United States Patent [19]
Davis et al.

[11] Patent Number: 6,136,596
[45] Date of Patent: Oct. 24, 2000

[54] CYTOKINE-, STRESS-, AND ONCOPROTEIN-ACTIVATED HUMAN PROTEIN KINASE KINASES

[75] Inventors: Roger J. Davis, Princeton; Alan Whitmarsh, Shrewsbury; Cathy Tournier, Worcester, all of Mass.

[73] Assignee: University of Massachusetts, Boston, Mass.

[21] Appl. No.: 08/888,429

[22] Filed: Jul. 7, 1997

Related U.S. Application Data

[63] Continuation-in-part of application No. 08/530,950, Sep. 19, 1995, Pat. No. 5,736,381, which is a continuation-in-part of application No. 08/446,083, May 19, 1995, Pat. No. 5,804,427.

[51] Int. Cl.$^7$ ............... C12N 9/12; C12N 15/54; C12N 5/10; C12N 15/63

[52] U.S. Cl. ............ 435/325; 536/23.2; 435/252.3; 435/320.1; 435/194

[58] Field of Search ............ 536/23.2; 435/252.3, 435/325, 320.1, 194

[56] References Cited

U.S. PATENT DOCUMENTS

| | | | |
|---|---|---|---|
| 5,753,446 | 5/1998 | Johnson | 435/1 |
| 5,804,427 | 9/1998 | Davis et al. | 435/194 |

FOREIGN PATENT DOCUMENTS

WO 94/24159  10/1994  WIPO.
WO 95/28421  10/1995  WIPO.

OTHER PUBLICATIONS

Davis, "MAPKs: new JNK expands group" Elsevier Science Ltd TIBS 19:470–473, 1994.

Dérijard et al., "Independent human MAP kinase signal transduction pathways defined by MEK and MKK isoforms" Science 267:682–685, 1995.

Déijard et al., "JNK1: a protein kinase stimulated by UV light and Ha-Ras that binds and phosphorylates . . . " Cell 76:1025–1037, 1994.

English, et al., "Isolation of MEK5 and differential Expression of Alternatively Spliced Forms" J. of Biol. Chem. 270:28897–28902, 1995.

Freshney et al., "Interleukin–1 activates a novel protein kinase cascade that results in the phosphorylation of Hsp27" Cell 78:1039–1049, 1994.

Galcheva–Gargova et al., "An osmosensing signal transduction pathway in mammalian cells" Science 265:806–808, 1994.

Gupta et al., "Transcription factor ATF2 regulation by the JNK signal transduction pathway" Science 267:389–393, 1995.

Han, et al., "Characterization of the structure and function of a novel MAP kinase kinase (MKK6)" J. of Biol. Chem. 271:2886–2891, 1996.

Hibi, et al, "Identification of an oncoprotein–and UV–responsive protein that binds and potentiates . . . " Genes & Dev. 7:2135–2148, 1993.

Lin et al., "Identification of a dual specificity kinase that activate the Jun kinases and p38–Mpk2" Science 268:286–290, 1995.

Minden et al., "Differential activation of ERK and JNK mitogen–activated protein kinases by Raf–1 and MEKK" Science 266:1719–1723, 1994.

Meirer, et. al., "Cellular stresses and cytokines activate multiple mitogen–activated–protein kinase . . . " Europ. J. of Biochem. 236:747–1040, 1996.

Moriguchi, et al., "Evidence for multiple activators for stress–activated protein kinases/c–Jun Amino . . . " J. of Biol. Chem. 270:12949–13579, 1995.

Moriguchi, et al., "Purification and Identification of a major activator for p38 from osmotically shocked cells" J. Biol. Chem. 271:26891–26988, 1996.

Nishina, et al., "Stress–signalling kinase Sek1 protects thymocytes from apoptosis". . . Nature 385:351–53, 1997.

Raingeaud et al., "Pro–inflammatory cytokines and environmental stress cause p38 mitogen–activated . . . " J. of Biol. Chem. 270:7420–7426, 1995.

Raingeaud et al., "MKK3– and MKK6–Regulated gene expression is mediated by the p38 mitogen–activated . . . " Mol. and Cell. Biol. 16:1247–1255, 1996.

Rouse et al., "A novel kinase cascade triggered by stress and heat shock that stimulates MAPKAP kinase . . . " Cell 78:1027–1037, 1994.

Sanchez et al., "Role of SAPK/ERK kinase–1 in the stress–activated pathway regulating transcription . . . " Nature 372:794–798, 1994.

Seger et al., "Human T–Cell Mitogen–Activated Protein Kinases Are Related to Yeast Signal Transduction Kinases," J. Biological Chemistry, 267:25628–25631 (1992).

Sluss, et al, "Signal transduction by tumor necrosis factor mediated by JNK protein kinases" Mol. and Cell. Biol. 14:8376–8384, 1994.

Whitmarsh et al., "Inteegration of MAP kinase signal transduction pathways at the serum response element" Science 269:403–407, 1995.

Wu et al., "Identification and Characterization of a New Mammlian Mitogen–Activated Protein Kinase Kinases, MKK2," Molecular and Cellular Biology, 13:4539–4548 (1993).

Xia et al., "Opposing effects of ERK and JNK–p38 MAP kinases on apoptosis" Science 270:1326–1331, 1995.

(List continued on next page.)

*Primary Examiner*—Rebecca E. Prouty
*Attorney, Agent, or Firm*—Fish & Richardson P.C.

[57] ABSTRACT

Disclosed are human mitogen-activated (MAP) kinase kinase isoforms (MKKs). MKKs mediate unique signal transduction pathways that activate human MAP kinases p38 and JNK, which result in activation of other factors, including activating transcription factor-2 (ATF2) and c-Jun. The pathways are activated by a number of factors, including cytokines and environmental stress. Methods are provided for identifying reagents that modulate MKK function or activity and for the use of such reagents in the treatment of MKK-mediated disorders.

9 Claims, 54 Drawing Sheets

OTHER PUBLICATIONS

Yan et al., "Activation of stress–activated protein kinase by MEKK1 phosphorylation of its activator SEK1" Nature 372:798–800, 1994.

Yang, et al., "Targeted disruption of the MKK4 gene causes embryonic death, inhibition of c–Jun . . ." Proc. Nat'l. Acad. Sci. USA 94:3004–3009, 1997.

Yashar et al., "Novel members of the mitogen–activated protein kinase activator family in *Xenopus laevis*" Mol. and Cell. Biol. 13:5738–5748, 1993.

Cuenda et al., "Differential activation of stress–activated protein kinase kinases SKK4/MKK7 and SKK1/MKK4 by the . . . " Biochem. J. 333:11–15, 1998.

Dent et al., "Activation of Mitogen–Activated Protein Kinase Kinase by v–Raf in NIH 3T3 Cells and in Vitro" Science 257:1404–1407, 1992.

Irie et al., "MKK1 and MKK2, Which Encode *Saccharomyces cerevisiae* Mitogen–Activated Protein Kinase–Kinase Homologs, . . . " Mol. and Cell. Biol. 13(5):3076–3083, 1993.

Moodie et al., "Complexes of Ras–GTP with Raf–1 and Mitogen–Activated Protein Kinase Kinase" Science 260:1658–1661, 1993.

Tournier et al., "Mitogen–activated protein kinase kinase 7 is an activator of the c–Jun $NH_2$–terminal kinase" Proc. Nat'l. Acad. Sci. USA 94:7337–7342, 1997.

Traverse et al., "Sustained activation of the mitogen–activated protein (MAP) kinase cascade may be required for differentiation of PC12 cells" Biochem. J. 288:351–355, 1992.

```
                                                                                              71
MKK3              MSKPP------APNPTPPRN------LDSRTFITIG------DRNFEVEADD
MKK4     MQGKRKALKLNFAN..FKSTARFTLN...GVQ.PHIERLRTHSIE.SGKLK.SP------EQHWDFT.E.
MEK1     MPKKKP--TPIQLN.A-PDGSAVNGTSSAETNLEALQKKLEELE..EQQRKRLEAFLTQKQKVG.LKD..
MEK2     MLARRKPVLPALTIN.TIAEGPSPTSEGASEANLVDLQKKLEELE..EQOKKRLEAFLTQKAKVG.LKD..
PBS2     <GTTPRTGNSNNS-NSGSGGGGLFANFSKYVDIKSGSLNFAGKLSL.SKG.DFSN----GSSSRITL.E
Consensus 72                                                                                  142
MKK3     LVTISELGRGAYGVVEKVRHAQSGTIMAVKRIRATVNSQEQKRLLMDLDINMRTVDCFYTVTFYGALFREG
MKK4     .KDLG.I......S.N.MV.KP.Q.......S..DEK..Q......VV..SS..P.I.Q.........
MEK1     FEK.....A.NG....F.VS.KP.LV..R.L.HLEIKPAIRNQIIRE.QV-LHECNSP.I.G.....FYSD.
MEK2     FER.....A.NG....T.VQ.RP.L....R.L.HLEIKPAIRNQIIRE.QV-LHECNSP.I.G.....FYSD.
PBS2     .EFLD...H.N..N.S.VL.KPTNV...T.EV.LELDEAKFRQI..E.EV-LHKCNSP.I.D....F.I..
Consensus         E G G G V K H     MA K             L      Y V FYGA    G 143                                                                                 213
MKK3     DWWICMELMD-TSLDKFYR---KVLDKNMTIPEDILGEIAVSIVRALEHLHSKLSVIHRDVKPSNVL-INK
MKK4     .C......S-..F...KYVYS...D-V...E...K.TLAT.K..N..KEN.KI.....I.....I.-LDR
MEK1     EIS.....H..GG...Q-------K.AGR...Q...KVSIAVIKG.TY.RE.HKIM........I.-V.S
MEK2     EIS.....H..GG...Q-------KEAKR....E...KVSIAVL.G.AY.RE.HQIM........I.-V.S
PBS2     A.YM....Y..GG....IYDESSEIGG-----D.PQ.AF..NAVIHG.KE.KEQHNI......T.I.CSAN
Consensus       CME M  S D        *      I E L       L   L       HRD KP N L 214                                                                                 284
MKK3     EGHVKMCDFGISGYLVDSVAKTMDAGCKPYMAPERINP-ELNQKGYNVKSDVWSLGITMIEMAILRFPY--
MKK4     S.NI.L.....Q....I...R....R......D.-SASRQ..D.R.......IY.L.TG......
MEK1     R.EI.L.....V..Q.I..M.NSF-V.TRS..S......LQGTH-----S.Q..I..M.LSLV..VG.Y.IPP
MEK2     R.EI.L.....V..Q.I..M.NSF-V.TRS......LQGTH-----S.Q..I..M.LSLV.L.VG.Y.IPP
PBS2     Q.T..L.....V.N..A.L....NI..QS......KSLNPDRAT.T.Q..I....LSIL...LG.Y..PP
Consensus  G  K CDFG SG L S A      G  YM PER      Y V SD WS G   E A R P 285                                                                                 355
MKK3     ESWG------------TPFQQLKQVVEEPSPQLPAD---R
MKK4     PK.N--------------SV.D..T...KGDP...SNSEERE
MEK1     PDAKELELMFGCQV-----EGDAAETPPRPRTPGRPLSSYGMDSRPPMAI.EL.DYI.N..P.K..SGV---
MEK2     PDAKELEAIFGRPVVDGEEGEPHSISPRPRPPGRPVSGHGMDSRPAMAI.EL.DYI.N..P.K..NGV---
PBS2     .TYD------------NI.S..SAI.DG.P.R..S.---K
Consensus                                  F L V  P L 356                                                                                 426
MKK3     FSPEFVDFTAQCLRKNPAERMSYLELMEHPFFTLHKTKKTDIAAFVK------KILGEDS           (SEQ ID NO: 2)
MKK4     ...S.IN.VNL..T.DESK.PK.K..LK...ILMYEERAVEV.CY.C-------.DQMPATPSSPMYD   (SEQ ID NO: 6)
MEK1     ..L..Q..VNK...I......ADLKQ..V.A.IKRSDAEEV.F.GWLCSTIGLNQPSTPTHAAGV     (SEQ ID NO: 11)
MEK2     .T.D.QE.VNK......I......ADLKM.TN..T.IKRSEVEEV.F.GWLCKTLRLNQPGTPTRTA    (SEQ ID NO: 12)
PBS2     ..SDAQD.VSL..Q.I.ER..PT.AA.T..PWLVKYRNQDVHMSEYITERLERRN...R.RGENGLSKNVP> (SEQ ID NO: 13)
Consensus        F    F  CL K   R      L   H                                       (SEQ ID NO: 34)
```

FIG. 1

```
          5         10        15        20        25        30        35        40        45        50        55        60
          *                             *                             *                             *
TGGCTGGCAA TGGCCTTGCT GACCTCGAGC CGGGCCCACG TGGGGACCTT TGGAGCACAG
ACCGACCGTT ACCGGAACGA CTGGAGCTCG GCCCGGGTGC ACCCCTGGAA ACCTCGTGTC 65        70        75        80        85        90        95        100       105       110       115       120
                              *                             *                             *                             *
CCTACGATCC TGGTGCAAGG CCGGTGGATG CAGAGGCCAG TCCATATACC ACCCAGGCCT
GGATGCTAGG ACCACGTTCC GGCCACCTAC GTCTCCGGTC AGGTATATGG TGGGTCCGGA 125       130       135       140       145       150       155       160       165       170       175       180
          *                             *                             *                             *
GCGAGGAGCG TGGTCCCCAC CCATCCAGCC CATATGTGCA AGTGCCCTTG ACAGAGAGGC
CGCTCCTCGC ACCAGGGGTG GGTAGGTCGG GTATACACGT TCACGGGAAC TGTCTCTCCG 185       190       195       200       205       210       215       220       225       230       235       240
                    *                             *                             *                             *
TGGTCATATC CATGGTGACC ATTTATGGGC CACAACAGGT CCCCATCTGC GCAGTGAACC
ACCAGTATAG GTACCACTGG TAAATACCCG GTGTTGTCCA GGGGTAGACG CGTCACTTGG 245       250       255       260       265       270       275       280       285       290       295       300
                    *                             *                             *                             *
CTGTGCTGAG CACCTTGCAG ACGTGATCTT GCTTCGTCCT GCAGCACTGT GCGGGGCAGG
GACACGACTC GTGGAACGTC TGCACTAGAA CGAAGCAGGA CGTCGTGACA CGCCCCGTCC 305       310       315       320       325       330       335       340       345       350       355
                              *                             *                             *
AAAATCCAAG AGGAAGAAGG ATCTACGGAT ATCCTGC ATG TCC AAG CCA CCC GCA
TTTTAGGTTC TCCTTCTTCC TAGATGCCTA TAGGACG TAC AGG TTC GGT GGG CGT
                                        Met Ser Lys Pro Pro Ala>

360       365       370       375       380       385       390       395       400
                    *                             *                             *
CCC AAC CCC ACA CCC CCC CGG AAC CTG GAC TCC CGG ACC TTC ATC ACC
GGG TTG GGG TGT GGG GGG GCC TTG GAC CTG AGG GCC TGG AAG TAG TGG
Pro Asn Pro Thr Pro Pro Arg Asn Leu Asp Ser Arg Thr Phe Ile Thr>

405       410       415       420       425       430       435       440       445       450
                              *                             *                             *
ATT GGA GAC AGA AAC TTT GAG GTG GAG GCT GAT GAC TTG GTG ACC ATC
TAA CCT CTG TCT TTG AAA CTC CAC CTC CGA CTA CTG AAC CAC TGG TAG
Ile Gly Asp Arg Asn Phe Glu Val Glu Ala Asp Asp Leu Val Thr Ile>

455       460       465       470       475       480       485       490       495
                              *                             *                             *
TCA GAA CTG GGC CGT GGA GCC TAT GGG GTG GTA GAG AAG GTG CGG CAC
AGT CTT GAC CCG GCA CCT CGG ATA CCC CAC CAT CTC TTC CAC GCC GTG
Ser Glu Leu Gly Arg Gly Ala Tyr Gly Val Val Glu Lys Val Arg His>

500       505       510       515       520       525       530       535       540       545
          *                             *                             *                             *
GCC CAG AGC GGC ACC ATC ATG GCC GTG AAG CGG ATC CGG GCC ACC GTG
CGG GTC TCG CCG TGG TAG TAC CGG CAC TTC GCC TAG GCC CGG TGG CAC
Ala Gln Ser Gly Thr Ile Met Ala Val Lys Arg Ile Arg Ala Thr Val>

550       555       560       565       570       575       580       585       590       595
          *                   *                             *                             *
AAC TCA CAG GAG CAG AAG CGG CTG CTC ATG GAC CTG GAC ATC AAC ATG
TTG AGT GTC CTC GTC TTC GCC GAC GAG TAC CTG GAC CTG TAG TTG TAC
Asn Ser Gln Glu Gln Lys Arg Leu Leu Met Asp Leu Asp Ile Asn Met>
```

FIG. 4A

```
      600       605       610       615       620       625       630       635       640
       *                   *                   *                   *                   *
CGC ACG GTC GAC TGT TTC TAC ACT GTC ACC TTC TAC GGG GCA CTA TTC
GCG TGC CAG CTG ACA AAG ATG TGA CAG TGG AAG ATG CCC CGT GAT AAG
Arg Thr Val Asp Cys Phe Tyr Thr Val Thr Phe Tyr Gly Ala Leu Phe>

645       650       655       660       665       670       675       680       685       690
   *                   *                   *                   *                   *
AGA GAG GGA GAC GTG TGG ATC TGC ATG GAG CTC ATG GAC ACA TCC TTG
TCT CTC CCT CTG CAC ACC TAG ACG TAC CTC GAG TAC CTG TGT AGG AAC
Arg Glu Gly Asp Val Trp Ile Cys Met Glu Leu Met Asp Thr Ser Leu>

695       700       705       710       715       720       725       730       735
        *                   *                   *                   *
GAC AAG TTC TAC CGG AAG GTG CTG GAT AAA AAC ATG ACA ATT CCA GAG
CTG TTC AAG ATG GCC TTC CAC GAC CTA TTT TTG TAC TGT TAA GGT CTC
Asp Lys Phe Tyr Arg Lys Val Leu Asp Lys Asn Met Thr Ile Pro Glu>

740       745       750       755       760       765       770       775       780       785
  *                   *                   *                   *                   *
GAC ATC CTT GGG GAG ATT GCT GTG TCT ATC GTG CGG GCC CTG GAG CAT
CTG TAG GAA CCC CTC TAA CGA CAC AGA TAG CAC GCC CGG GAC CTC GTA
Asp Ile Leu Gly Glu Ile Ala Val Ser Ile Val Arg Ala Leu Glu His>

790       795       800       805       810       815       820       825       830       835
  *                   *                   *                   *                   *
CTG CAC AGC AAG CTG TCG GTG ATC CAC AGA GAT GTG AAG CCC TCC AAT
GAC GTG TCG TTC GAC AGC CAC TAG GTG TCT CTA CAC TTC GGG AGG TTA
Leu His Ser Lys Leu Ser Val Ile His Arg Asp Val Lys Pro Ser Asn>

840       845       850       855       860       865       870       875       880
        *                   *                   *                   *                   *
GTC CTT ATC AAC AAG GAG GGC CAT GTG AAG ATG TGT GAC TTT GGC ATC
CAG GAA TAG TTG TTC CTC CCG GTA CAC TTC TAC ACA CTG AAA CCG TAG
Val Leu Ile Asn Lys Glu Gly His Val Lys Met Cys Asp Phe Gly Ile>

885       890       895       900       905       910       915       920       925       930
   *                   *                   *                   *                   *
AGT GGC TAC TTG GTG GAC TCT GTG GCC AAG ACG ATG GAT GCC GGC TGC
TCA CCG ATG AAC CAC CTG AGA CAC CGG TTC TGC TAC CTA CGG CCG ACG
Ser Gly Tyr Leu Val Asp Ser Val Ala Lys Thr Met Asp Ala Gly Cys>

935       940       945       950       955       960       965       970       975
        *                   *                   *                   *
AAG CCC TAC ATG GCC CCT GAG AGG ATC AAC CCA GAG CTG AAC CAG AAG
TTC GGG ATG TAC CGG GGA CTC TCC TAG TTG GGT CTC GAC TTG GTC TTC
Lys Pro Tyr Met Ala Pro Glu Arg Ile Asn Pro Glu Leu Asn Gln Lys>

980       985       990       995      1000      1005      1010      1015      1020      1025
  *                   *                   *                   *                   *
GGC TAC AAT GTC AAG TCC GAC GTC TGG AGC CTG GGC ATC ACC ATG ATT
CCG ATG TTA CAG TTC AGG CTG CAG ACC TCG GAC CCG TAG TGG TAC TAA
Gly Tyr Asn Val Lys Ser Asp Val Trp Ser Leu Gly Ile Thr Met Ile>

1030      1035      1040 1045      1050      1055      1060      1065      1070 1075
  *                   *                   *                   *                   *
GAG ATG GCC ATC CTG CGG TTC CCT TAC GAG TCC TGG GGG ACC CCG TTC
CTC TAC CGG TAG GAC GCC AAG GGA ATG CTC AGG ACC CCC TGG GGC AAG
Glu Met Ala Ile Leu Arg Phe Pro Tyr Glu Ser Trp Gly Thr Pro Phe>

```
             *              *              *              *              *
        CAG CAG CTG AAG CAG GTG GTG GAG GAG CCG TCC CCC CAG CTC CCA GCC
        GTC GTC GAC TTC GTC CAC CAC CTC CTC GGC AGG GGG GTC GAG GGT CGG
        Gln Gln Leu Lys Gln Val Val Glu Glu Pro Ser Pro Gln Leu Pro Ala>

1125  1130  1135  1140  1145  1150  1155  1160  1165  1170
             *              *              *              *              *
        GAC CGT TTC TCC CCC GAG TTT GTG GAC TTC ACT GCT CAG TGC CTG AGG
        CTG GCA AAG AGG GGG CTC AAA CAC CTG AAG TGA CGA GTC ACG GAC TCC
        Asp Arg Phe Ser Pro Glu Phe Val Asp Phe Thr Ala Gln Cys Leu Arg>

1175  1180  1185  1190  1195  1200  1205  1210  1215
                    *              *              *              *
        AAG AAC CCC GCA GAG CGT ATG AGC TAC CTG GAG CTG ATG GAG CAC CCC
        TTC TTG GGG CGT CTC GCA TAC TCG ATG GAC CTC GAC TAC CTC GTG GGG
        Lys Asn Pro Ala Glu Arg Met Ser Tyr Leu Glu Leu Met Glu His Pro>

1220 1225  1230  1235  1240  1245  1250  1255  1260  1265
        *              *              *              *              *
        TTC TTC ACC TTG CAC AAA ACC AAG AAG ACG GAC ATT GCT GCC TTC GTG
        AAG AAG TGG AAC GTG TTT TGG TTC TTC TGC CTG TAA CGA CGG AAG CAC
        Phe Phe Thr Leu His Lys Thr Lys Lys Thr Asp Ile Ala Ala Phe Val>

1270  1275  1280  1285  1290  1295  1300  1305  1310  1315 1320
             *              *              *              *              *
        AAG AAG ATC CTG GGA GAA GAC TCA TAGGGGCTG GGCCTCGGAC CCCACTCCGG
        TTC TTC TAG GAC CCT CTT CTG AGT ATCCCCGAC CCGGAGCCTG GGGTGAGGCC
        Lys Lys Ile Leu Gly Glu Asp Ser> (SEQ ID NO:2)

1325 1330  1335 1340  1345 1350  1355 1360  1365 1370  1375 1380
             *              *              *              *              *
        CCCTCCAGAG CCCCACAGCC CCATCTGCGG GGGCAGTGCT CACCCACACC ATAAGCTACT
        GGGAGGTCTC GGGGTGTCGG GGTAGACGCC CCCGTCACGA GTGGGTGTGG TATTCGATGA 1385 1390  1395 1400  1405 1410  1415 1420  1425 1430  1435 1440
             *              *              *              *              *
        GCCATCCTGG CCCAGGGCAT CTGGGAGGAA CCGAGGGGGC TGCTCCCACC TGGCTCTGTG
        CGGTAGGACC GGGTCCCGTA GACCCTCCTT GGCTCCCCCG ACGAGGGTGG ACCGAGACAC 1445 1450  1455 1460  1465 1470  1475 1480  1485 1490  1495 1500
             *              *              *              *              *
        GCGAGCCATT TGTCCCAAGT GCCAAAGAAG CAGACCATTG GGGCTCCCAG CCAGGCCCTT
        CGCTCGGTAA ACAGGGTTCA CGGTTTCTTC GTCTGGTAAC CCCGAGGGTC GGTCCGGGAA 1505 1510  1515 1520  1525 1530  1535 1540  1545 1550  1555 1560
             *              *              *              *              *
        GTCGGCCCCA CCAGTGCCTC TCCCTGCTGC TCCTAGGACC CGTCTCCAGC TGCTGAGATC
        CAGCCGGGGT GGTCACGGAG AGGGACGACG AGGATCCTGG GCAGAGGTCG ACGACTCTAG 1565 1570  1575 1580  1585 1590  1595 1600  1605 1610  1615 1620
             *              *              *              *              *
        CTGGACTGAG GGGGCCTGGA TGCCCCCTGT GGATGCTGCT GCCCCTGCAC AGCAGGCTGC
        GACCTGACTC CCCCGGACCT ACGGGGGACA CCTACGACGA CGGGGACGTG TCGTCCGACG 1625 1630  1635 1640  1645 1650  1655 1660  1665 1670  1675 1680
             *              *              *              *              *
        CAGTGCCTGG GTGGATGGGC CACCGCCTTG CCCAGCCTGG ATGCCATCCA AGTTGTATAT
        GTCACGGACC CACCTACCCG GTGGCGGAAC GGGTCGGACC TACGGTAGGT TCAACATATA 1685 1690  1695 1700  1705 1710  1715 1720  1725 1730  1735 1740
             *              *              *              *              *
        TTTTTTAATC TCTCGACTGA ATGGACTTTG CACACTTTGG CCCAGGGTGG CCACACCTCT
```

FIG. 4C

```
AAAAAATTAG AGAGCTGACT TACCTGAAAC GTGTGAAACC GGGTCCCACC GGTGTGGAGA 1745 1750  1755 1760  1765 1770  1775 1780  1785 1790  1795 1800
     *          *          *          *          *          *
ATCCCGGCTT TGGTGCGGGG TACACAAGAG GGGATGAGTT GTGTGAATAC CCCAAGACTC
TAGGGCCGAA ACCACGCCCC ATGTGTTCTC CCCTACTCAA CACACTTATG GGGTTCTGAG 1805 1810  1815 1820  1825 1830  1835 1840  1845 1850  1855 1860
     *          *          *          *          *          *
CCATGAGGGA GATGCCATGA GCCGCCCAAG GCCTTCCCCT GGCACTGGCA AACAGGGCCT
GGTACTCCCT CTACGGTACT CGGCGGGTTC CGGAAGGGGA CCGTGACCGT TTGTCCCGGA 1865 1870  1875 1880  1885 1890  1895 1900  1905 1910  1915 1920
     *          *          *          *          *          *
CTGCGGAGCA CACTGGCTCA CCCAGTCCTG CCCGCCACCG TTATCGGTGT CATTCACCTT
GACGCCTCGT GTGACCGAGT GGGTCAGGAC GGGCGGTGGC AATAGCCACA GTAAGTGGAA 1925 1930  1935 1940  1945 1950  1955 1960  1965 1970  1975 1980
     *          *          *          *          *          *
TCGTGTTTTT TTTAATTTAT CCTCTGTTGA TTTTTTCTTT TGCTTTATGG GTTTGGCTTG
AGCACAAAAA AAATTAAATA GGAGACAACT AAAAAAGAAA ACGAAATACC CAAACCGAAC 1985 1990  1995 2000  2005 2010  2015 2020  2025 2030
     *          *          *          *          *
TTTTTCTTGC ATGGTTTGGA GCTGATCGCT TCTCCCCCAC CCCCTAGGGG   (SEQ ID NO: 1)
AAAAAGAACG TACCAAACCT CGACTAGCGA AGAGGGGGTG GGGGATCCCC
```

FIG. 4D

```
          5         10        15        20        25        30        35        40        45        50        55        60
                              *                             *                             *                             *
TAGCTGCAGC ACAGCCTTCC CTAACGTTGC AACTGGGGGA AAAATCACTT TCCAGTCTGT
ATCGACGTCG TGTCGGAAGG GATTGCAACG TTGACCCCCT TTTTAGTGAA AGGTCAGACA 65        70        75        80        85        90        95       100       105       110       115       120
                              *                             *                             *                             *
TTTGCAAGGT GTGCATTTCC ATCTTGATTC CCTGAAAGTC CATCTGCTGC ATCGGTCAAG
AAACGTTCCA CACGTAAAGG TAGAACTAAG GGACTTTCAG GTAGACGACG TAGCCAGTTC 125       130       135       140       145       150       155       160       165       170       175       180
                              *                             *                             *                             *
AGAAACTCCA CTTGCATGAA GATTGCACGC CTGCAGCTTG CATCTTTGTT GCAAAACTAG
TCTTTGAGGT GAACGTACTT CTAACGTGCG GACGTCGAAC GTAGAAACAA CGTTTTGATC 185       190       195       200       205       210       215       220       225       230       235       240
                              *                             *                             *                             *
CTACAGAAGA GAAGCAAGGC AAAGTCTTTT GTGCTCCCCT CCCCCATCAA AGGAAAGGGG
GATGTCTTCT CTTCGTTCCG TTTCAGAAAA CACGAGGGGA GGGGGTAGTT TCCTTTCCCC 245       250       255       260       265       270       275       280       285
                              *                             *                             *
AAA ATG TCT CAG TCG AAA GGC AAG AAG CGA AAC CCT GGC CTT AAA ATT
TTT TAC AGA GTC AGC TTT CCG TTC TTC GCT TTG GGA CCG GAA TTT TAA
    Met Ser Gln Ser Lys Gly Lys Lys Arg Asn Pro Gly Leu Lys Ile>

290       295       300       305       310       315       320       325       330       335
                              *                             *                             *
CCA AAA GAA GCA TTT GAA CAA CCT CAG ACC AGT TCC ACA CCA CCT AGA
GGT TTT CTT CGT AAA CTT GTT GGA GTC TGG TCA AGG TGT GGT GGA TCT
Pro Lys Glu Ala Phe Glu Gln Pro Gln Thr Ser Ser Thr Pro Pro Arg>

340       345       350       355       360       365       370       375       380
                              *                             *                             *
GAT TTA GAC TCC AAG GCT TGC ATT TCT ATT GGA AAT CAG AAC TTT GAG
CTA AAT CTG AGG TTC CGA ACG TAA AGA TAA CCT TTA GTC TTG AAA CTC
Asp Leu Asp Ser Lys Ala Cys Ile Ser Ile Gly Asn Gln Asn Phe Glu>

385       390       395       400       405       410       415       420       425       430
                              *                             *                             *
GTG AAG GCA GAT GAC CTG GAG CCT ATA ATG GAA CTG GGA CGA GGT GCG
CAC TTC CGT CTA CTG GAC CTC GGA TAT TAC CTT GAC CCT GCT CCA CGC
Val Lys Ala Asp Asp Leu Glu Pro Ile Met Glu Leu Gly Arg Gly Ala>

435       440       445       450       455       460       465       470       475       480
                              *                             *                             *
TAC GGG GTG GTG GAG AAG ATG CGG CAC GTG CCC AGC GGG CAG ATC ATG
ATG CCC CAC CAC CTC TTC TAC GCC GTG CAC GGG TCG CCC GTC TAG TAC
Tyr Gly Val Val Glu Lys Met Arg His Val Pro Ser Gly Gln Ile Met>

485       490       495       500       505       510       515       520       525
                              *                             *                             *
GCA GTG AAG CGG ATC CGA GCC ACA GTA AAT AGC CAG GAA CAG AAA CGG
CGT CAC TTC GCC TAG GCT CGG TGT CAT TTA TCG GTC CTT GTC TTT GCC
Ala Val Lys Arg Ile Arg Ala Thr Val Asn Ser Gln Glu Gln Lys Arg>

530       535       540       545       550       555       560       565       570       575
                              *                             *                             *
CTA CTG ATG GAT TTG GAT ATT TCC ATG AGG ACG GTG GAC TGT CCA TTC
GAT GAC TAC CTA AAC CTA TAA AGG TAC TCC TGC CAC CTG ACA GGT AAG
```

FIG. 5A

```
       Leu Leu Met Asp Leu Asp Ile Ser Met Arg Thr Val Asp Cys Pro Phe>

580    585    590    595    600    605    610    615    620
         *      *      *      *      *      *      *      *      *
       ACT GTC ACC TTT TAT GGC GCA CTG TTT CGG GAG GGT GAT GTG TGG ATC
       TGA CAG TGG AAA ATA CCG CGT GAC AAA GCC CTC CCA CTA CAC ACC TAG
       Thr Val Thr Phe Tyr Gly Ala Leu Phe Arg Glu Gly Asp Val Trp Ile>

625    630    635    640    645    650    655    660    665    670
    *      *      *      *      *      *      *      *      *      *
   TGC ATG GAG CTC ATG GAT ACA TCA CTA GAT AAA TTC TAC AAA CAA GTT
   ACG TAC CTC GAG TAC CTA TGT AGT GAT CTA TTT AAG ATG TTT GTT CAA
   Cys Met Glu Leu Met Asp Thr Ser Leu Asp Lys Phe Tyr Lys Gln Val>

675    680    685    690    695    700    705    710    715    720
       *      *      *      *      *      *      *      *      *      *
      ATT GAT AAA GGC CAG ACA ATT CCA GAG GAC ATC TTA GGG AAA ATA GCA
      TAA CTA TTT CCG GTC TGT TAA GGT CTC CTG TAG AAT CCC TTT TAT CGT
      Ile Asp Lys Gly Gln Thr Ile Pro Glu Asp Ile Leu Gly Lys Ile Ala>

725    730    735    740    745    750    755    760    765
          *      *      *      *      *      *      *      *      *
         GTT TCT ATT GTA AAA GCA TTA GAA CAT TTA CAT AGT AAG CTG TCT GTC
         CAA AGA TAA CAT TTT CGT AAT CTT GTA AAT GTA TCA TTC GAC AGA CAG
         Val Ser Ile Val Lys Ala Leu Glu His Leu His Ser Lys Leu Ser Val>

770    775    780    785    790    795    800    805    810    815
    *      *      *      *      *      *      *      *      *      *
   ATT CAC AGA GAC GTC AAG CCT TCT AAT GTA CTC ATC AAT GCT CTC GGT
   TAA GTG TCT CTG CAG TTC GGA AGA TTA CAT GAG TAG TTA CGA GAG CCA
   Ile His Arg Asp Val Lys Pro Ser Asn Val Leu Ile Asn Ala Leu Gly>

820    825    830    835    840    845    850    855    860
       *      *      *      *      *      *      *      *      *
      CAA GTG AAG ATG TGC GAT TTT GGA ATC AGT GGC TAC TTG GTG GAC TCT
      GTT CAC TTC TAC ACG CTA AAA CCT TAG TCA CCG ATG AAC CAC CTG AGA
      Gln Val Lys Met Cys Asp Phe Gly Ile Ser Gly Tyr Leu Val Asp Ser>

865    870    875    880    885    890    895    900    905    910
    *      *      *      *      *      *      *      *      *      *
   GTT GCT AAA ACA ATT GAT GCA GGT TGC AAA CCA TAC ATG GCC CCT GAA
   CAA CGA TTT TGT TAA CTA CGT CCA ACG TTT GGT ATG TAC CGG GGA CTT
   Val Ala Lys Thr Ile Asp Ala Gly Cys Lys Pro Tyr Met Ala Pro Glu>

915    920    925    930    935    940    945    950    955    960
       *      *      *      *      *      *      *      *      *      *
      AGA ATA AAC CCA GAG CTC AAC CAG AAG GGA TAC AGT GTG AAG TCT GAC
      TCT TAT TTG GGT CTC GAG TTG GTC TTC CCT ATG TCA CAC TTC AGA CTG
      Arg Ile Asn Pro Glu Leu Asn Gln Lys Gly Tyr Ser Val Lys Ser Asp>

965    970    975    980    985    990    995   1000   1005
          *      *      *      *      *      *      *      *      *
         ATT TGG AGT CTG GGC ATC ACG ATG ATT GAG TTG GCC ATC CTT CGA TTT
         TAA ACC TCA GAC CCG TAG TGC TAC TAA CTC AAC CGG TAG GAA GCT AAA
         Ile Trp Ser Leu Gly Ile Thr Met Ile Glu Leu Ala Ile Leu Arg Phe>

1010   1015   1020   1025   1030   1035   1040   1045   1050   1055
    *      *      *      *      *      *      *      *      *      *
   CCC TAT GAT TCA TGG GGA ACT CCA TTT CAG CAG CTC AAA CAG GTG GTA
   GGG ATA CTA AGT ACC CCT TGA GGT AAA GTC GTC GAG TTT GTC CAC CAT
   Pro Tyr Asp Ser Trp Gly Thr Pro Phe Gln Gln Leu Lys Gln Val Val>
```

FIG. 5B

```
      1060      1065      1070      1075      1080      1085      1090  1095      1100
         *                   *                   *                   *              *
      GAG GAG CCA TCG CCA CAA CTC CCA GCA GAC AAG TTC TCT GCA GAG TTT
      CTC CTC GGT AGC GGT GTT GAG GGT CGT CTG TTC AAG AGA CGT CTC AAA
      Glu Glu Pro Ser Pro Gln Leu Pro Ala Asp Lys Phe Ser Ala Glu Phe>

1105    1110      1115      1120      1125      1130      1135      1140      1145      1150
    *                   *                   *                   *                   *
    GTT GAC TTT ACC TCA CAG TGC TTA AAG AAG AAT TCC AAA GAA CGG CCT
    CAA CTG AAA TGG AGT GTC ACG AAT TTC TTC TTA AGG TTT CTT GCC GGA
    Val Asp Phe Thr Ser Gln Cys Leu Lys Lys Asn Ser Lys Glu Arg Pro>

1155      1160      1165      1170      1175      1180      1185      1190      1195      1200
      *                   *                   *                   *                   *
    ACA TAC CCA GAG CTA ATG CAA CAT CCA TTT TTC ACC CTA CAT GAA TCC
    TGT ATG GGT CTC GAT TAC GTT GTA GGT AAA AAG TGG GAT GTA CTT AGG
    Thr Tyr Pro Glu Leu Met Gln His Pro Phe Phe Thr Leu His Glu Ser>

1205      1210  1215      1220      1225  1230      1235      1240      1245      1250
         *                   *                   *                   *              *
    AAA GGA ACA GAT GTG GCA TCT TTT GTA AAA CTG ATT CTT GGA GAC TAAAA
    TTT CCT TGT CTA CAC CGT AGA AAA CAT TTT GAC TAA GAA CCT CTG ATTTT
    Lys Gly Thr Asp Val Ala Ser Phe Val Lys Leu Ile Leu Gly Asp> (SEQ ID NO:4)

1255 1260      1265 1270      1275 1280      1285 1290      1295 1300      1305 1310
              *                 *                 *                 *                 *
    AGCAGTGGAC TTAATCGGTT GACCCTACTG TGGATTGGTG GGTTTCGGGG TGAAGCAAGT
    TCGTCACCTG AATTAGCCAA CTGGGATGAC ACCTAACCAC CCAAAGCCCC ACTTCGTTCA 1315 1320      1325 1330      1335 1340      1345 1350      1355 1360      1365 1370
              *                 *                 *                 *                 *
    TCACTACAGC ATCAATAGAA AGTCATCTTT GAGATAATTT AACCCTGCCT CTCAGAGGGT
    AGTGATGTCG TAGTTATCTT TCAGTAGAAA CTCTATTAAA TTGGGACGGA GAGTCTCCCA 1375 1380      1385 1390      1395 1400      1405 1410      1415 1420      1425 1430
              *                 *                 *                 *                 *
    TTTCTCTCCC AATTTTCTTT TTACTCCCCC TCTTAAGGGG GCCTTGGAAT CTATAGTATA
    AAAGAGAGGG TTAAAAGAAA AATGAGGGGG AGAATTCCCC CGGAACCTTA GATATCATAT 1435 1440      1445 1450      1455 1460      1465 1470      1475 1480      1485 1490
              *                 *                 *                 *                 *
    GAATGAACTG TCTAGATGGA TGAATTATGA TAAAGGCTTA GGACTTCAAA AGGTGATTAA
    CTTACTTGAC AGATCTACCT ACTTAATACT ATTTCCGAAT CCTGAAGTTT TCCACTAATT 1495 1500      1505 1510      1515 1520      1525 1530      1535 1540      1545 1550
              *                 *                 *                 *                 *
    ATATTTAATG ATGTGTCATA TGAGTCCTCA AAAAAAAAAA AAAAAAAAAA AAAAAAAAAA
    TATAAATTAC TACACAGTAT ACTCAGGAGT TTTTTTTTTT TTTTTTTTTT TTTTTTTTTT 1555 1560      1565 1570      1575 1580      1585 1590      1595 1600
              *                 *                 *                 *
    AAAAAAAAAA AAAAAAAAAA AAAAAAAAAA AAAAAAAAAA AAAAAAAAAA AA (SEQ ID NO:3)
    TTTTTTTTTT TTTTTTTTTT TTTTTTTTTT TTTTTTTTTT TTTTTTTTTT TT
```

FIG. 5C

```
              5         10         15         20         25         30         35         40         45         50         55
              *          *          *          *          *          *          *          *          *          *          *
          CTAGGGTCCC CGGCGCCAGG CCACCCGGCC GTCAGCAGC  ATG CAG GGT AAA CGC AAA
          GATCCCAGGG GCCGCGGTCC GGTGGGCCGG CAGTCGTCG  TAC GTC CCA TTT GCG TTT
                                                      Met Gln Gly Lys Arg Lys>

60         65         70         75         80         85         90         95        100        105
          *          *          *          *          *          *          *          *          *          *
        GCA CTG AAG TTG AAT TTT GCA AAT CCA CCT TTC AAA TCT ACA GCA AGG
        CGT GAC TTC AAC TTA AAA CGT TTA GGT GGA AAG TTT AGA TGT CGT TCC
        Ala Leu Lys Leu Asn Phe Ala Asn Pro Pro Phe Lys Ser Thr Ala Arg>

110        115        120        125        130        135        140        145        150
             *          *          *          *          *          *          *          *          *
        TTT ACT CTG AAT CCC AAT CCT ACA GGA GTT CAA AAC CCA CAC ATA GAG
        AAA TGA GAC TTA GGG TTA GGA TGT CCT CAA GTT TTG GGT GTG TAT CTC
        Phe Thr Leu Asn Pro Asn Pro Thr Gly Val Gln Asn Pro His Ile Glu>

155        160        165        170        175        180        185        190        195        200
        *          *          *          *          *          *          *          *          *          *
        AGA CTG AGA ACA CAC AGC ATT GAG TCA TCA GGA AAA CTG AAG ATC TCC
        TCT GAC TCT TGT GTG TCG TAA CTC AGT AGT CCT TTT GAC TTC TAG AGG
        Arg Leu Arg Thr His Ser Ile Glu Ser Ser Gly Lys Leu Lys Ile Ser>

205        210        215        220        225        230        235        240        245
             *          *          *          *          *          *          *          *          *
        CCT GAA CAA CAC TGG GAT TTC ACT GCA GAG GAC TTG AAA GAC CTT GGA
        GGA CTT GTT GTG ACC CTA AAG TGA CGT CTC CTG AAC TTT CTG GAA CCT
        Pro Glu Gln His Trp Asp Phe Thr Ala Glu Asp Leu Lys Asp Leu Gly>

250        255        260        265        270        275        280        285        290        295
        *          *          *          *          *          *          *          *          *          *
        GAA ATT GGA CGA GGA GCT TAT GGT TCT GTC AAC AAA ATG GTC CAC AAA
        CTT TAA CCT GCT CCT CGA ATA CCA AGA CAG TTG TTT TAC CAG GTG TTT
        Glu Ile Gly Arg Gly Ala Tyr Gly Ser Val Asn Lys Met Val His Lys>

300        305        310        315        320        325        330        335        340        345
        *          *          *          *          *          *          *          *          *          *
        CCA AGT GGG CAA ATA ATG GCA GTT AAA AGA ATT CGG TCA ACA GTG GAT
        GGT TCA CCC GTT TAT TAC CGT CAA TTT TCT TAA GCC AGT TGT CAC CTA
        Pro Ser Gly Gln Ile Met Ala Val Lys Arg Ile Arg Ser Thr Val Asp>

350        355        360        365        370        375        380        385        390
             *          *          *          *          *          *          *          *          *
        GAA AAA GAA CAA AAA CAA CTT CTT ATG GAT TTG GAT GTA GTA ATG CGG
        CTT TTT CTT GTT TTT GTT GAA GAA TAC CTA AAC CTA CAT CAT TAC GCC
        Glu Lys Glu Gln Lys Gln Leu Leu Met Asp Leu Asp Val Val Met Arg>

395        400        405        410        415        420        425        430        435        440
        *          *          *          *          *          *          *          *          *          *
        AGT AGT GAT TGC CCA TAC ATT GTT CAG TTT TAT GGT GCA CTC TTC AGA
        TCA TCA CTA ACG GGT ATG TAA CAA GTC AAA ATA CCA CGT GAG AAG TCT
        Ser Ser Asp Cys Pro Tyr Ile Val Gln Phe Tyr Gly Ala Leu Phe Arg>

445        450        455        460        465        470        475        480        485
        *          *          *          *          *          *          *          *
        GAG GGT GAC TGT TGG ATC TGT ATG GAA CTC ATG TCT ACC TCG TTT GAT
        CTC CCA CTG ACA ACC TAG ACA TAC CTT GAG TAC AGA TGG AGC AAA CTA
        Glu Gly Asp Cys Trp Ile Cys Met Glu Leu Met Ser Thr Ser Phe Asp>
```

FIG. 6A

```
      490       495       500       505       510       515       520       525       530       535
       *                   *                   *                   *                   *
     AAG  TTT  TAC  AAA  TAT  GTA  TAT  AGT  GTA  TTA  GAT  GAT  GTT  ATT  CCA  GAA
     TTC  AAA  ATG  TTT  ATA  CAT  ATA  TCA  CAT  AAT  CTA  CTA  CAA  TAA  GGT  CTT
     Lys  Phe  Tyr  Lys  Tyr  Val  Tyr  Ser  Val  Leu  Asp  Asp  Val  Ile  Pro  Glu>

540       545       550       555       560       565       570       575       580       585
       *                   *                   *                   *                   *
     GAA  ATT  TTA  GGC  AAA  ATC  ACT  TTA  GCA  ACT  GTG  AAA  GCA  CTA  AAC  CAC
     CTT  TAA  AAT  CCG  TTT  TAG  TGA  AAT  CGT  TGA  CAC  TTT  CGT  GAT  TTG  GTG
     Glu  Ile  Leu  Gly  Lys  Ile  Thr  Leu  Ala  Thr  Val  Lys  Ala  Leu  Asn  His>

590       595       600       605       610       615       620       625       630
            *                   *                   *                   *                   *
        TTA  AAA  GAA  AAC  TTG  AAA  ATT  ATT  CAC  AGA  GAT  ATC  AAA  CCT  TCC  AAT
        AAT  TTT  CTT  TTG  AAC  TTT  TAA  TAA  GTG  TCT  CTA  TAG  TTT  GGA  AGG  TTA
        Leu  Lys  Glu  Asn  Leu  Lys  Ile  Ile  His  Arg  Asp  Ile  Lys  Pro  Ser  Asn>

635       640       645       650       655       660       665       670       675       680
       *                   *                   *                   *                   *
     ATT  CTT  CTG  GAC  AGA  AGT  GGA  AAT  ATT  AAG  CTC  TGT  GAC  TTC  GGC  ATC
     TAA  GAA  GAC  CTG  TCT  TCA  CCT  TTA  TAA  TTC  GAG  ACA  CTG  AAG  CCG  TAG
     Ile  Leu  Leu  Asp  Arg  Ser  Gly  Asn  Ile  Lys  Leu  Cys  Asp  Phe  Gly  Ile>

685       690       695       700       705       710       715       720       725
       *                   *                   *                   *                   *
     AGT  GGA  CAG  CTT  GTG  GAC  TCT  ATT  GCC  AAG  ACA  AGA  GAT  GCT  GGC  TGT
     TCA  CCT  GTC  GAA  CAC  CTG  AGA  TAA  CGG  TTC  TGT  TCT  CTA  CGA  CCG  ACA
     Ser  Gly  Gln  Leu  Val  Asp  Ser  Ile  Ala  Lys  Thr  Arg  Asp  Ala  Gly  Cys>

730       735       740       745       750       755       760       765       770       775
     *                   *                   *                   *                   *
   AGG  CCA  TAC  ATG  GCA  CCT  GAA  AGA  ATA  GAC  CCA  AGC  GCA  TCA  CGA  CAA
   TCC  GGT  ATG  TAC  CGT  GGA  CTT  TCT  TAT  CTG  GGT  TCG  CGT  AGT  GCT  GTT
   Arg  Pro  Tyr  Met  Ala  Pro  Glu  Arg  Ile  Asp  Pro  Ser  Ala  Ser  Arg  Gln>

780       785       790       795       800       805       810       815       820       825
     *                   *                   *                   *                   *
   GGA  TAT  GAT  GTC  CGC  TCT  GAT  GTC  TGG  AGT  TTG  GGG  ATC  ACA  TTG  TAT
   CCT  ATA  CTA  CAG  GCG  AGA  CTA  CAG  ACC  TCA  AAC  CCC  TAG  TGT  AAC  ATA
   Gly  Tyr  Asp  Val  Arg  Ser  Asp  Val  Trp  Ser  Leu  Gly  Ile  Thr  Leu  Tyr>

830       835       840       845       850       855       860       865       870
           *                   *                   *                   *                   *
       GAG  TTG  GCC  ACA  GGC  CGA  TTT  CCT  TAT  CCA  AAG  TGG  AAT  AGT  GTA  TTT
       CTC  AAC  CGG  TGT  CCG  GCT  AAA  GGA  ATA  GGT  TTC  ACC  TTA  TCA  CAT  AAA
       Glu  Leu  Ala  Thr  Gly  Arg  Phe  Pro  Tyr  Pro  Lys  Trp  Asn  Ser  Val  Phe>

875       880       885       890       895       900       905       910       915       920
     *                   *                   *                   *                   *
   GAT  CAA  CTA  ACA  CAA  GTC  GTG  AAA  GGA  GAT  CCT  CCG  CAG  CTG  AGT  AAT
   CTA  GTT  GAT  TGT  GTT  CAG  CAC  TTT  CCT  CTA  GGA  GGC  GTC  GAC  TCA  TTA
   Asp  Gln  Leu  Thr  Gln  Val  Val  Lys  Gly  Asp  Pro  Pro  Gln  Leu  Ser  Asn>

925       930       935       940       945       950       955       960       965
           *                   *                   *                   *                   *
       TCT  GAG  GAA  AGG  GAA  TTC  TCC  CCG  AGT  TTC  ATC  AAC  TTT  GTC  AAC  TTG
       AGA  CTC  CTT  TCC  CTT  AAG  AGG  GGC  TCA  AAG  TAG  TTG  AAA  CAG  TTG  AAC
       Ser  Glu  Glu  Arg  Glu  Phe  Ser  Pro  Ser  Phe  Ile  Asn  Phe  Val  Asn  Leu>

```
TGC CTT ACG AAG GAT GAA TCC AAA AGG CCA AAG TAT AAA GAG CTT CTG
ACG GAA TGC TTC CTA CTT AGG TTT TCC GGT TTC ATA TTT CTC GAA GAC
Cys Leu Thr Lys Asp Glu Ser Lys Arg Pro Lys Tyr Lys Glu Leu Leu>

1020    1025    1030 1035    1040    1045 1050    1055    1060 1065
  *              *              *              *              *
AAA CAT CCC TTT ATT TTG ATG TAT GAA GAA CGT GCC GTT GAG GTC GCA
TTT GTA GGG AAA TAA AAC TAC ATA CTT CTT GCA CGG CAA CTC CAG CGT
Lys His Pro Phe Ile Leu Met Tyr Glu Glu Arg Ala Val Glu Val Ala>

1070   1075 1080   1085   1090 1095   1100   1105 1110
     *            *            *            *            *
TGC TAT GTT TGT AAA ATC CTG GAT CAA ATG CCA GCT ACT CCC AGC TCT
ACG ATA CAA ACA TTT TAG GAC CTA GTT TAC GGT CGA TGA GGG TCG AGA
Cys Tyr Val Cys Lys Ile Leu Asp Gln Met Pro Ala Thr Pro Ser Ser>

1115    1120 1125    1130    1135 1140    1145 1150    1155 1160    1165 1170
  *              *              *              *              *              *
CCC ATG TAT GTC GAT TG ATATCGYTGC TACATCAGAC TCTAGAAAAA AGGGCTGAGA
GGG TAC ATA CAG CTA AC TATAGCRACG ATGTAGTCTG AGATCTTTTT TCCCGACTCT
Pro Met Tyr Val Asp>    (SEQ ID NO:6)

1175 1180    1185 1190    1195 1200    1205 1210    1215 1220    1225 1230
     *              *              *              *              *              *
GGAAGCAAGA CGTAAAGAAT TTTCATCCCG TATCACAGTG TTTTTATTGC TCGCCCAGAC
CCTTCGTTCT GCATTTCTTA AAAGTAGGGC ATAGTGTCAC AAAAATAACG AGCGGGTCTG 1235 1240    1245 1250    1255 1260    1265 1270    1275 1280    1285 1290
     *              *              *              *              *              *
ACCATGTGCA ATAAGATTGG TGTTCGTTTC CATCATGTCT GTATACTCCT GTCACCTAGA
TGGTACACGT TATTCTAACC ACAAGCAAAG GTAGTACAGA CATATGAGGA CAGTGGATCT 1295 1300    1305 1310    1315 1320    1325 1330    1335 1340    1345 1350
     *              *              *              *              *              *
ACGTGCATCC TTGTAATACC TGATTGATCA CACAGTGTTA GTGCTGGTCA GAGAGACCTC
TGCACGTAGG AACATTATGG ACTAACTAGT GTGTCACAAT CACGACCAGT CTCTCTGGAG 1355 1360    1365 1370    1375 1380    1385 1390    1395 1400    1405 1410
     *              *              *              *              *              *
ATCCTGCTCT TTTGTGATGA ACATATTCAT GAAATGTGGA AGTCAGTACG ATCAAGTTGT
TAGGACGAGA AAACACTACT TGTATAAGTA CTTTACACCT TCAGTCATGC TAGTTCAACA 1415 1420    1425 1430    1435 1440    1445 1450    1455 1460    1465 1470
     *              *              *              *              *              *
TGACTGTGAT TAGATCACAT CTTAAATTCA TTTCTAGACT CAAAACCTGG AGATGCAGCT
ACTGACACTA ATCTAGTGTA GAATTTAAGT AAAGATCTGA GTTTTGGACC TCTACGTCGA 1475 1480    1485 1490    1495 1500    1505 1510    1515 1520    1525 1530
     *              *              *              *              *              *
ACTGGAATGG TGTTTTGTCA GACTTCCAAA TCCTGGAAGG ACACAGTGAT GAATGTACTA
TGACCTTACC ACAAAACAGT CTGAAGGTTT AGGACCTTCC TGTGTCACTA CTTACATGAT 1535 1540    1545 1550    1555 1560    1565 1570    1575 1580    1585 1590
     *              *              *              *              *              *
TATCTGAACA TAGAAACTCG GGCTTGAGTG AGAAGAGCTT GCACAGCCAA CGAGACACAT
ATAGACTTGT ATCTTTGAGC CCGAACTCAC TCTTCTCGAA CGTGTCGGTT GCTCTGTGTA 1595 1600    1605 1610    1615 1620    1625 1630    1635 1640    1645 1650
     *              *              *              *              *              *
TGCCTTCTGG AGCTGGGAGA CAAAGGAGGA ATTTACTTTC TTCACCAAGT GCAATAGATT
ACGGAAGACC TCGACCCTCT GTTTCCTCCT TAAATGAAAG AAGTGGTTCA CGTTATCTAA
```

FIG. 6C

```
1655 1660  1665 1670  1675 1680  1685 1690  1695 1700  1705 1710
     *          *          *          *          *          *
ACTGATGTGA TATTCTGTTG CTTTACAGTT ACAGTTGATG TTTGGGGATC GATGTGCTCA
TGACTACACT ATAAGACAAC GAAATGTCAA TGTCAACTAC AAACCCCTAG CTACACGAGT 1715 1720  1725 1730  1735 1740  1745 1750  1755 1760  1765 1770
     *          *          *          *          *          *
GCCAAATTTC CTGTTTGAAA TATCATGTTA AATTAGAATG AATTTATCTT TACCAAAAAC
CGGTTTAAAG GACAAACTTT ATAGTACAAT TTAATCTTAC TTAAATAGAA ATGGTTTTTG 1775 1780  1785 1790  1795 1800  1805 1810  1815 1820  1825 1830
     *          *          *          *          *          *
CATGTTGCGT TCAAAGAGGT GAACATTAAA ATATAGAGAC AGGACAGAAT GTGTTCTTTT
GTACAACGCA AGTTTCTCCA CTTGTAATTT TATATCTCTG TCCTGTCTTA CACAAGAAAA 1835 1840  1845 1850  1855 1860  1865 1870  1875 1880  1885 1890
     *          *          *          *          *          *
CTCCTCTACC AGTCCTATTT TTCAATGGGA AGACTCAGGA GTCTGCCACT TGTCAAAGAA
GAGGAGATGG TCAGGATAAA AAGTTACCCT TCTGAGTCCT CAGACGGTGA ACAGTTTCTT 1895 1900  1905 1910  1915 1920  1925 1930  1935 1940  1945 1950
     *          *          *          *          *          *
GGTGCTGATC CTAAGAATTT TTCATTCTCA GAATTCGGTG TGCTGCCAAC TTGATGTTCC
CCACGACTAG GATTCTTAAA AAGTAAGAGT CTTAAGCCAC ACGACGGTTG AACTACAAGG 1955 1960  1965 1970  1975 1980  1985 1990  1995 2000  2005 2010
     *          *          *          *          *          *
ACCTGCCACA AACCACCAGG ACTGAAAGAA GAAAACAGTA CAGAAGGCAA AGTTTACAGA
TGGACGGTGT TTGGTGGTCC TGACTTTCTT CTTTTGTCAT GTCTTCCGTT TCAAATGTCT 2015 2020  2025 2030  2035 2040  2045 2050  2055 2060  2065 2070
     *          *          *          *          *          *
TGTTTTTAAT TCTAGTATTT TATCTGGAAC AACTTGTAGC AGCTATATAT TTCCCCTTGG
ACAAAAATTA AGATCATAAA ATAGACCTTG TTGAACATCG TCGATATATA AAGGGGAACC 2075 2080  2085 2090  2095 2100  2105 2110  2115 2120  2125 2130
     *          *          *          *          *          *
TCCCAAGCCT GATACTTTAG CCATCATAAC TCACTAACAG GGAGAAGTAG CTAGTAGCAA
AGGGTTCGGA CTATGAAATC GGTAGTATTG AGTGATTGTC CCTCTTCATC GATCATCGTT 2135 2140  2145 2150  2155 2160  2165 2170  2175 2180  2185 2190
     *          *          *          *          *          *
TGTGCCTTGA TTGATTAGAT AAAGATTTCT AGTAGGCAGC AAAAGACCAA ATCTCAGTTG
ACACGGAACT AACTAATCTA TTTCTAAAGA TCATCCGTCG TTTTCTGGTT TAGAGTCAAC 2195 2200  2205 2210  2215 2220  2225 2230  2235 2240  2245 2250
     *          *          *          *          *          *
TTTGCTTCTT GCCATCACTG GTCCAGGTCT TCAGTTTCCG AATCTCTTTC CCTTCCCCTG
AAACGAAGAA CGGTAGTGAC CAGGTCCAGA AGTCAAAGGC TTAGAGAAAG GGAAGGGGAC 2255 2260  2265 2270  2275 2280  2285 2290  2295 2300  2305 2310
     *          *          *          *          *          *
TGGTCTATTG TCGCTATGTG ACTTGCGCTT AATCCAATAT TTTGCCTTTT TTCTATATCA
ACCAGATAAC AGCGATACAC TGAACGCGAA TTAGGTTATA AAACGGAAAA AAGATATAGT 2315 2320  2325 2330  2335 2340  2345 2350  2355 2360  2365 2370
     *          *          *          *          *          *
AAAAACCTTT ACAGTTAGCA GGGATGTTCC TTACCGAGGA TTTTTAACCC CCAATCTCTC
TTTTTGGAAA TGTCAATCGT CCCTACAAGG AATGGCTCCT AAAAATTGGG GGTTAGAGAG 2375 2380  2385 2390  2395 2400  2405 2410  2415 2420  2425 2430
     *          *          *          *          *          *
```

FIG. 6D

```
ATAATCGCTA GTGTTTAAAA GGCTAAGAAT AGTGGGGCCC AACCGATGTG GTAGGTGATA
TATTAGCGAT CACAAATTTT CCGATTCTTA TCACCCCGGG TTGGCTACAC CATCCACTAT 2435 2440  2445 2450  2455 2460  2465 2470  2475 2480  2485 2490
       *          *          *          *          *          *
AAGAGGCATC TTTTCTAGAG ACACATTGGA CCAGATGAGG ATCCGAAACG GCAGCCTTTA
TTCTCCGTAG AAAAGATCTC TGTGTAACCT GGTCTACTCC TAGGCTTTGC CGTCGGAAAT 2495 2500  2505 2510  2515 2520  2525 2530  2535 2540  2545 2550
       *          *          *          *          *          *
CGTTCATCAC CTGCTAGAAC CTCTCGTAGT CCATCACCAT TTCTTGGCAT TGGAATTCTA
GCAAGTAGTG GACGATCTTG GAGAGCATCA GGTAGTGGTA AAGAACCGTA ACCTTAAGAT 2555 2560  2565 2570  2575 2580  2585 2590  2595 2600  2605 2610
       *          *          *          *          *          *
CTGGAAAAAA ATACAAAAAG CAAAACAAAA CCCTCAGCAC TGTTACAAGA GGCCATTTAA
GACCTTTTTT TATGTTTTTC GTTTTGTTTT GGGAGTCGTG ACAATGTTCT CCGGTAAATT 2615 2620  2625 2630  2635 2640  2645 2650  2655 2660  2665 2670
       *          *          *          *          *          *
GTATCTTGTG CTTCTTCACT TACCCATTAG CCAGGTTCTC ATTAGGTTTT GCTTGGGCCT
CATAGAACAC GAAGAAGTGA ATGGGTAATC GGTCCAAGAG TAATCCAAAA CGAACCCGGA 2675 2680  2685 2690  2695 2700  2705 2710  2715 2720  2725 2730
       *          *          *          *          *          *
CCCTGGCACT GAACCTTAGG CTTTGTATGA CAGTGAAGCA GCACTGTGAG TGGTTCAAGC
GGGACCGTGA CTTGGAATCC GAAACATACT GTCACTTCGT CGTGACACTC ACCAAGTTCG 2735 2740  2745 2750  2755 2760  2765 2770  2775 2780  2785 2790
       *          *          *          *          *          *
ACACTGGAAT ATAAAACAGT CATGGCCTGA GATGCAGGTG ATGCCATTAC AGAACCAAAT
TGTGACCTTA TATTTTGTCA GTACCGGACT CTACGTCCAC TACGGTAATG TCTTGGTTTA 2795 2800  2805 2810  2815 2820  2825 2830  2835 2840  2845 2850
       *          *          *          *          *          *
CGTGGCACGT ATTGCTGTGT CTCCTCTCAG AGTGACAGTC ATAAATACTG TCAAACAATA
GCACCGTGCA TAACGACACA GAGGAGAGTC TCACTGTCAG TATTTATGAC AGTTTGTTAT 2855 2860  2865 2870  2875 2880  2885 2890  2895 2900  2905 2910
       *          *          *          *          *          *
AAGGGAGAAT GGTGCTGTTT AAAGTCACAT CCCTGTAAAT TGCAGAATTC AAAAGTGATT
TTCCCTCTTA CCACGACAAA TTTCAGTGTA GGGACATTTA ACGTCTTAAG TTTTCACTAA 2915 2920  2925 2930  2935 2940  2945 2950  2955 2960  2965 2970
       *          *          *          *          *          *
ATCTCTTTGA TCTACTTGCC TCATTTCCCT ATCTTCTCCC CCACGGTATC CTAAACTTTA
TAGAGAAACT AGATGAACGG AGTAAAGGGA TAGAAGAGGG GGTGCCATAG GATTTGAAAT 2975 2980  2985 2990  2995 3000  3005 3010  3015 3020  3025 3030
       *          *          *          *          *          *
GACTTCCCAC TGTTCTGAAA GGAGACATTG CTCTATGTCT GCCTTCGACC ACAGCAAGCC
CTGAAGGGTG ACAAGACTTT CCTCTGTAAC GAGATACAGA CGGAAGCTGG TGTCGTTCGG 3035 3040  3045 3050  3055 3060  3065 3070  3075 3080  3085 3090
       *          *          *          *          *          *
ATCATCCTCC ATTGCTCCCG GGGACTCAAG AGGAATCTGT TTCTCTGCTG TCAACTTCCC
TAGTAGGAGG TAACGAGGGC CCCTGAGTTC TCCTTAGACA AAGAGACGAC AGTTGAAGGG 3095 3100  3105 3110  3115 3120  3125 3130  3135 3140  3145 3150
       *          *          *          *          *          *
ATCTGGCTCA GCATAGGGTC ACTTTGCCAT TATGCAAATG GAGATAAAAG CAATTCTGGC
TAGACCGAGT CGTATCCCAG TGAAACGGTA ATACGTTTAC CTCTATTTTC GTTAAGACCG
```

FIG. 6E

```
3155 3160   3165 3170   3175 3180   3185 3190   3195 3200   3205 3210
     *           *           *           *           *           *
TGTCCAGGAG  CTAATCTGAC  CGTTCTATTG  TGTGGATGAC  CACATAAGAA  GGCAATTTTA
ACAGGTCCTC  GATTAGACTG  GCAAGATAAC  ACACCTACTG  GTGTATTCTT  CCGTTAAAAT 3215 3220   3225 3230   3235 3240   3245 3250   3255 3260   3265 3270
     *           *           *           *           *           *
GTGTATTAAT  CATAGATTAT  TATAAACTAT  AAACTTAAGG  GCAAGGAGTT  TATTACAATG
CACATAATTA  GTATCTAATA  ATATTTGATA  TTTGAATTCC  CGTTCCTCAA  ATAATGTTAC 3275 3280   3285 3290   3295 3300   3305 3310   3315 3320   3325 3330
     *           *           *           *           *           *
TATCTTTATT  AAAACAAAAG  GGTGTATAGT  GTTCACAAAC  TGTGAAAATA  GTGTAAGAAC
ATAGAAATAA  TTTTGTTTTC  CCACATATCA  CAAGTGTTTG  ACACTTTTAT  CACATTCTTG 3335 3340   3345 3350   3355 3360   3365 3370   3375 3380   3385 3390
     *           *           *           *           *           *
TGTACATTGT  GAGCTCTGGT  TATTTTTCTC  TTGTACCATA  GAAAAATGTA  TAAAAATTAT
ACATGTAACA  CTCGAGACCA  ATAAAAGAG   AACATGGTAT  CTTTTTACAT  ATTTTTAATA 3395 3400   3405 3410   3415 3420   3425 3430   3435 3440   3445 3450
     *           *           *           *           *           *
CAAAAAGCTA  ATGTGCAGGG  ATATTGCCTT  ATTTGTCTGT  AAAAAATGGA  GCTCAGTAAC
GTTTTTCGAT  TACACGTCCC  TATAACGGAA  TAAACAGACA  TTTTTTACCT  CGAGTCATTG 3455 3460   3465 3470   3475 3480   3485 3490   3495
     *           *           *           *
ATAACTGCTT  CTTGGAGCTT  TGGAATATTT  TATCCTGTAT  TCTTGTTT     (SEQ ID NO:5)
TATTGACGAA  GAACCTCGAA  ACCTTATAAA  ATAGGACATA  AGAACAAA
```

FIG. 6F

```
       5         10        15        20        25        30        35        40        45        50
       *         *         *         *         *         *         *         *         *         *
CAACA ATG GCG GCT CCG AGC CCG AGC GGT GGC GGC GGC AGC GGC ACC CCC
GTTGT TAC CGC CGA GGC TCG GGC TCG CCA CCG CCG CCG TCG CCG TGG GGG
      Met Ala Ala Pro Ser Pro Ser Gly Gly Gly Gly Ser Gly Thr Pro>

55        60        65        70        75        80        85        90        95
       *         *         *         *         *         *         *         *         *
GGC CCC GTA GGG TCC CCG GCG CCA GGC CAC CCG GCC GTC AGC AGC ATG
CCG GGG CAT CCC AGG GGC CGC GGT CCG GTG GGC CGG CAG TCG TCG TAC
Gly Pro Val Gly Ser Pro Ala Pro Gly His Pro Ala Val Ser Ser Met>

100       105       110       115       120       125       130       135       140       145
   *         *         *         *         *         *         *         *         *         *
CAG GGT AAA CGC AAA GCA CTG AAG TTG AAT TTT GCA AAT CCA CCT TTC
GTC CCA TTT GCG TTT CGT GAC TTC AAC TTA AAA CGT TTA GGT GGA AAG
Gln Gly Lys Arg Lys Ala Leu Lys Leu Asn Phe Ala Asn Pro Pro Phe>

150       155       160       165       170       175       180       185       190
       *         *         *         *         *         *         *         *         *
AAA TCT ACA GCA AGG TTT ACT CTG AAT CCC AAT CCT ACA GGA GTT CAA
TTT AGA TGT CGT TCC AAA TGA GAC TTA GGG TTA GGA TGT CCT CAA GTT
Lys Ser Thr Ala Arg Phe Thr Leu Asn Pro Asn Pro Thr Gly Val Gln>

195       200       205       210       215       220       225       230       235       240
   *         *         *         *         *         *         *         *         *         *
AAC CCA CAC ATA GAG AGA CTG AGA ACA CAC AGC ATT GAG TCA TCA GGA
TTG GGT GTG TAT CTC TCT GAC TCT TGT GTG TCG TAA CTC AGT AGT CCT
Asn Pro His Ile Glu Arg Leu Arg Thr His Ser Ile Glu Ser Ser Gly>

245       250       255       260       265       270       275       280       285       290
   *         *         *         *         *         *         *         *         *         *
AAA CTG AAG ATC TCC CCT GAA CAA CAC TGG GAT TTC ACT GCA GAG GAC
TTT GAC TTC TAG AGG GGA CTT GTT GTG ACC CTA AAG TGA CGT CTC CTG
Lys Leu Lys Ile Ser Pro Glu Gln His Trp Asp Phe Thr Ala Glu Asp>

295       300       305       310       315       320       325       330       335
       *         *         *         *         *         *         *         *         *
TTG AAA GAC CTT GGA GAA ATT GGA CGA GGA GCT TAT GGT TCT GTC AAC
AAC TTT CTG GAA CCT CTT TAA CCT GCT CCT CGA ATA CCA AGA CAG TTG
Leu Lys Asp Leu Gly Glu Ile Gly Arg Gly Ala Tyr Gly Ser Val Asn>

340       345       350       355       360       365       370       375       380       385
   *         *         *         *         *         *         *         *         *         *
AAA ATG GTC CAC AAA CCA AGT GGG CAA ATA ATG GCA GTT AAA AGA ATT
TTT TAC CAG GTG TTT GGT TCA CCC GTT TAT TAC CGT CAA TTT TCT TAA
Lys Met Val His Lys Pro Ser Gly Gln Ile Met Ala Val Lys Arg Ile>

390       395       400       405       410       415       420       425       430
       *         *         *         *         *         *         *         *         *
CGG TCA ACA GTG GAT GAA AAA GAA CAA AAA CAA CTT CTT ATG GAT TTG
GCC AGT TGT CAC CTA CTT TTT CTT GTT TTT GTT GAA GAA TAC CTA AAC
Arg Ser Thr Val Asp Glu Lys Glu Gln Lys Gln Leu Leu Met Asp Leu>

435       440       445       450       455       460       465       470       475       480
   *         *         *         *         *         *         *         *         *         *
GAT GTA GTA ATG CGG AGT AGT GAT TGC CCA TAC ATT GTT CAG TTT TAT
CTA CAT CAT TAC GCC TCA TCA CTA ACG GGT ATG TAA CAA GTC AAA ATA
Asp Val Val Met Arg Ser Ser Asp Cys Pro Tyr Ile Val Gln Phe Tyr>
```

FIG. 7A

```
      485       490       495       500       505       510       515       520       525       530
        *                   *                   *                   *                   *
GGT  GCA  CTC  TTC  AGA  GAG  GGT  GAC  TGT  TGG  ATC  TGT  ATG  GAA  CTC  ATG
CCA  CGT  GAG  AAG  TCT  CTC  CCA  CTG  ACA  ACC  TAG  ACA  TAC  CTT  GAG  TAC
Gly  Ala  Leu  Phe  Arg  Glu  Gly  Asp  Cys  Trp  Ile  Cys  Met  Glu  Leu  Met>

535       540       545       550       555       560       565       570       575
        *                   *                   *                   *
TCT  ACC  TCG  TTT  GAT  AAG  TTT  TAC  AAA  TAT  GTA  TAT  AGT  GTA  TTA  GAT
AGA  TGG  AGC  AAA  CTA  TTC  AAA  ATG  TTT  ATA  CAT  ATA  TCA  CAT  AAT  CTA
Ser  Thr  Ser  Phe  Asp  Lys  Phe  Tyr  Lys  Tyr  Val  Tyr  Ser  Val  Leu  Asp>

580       585       590       595       600       605       610       615       620       625
  *                   *                   *                   *                   *
GAT  GTT  ATT  CCA  GAA  GAA  ATT  TTA  GGC  AAA  ATC  ACT  TTA  GCA  ACT  GTG
CTA  CAA  TAA  GGT  CTT  CTT  TAA  AAT  CCG  TTT  TAG  TGA  AAT  CGT  TGA  CAC
Asp  Val  Ile  Pro  Glu  Glu  Ile  Leu  Gly  Lys  Ile  Thr  Leu  Ala  Thr  Val>

630       635       640       645       650       655       660       665       670
        *                   *                   *                   *                   *
AAA  GCA  CTA  AAC  CAC  TTA  AAA  GAA  AAC  TTG  AAA  ATT  ATT  CAC  AGA  GAT
TTT  CGT  GAT  TTG  GTG  AAT  TTT  CTT  TTG  AAC  TTT  TAA  TAA  GTG  TCT  CTA
Lys  Ala  Leu  Asn  His  Leu  Lys  Glu  Asn  Leu  Lys  Ile  Ile  His  Arg  Asp>

675       680       685       690       695       700       705       710       715       720
  *                   *                   *                   *                   *
ATC  AAA  CCT  TCC  AAT  ATT  CTT  CTG  GAC  AGA  AGT  GGA  AAT  ATT  AAG  CTC
TAG  TTT  GGA  AGG  TTA  TAA  GAA  GAC  CTG  TCT  TCA  CCT  TTA  TAA  TTC  GAG
Ile  Lys  Pro  Ser  Asn  Ile  Leu  Leu  Asp  Arg  Ser  Gly  Asn  Ile  Lys  Leu>

725       730       735       740       745       750       755       760       765       770
        *                   *                   *                   *                   *
TGT  GAC  TTC  GGC  ATC  AGT  GGA  CAG  CTT  GTG  GAC  TCT  ATT  GCC  AAG  ACA
ACA  CTG  AAG  CCG  TAG  TCA  CCT  GTC  GAA  CAC  CTG  AGA  TAA  CGG  TTC  TGT
Cys  Asp  Phe  Gly  Ile  Ser  Gly  Gln  Leu  Val  Asp  Ser  Ile  Ala  Lys  Thr>

775       780       785       790       795       800       805       810       815
               *                   *                   *                   *
AGA  GAT  GCT  GGC  TGT  AGG  CCA  TAC  ATG  GCA  CCT  GAA  AGA  ATA  GAC  CCA
TCT  CTA  CGA  CCG  ACA  TCC  GGT  ATG  TAC  CGT  GGA  CTT  TCT  TAT  CTG  GGT
Arg  Asp  Ala  Gly  Cys  Arg  Pro  Tyr  Met  Ala  Pro  Glu  Arg  Ile  Asp  Pro>

820       825       830       835       840       845       850       855       860       865
  *                   *                   *                   *                   *
AGC  GCA  TCA  CGA  CAA  GGA  TAT  GAT  GTC  CGC  TCT  GAT  GTC  TGG  AGT  TTG
TCG  CGT  AGT  GCT  GTT  CCT  ATA  CTA  CAG  GCG  AGA  CTA  CAG  ACC  TCA  AAC
Ser  Ala  Ser  Arg  Gln  Gly  Tyr  Asp  Val  Arg  Ser  Asp  Val  Trp  Ser  Leu>

870       875       880       885       890       895       900       905       910
        *                   *                   *                   *                   *
GGG  ATC  ACA  TTG  TAT  GAG  TTG  GCC  ACA  GGC  CGA  TTT  CCT  TAT  CCA  AAG
CCC  TAG  TGT  AAC  ATA  CTC  AAC  CGG  TGT  CCG  GCT  AAA  GGA  ATA  GGT  TTC
Gly  Ile  Thr  Leu  Tyr  Glu  Leu  Ala  Thr  Gly  Arg  Phe  Pro  Tyr  Pro  Lys>

915       920       925       930       935       940       945       950       955       960
  *                   *                   *                   *                   *
TGG  AAT  AGT  GTA  TTT  GAT  CAA  CTA  ACA  CAA  GTC  GTG  AAA  GGA  GAT  CCT
ACC  TTA  TCA  CAT  AAA  CTA  GTT  GAT  TGT  GTT  CAG  CAC  TTT  CCT  CTA  GGA
Trp  Asn  Ser  Val  Phe  Asp  Gln  Leu  Thr  Gln  Val  Val  Lys  Gly  Asp  Pro>

```
CCG CAG CTG AGT AAT TCT GAG GAA AGG GAA TTC TCC CCG AGT TTC ATC
GGC GTC GAC TCA TTA AGA CTC CTT TCC CTT AAG AGG GGC TCA AAG TAG
Pro Gln Leu Ser Asn Ser Glu Glu Arg Glu Phe Ser Pro Ser Phe Ile>

1015  1020  1025  1030  1035  1040  1045  1050  1055
                  *           *           *           *
AAC TTT GTC AAC TTG TGC CTT ACG AAG GAT GAA TCC AAA AGG CCA AAG
TTG AAA CAG TTG AAC ACG GAA TGC TTC CTA CTT AGG TTT TCC GGT TTC
Asn Phe Val Asn Leu Cys Leu Thr Lys Asp Glu Ser Lys Arg Pro Lys>

1060  1065  1070  1075  1080  1085  1090  1095  1100   1105
  *           *           *           *           *
TAT AAA GAG CTT CTG AAA CAT CCC TTT ATT TTG ATG TAT GAA GAA CGT
ATA TTT CTC GAA GAC TTT GTA GGG AAA TAA AAC TAC ATA CTT CTT GCA
Tyr Lys Glu Leu Leu Lys His Pro Phe Ile Leu Met Tyr Glu Glu Arg>

1110  1115  1120  1125  1130  1135  1140  1145  1150
           *           *           *           *           *
GCC GTT GAG GTC GCA TGC TAT GTT TGT AAA ATC CTG GAT CAA ATG CCA
CGG CAA CTC CAG CGT ACG ATA CAA ACA TTT TAG GAC CTA GTT TAC GGT
Ala Val Glu Val Ala Cys Tyr Val Cys Lys Ile Leu Asp Gln Met Pro>

1155  1160  1165  1170  1175  1180   1185 1190  1195 1200
  *           *           *              *           *
GCT ACT CCC AGC TCT CCC ATG TAT GTC GAT TGATAT CGYTGCTACA
CGA TGA GGG TCG AGA GGG TAC ATA CAG CTA ACTATA GCRACGATGT
Ala Thr Pro Ser Ser Pro Met Tyr Val Asp> (SEQ ID NO:8)

1205 1210  1215 1220  1225 1230  1235 1240  1245 1250  1255 1260
         *           *           *           *           *           *
TCAGACTCTA GAAAAAGGG CTGAGAGGAA GCAAGACGTA AAGAATTTTC ATCCCGTATC
AGTCTGAGAT CTTTTTTCCC GACTCTCCTT CGTTCTGCAT TTCTTAAAAG TAGGGCATAG 1265 1270  1275 1280  1285 1290  1295 1300  1305 1310  1315 1320
         *           *           *           *           *           *
ACAGTGTTTT TATTGCTCGC CCAGACACCA TGTGCAATAA GATTGGTGTT CGTTTCCATC
TGTCACAAAA ATAACGAGCG GGTCTGTGGT ACACGTTATT CTAACCACAA GCAAAGGTAG 1325 1330  1335 1340  1345 1350  1355 1360  1365 1370  1375 1380
         *           *           *           *           *           *
ATGTCTGTAT ACTCCTGTCA CCTAGAACGT GCATCCTTGT AATACCTGAT TGATCACACA
TACAGACATA TGAGGACAGT GGATCTTGCA CGTAGGAACA TTATGGACTA ACTAGTGTGT 1385 1390  1395 1400  1405 1410  1415 1420  1425 1430  1435 1440
         *           *           *           *           *           *
GTGTTAGTGC TGGTCAGAGA GACCTCATCC TGCTCTTTTG TGATGAACAT ATTCATGAAA
CACAATCACG ACCAGTCTCT CTGGAGTAGG ACGAGAAAAC ACTACTTGTA TAAGTACTTT 1445 1450  1455 1460  1465 1470  1475 1480  1485 1490  1495 1500
         *           *           *           *           *           *
TGTGGAAGTC AGTACGATCA AGTTGTTGAC TGTGATTAGA TCACATCTTA AATTCATTTC
ACACCTTCAG TCATGCTAGT TCAACAACTG ACACTAATCT AGTGTAGAAT TTAAGTAAAG 1505 1510  1515 1520  1525 1530  1535 1540  1545 1550  1555 1560
         *           *           *           *           *           *
TAGACTCAAA ACCTGGAGAT GCAGCTACTG GAATGGTGTT TTGTCAGACT TCCAAATCCT
ATCTGAGTTT TGGACCTCTA CGTCGATGAC CTTACCACAA AACAGTCTGA AGGTTTAGGA 1565 1570  1575 1580  1585 1590  1595 1600  1605 1610  1615 1620
         *           *           *           *           *           *
GGAAGGACAC AGTGATGAAT GTACTATATC TGAACATAGA AACTCGGGCT TGAGTGAGAA
CCTTCCTGTG TCACTACTTA CATGATATAG ACTTGTATCT TTGAGCCCGA ACTCACTCTT
```

FIG. 7C

```
1625 1630   1635 1640   1645 1650   1655 1660   1665 1670   1675 1680
    *           *           *           *           *           *
GAGCTTGCAC  AGCCAACGAG  ACACATTGCC  TTCTGGAGCT  GGGAGACAAA  GGAGGAATTT
CTCGAACGTG  TCGGTTGCTC  TGTGTAACGG  AAGACCTCGA  CCCTCTGTTT  CCTCCTTAAA 1685 1690   1695 1700   1705 1710   1715 1720   1725 1730   1735 1740
    *           *           *           *           *           *
ACTTTCTTCA  CCAAGTGCAA  TAGATTACTG  ATGTGATATT  CTGTTGCTTT  ACAGTTACAG
TGAAAGAAGT  GGTTCACGTT  ATCTAATGAC  TACACTATAA  GACAACGAAA  TGTCAATGTC 1745 1750   1755 1760   1765 1770   1775 1780   1785 1790   1795 1800
    *           *           *           *           *           *
TTGATGTTTG  GGGATCGATG  TGCTCAGCCA  AATTTCCTGT  TTGAAATATC  ATGTTAAATT
AACTACAAAC  CCCTAGCTAC  ACGAGTCGGT  TTAAAGGACA  AACTTTATAG  TACAATTTAA 1805 1810   1815 1820   1825 1830   1835 1840   1845 1850   1855 1860
    *           *           *           *           *           *
AGAATGAATT  TATCTTTACC  AAAAACCATG  TTGCGTTCAA  AGAGGTGAAC  ATTAAAATAT
TCTTACTTAA  ATAGAAATGG  TTTTTGGTAC  AACGCAAGTT  TCTCCACTTG  TAATTTTATA 1865 1870   1875 1880   1885 1890   1895 1900   1905 1910   1915 1920
    *           *           *           *           *           *
AGAGACAGGA  CAGAATGTGT  TCTTTTCTCC  TCTACCAGTC  CTATTTTTCA  ATGGAAGAC
TCTCTGTCCT  GTCTTACACA  AGAAAAGAGG  AGATGGTCAG  GATAAAAAGT  TACCCTTCTG 1925 1930   1935 1940   1945 1950   1955 1960   1965 1970   1975 1980
    *           *           *           *           *           *
TCAGGAGTCT  GCCACTTGTC  AAAGAAGGTG  CTGATCCTAA  GAATTTTTCA  TTCTCAGAAT
AGTCCTCAGA  CGGTGAACAG  TTTCTTCCAC  GACTAGGATT  CTTAAAAAGT  AAGAGTCTTA 1985 1990   1995 2000   2005 2010   2015 2020   2025 2030   2035 2040
    *           *           *           *           *           *
TCGGTGTGCT  GCCAACTTGA  TGTTCCACCT  GCCACAAACC  ACCAGGACTG  AAAGAAGAAA
AGCCACACGA  CGGTTGAACT  ACAAGGTGGA  CGGTGTTTGG  TGGTCCTGAC  TTTCTTCTTT 2045 2050   2055 2060   2065 2070   2075 2080   2085 2090   2095 2100
    *           *           *           *           *           *
ACAGTACAGA  AGGCAAAGTT  TACAGATGTT  TTTAATTCTA  GTATTTTATC  TGGAACAACT
TGTCATGTCT  TCCGTTTCAA  ATGTCTACAA  AAATTAAGAT  CATAAAATAG  ACCTTGTTGA 2105 2110   2115 2120   2125 2130   2135 2140   2145 2150   2155 2160
    *           *           *           *           *           *
TGTAGCAGCT  ATATATTTCC  CCTTGGTCCC  AAGCCTGATA  CTTTAGCCAT  CATAACTCAC
ACATCGTCGA  TATATAAAGG  GGAACCAGGG  TTCGGACTAT  GAAATCGGTA  GTATTGAGTG 2165 2170   2175 2180   2185 2190   2195 2200   2205 2210   2215 2220
    *           *           *           *           *           *
TAACAGGGAG  AAGTAGCTAG  TAGCAATGTG  CCTTGATTGA  TTAGATAAAG  ATTTCTAGTA
ATTGTCCCTC  TTCATCGATC  ATCGTTACAC  GGAACTAACT  AATCTATTTC  TAAAGATCAT 2225 2230   2235 2240   2245 2250   2255 2260   2265 2270   2275 2280
    *           *           *           *           *           *
GGCAGCAAAA  GACCAAATCT  CAGTTGTTTG  CTTCTTGCCA  TCACTGGTCC  AGGTCTTCAG
CCGTCGTTTT  CTGGTTTAGA  GTCAACAAAC  GAAGAACGGT  AGTGACCAGG  TCCAGAAGTC 2285 2290   2295 2300   2305 2310   2315 2320   2325 2330   2335 2340
    *           *           *           *           *           *
TTTCCGAATC  TCTTTCCCTT  CCCCTGTGGT  CTATTGTCGC  TATGTGACTT  GCGCTTAATC
AAAGGCTTAG  AGAAAGGGAA  GGGGACACCA  GATAACAGCG  ATACACTGAA  CGCGAATTAG 2345 2350   2355 2360   2365 2370   2375 2380   2385 2390   2395 2400
```

FIG. 7D

```
                *          *          *          *          *          *
          CAATATTTTG CCTTTTTTCT ATATCAAAAA ACCTTTACAG TTAGCAGGGA TGTTCCTTAC
          GTTATAAAAC GGAAAAAAGA TATAGTTTTT TGGAAATGTC AATCGTCCCT ACAAGGAATG 2405 2410  2415 2420  2425 2430  2435 2440  2445 2450  2455 2460
                *          *          *          *          *          *
          CGAGGATTTT TAACCCCCAA TCTCTCATAA TCGCTAGTGT TTAAAAGGCT AAGAATAGTG
          GCTCCTAAAA ATTGGGGGTT AGAGAGTATT AGCGATCACA AATTTTCCGA TTCTTATCAC 2465 2470  2475 2480  2485 2490  2495 2500  2505 2510  2515 2520
                *          *          *          *          *          *
          GGGCCCAACC GATGTGGTAG GTGATAAAGA GGCATCTTTT CTAGAGACAC ATTGGACCAG
          CCCGGGTTGG CTACACCATC CACTATTTCT CCGTAGAAAA GATCTCTGTG TAACCTGGTC 2525 2530  2535 2540  2545 2550  2555 2560  2565 2570  2575 2580
                *          *          *          *          *          *
          ATGAGGATCC GAAACGGCAG CCTTTACGTT CATCACCTGC TAGAACCTCT CGTAGTCCAT
          TACTCCTAGG CTTTGCCGTC GGAAATGCAA GTAGTGGACG ATCTTGGAGA GCATCAGGTA 2585 2590  2595 2600  2605 2610  2615 2620  2625 2630  2635 2640
                *          *          *          *          *          *
          CACCATTTCT TGGCATTGGA ATTCTACTGG AAAAAAATAC AAAAAGCAAA ACAAAACCCT
          GTGGTAAAGA ACCGTAACCT TAAGATGACC TTTTTTTATG TTTTTCGTTT TGTTTTGGGA 2645 2650  2655 2660  2665 2670  2675 2680  2685 2690  2695 2700
                *          *          *          *          *          *
          CAGCACTGTT ACAAGAGGCC ATTTAAGTAT CTTGTGCTTC TTCACTTACC CATTAGCCAG
          GTCGTGACAA TGTTCTCCGG TAAATTCATA GAACACGAAG AAGTGAATGG GTAATCGGTC 2705 2710  2715 2720  2725 2730  2735 2740  2745 2750  2755 2760
                *          *          *          *          *          *
          GTTCTCATTA GGTTTTGCTT GGGCCTCCCT GGCACTGAAC CTTAGGCTTT GTATGACAGT
          CAAGAGTAAT CCAAAACGAA CCCGGAGGGA CCGTGACTTG GAATCCGAAA CATACTGTCA 2765 2770  2775 2780  2785 2790  2795 2800  2805 2810  2815 2820
                *          *          *          *          *          *
          GAAGCAGCAC TGTGAGTGGT TCAAGCACAC TGGAATATAA AACAGTCATG GCCTGAGATG
          CTTCGTCGTG ACACTCACCA AGTTCGTGTG ACCTTATATT TTGTCAGTAC CGGACTCTAC 2825 2830  2835 2840  2845 2850  2855 2860  2865 2870  2875 2880
                *          *          *          *          *          *
          CAGGTGATGC CATTACAGAA CCAAATCGTG GCACGTATTG CTGTGTCTCC TCTCAGAGTG
          GTCCACTACG GTAATGTCTT GGTTTAGCAC CGTGCATAAC GACACAGAGG AGAGTCTCAC 2885 2890  2895 2900  2905 2910  2915 2920  2925 2930  2935 2940
                *          *          *          *          *          *
          ACAGTCATAA ATACTGTCAA ACAATAAAGG GAGAATGGTG CTGTTTAAAG TCACATCCCT
          TGTCAGTATT TATGACAGTT TGTTATTTCC CTCTTACCAC GACAAATTTC AGTGTAGGGA 2945 2950  2955 2960  2965 2970  2975 2980  2985 2990  2995 3000
                *          *          *          *          *          *
          GTAAATTGCA GAATTCAAAA GTGATTATCT CTTTGATCTA CTTGCCTCAT TTCCCTATCT
          CATTTAACGT CTTAAGTTTT CACTAATAGA GAAACTAGAT GAACGGAGTA AAGGGATAGA 3005 3010  3015 3020  3025 3030  3035 3040  3045 3050  3055 3060
                *          *          *          *          *          *
          TCTCCCCCAC GGTATCCTAA ACTTTAGACT TCCCACTGTT CTGAAAGGAG ACATTGCTCT
          AGAGGGGGTG CCATAGGATT TGAAATCTGA AGGGTGACAA GACTTTCCTC TGTAACGAGA 3065 3070  3075 3080  3085 3090  3095 3100  3105 3110  3115 3120
                *          *          *          *          *          *
          ATGTCTGCCT TCGACCACAG CAAGCCATCA TCCTCCATTG CTCCCGGGGA CTCAAGAGGA
```

FIG. 7E

```
TACAGACGGA AGCTGGTGTC GTTCGGTAGT AGGAGGTAAC GAGGGCCCCT GAGTTCTCCT
3125 3130  3135 3140  3145 3150  3155 3160  3165 3170  3175 3180
     *          *          *          *          *          *
ATCTGTTTCT CTGCTGTCAA CTTCCCATCT GGCTCAGCAT AGGGTCACTT TGCCATTATG
TAGACAAAGA GACGACAGTT GAAGGGTAGA CCGAGTCGTA TCCCAGTGAA ACGGTAATAC 3185 3190  3195 3200  3205 3210  3215 3220  3225 3230  3235 3240
     *          *          *          *          *          *
CAAATGGAGA TAAAAGCAAT TCTGGCTGTC CAGGAGCTAA TCTGACCGTT CTATTGTGTG
GTTTACCTCT ATTTTCGTTA AGACCGACAG GTCCTCGATT AGACTGGCAA GATAACACAC 3245 3250  3255 3260  3265 3270  3275 3280  3285 3290  3295 3300
     *          *          *          *          *          *
GATGACCACA TAAGAAGGCA ATTTTAGTGT ATTAATCATA GATTATTATA AACTATAAAC
CTACTGGTGT ATTCTTCCGT TAAAATCACA TAATTAGTAT CTAATAATAT TTGATATTTG 3305 3310  3315 3320  3325 3330  3335 3340  3345 3350  3355 3360
     *          *          *          *          *          *
TTAAGGGCAA GGAGTTTATT ACAATGTATC TTTATTAAAA CAAAAGGGTG TATAGTGTTC
AATTCCCGTT CCTCAAATAA TGTTACATAG AAATAATTTT GTTTTCCCAC ATATCACAAG 3365 3370  3375 3380  3385 3390  3395 3400  3405 3410  3415 3420
     *          *          *          *          *          *
ACAAACTGTG AAAATAGTGT AAGAACTGTA CATTGTGAGC TCTGGTTATT TTTCTCTTGT
TGTTTGACAC TTTTATCACA TTCTTGACAT GTAACACTCG AGACCAATAA AAAGAGAACA 3425 3430  3435 3440  3445 3450  3455 3460  3465 3470  3475 3480
     *          *          *          *          *          *
ACCATAGAAA AATGTATAAA AATTATCAAA AAGCTAATGT GCAGGGATAT TGCCTTATTT
TGGTATCTTT TTACATATTT TTAATAGTTT TTCGATTACA CGTCCCTATA ACGGAATAAA 3485 3490  3495 3500  3505 3510  3515 3520  3525 3530  3535 3540
     *          *          *          *          *          *
GTCTGTAAAA AATGGAGCTC AGTAACATAA CTGCTTCTTG GAGCTTTGGA ATATTTTATC
CAGACATTTT TTACCTCGAG TCATTGTATT GACGAAGAAC CTCGAAACCT TATAAAATAG 3545 3550
     *
CTGTATTCTT GTTT  (SEQ ID NO:7)
GACATAAGAA CAAA
```

FIG. 7F

```
        5        10       15       20       25       30       35       40       45       50
                                            *                                   *        *
CTCCCAACA ATG GCG GCT CCG AGC CCG AGC GGC GGC GGC GGC TCC GGG GGC
GAGGGTTGT TAC CGC CGA GGC TCG GGC TCG CCG CCG CCG CCG AGG CCC CCG
          Met Ala Ala Pro Ser Pro Ser Gly Gly Gly Gly Ser Gly Gly>

55       60       65       70       75       80       85       90       95
    *                          *                 *        *        *
GGC AGC GGC AGC GGC ACC CCC GGC CCC GTA GGG TCC CCG GCA CCA GGC
CCG TCG CCG TCG CCG TGG GGG CCG GGG CAT CCC AGG GGC CGT GGT CCG
Gly Ser Gly Ser Gly Thr Pro Gly Pro Val Gly Ser Pro Ala Pro Gly>

100      105      110      115      120      125      130      135      140      145
 *                 *                 *                 *                 *
CAC CCG GCC GTC AGC AGC ATG CAG GGT AAA CGC AAA GCA CTG AAG TTG
GTG GGC CGG CAG TCG TCG TAC GTC CCA TTT GCG TTT CGT GAC TTC AAC
His Pro Ala Val Ser Ser Met Gln Gly Lys Arg Lys Ala Leu Lys Leu>

150      155      160      165      170      175      180      185      190      195
 *                          *                          *                 *
AAT TTT GCA AAT CCA CCT TTC AAA TCT ACA GCA AGG TTT ACT CTG AAT
TTA AAA CGT TTA GGT GGA AAG TTT AGA TGT CGT TCC AAA TGA GAC TTA
Asn Phe Ala Asn Pro Pro Phe Lys Ser Thr Ala Arg Phe Thr Leu Asn>

200      205      210      215      220      225      230      235      240
     *                 *                 *                 *                 *
CCC AAT CCT ACA GGA GTT CAA AAC CCA CAC ATA GAG AGA CTG AGA ACA
GGG TTA GGA TGT CCT CAA GTT TTG GGT GTG TAT CTC TCT GAC TCT TGT
Pro Asn Pro Thr Gly Val Gln Asn Pro His Ile Glu Arg Leu Arg Thr>

245      250      255      260      265      270      275      280      285      290
 *                          *                 *                 *                 *
CAC AGC ATT GAG TCA TCA GGA AAA CTG AAG ATC TCC CCT GAA CAA CAC
GTG TCG TAA CTC AGT AGT CCT TTT GAC TTC TAG AGG GGA CTT GTT GTG
His Ser Ile Glu Ser Ser Gly Lys Leu Lys Ile Ser Pro Glu Gln His>

295      300      305      310      315      320      325      330      335
                       *                 *                 *
TGG GAT TTC ACT GCA GAG GAC TTG AAA GAC CTT GGA GAA ATT GGA CGA
ACC CTA AAG TGA CGT CTC CTG AAC TTT CTG GAA CCT CTT TAA CCT GCT
Trp Asp Phe Thr Ala Glu Asp Leu Lys Asp Leu Gly Glu Ile Gly Arg>

340      345      350      355      360      365      370      375      380      385
 *                 *                 *                 *                 *
GGA GCT TAT GGT TCT GTC AAC AAA ATG GTC CAC AAA CCA AGT GGG CAA
CCT CGA ATA CCA AGA CAG TTG TTT TAC CAG GTG TTT GGT TCA CCC GTT
Gly Ala Tyr Gly Ser Val Asn Lys Met Val His Lys Pro Ser Gly Gln>

390      395      400      405      410      415      420      425      430      435
 *                 *                 *                 *        *        *
ATA ATG GCA GTT AAA AGA ATT CGG TCA ACA GTG GAT GAA AAA GAA CAA
TAT TAC CGT CAA TTT TCT TAA GCC AGT TGT CAC CTA CTT TTT CTT GTT
Ile Met Ala Val Lys Arg Ile Arg Ser Thr Val Asp Glu Lys Glu Gln>

440      445      450      455      460      465      470      475      480
     *                 *                 *                 *        *
AAA CAA CTT CTT ATG GAT TTG GAT GTA GTA ATG CGG AGT AGT GAT TGC
TTT GTT GAA GAA TAC CTA AAC CTA CAT CAT TAC GCC TCA TCA CTA ACG
Lys Gln Leu Leu Met Asp Leu Asp Val Val Met Arg Ser Ser Asp Cys>
```

FIG. 8A

```
485      490      495      500      505      510      515      520      525      530
 *                 *                 *                 *                 *
CCA TAC ATT GTT CAG TTT TAT GGT GCA CTC TTC AGA GAG GGT GAC TGT
GGT ATG TAA CAA GTC AAA ATA CCA CGT GAG AAG TCT CTC CCA CTG ACA
Pro Tyr Ile Val Gln Phe Tyr Gly Ala Leu Phe Arg Glu Gly Asp Cys>

535      540      545      550      555      560      565      570      575
      *                 *                 *                 *
TGG ATC TGT ATG GAA CTC ATG TCT ACC TCG TTT GAT AAG TTT TAC AAA
ACC TAG ACA TAC CTT GAG TAC AGA TGG AGC AAA CTA TTC AAA ATG TTT
Trp Ile Cys Met Glu Leu Met Ser Thr Ser Phe Asp Lys Phe Tyr Lys>

580      585      590      595      600      605      610      615      620      625
 *                 *                 *                 *                 *
TAT GTA TAT AGT GTA TTA GAT GAT GTT ATT CCA GAA GAA ATT TTA GGC
ATA CAT ATA TCA CAT AAT CTA CTA CAA TAA GGT CTT CTT TAA AAT CCG
Tyr Val Tyr Ser Val Leu Asp Asp Val Ile Pro Glu Glu Ile Leu Gly>

630      635      640      645      650      655      660      665      670      675
 *                 *                 *                 *                 *
AAA ATC ACT TTA GCA ACT GTG AAA GCA CTA AAC CAC TTA AAA GAA AAC
TTT TAG TGA AAT CGT TGA CAC TTT CGT GAT TTG GTG AAT TTT CTT TTG
Lys Ile Thr Leu Ala Thr Val Lys Ala Leu Asn His Leu Lys Glu Asn>

680      685      690      695      700      705      710      715      720
      *                 *                 *                 *
TTG AAA ATT ATT CAC AGA GAT ATC AAA CCT TCC AAT ATT CTT CTG GAC
AAC TTT TAA TAA GTG TCT CTA TAG TTT GGA AGG TTA TAA GAA GAC CTG
Leu Lys Ile Ile His Arg Asp Ile Lys Pro Ser Asn Ile Leu Leu Asp>

725      730      735      740      745      750      755      760      765      770
 *                 *                 *                 *                 *
AGA AGT GGA AAT ATT AAG CTC TGT GAC TTC GGC ATC AGT GGA CAG CTT
TCT TCA CCT TTA TAA TTC GAG ACA CTG AAG CCG TAG TCA CCT GTC GAA
Arg Ser Gly Asn Ile Lys Leu Cys Asp Phe Gly Ile Ser Gly Gln Leu>

775      780      785      790      795      800      805      810      815
      *                 *                 *                 *
GTG GAC TCT ATT GCC AAG ACA AGA GAT GCT GGC TGT AGG CCA TAC ATG
CAC CTG AGA TAA CGG TTC TGT TCT CTA CGA CCG ACA TCC GGT ATG TAC
Val Asp Ser Ile Ala Lys Thr Arg Asp Ala Gly Cys Arg Pro Tyr Met>

820      825      830      835      840      845      850      855      860      865
 *                 *                 *                 *                 *
GCA CCT GAA AGA ATA GAC CCA AGC GCA TCA CGA CAA GGA TAT GAT GTC
CGT GGA CTT TCT TAT CTG GGT TCG CGT AGT GCT GTT CCT ATA CTA CAG
Ala Pro Glu Arg Ile Asp Pro Ser Ala Ser Arg Gln Gly Tyr Asp Val>

870      875      880      885      890      895      900      905      910      915
 *                 *                 *                 *                 *
CGC TCT GAT GTC TGG AGT TTG GGG ATC ACA TTG TAT GAG TTG GCC ACA
GCG AGA CTA CAG ACC TCA AAC CCC TAG TGT AAC ATA CTC AAC CGG TGT
Arg Ser Asp Val Trp Ser Leu Gly Ile Thr Leu Tyr Glu Leu Ala Thr>

920      925      930      935      940      945      950      955      960
      *                 *                 *                 *
GGC CGA TTT CCT TAT CCA AAG TGG AAT AGT GTA TTT GAT CAA CTA ACA
CCG GCT AAA GGA ATA GGT TTC ACC TTA TCA CAT AAA CTA GTT GAT TGT
Gly Arg Phe Pro Tyr Pro Lys Trp Asn Ser Val Phe Asp Gln Leu Thr>

```
CAA GTC GTG AAA GGA GAT CCT CCG CAG CTG AGT AAT TCT GAG GAA AGG
GTT CAG CAC TTT CCT CTA GGA GGC GTC GAC TCA TTA AGA CTC CTT TCC
Gln Val Val Lys Gly Asp Pro Pro Gln Leu Ser Asn Ser Glu Glu Arg>

1015  1020  1025  1030  1035  1040  1045  1050  1055
            *           *           *           *
GAA TTC TCC CCG AGT TTC ATC AAC TTT GTC AAC TTG TGC CTT ACG AAG
CTT AAG AGG GGC TCA AAG TAG TTG AAA CAG TTG AAC ACG GAA TGC TTC
Glu Phe Ser Pro Ser Phe Ile Asn Phe Val Asn Leu Cys Leu Thr Lys>

1060 1065  1070  1075  1080  1085  1090  1095  1100  1105
  *           *           *           *           *
GAT GAA TCC AAA AGG CCA AAG TAT AAA GAG CTT CTG AAA CAT CCC TTT
CTA CTT AGG TTT TCC GGT TTC ATA TTT CTC GAA GAC TTT GTA GGG AAA
Asp Glu Ser Lys Arg Pro Lys Tyr Lys Glu Leu Leu Lys His Pro Phe>

1110  1115  1120  1125  1130  1135  1140  1145  1150  1155
            *           *           *           *           *
ATT TTG ATG TAT GAA GAA CGT GCC GTT GAG GTC GCA TGC TAT GTT TGT
TAA AAC TAC ATA CTT CTT GCA CGG CAA CTC CAG CGT ACG ATA CAA ACA
Ile Leu Met Tyr Glu Glu Arg Ala Val Glu Val Ala Cys Tyr Val Cys>

1160  1165  1170  1175  1180  1185  1190  1195  1200
               *           *           *           *           *
AAA ATC CTG GAT CAA ATG CCA GCT ACT CCC AGC TCT CCC ATG TAT GTC
TTT TAG GAC CTA GTT TAC GGT CGA TGA GGG TCG AGA GGG TAC ATA CAG
Lys Ile Leu Asp Gln Met Pro Ala Thr Pro Ser Ser Pro Met Tyr Val>

1205  1210  1215  1220  1225  1230  1235  1240  1245  1250  1255  1260
         *           *           *           *           *           *
GAT TGAT ATCGCTGCTA CATCAGACTC TAGAAAAAAG GGCTGAGAGG AAGCAAGACG
CTA ACTA TAGCGACGAT GTAGTCTGAG ATCTTTTTTC CCGACTCTCC TTCGTTCTGC
Asp> (SEQ ID NO:10)

1265  1270  1275  1280  1285  1290  1295  1300  1305  1310  1315  1320
            *           *           *           *           *           *
TAAAGAATTT TCATCCCGTA TCACAGTGTT TTTATTGCTC GCCCAGACAC CATGTGCAAT
ATTTCTTAAA AGTAGGGCAT AGTGTCACAA AAATAACGAG CGGGTCTGTG GTACACGTTA 1325  1330  1335  1340  1345  1350  1355  1360  1365  1370  1375  1380
            *           *           *           *           *           *
AAGATTGGTG TTCGTTTCCA TCATGTCTGT ATACTCCTGT CACCTAGAAC GTGCATCCTT
TTCTAACCAC AAGCAAAGGT AGTACAGACA TATGAGGACA GTGGATCTTG CACGTAGGAA 1385  1390  1395  1400  1405  1410  1415  1420  1425  1430  1435  1440
            *           *           *           *           *           *
GTAATACCTG ATTGATCACA CAGTGTTAGT GCTGGTCAGA GAGACCTCAT CCTGCTCTTT
CATTATGGAC TAACTAGTGT GTCACAATCA CGACCAGTCT CTCTGGAGTA GGACGAGAAA 1445  1450  1455  1460  1465  1470  1475  1480  1485  1490  1495  1500
            *           *           *           *           *           *
TGTGATGAAC ATATTCATGA AATGTGGAAG TCAGTACGAT CAAGTTGTTG ACTGTGATTA
ACACTACTTG TATAAGTACT TTACACCTTC AGTCATGCTA GTTCAACAAC TGACACTAAT 1505  1510  1515  1520  1525  1530  1535  1540  1545  1550  1555  1560
            *           *           *           *           *           *
GATCACATCT TAAATTCATT TCTAGACTCA AAACCTGGAG ATGCAGCTAC TGGAATGGTG
CTAGTGTAGA ATTTAAGTAA AGATCTGAGT TTTGGACCTC TACGTCGATG ACCTTACCAC 1565  1570  1575  1580  1585  1590  1595  1600  1605  1610  1615  1620
            *           *           *           *           *           *
TTTTGTCAGA CTTCCAAATC CTGGAAGGAC ACAGTGATGA ATGTACTATA TCTGAACATA
```

FIG. 8C

```
AAAACAGTCT GAAGGTTTAG GACCTTCCTG TGTCACTACT TACATGATAT AGACTTGTAT 1625 1630  1635 1640  1645 1650  1655 1660  1665 1670  1675 1680
         *          *          *          *          *          *
GAAACTCGGG CTTGAGTGAG AAGAGCTTGC ACAGCCAACG AGACACATTG CCTTCTGGAG
CTTTGAGCCC GAACTCACTC TTCTCGAACG TGTCGGTTGC TCTGTGTAAC GGAAGACCTC 1685 1690  1695 1700  1705 1710  1715 1720  1725 1730  1735 1740
         *          *          *          *          *          *
CTGGGAGACA AAGGAGGAAT TTACTTTCTT CACCAAGTGC AATAGATTAC TGATGTGATA
GACCCTCTGT TTCCTCCTTA AATGAAAGAA GTGGTTCACG TTATCTAATG ACTACACTAT 1745 1750  1755 1760  1765 1770  1775 1780  1785 1790  1795 1800
         *          *          *          *          *          *
TTCTGTTGCT TTACAGTTAC AGTTGATGTT TGGGGATCGA TGTGCTCAGC CAAATTTCCT
AAGACAACGA AATGTCAATG TCAACTACAA ACCCCTAGCT ACACGAGTCG GTTTAAAGGA 1805 1810  1815 1820  1825 1830  1835 1840  1845 1850  1855 1860
         *          *          *          *          *          *
GTTTGAAATA TCATGTTAAA TTAGAATGAA TTTATCTTTA CCAAAAACCA TGTTGCGTTC
CAAACTTTAT AGTACAATTT AATCTTACTT AAATAGAAAT GGTTTTTGGT ACAACGCAAG 1865 1870  1875 1880  1885 1890  1895 1900  1905 1910  1915 1920
         *          *          *          *          *          *
AAAGAGGTGA ACATTAAAAT ATAGAGACAG GACAGAATGT GTTCTTTTCT CCTCTACCAG
TTTCTCCACT TGTAATTTTA TATCTCTGTC CTGTCTTACA CAAGAAAAGA GGAGATGGTC 1925 1930  1935 1940  1945 1950  1955 1960  1965 1970  1975 1980
         *          *          *          *          *          *
TCCTATTTTT CAATGGGAAG ACTCAGGAGT CTGCCACTTG TCAAAGAAGG TGCTGATCCT
AGGATAAAAA GTTACCCTTC TGAGTCCTCA GACGGTGAAC AGTTTCTTCC ACGACTAGGA 1985 1990  1995 2000  2005 2010  2015 2020  2025 2030  2035 2040
         *          *          *          *          *          *
AAGAATTTTT CATTCTCAGA ATTCGGTGTG CTGCCAACTT GATGTTCCAC CTGCCACAAA
TTCTTAAAAA GTAAGAGTCT TAAGCCACAC GACGGTTGAA CTACAAGGTG GACGGTGTTT 2045 2050  2055 2060  2065 2070  2075 2080  2085 2090  2095 2100
         *          *          *          *          *          *
CCACCAGGAC TGAAAGAAGA AAACAGTACA GAAGGCAAAG TTTACAGATG TTTTTAATTC
GGTGGTCCTG ACTTTCTTCT TTTGTCATGT CTTCCGTTTC AAATGTCTAC AAAAATTAAG 2105 2110  2115 2120  2125 2130  2135 2140  2145 2150  2155 2160
         *          *          *          *          *          *
TAGTATTTTA TCTGGAACAA CTTGTAGCAG CTATATATTT CCCCTTGGTC CCAAGCCTGA
ATCATAAAAT AGACCTTGTT GAACATCGTC GATATATAAA GGGGAACCAG GGTTCGGACT 2165 2170  2175 2180  2185 2190  2195 2200  2205 2210  2215 2220
         *          *          *          *          *          *
TACTTTAGCC ATCATAACTC ACTAACAGGG AGAAGTAGCT AGTAGCAATG TGCCTTGATT
ATGAAATCGG TAGTATTGAG TGATTGTCCC TCTTCATCGA TCATCGTTAC ACGGAACTAA 2225 2230  2235 2240  2245 2250  2255 2260  2265 2270  2275 2280
         *          *          *          *          *          *
GATTAGATAA AGATTTCTAG TAGGCAGCAA AAGACCAAAT CTCAGTTGTT TGCTTCTTGC
CTAATCTATT TCTAAAGATC ATCCGTCGTT TTCTGGTTTA GAGTCAACAA ACGAAGAACG 2285 2290  2295 2300  2305 2310  2315 2320  2325 2330  2335 2340
         *          *          *          *          *          *
CATCACTGGT CCAGGTCTTC AGTTTCCGAA TCTCTTTCCC TTCCCCTGTG GTCTATTGTC
GTAGTGACCA GGTCCAGAAG TCAAAGGCTT AGAGAAAGGG AAGGGGACAC CAGATAACAG
```

FIG. 8D

```
2345 2350  2355 2360  2365 2370  2375 2380  2385 2390  2395 2400
         *          *          *          *          *          *
GCTATGTGAC TTGCGCTTAA TCCAATATTT TGCCTTTTTT CTATATCAAA AAACCTTTAC
CGATACACTG AACGCGAATT AGGTTATAAA ACGGAAAAAA GATATAGTTT TTTGGAAATG 2405 2410  2415 2420  2425 2430  2435 2440  2445 2450  2455 2460
         *          *          *          *          *          *
AGTTAGCAGG GATGTTCCTT ACCGAGGATT TTTAACCCCC AATCTCTCAT AATCGCTAGT
TCAATCGTCC CTACAAGGAA TGGCTCCTAA AAATTGGGGG TTAGAGAGTA TTAGCGATCA 2465 2470  2475 2480  2485 2490  2495 2500  2505 2510  2515 2520
         *          *          *          *          *          *
GTTTAAAAGG CTAAGAATAG TGGGGCCCAA CCGATGTGGT AGGTGATAAA GAGGCATCTT
CAAATTTTCC GATTCTTATC ACCCCGGGTT GGCTACACCA TCCACTATTT CTCCGTAGAA 2525 2530  2535 2540  2545 2550  2555 2560  2565 2570  2575 2580
         *          *          *          *          *          *
TTCTAGAGAC ACATTGGACC AGATGAGGAT CCGAAACGGC AGCCTTTACG TTCATCACCT
AAGATCTCTG TGTAACCTGG TCTACTCCTA GGCTTTGCCG TCGGAAATGC AAGTAGTGGA 2585 2590  2595 2600  2605 2610  2615 2620  2625 2630  2635 2640
         *          *          *          *          *          *
GCTAGAACCT CTCGTAGTCC ATCACCATTT CTTGGCATTG GAATTCTACT GGAAAAAAAT
CGATCTTGGA GAGCATCAGG TAGTGGTAAA GAACCGTAAC CTTAAGATGA CCTTTTTTTA 2645 2650  2655 2660  2665 2670  2675 2680  2685 2690  2695 2700
         *          *          *          *          *          *
ACAAAAAGCA AAACAAAACC CTCAGCACTG TTACAAGAGG CCATTTAAGT ATCTTGTGCT
TGTTTTTCGT TTTGTTTTGG GAGTCGTGAC AATGTTCTCC GGTAAATTCA TAGAACACGA 2705 2710  2715 2720  2725 2730  2735 2740  2745 2750  2755 2760
         *          *          *          *          *          *
TCTTCACTTA CCCATTAGCC AGGTTCTCAT TAGGTTTTGC TTGGGCCTCC CTGGCACTGA
AGAAGTGAAT GGGTAATCGG TCCAAGAGTA ATCCAAAACG AACCCGGAGG GACCGTGACT 2765 2770  2775 2780  2785 2790  2795 2800  2805 2810  2815 2820
         *          *          *          *          *          *
ACCTTAGGCT TTGTATGACA GTGAAGCAGC ACTGTGAGTG GTTCAAGCAC ACTGGAATAT
TGGAATCCGA AACATACTGT CACTTCGTCG TGACACTCAC CAAGTTCGTG TGACCTTATA 2825 2830  2835 2840  2845 2850  2855 2860  2865 2870  2875 2880
         *          *          *          *          *          *
AAAACAGTCA TGGCCTGAGA TGCAGGTGAT GCCATTACAG AACCAAATCG TGGCACGTAT
TTTTGTCAGT ACCGGACTCT ACGTCCACTA CGGTAATGTC TTGGTTTAGC ACCGTGCATA 2885 2890  2895 2900  2905 2910  2915 2920  2925 2930  2935 2940
         *          *          *          *          *          *
TGCTGTGTCT CCTCTCAGAG TGACAGTCAT AAATACTGTC AAACAATAAA GGGAGAATGG
ACGACACAGA GGAGAGTCTC ACTGTCAGTA TTTATGACAG TTTGTTATTT CCCTCTTACC 2945 2950  2955 2960  2965 2970  2975 2980  2985 2990  2995 3000
         *          *          *          *          *          *
TGCTGTTTAA AGTCACATCC CTGTAAATTG CAGAATTCAA AAGTGATTAT CTCTTTGATC
ACGACAAATT TCAGTGTAGG GACATTTAAC GTCTTAAGTT TTCACTAATA GAGAAACTAG 3005 3010  3015 3020  3025 3030  3035 3040  3045 3050  3055 3060
         *          *          *          *          *          *
TACTTGCCTC ATTTCCCTAT CTTCTCCCCC ACGGTATCCT AAACTTTAGA CTTCCCACTG
ATGAACGGAG TAAAGGGATA GAAGAGGGGG TGCCATAGGA TTTGAAATCT GAAGGGTGAC 3065 3070  3075 3080  3085 3090  3095 3100  3105 3110  3115 3120
         *          *          *          *          *          *
```

FIG. 8E

```
TTCTGAAAGG AGACATTGCT CTATGTCTGC CTTCGACCAC AGCAAGCCAT CATCCTCCAT
AAGACTTTCC TCTGTAACGA GATACAGACG GAAGCTGGTG TCGTTCGGTA GTAGGAGGTA 3125 3130  3135 3140  3145 3150  3155 3160  3165 3170  3175 3180
           *         *         *         *         *         *
TGCTCCCGGG GACTCAAGAG GAATCTGTTT CTCTGCTGTC AACTTCCCAT CTGGCTCAGC
ACGAGGGCCC CTGAGTTCTC CTTAGACAAA GAGACGACAG TTGAAGGGTA GACCGAGTCG 3185 3190  3195 3200  3205 3210  3215 3220  3225 3230  3235 3240
           *         *         *         *         *         *
ATAGGGTCAC TTTGCCATTA TGCAAATGGA GATAAAAGCA ATTCTGGCTG TCCAGGAGCT
TATCCCAGTG AAACGGTAAT ACGTTTACCT CTATTTTCGT TAAGACCGAC AGGTCCTCGA 3245 3250  3255 3260  3265 3270  3275 3280  3285 3290  3295 3300
           *         *         *         *         *         *
AATCTGACCG TTCTATTGTG TGGATGACCA CATAAGAAGG CAATTTTAGT GTATTAATCA
TTAGACTGGC AAGATAACAC ACCTACTGGT GTATTCTTCC GTTAAAATCA CATAATTAGT 3305 3310  3315 3320  3325 3330  3335 3340  3345 3350  3355 3360
           *         *         *         *         *         *
TAGATTATTA TAAACTATAA ACTTAAGGGC AAGGAGTTTA TTACAATGTA TCTTTATTAA
ATCTAATAAT ATTTGATATT TGAATTCCCG TTCCTCAAAT AATGTTACAT AGAAATAATT 3365 3370  3375 3380  3385 3390  3395 3400  3405 3410  3415 3420
           *         *         *         *         *         *
AACAAAAGGG TGTATAGTGT TCACAAACTG TGAAAATAGT GTAAGAACTG TACATTGTGA
TTGTTTTCCC ACATATCACA AGTGTTTGAC ACTTTTATCA CATTCTTGAC ATGTAACACT 3425 3430  3435 3440  3445 3450  3455 3460  3465 3470  3475 3480
           *         *         *         *         *         *
GCTCTGGTTA TTTTTCTCTT GTACCATAGA AAAATGTATA AAAATTATCA AAAAGCTAAT
CGAGACCAAT AAAAAGAGAA CATGGTATCT TTTTACATAT TTTTAATAGT TTTTCGATTA 3485 3490  3495 3500  3505 3510  3515 3520  3525 3530  3535 3540
           *         *         *         *         *         *
GTGCAGGGAT ATTGCCTTAT TTGTCTGTAA AAAATGGAGC TCAGTAACAT AACTGCTTCT
CACGTCCCTA TAACGGAATA AACAGACATT TTTTACCTCG AGTCATTGTA TTGACGAAGA 3545 3550  3555 3560  3565 3570  3575
           *         *         *
TGGAGCTTTG GAATATTTTA TCCTGTATTC TTGTTT    (SEQ ID NO:9)
ACCTCGAAAC CTTATAAAAT AGGACATAAG AACAAA
```

FIG. 8F

```
                   1                                                                               70
         MKK7                                                                          MLGLPSTLFTPRSMES
         HEP              <SASSSSSSASAFASAAPATGTFGGTYTPPTTRVSRATPTLPMLSSGPGGGLNRTRPVILP.PT.PHPPV
         MKK1                                                        MPKKKP--TPIQ.NPA-PDGSAVNG
         MKK2                                                       MLARRKPVLPA.TINP.IAEGP.PT.
         MKK3                                                              MSKPPA-----PN.TPPRN
         MKK4             MAAPSPSGGGGSGGGSGSGTPGPVGSPAPGHPAVSSMQGKRKALKLNFANPPFKSTARFTLNPN.TGVQN
         MKK5             <IGQVLPEATTTAFEYEDEDGDRITVRSDEEMKAMLSYYYSTVMEQQVNGQLIEP.QIFPRACK.PGERN
         MKK6                                        MSQSKGKKRNPGLKIPKEAFEQPQ-----TSSTPPRD
         Consensus 71                                                                              140
                                                                     I
         MKK7      IEIDQKLQEIMKQT-GYLTIG------GQRYQAEI-----------------NDLENLGEMGSGTCGQVWKMRFR
         HEP       S.T.M..KI..E...-.K.N.N------.RQ.PTD.------------------..KH..DL.N..S.N.V..MHL
         MKK1      TSSAETNL.ALQKKLEE.ELDE-----Q...KRL.AFLTQKQKVGELKDD.F.KIS.L.A.NG.V.F.VSHK
         MKK2      EGASEANLVDLQKKLEE.ELDE-----Q.KKRL.AFLTQKAKVGELKDD.F.RIS.L.A.NG.V.T.VQH.
         MKK3      ------LDSR-TFI..G------DRNFEV.A---------------------D..VTIS.L.R.AY.V.E.V.HA
         MKK4      PH.ERLRTHSIESS-.K.K.SP---E.HWDFTA----------------E..KD...I.R.AY.S.N..VHK
         MKK5      .HGLKVNTRAGPSQHSSPAVSDSLPSNSLKKSSAELKKILANGQMNEQ.IRYRDTL.H.NG.T.Y.AYHV
         MKK6      ------LDSK-ACIS.G------N.NFEVKA----------------D.L.PIM.L.R.AY.E...HV
         Consensus                                                        D       GGGVK
                                                                                  D 141              II                                   III              IV         210
         MKK7      KTGHIIAVKQMRRSGNKEENKRILMDLDVVLKSHDCPYIVQCFGTFITNTDVFIAMELM-GTCAEKLKK-
         HEP       SSNT.........T..A..........K...K.L.C.VRDP..W.C.....-SM.FD..L.-
         MKK1      PS.LVM.R.LIHLEIKPAIRNQ.IRE.Q.-.HECNSP...GFY.A.YSDGEIS.C..H.D.GSLDQVL.K
         MKK2      PS.L.M.R.LIHLEIKPAIRNQ.IRE.Q.--HECNSP...GFY.A.YSDGEIS.C..H.D.GSLDQVL.E
         MKK3      QS.T.M...RI.A.V.SQ.Q..LL....INMRTV..F.T.TFY.ALFREG..W.C.....D--.SLD.FYRK
         MKK4      PS.Q.M....RI.S.VDEK.Q.QLL......MRSS.......FY.ALFREG.CW.C.....-S.SFD.FY.Y
         MKK5      PS.K.L...VILLDITL.LQ.Q.MSE.EILI.-C.SS..IGFY.A.FVENRIS.CTEF.D.GSLDDIG.-
         MKK6      PS.Q.M....RI.A.V.SQ.Q..LL.....ISMRTV...FTVTFY.ALFREG..W.C......D--.SLD.FY.Q
         Consensus          IAK                L                      G         I    M
```

FIG. 9A

```
                              VI                              VII            *   280
MKK7       211 ---RMQGPIPERILGKMTVAIVKALYYLKEKHGVIHRDVKPSNILLDERGQIKLCDFGISGRLVDSKAKT
HEP            ---LSKK.V..Q....V...T.N..S...D...............I...N...................N.
MKK1           ---A.R...Q.....VSI.VIKG.T..R...KIM..................V...Q.I..M.NS
MKK2           ----AKR...E.....VSI.VLRG.A..R...QIM.................VNS..E........V...Q.I..M.NS
MKK3           VLDK-NMT...D.....EIA..S..R...EH.HS.LS.I..........V.INKE.HV.M.........Y....V...
MKK4           VYSVLDDV...E....I.L.T.K..NH...NLKII......I.......DRS.N.............Q...I...
MKK5           ------M..HV..RIA..V.KG.T..WS-LKIL.........M.VNT...V.......V.TQ..N.I...
MKK6           VIDK-GQT...D....IA..S......EH.HS.LS.I.......V.INAL..V.M.........Y....V...
Consensus             PE ILG       L       L        HRD KPSN L       G  K CDFG  S   LV S  A VIII                  IX                                       350
MKK7       281 RSAGCAAYMAPERIDPPDPTKPDYDIRADVWSLGISLVELATGQFPYKNCKTD-----------------
HEP            .....K...K...........T......ARS..EG.N...........................
MKK1           F-V.TRS..S.....LQGTH------.SVQS.I..M.L....M.V.RY.IPPPDAKELELMFGCQV----EGD
MKK2           F-V.TRS........LQGTH------.SVQS.I..M.L......V.RY.IPPPDAKELEAIFGRPVVDGEEGE
MKK3           MD...KP........N--.ELNQKG.NVKS.......TMI.M.ILR...ESWG.P-----------------
MKK4           .D...RP.........SASRQG...V.S.........T.Y.....R...PKWNSV----------------
MKK5           Y-V.TN.........SGEQ------.G.HS.......FM.IQKN.GSLMP----------------
MKK6           ID...KP........N--.ELNQKG.SVKS.I.....TMI..ILR...DSWG.P-----------------
Consensus                        Y    D WSLG   E X                                      XI    420
MKK7       351 ------------------------FEVLTKVLQEEPLLP-G-HMGFSGDFQSFVKDCLTKDHRKR
HEP            .................DS....C..Y.EGYN..QQ.RD..IK....N.QD.
MKK1           AAETPPRRTPGRPLSSYGMDSRPPMAI..L.DYIVN.P..K..S.V-----.LE..D..NK...I.NPAE.
MKK2           PHSISPRRPPGRPVSGHGMDSRPAMAI..L.DYIVN.P..K..N.V-----.TP...E..NK...I.NPAE.
MKK3           ................QQ.KQ.VE.PS.Q..AD----R..PE.VD.TAQ..R.NPAE.
MKK4           ................DQ..Q.VKGD..Q.SNSEERE..PS.IN..NL....ES..
MKK5           ................LQL.QCIVD.DS.V..V.E----..EP.VH.ITQ.MR.QPKE.
MKK6           ................QQ.KQ.V...S.Q..AD----K..AE.VD.TSQ..K.NSKE.
Consensus                                   L         P L           F      CL K       R 473
MKK7       421 PKYNKLLEHSFIKHYEILEVDVAS-WFKDVMAKTESPRTSGVLSQHHLPFFR    (SEQ ID NO: 18)
HEP            ...PE..AQP..RI..SAK...PN-..QSI--.DNRL.AN.DPTLQR...NS    (SEQ ID NO: 21)
MKK1           ADLKQ.MV.A...RSDAE...F.G-.LCSTIGLNQPSTPTHAAGV           (SEQ ID NO: 11)
MKK2           ADLKM.TN.T...RS.VE...F.G-.LCKTLRLNQPGTPTRTAV            (SEQ ID NO: 12)
MKK3           MS.LE.M..P.FTLHKTKKT.I.A-FV.KILGEDS                     (SEQ ID NO: 2)
MKK4           ...KE..K.P..LMY.ERA.E...C-YVCKILDQMPATP.SPMYVD          (SEQ ID NO: 10)
MKK5           .APEE.MG.P..VQFNDGNAA.VSM.VCRALEERRTSRGPREAAAGH         (SEQ ID NO: 22)
MKK6           .T.PE.MQ.P.FTLH.SKGT....-FVKLILGD                       (SEQ ID NO: 4)
Consensus            L    F                                             (SEQ ID NO: 27)
```

FIG. 9B

MKK7
Sequence Range: 1 to 1623

```
          10         20         30         40         50         60
           .          .          .          .          .          .
    GGAAAGGCAG CCTCCTGTAG GTGAAAATTC TGTTCACTAC CTGGCCACCT GGCCTGACTG
    CCTTTCCGTC GGAGGACATC CACTTTTAAG ACAAGTGATG GACCGGTGGA CCGGACTGAC 70         80         90        100        110        120
           .          .          .          .          .          .
    ACCTTCACAG CTTGATCATC TTCCTGAAGA GGCATTCAGG ATTCCCTCCA TCCCTACCCC
    TGGAAGTGTC GAACTAGTAG AAGGACTTCT CCGTAAGTCC TAAGGGAGGT AGGGATGGGG 130        140        150        160        170        180
           .          .          .          .          .          .
    TTCTGGACAA AGTCTTCCAC GTTTCCTTCC TGGGAGTTTC TTCCAGGAAC TGGAGATACC
    AAGACCTGTT TCAGAAGGTG CAAAGGAAGG ACCCTCAAAG AAGGTCCTTG ACCTCTATGG 190        200        210        220        230        240
           .          .          .          .          .          .
    CAGAGCCCTG CAACTCCCAC TGGCCAACGA TGGGGGCAGC CGCTCACCAT CCTCAGAGAG
    GTCTCGGGAC GTTGAGGGTG ACCGGTTGCT ACCCCCGTCG GCGAGTGGTA GGAGTCTCTC 250        260        270        280        290
           .          .          .          .          .          .
    CTCCCCACAG CACCCTACAC CCCCCACCCG GCCCCGCCAC ATG CTG GGG CTC CCA
    GAGGGGTGTC GTGGGATGTG GGGGGTGGGC CGGGGCGGTG TAC GAC CCC GAG GGT
                                                 Met Leu Gly Leu Pro>

300        310        320        330        340
           .          .          .          .          .
    TCA ACC TTG TTC ACA CCG CGC AGT ATG GAG AGC ATC GAG ATT GAC CAG
    AGT TGG AAC AAG TGT GGC GCG TCA TAC CTC TCG TAG CTC TAA CTG GTC
    Ser Thr Leu Phe Thr Pro Arg Ser Met Glu Ser Ile Glu Ile Asp Gln>

350        360        370        380        390
           .          .          .          .          .
    AAG CTG CAG GAG ATC ATG AAG CAG ACA GGG TAC CTG ACT ATC GGG GGC
    TTC GAC GTC CTC TAG TAC TTC GTC TGT CCC ATG GAC TGA TAG CCC CCG
    Lys Leu Gln Glu Ile Met Lys Gln Thr Gly Tyr Leu Thr Ile Gly Gly>

400        410        420        430
           .          .          .          .          .
    CAG CGT TAT CAG GCA GAA ATC AAT GAC TTG GAG AAC TTG GGT GAG ATG
    GTC GCA ATA GTC CGT CTT TAG TTA CTG AAC CTC TTG AAC CCA CTC TAC
    Gln Arg Tyr Gln Ala Glu Ile Asn Asp Leu Glu Asn Leu Gly Glu Met>

440        450        460        470        480
      .          .          .          .          .          .
    GGC AGT GGT ACC TGT GGT CAG GTG TGG AAG ATG CGG TTC CGG AAG ACA
    CCG TCA CCA TGG ACA CCA GTC CAC ACC TTC TAC GCC AAG GCC TTC TGT
    Gly Ser Gly Thr Cys Gly Gln Val Trp Lys Met Arg Phe Arg Lys Thr>

490        500        510        520        530
           .          .          .          .          .
    GGC CAC ATC ATT GCT GTT AAG CAA ATG CGG CGC TCT GGG AAC AAG GAA
    CCG GTG TAG TAA CGA CAA TTC GTT TAC GCC GCG AGA CCC TTG TTC CTT
    Gly His Ile Ile Ala Val Lys Gln Met Arg Arg Ser Gly Asn Lys Glu
```

FIG. 10A

MKK7

```
        540         550         560         570         580
         *           *           *           *           *
GAG AAT AAG CGC ATT TTG ATG GAC CTG GAT GTA GTA CTC AAG AGC CAT
CTC TTA TTC GCG TAA AAC TAC CTG GAC CTA CAT CAT GAG TTC TCG GTA
Glu Asn Lys Arg Ile Leu Met Asp Leu Asp Val Val Leu Lys Ser His>

590         600         610         620         630
         *           *           *           *           *
GAC TGC CCT TAC ATC GTT CAG TGC TTT GGC ACC TTC ATC ACC AAC ACA
CTG ACG GGA ATG TAG CAA GTC ACG AAA CCG TGG AAG TAG TGG TTG TGT
Asp Cys Pro Tyr Ile Val Gln Cys Phe Gly Thr Phe Ile Thr Asn Thr>

640         650         660         670
         *           *           *           *           *
GAC GTC TTT ATT GCC ATG GAG CTC ATG GGC ACA TGT GCA GAG AAG CTG
CTG CAG AAA TAA CGG TAC CTC GAG TAC CCG TGT ACA CGT CTC TTC GAC
Asp Val Phe Ile Ala Met Glu Leu Met Gly Thr Cys Ala Glu Lys Leu>

680         690         700         710         720
  *           *           *           *           *           *
AAG AAA CGA ATG CAG GGC CCC ATT CCA GAG CGA ATC CTG GGC AAG ATG
TTC TTT GCT TAC GTC CCG GGG TAA GGT CTC GCT TAG GAC CCG TTC TAC
Lys Lys Arg Met Gln Gly Pro Ile Pro Glu Arg Ile Leu Gly Lys Met>

730         740         750         760         770
         *           *           *           *           *
ACT GTG GCG ATT GTG AAA GCA CTG TAC TAT CTG AAG GAG AAG CAT GGC
TGA CAC CGC TAA CAC TTT CGT GAC ATG ATA GAC TTC CTC TTC GTA CCG
Thr Val Ala Ile Val Lys Ala Leu Tyr Tyr Leu Lys Glu Lys His Gly>

780         790         800         810         820
         *           *           *           *           *
GTC ATC CAT CGC GAT GTC AAA CCC TCC AAC ATC CTG CTA GAT GAG CGG
CAG TAG GTA GCG CTA CAG TTT GGG AGG TTG TAG GAC GAT CTA CTC GCC
Val Ile His Arg Asp Val Lys Pro Ser Asn Ile Leu Leu Asp Glu Arg>

830         840         850         860         870
         *           *           *           *           *
GGC CAG ATC AAG CTC TGT GAC TTT GGC ATC AGT GGC CGC CTT GTT GAC
CCG GTC TAG TTC GAG ACA CTG AAA CCG TAG TCA CCG GCG GAA CAA CTG
Gly Gln Ile Lys Leu Cys Asp Phe Gly Ile Ser Gly Arg Leu Val Asp>

880         890         900         910
         *           *           *           *           *
TCC AAA GCC AAA ACA CGG AGT GCT GGC TGT GCT GCC TAT ATG GCT CCC
AGG TTT CGG TTT TGT GCC TCA CGA CCG ACA CGA CGG ATA TAC CGA GGG
Ser Lys Ala Lys Thr Arg Ser Ala Gly Cys Ala Ala Tyr Met Ala Pro>

920         930         940         950         960
  *           *           *           *           *           *
GAG CGC ATC GAC CCT CCA GAT CCC ACC AAG CCT GAC TAT GAC ATC CGA
CTC GCG TAG CTG GGA GGT CTA GGG TGG TTC GGA CTG ATA CTG TAG GCT
Glu Arg Ile Asp Pro Pro Asp Pro Thr Lys Pro Asp Tyr Asp Ile Arg>
```

FIG. 10B

MKK7

```
        970          980          990         1000         1010
         *            *            *            *            *
      GCT GAT GTG TGG AGC CTG GGC ATC TCA CTG GTG GAG CTG GCA ACA GGA
      CGA CTA CAC ACC TCG GAC CCG TAG AGT GAC CAC CTC GAC CGT TGT CCT
      Ala Asp Val Trp Ser Leu Gly Ile Ser Leu Val Glu Leu Ala Thr Gly>

1020         1030         1040         1050         1060
         *            *            *            *            *
      CAG TTC CCC TAT AAG AAC TGC AAG ACG GAC TTT GAG GTC CTC ACC AAA
      GTC AAG GGG ATA TTC TTG ACG TTC TGC CTG AAA CTC CAG GAG TGG TTT
      Gln Phe Pro Tyr Lys Asn Cys Lys Thr Asp Phe Glu Val Leu Thr Lys>

1070         1080         1090         1100         1110
         *            *            *            *            *
      GTC CTA CAG GAA GAG CCC CCA CTC CTG CCT GGT CAC ATG GGC TTC TCA
      CAG GAT GTC CTT CTC GGG GGT GAG GAC GGA CCA GTG TAC CCG AAG AGT
      Val Leu Gln Glu Glu Pro Pro Leu Leu Pro Gly His Met Gly Phe Ser>

1120         1130         1140         1150
         *            *            *            *
      GGG GAC TTC CAG TCA TTT GTC AAA GAC TGC CTT ACT AAA GAT CAC AGG
      CCC CTG AAG GTC AGT AAA CAG TTT CTG ACG GAA TGA TTT CTA GTG TCC
      Gly Asp Phe Gln Ser Phe Val Lys Asp Cys Leu Thr Lys Asp His Arg>

1160         1170         1180         1190         1200
   *            *            *            *            *
AAG AGA CCA AAG TAT AAT AAG CTA CTT GAA CAC AGC TTC ATC AAG CAC
TTC TCT GGT TTC ATA TTA TTC GAT GAA CTT GTG TCG AAG TAG TTC GTG
Lys Arg Pro Lys Tyr Asn Lys Leu Leu Glu His Ser Phe Ile Lys His>

1210         1220         1230         1240         1250
         *            *            *            *            *
      TAT GAG ATA CTC GAG GTG GAT GTC GCG TCC TGG TTT AAG GAT GTC ATG
      ATA CTC TAT GAG CTC CAC CTA CAG CGC AGG ACC AAA TTC CTA CAG TAC
      Tyr Glu Ile Leu Glu Val Asp Val Ala Ser Trp Phe Lys Asp Val Met>

1260         1270         1280         1290         1300
         *            *            *            *            *
      GCG AAG ACC GAG TCC CCA AGG ACT AGT GGA GTC CTG AGT CAG CAC CAT
      CGC TTC TGG CTC AGG GGT TCC TGA TCA CCT CAG GAC TCA GTC GTG GTA
      Ala Lys Thr Glu Ser Pro Arg Thr Ser Gly Val Leu Ser Gln His His>

1310         1320         1330         1340         1350         1360
          *            *            *            *            *            *
      CTG CCC TTC TTC AGG TA GCCTCATGGC AGCGGCCAGC CCCGCAGGGG CCCCGGGCCA
      GAC GGG AAG AAG TCC AT CGGAGTACCG TCGCCGGTCG GGGCGTCCCC GGGGCCCGGT
      Leu Pro Phe Phe Arg>

1370         1380         1390         1400         1410         1420
           *            *            *            *            *            *
      CGGCCACCGA CCCCCCCCCC AACCTGGCCA ACCCAGCTGC CCATCAGGGG ACCTGGGACC
      GCCGGTGGCT GGGGGGGGGG TTGGACCGGT TGGGTCGACG GGTAGTCCCC TGGACCCTGG
```

FIG. 10C

MKK7

```
        1430       1440       1450       1460       1470       1480
         *  *       *  *       *  *       *  *       *  *       *  *
     TGGACGACTG CCAAGGACTG AGGACAGAAA GTAGGGGGTT CCCATCCAGC TCTGACTCCC
     ACCTGCTGAC GGTTCCTGAC TCCTGTCTTT CATCCCCCAA GGGTAGGTCG AGACTGAGGG 1490       1500       1510       1520       1530       1540
         *  *       *  *       *  *       *  *       *  *       *  *
     TGCCTACCAG CTGTGGACAA AAGGGCATGC TGGTTCCTAA TCCCTCCCAC TCTGGGGTCA
     ACGGATGGTC GACACCTGTT TTCCCGTACG ACCAAGGATT AGGGAGGGTG AGACCCCAGT 1550       1560       1570       1580       1590       1600
         *  *       *  *       *  *       *  *       *  *       *  *
     GCCAGCAGTG TGAGCCCCAT CCCACCCCGA CAGACACTGT GAACGGAAGA CAGCAGGCCA
     CGGTCGTCAC ACTCGGGGTA GGGTGGGGCT GTCTGTGACA CTTGCCTTCT GTCGTCCGGT 1610       1620
         *  *       *  *
     AAAAAAAAAA AAAAAAAAAA AAA  (SEQ ID NO: 17)
     TTTTTTTTTT TTTTTTTTTT TTT
```

FIG. 10D

MKK7b
Sequence Range: 1 to 1465

```
         10          20          30          40          50
         .           .           .           .           .
GC ACG AGC CCT GCT CCT GCC CCG TCC CAG CGA GCA GCC CTG CAA CTC CCA
CG TGC TCG GGA CGA GGA CGG GGC AGG GTC GCT CGT CGG GAC GTT GAG GGT
   Thr Ser Pro Ala Pro Ala Pro Ser Gln Arg Ala Ala Leu Gln Leu Pro>

60          70          80          90
              .           .           .           .
CTG GCC AAC GAT GGG GGC AGC CGC TCA CCA TCC TCA GAG AGC TCC CCA
GAC CGG TTG CTA CCC CCG TCG GCG AGT GGT AGG AGT CTC TCG AGG GGT
Leu Ala Asn Asp Gly Gly Ser Arg Ser Pro Ser Ser Glu Ser Ser Pro>

100         110         120         130         140
 .           .           .           .           .
CAG CAC CCT ACA CCC CCC ACC CGG CCC CGC CAC ATG CTG GGG CTC CCA
GTC GTG GGA TGT GGG GGG TGG GCC GGG GCG GTG TAC GAC CCC GAG GGT
Gln His Pro Thr Pro Pro Thr Arg Pro Arg His Met Leu Gly Leu Pro>

150         160         170         180         190
          .           .           .           .           .
TCA ACC TTG TTC ACA CCG CGC AGT ATG GAG AGC ATC GAG ATT GAC CAG
AGT TGG AAC AAG TGT GGC GCG TCA TAC CTC TCG TAG CTC TAA CTG GTC
Ser Thr Leu Phe Thr Pro Arg Ser Met Glu Ser Ile Glu Ile Asp Gln>

200         210         220         230         240
          .           .           .           .           .
AAG CTG CAG GAG ATC ATG AAG CAG ACA GGG TAC CTG ACT ATC GGG GGC
TTC GAC GTC CTC TAG TAC TTC GTC TGT CCC ATG GAC TGA TAG CCC CCG
Lys Leu Gln Glu Ile Met Lys Gln Thr Gly Tyr Leu Thr Ile Gly Gly>

250         260         270         280         290
              .           .           .           .           .
CAG CGT TAT CAG GCA GAA ATC AAT GAC TTG GAG AAC TTG GGT GAG ATG
GTC GCA ATA GTC CGT CTT TAG TTA CTG AAC CTC TTG AAC CCA CTC TAC
Gln Arg Tyr Gln Ala Glu Ile Asn Asp Leu Glu Asn Leu Gly Glu Met>

300         310         320         330
              .           .           .           .
GGC AGT GGT ACC TGT GGT CAG GTG TGG AAG ATG CGG TTC CGG AAG ACA
CCG TCA CCA TGG ACA CCA GTC CAC ACC TTC TAC GCC AAG GCC TTC TGT
Gly Ser Gly Thr Cys Gly Gln Val Trp Lys Met Arg Phe Arg Lys Thr>

340         350         360         370         380
 .           .           .           .           .
GGC CAC ATC ATT GCT GTT AAG CAA ATG CGG CGC TCT GGG AAC AAG GAA
CCG GTG TAG TAA CGA CAA TTC GTT TAC GCC GCG AGA CCC TTG TTC CTT
Gly His Ile Ile Ala Val Lys Gln Met Arg Arg Ser Gly Asn Lys Glu>

390         400         410         420         430
          .           .           .           .           .
GAG AAT AAG CGC ATT TTG ATG GAC CTG GAT GTA GTA CTC AAG AGC CAT
CTC TTA TTC GCG TAA AAC TAC CTG GAC CTA CAT CAT GAG TTC TCG GTA
Glu Asn Lys Arg Ile Leu Met Asp Leu Asp Val Val Leu Lys Ser His>
```

FIG. 11A

MKK7b

```
      440           450           460           470           480
       *             *             *             *             *
GAC TGC CCT TAC ATC GTT CAG TGC TTT GGC ACC TTC ATC ACC AAC ACA
CTG ACG GGA ATG TAG CAA GTC ACG AAA CCG TGG AAG TAG TGG TTG TGT
Asp Cys Pro Tyr Ile Val Gln Cys Phe Gly Thr Phe Ile Thr Asn Thr>

490           500           510           520           530
       *             *             *             *             *
GAC GTC TTT ATT GCC ATG GAG CTC ATG GGC ACA TGT GCA GAG AAG CTG
CTG CAG AAA TAA CGG TAC CTC GAG TAC CCG TGT ACA CGT CTC TTC GAC
Asp Val Phe Ile Ala Met Glu Leu Met Gly Thr Cys Ala Glu Lys Leu>

540           550           560           570
              *             *             *             *
AAG AAA CGA ATG CAG GGC CCC ATT CCA GAG CGA ATC CTG GGC AAG ATG
TTC TTT GCT TAC GTC CCG GGG TAA GGT CTC GCT TAG GAC CCG TTC TAC
Lys Lys Arg Met Gln Gly Pro Ile Pro Glu Arg Ile Leu Gly Lys Met>

580           590           600           610           620
  *             *             *             *             *
ACT GTG GCG ATT GTG AAA GCA CTG TAC TAT CTG AAG GAG AAG CAT GGC
TGA CAC CGC TAA CAC TTT CGT GAC ATG ATA GAC TTC CTC TTC GTA CCG
Thr Val Ala Ile Val Lys Ala Leu Tyr Tyr Leu Lys Glu Lys His Gly>

630           640           650           660           670
         *             *             *             *             *
GTC ATC CAT CGC GAT GTC AAA CCC TCC AAC ATC CTG CTA GAT GAG CGG
CAG TAG GTA GCG CTA CAG TTT GGG AGG TTG TAG GAC GAT CTA CTC GCC
Val Ile His Arg Asp Val Lys Pro Ser Asn Ile Leu Leu Asp Glu Arg>

680           690           700           710           720
          *             *             *             *             *
GGC CAG ATC AAG CTC TGT GAC TTT GGC ATC AGT GGC CGC CTT GTT GAC
CCG GTC TAG TTC GAG ACA CTG AAA CCG TAG TCA CCG GCG GAA CAA CTG
Gly Gln Ile Lys Leu Cys Asp Phe Gly Ile Ser Gly Arg Leu Val Asp>

730           740           750           760           770
             *             *             *             *             *
TCC AAA GCC AAA ACA CGG AGT GCT GGC TGT GCT GCC TAT ATG GCT CCC
AGG TTT CGG TTT TGT GCC TCA CGA CCG ACA CGA CGG ATA TAC CGA GGG
Ser Lys Ala Lys Thr Arg Ser Ala Gly Cys Ala Ala Tyr Met Ala Pro>

780           790           800           810
             *             *             *             *
GAG CGC ATC GAC CCT CCA GAT CCC ACC AAG CCT GAC TAT GAC ATC CGA
CTC GCG TAG CTG GGA GGT CTA GGG TGG TTC GGA CTG ATA CTG TAG GCT
Glu Arg Ile Asp Pro Pro Asp Pro Thr Lys Pro Asp Tyr Asp Ile Arg>
```

FIG. 11B

MKK7b

```
  820         830         840         850         860
   .           .           .           .           .
GCT GAT GTG TGG AGC CTG GGC ATC TCA CTG GTG GAG CTG GCA ACA GGA
CGA CTA CAC ACC TCG GAC CCG TAG AGT GAC CAC CTC GAC CGT TGT CCT
Ala Asp Val Trp Ser Leu Gly Ile Ser Leu Val Glu Leu Ala Thr Gly>

870         880         890         900         910
        .           .           .           .           .
CAG TTC CCC TAT AAG AAC TGC AAG ACG GAC TTT GAG GTC CTC ACC AAA
GTC AAG GGG ATA TTC TTG ACG TTC TGC CTG AAA CTC CAG GAG TGG TTT
Gln Phe Pro Tyr Lys Asn Cys Lys Thr Asp Phe Glu Val Leu Thr Lys>

920         930         940         950         960
        .           .           .           .           .
GTC CTA CAG GAA GAG CCC CCA CTC CTG CCT GGT CAC ATG GGC TTC TCA
CAG GAT GTC CTT CTC GGG GGT GAG GAC GGA CCA GTG TAC CCG AAG AGT
Val Leu Gln Glu Glu Pro Pro Leu Leu Pro Gly His Met Gly Phe Ser>

970         980         990        1000        1010
            .           .           .           .           .
GGG GAC TTC CAG TCA TTT GTC AAA GAC TGC CTT ACT AAA GAT CAC AGG
CCC CTG AAG GTC AGT AAA CAG TTT CTG ACG GAA TGA TTT CTA GTG TCC
Gly Asp Phe Gln Ser Phe Val Lys Asp Cys Leu Thr Lys Asp His Arg>

1020        1030        1040        1050
               .           .           .           .
AAG AGA CCA AAG TAT AAT AAG CTA CTT GAA CAC AGC TTC ATC AAG CAC
TTC TCT GGT TTC ATA TTA TTC GAT GAA CTT GTG TCG AAG TAG TTC GTG
Lys Arg Pro Lys Tyr Asn Lys Leu Leu Glu His Ser Phe Ile Lys His>

1060        1070        1080        1090        1100
 .           .           .           .           .
TAT GAG ATA CTC GAG GTG GAT GTC GCG TCC TGG TTT AAG GAT GTC ATG
ATA CTC TAT GAG CTC CAC CTA CAG CGC AGG ACC AAA TTC CTA CAG TAC
Tyr Glu Ile Leu Glu Val Asp Val Ala Ser Trp Phe Lys Asp Val Met>

1110        1120        1130        1140        1150
      .           .           .           .           .
GCG AAG ACC GAG TCC CCA AGG ACT AGT GGA GTC CTG AGT CAG CAC CAT
CGC TTC TGG CTC AGG GGT TCC TGA TCA CCT CAG GAC TCA GTC GTG GTA
Ala Lys Thr Glu Ser Pro Arg Thr Ser Gly Val Leu Ser Gln His His>

1160        1170        1180        1190        1200        1210
        .           .           .           .           .           .
CTG CCC TTC TTC AGG T  AGCCTCATGG CAGCGGCCAG CCCCGCAGGG GCCCCGGGCC
GAC GGG AAG AAG TCC A   TCGGAGTACC GTCGCCGGTC GGGGCGTCCC CGGGGCCCGG
Leu Pro Phe Phe Arg> (SEQ ID NO: 20)

1220        1230        1240        1250        1260        1270
          .           .           .           .           .           .
ACGGCCACCG ACCCCCCCCC CAACCTGGCC AACCCAGCTG CCCATCAGGG GACCTGGGAC
TGCCGGTGGC TGGGGGGGGG GTTGGACCGG TTGGGTCGAC GGGTAGTCCC CTGGACCCTG 1280        1290        1300        1310        1320        1330
          .           .           .           .           .           .
CTGGACGACT GCCAAGGACT GAGGACAGAA AGTAGGGGGT TCCCATCCAG CTCTGACTCC
GACCTGCTGA CGGTTCCTGA CTCCTGTCTT TCATCCCCCA AGGGTAGGTC GAGACTGAGG
```

FIG. 11C

MKK7b

```
           1340       1350       1360       1370       1380       1390
            *         *          *          *          *          *
         CTGCCTACCA GCTGTGGACA AAAGGGCATG CTGGTTCCTA ATCCCTCCCA CTCTGGGGTC
         GACGGATGGT CGACACCTGT TTTCCCGTAC GACCAAGGAT TAGGGAGGGT GAGACCCCAG 1400       1410       1420       1430       1440       1450
            *         *          *          *          *          *
         AGCCAGCAGT GTGAGCCCCA TCCCACCCCG ACAGACACTG TGAACGGAAG ACAGCAAAAA
         TCGGTCGTCA CACTCGGGGT AGGGTGGGGC TGTCTGTGAC ACTTGCCTTC TGTCGTTTTT

1460
            *
         AAAAAAAAAA AAAAA    (SEQ ID NO: 19)
         TTTTTTTTTT TTTTT
```

FIG. 11D

Human MKK7
Sequence Range: 1 to 843

```
              10         20         30         40         50         60
              *          *          *          *          *          *
         TGTTTGTCTG CCGGACTGAC GGGCGGCCGG GCGGTGCGCG GCGGCGGTGG CGGCGGGGAA
         ACAAACAGAC GGCCTGACTG CCCGCCGGCC CGCCACGCGC CGCCGCCACC GCCGCCCCTT 70              80              90            100
              *               *               *             *
       G ATG GCG GCG TCC TCC CTG GAA CAG AAG CTG TCC CGC CTG GAA GCA AAG
       C TAC CGC CGC AGG AGG GAC CTT GTC TTC GAC AGG GCG GAC CTT CGT TTC
         Met Ala Ala Ser Ser Leu Glu Gln Lys Leu Ser Arg Leu Glu Ala Lys>

110            120          130          140          150
      *              *            *            *            *
    CTG AAG CAG GAG AAC CGG GAG GCC CGG CGG AGG ATC GAC CTC AAC CTG
    GAC TTC GTC CTC TTG GCC CTC CGG GCC GCC TCC TAG CTG GAG TTG GAC
    Leu Lys Gln Glu Asn Arg Glu Ala Arg Arg Arg Ile Asp Leu Asn Leu>

160          170          180          190          200
         *            *            *            *            *
    GAT ATC AGC CCC CAG CGG CCC AGG CCC ACC CTG CAG CTC CCG CTG GCC
    CTA TAG TCG GGG GTC GCC GGG TCC GGG TGG GAC GTC GAG GGC GAC CGG
    Asp Ile Ser Pro Gln Arg Pro Arg Pro Thr Leu Gln Leu Pro Leu Ala>

210          220          230          240          250
         *            *            *            *            *
    AAC GAT GGG GGC AGC CGC TCG CCA TCC TCA GAG AGC TCC CCG CAG CAC
    TTG CTA CCC CCG TCG GCG AGC GGT AGG AGT CTC TCG AGG GGC GTC GTG
    Asn Asp Gly Gly Ser Arg Ser Pro Ser Ser Glu Ser Ser Pro Gln His>

260          270          280          290          300
           *            *            *            *            *
    CCC ACG CCC CCC GCC CGG CCC CGC CAC ATG CTG GGG CTC CCG TCA ACC
    GGG TGC GGG GGG CGG GCC GGG GCG GTG TAC GAC CCC GAG GGC AGT TGG
    Pro Thr Pro Pro Ala Arg Pro Arg His Met Leu Gly Leu Pro Ser Thr>

310          320          330          340
            *            *            *            *
    CTG TTC ACA CCC CGC AGC ATG GAG AGC ATT GAG ATT GAC CAG AAG CTG
    GAC AAG TGT GGG GCG TCG TAC CTC TCG TAA CTC TAA CTG GTC TTC GAC
    Leu Phe Thr Pro Arg Ser Met Glu Ser Ile Glu Ile Asp Gln Lys Leu>

350         360          370          380          390
   *           *            *            *            *
    CAG GAG ATC ATG AAG CAG ACG GGC TAC CTG ACC ATC GGG GGC CAG CGC
    GTC CTC TAG TAC TTC GTC TGC CCG ATG GAC TGG TAG CCC CCG GTC GCG
    Gln Glu Ile Met Lys Gln Thr Gly Tyr Leu Thr Ile Gly Gly Gln Arg>

400          410          420          430          440
         *            *            *            *            *
    TAC CAG GCA GAA ATC AAC GAC CTG GAG AAC TTG GGC GAG ATG GGC AGC
    ATG GTC CGT CTT TAG TTG CTG GAC CTC TTG AAC CCG CTC TAC CCG TCG
    Tyr Gln Ala Glu Ile Asn Asp Leu Glu Asn Leu Gly Glu Met Gly Ser>
```

FIG. 12A

Human MKK7

```
         450         460         470         480         490
          *           *           *           *           *
GGC ACC TGC GGC CAG GTG TGG AAG ATG CGC TTC CGG AAG ACC GGC CAC
CCG TGG ACG CCG GTC CAC ACC TTC TAC GCG AAG GCC TTC TGG CCG GTG
Gly Thr Cys Gly Gln Val Trp Lys Met Arg Phe Arg Lys Thr Gly His>

500         510         520         530         540
          *           *           *           *           *
GTC ATT GCC GTT AAG CAA ATG CGG CGC TCC GGG AAC AAG GAG GAG AAC
CAG TAA CGG CAA TTC GTT TAC GCC GCG AGG CCC TTG TTC CTC CTC TTG
Val Ile Ala Val Lys Gln Met Arg Arg Ser Gly Asn Lys Glu Glu Asn>

550         560         570         580
          *           *           *           *
AAG CGC ATC CTC ATG GAC CTG GAT GTG GTG CTG AAG AGC CAC GAC TGC
TTC GCG TAG GAG TAC CTG GAC CTA CAC CAC GAC TTC TCG GTG CTG ACG
Lys Arg Ile Leu Met Asp Leu Asp Val Val Leu Lys Ser His Asp Cys>

590         600         610         620         630
 *           *           *           *           *
CCC TAC ATC GTG CAG TGC TTT GGG ACG TTC ATC ACC AAC ACG GAC GTC
GGG ATG TAG CAC GTC ACG AAA CCC TGC AAG TAG TGG TTG TGC CTG CAG
Pro Tyr Ile Val Gln Cys Phe Gly Thr Phe Ile Thr Asn Thr Asp Val>

640         650         660         670         680
 *           *           *           *           *
TTC ATC GCC ATG GAG CTC ATG GGC ACC TGC GCT GAG AAG CTC AAG AAG
AAG TAG CGG TAC CTC GAG TAC CCG TGG ACG CGA CTC TTC GAG TTC TTC
Phe Ile Ala Met Glu Leu Met Gly Thr Cys Ala Glu Lys Leu Lys Lys>

690         700         710         720         730
          *           *           *           *           *
CGG ATG CAG GGC CCC ATC CCC GAG CGC ATT CTG GGC AAG ATG ACA GTG
GCC TAC GTC CCG GGG TAG GGG CTC GCG TAA GAC CCG TTC TAC TGT CAC
Arg Met Gln Gly Pro Ile Pro Glu Arg Ile Leu Gly Lys Met Thr Val>

740         750         760         770         780
          *           *           *           *           *
GCG ATT GTG AAG GCG CTG TAC TAC CTG AAG GAG AAG CAC GGT GTC ATC
CGC TAA CAC TTC CGC GAC ATG ATG GAC TTC CTC TTC GTG CCA CAG TAG
Ala Ile Val Lys Ala Leu Tyr Tyr Leu Lys Glu Lys His Gly Val Ile>

790         800         810         820
          *           *           *           *
CAC CGC GAC GTC AAG CCC TCC AAC ATC CTG CTG GAC GAG CGG GGC CAG
GTG GCG CTG CAG TTC GGG AGG TTG TAG GAC GAC CTG CTC GCC CCG GTC
His Arg Asp Val Lys Pro Ser Asn Ile Leu Leu Asp Glu Arg Gly Gln>

830         840
 *           *
ATC AAG CTC TGC GA  (SEQ ID NO: 25)
TAG TTC GAG ACG CT
Ile Lys Leu Cys>   (SEQ ID NO: 26)
```

FIG. 12B

Mouse MKK7c
Sequence Range: 1 to 1643

```
          10         20         30         40         50         60
    *    *     *    *     *    *     *    *     *    *     *    *
AGCGCAGGCG CAGTGCGGTG TTTGTCTACC CCGGACTGAC GGGTGGCCTG GCGGTGAGCG
TCGCGTCCGC GTCACGCCAC AAACAGATGG GGCCTGACTG CCCACCGGAC CGCCACTCGC 70         80         90        100        110
    *    *     *    *     *    *     *    *     *    *
GCGGCAGCGG CGGCGGGGAA G ATG GCG GCG TCC TCC CTG GAG CAG AAG CTG
CGCCGTCGCC GCCGCCCCTT C TAC CGC CGC AGG AGG GAC CTC GTC TTC GAC
                        Met Ala Ala Ser Ser Leu Glu Gln Lys Leu>

120        130        140        150
       *    *      *    *     *    *     *    *      *
TCC CGC CTG GAA GCC AAG CTG AAG CAG GAG AAC CGT GAG GCC CGC AGG
AGG GCG GAC CTT CGG TTC GAC TTC GTC CTC TTG GCA CTC CGG GCG TCC
Ser Arg Leu Glu Ala Lys Leu Lys Gln Glu Asn Arg Glu Ala Arg Arg>

160        170        180        190        200
   *     *    *     *    *     *    *     *    *     *
AGG ATC GAC CTC AAC TTG GAT ATC AGC CCA CAG CGG CCC AGG CCC ACC
TCC TAG CTG GAG TTG AAC CTA TAG TCG GGT GTC GCC GGG TCC GGG TGG
Arg Ile Asp Leu Asn Leu Asp Ile Ser Pro Gln Arg Pro Arg Pro Thr>

210        220        230        240        250
   *     *    *      *    *     *    *     *    *     *
CTG CAA CTC CCA CTG GCC AAC GAT GGG GGC AGC CGC TCA CCA TCC TCA
GAC GTT GAG GGT GAC CGG TTG CTA CCC CCG TCG GCG AGT GGT AGG AGT
Leu Gln Leu Pro Leu Ala Asn Asp Gly Gly Ser Arg Ser Pro Ser Ser>

260        270        280        290        300
        *    *     *    *      *    *     *    *     *
GAG AGC TCC CCA CAG CAC CCT ACA CCC CCC ACC CGG CCC CGC CAC ATG
CTC TCG AGG GGT GTC GTG GGA TGT GGG GGG TGG GCC GGG GCG GTG TAC
Glu Ser Ser Pro Gln His Pro Thr Pro Pro Thr Arg Pro Arg His Met>

310        320        330        340        350
         *    *     *    *      *    *     *    *     *    *
CTG GGG CTC CCA TCA ACC TTG TTC ACA CCG CGC AGT ATG GAG AGC ATC
GAC CCC GAG GGT AGT TGG AAC AAG TGT GGC GCG TCA TAC CTC TCG TAG
Leu Gly Leu Pro Ser Thr Leu Phe Thr Pro Arg Ser Met Glu Ser Ile>

360        370        380        390
         *    *     *    *      *    *     *    *     *
GAG ATT GAC CAG AAG CTG CAG GAG ATC ATG AAG CAG ACA GGG TAC CTG
CTC TAA CTG GTC TTC GAC GTC CTC TAG TAC TTC GTC TGT CCC ATG GAC
Glu Ile Asp Gln Lys Leu Gln Glu Ile Met Lys Gln Thr Gly Tyr Leu>

400        410        420        430        440
   *     *    *     *    *      *    *     *    *     *
ACT ATC GGG GGC CAG CGT TAT CAG GCA GAA ATC AAT GAC TTG GAG AAC
TGA TAG CCC CCG GTC GCA ATA GTC CGT CTT TAG TTA CTG AAC CTC TTG
Thr Ile Gly Gly Gln Arg Tyr Gln Ala Glu Ile Asn Asp Leu Glu Asn>
```

FIG. 13A

Mouse MKK7c

```
      450           460           470           480           490
       *             *             *             *             *
TTG GGT GAG ATG GGC AGT GGT ACC TGT GGT CAG GTG TGG AAG ATG CGG
AAC CCA CTC TAC CCG TCA CCA TGG ACA CCA GTC CAC ACC TTC TAC GCC
Leu Gly Glu Met Gly Ser Gly Thr Cys Gly Gln Val Trp Lys Met Arg>

500           510           520           530           540
       *             *             *             *             *
TTC CGG AAG ACA GGC CAC ATC ATT GCT GTT AAG CAA ATG CGG CGC TCT
AAG GCC TTC TGT CCG GTG TAG TAA CGA CAA TTC GTT TAC GCC GCG AGA
Phe Arg Lys Thr Gly His Ile Ile Ala Val Lys Gln Met Arg Arg Ser>

550           560           570           580           590
       *             *             *             *             *
GGG AAC AAG GAA GAG AAT AAG CGC ATT TTG ATG GAC CTG GAT GTA GTA
CCC TTG TTC CTT CTC TTA TTC GCG TAA AAC TAC CTG GAC CTA CAT CAT
Gly Asn Lys Glu Glu Asn Lys Arg Ile Leu Met Asp Leu Asp Val Val>

600           610           620           630
               *             *             *             *
CTC AAG AGC CAT GAC TGC CCT TAC ATC GTT CAG TGC TTT GGC ACC TTC
GAG TTC TCG GTA CTG ACG GGA ATG TAG CAA GTC ACG AAA CCG TGG AAG
Leu Lys Ser His Asp Cys Pro Tyr Ile Val Gln Cys Phe Gly Thr Phe>

640          650           660           670           680
   *           *             *             *             *
ATC ACC AAC ACA GAC GTC TTT ATT GCC ATG GAG CTC ATG GGC ACA TGT
TAG TGG TTG TGT CTG CAG AAA TAA CGG TAC CTC GAG TAC CCG TGT ACA
Ile Thr Asn Thr Asp Val Phe Ile Ala Met Glu Leu Met Gly Thr Cys>

690           700           710           720           730
       *             *             *             *             *
GCA GAG AAG CTG AAG AAA CGA ATG CAG GGC CCC ATT CCA GAG CGA ATC
CGT CTC TTC GAC TTC TTT GCT TAC GTC CCG GGG TAA GGT CTC GCT TAG
Ala Glu Lys Leu Lys Lys Arg Met Gln Gly Pro Ile Pro Glu Arg Ile>

740           750           760           770           780
       *             *             *             *             *
CTG GGC AAG ATG ACT GTG GCG ATT GTG AAA GCA CTG TAC TAT CTG AAG
GAC CCG TTC TAC TGA CAC CGC TAA CAC TTT CGT GAC ATG ATA GAC TTC
Leu Gly Lys Met Thr Val Ala Ile Val Lys Ala Leu Tyr Tyr Leu Lys>

790           800           810           820           830
            *             *             *             *             *
GAG AAG CAT GGC GTC ATC CAT CGC GAT GTC AAA CCC TCC AAC ATC CTG
CTC TTC GTA CCG CAG TAG GTA GCG CTA CAG TTT GGG AGG TTG TAG GAC
Glu Lys His Gly Val Ile His Arg Asp Val Lys Pro Ser Asn Ile Leu>

840           850           860           870
            *             *             *             *
CTA GAT GAG CGG GGC CAG ATC AAG CTC TGT GAC TTT GGC ATC AGT GGC
GAT CTA CTC GCC CCG GTC TAG TTC GAG ACA CTG AAA CCG TAG TCA CCG
Leu Asp Glu Arg Gly Gln Ile Lys Leu Cys Asp Phe Gly Ile Ser Gly>
```

FIG. 13B

Mouse MKK7c

```
    880         890         900         910         920
     *     *     *     *     *     *     *     *     *     *
    CGC CTT GTT GAC TCC AAA GCC AAA ACA CGG AGT GCT GGC TGT GCT GCC
    GCG GAA CAA CTG AGG TTT CGG TTT TGT GCC TCA CGA CCG ACA CGA CGG
    Arg Leu Val Asp Ser Lys Ala Lys Thr Arg Ser Ala Gly Cys Ala Ala>

930         940         950         960         970
     *     *     *     *     *     *     *     *     *     *
    TAT ATG GCT CCC GAG CGC ATC GAC CCT CCA GAT CCC ACC AAG CCT GAC
    ATA TAC CGA GGG CTC GCG TAG CTG GGA GGT CTA GGG TGG TTC GGA CTG
    Tyr Met Ala Pro Glu Arg Ile Asp Pro Pro Asp Pro Thr Lys Pro Asp>

980         990         1000        1010        1020
     *     *     *     *     *     *     *     *     *
    TAT GAC ATC CGA GCT GAT GTG TGG AGC CTG GGC ATC TCA CTG GTG GAG
    ATA CTG TAG GCT CGA CTA CAC ACC TCG GAC CCG TAG AGT GAC CAC CTC
    Tyr Asp Ile Arg Ala Asp Val Trp Ser Leu Gly Ile Ser Leu Val Glu>

1030        1040        1050        1060        1070
         *     *     *     *     *     *     *     *     *     *
        CTG GCA ACA GGA CAG TTC CCC TAT AAG AAC TGC AAG ACG GAC TTT GAG
        GAC CGT TGT CCT GTC AAG GGG ATA TTC TTG ACG TTC TGC CTG AAA CTC
        Leu Ala Thr Gly Gln Phe Pro Tyr Lys Asn Cys Lys Thr Asp Phe Glu>

1080        1090        1100        1110
         *     *     *     *     *     *     *     *     *
        GTC CTC ACC AAA GTC CTA CAG GAA GAG CCC CCA CTC CTG CCT GGT CAC
        CAG GAG TGG TTT CAG GAT GTC CTT CTC GGG GGT GAG GAC GGA CCA GTG
        Val Leu Thr Lys Val Leu Gln Glu Glu Pro Pro Leu Leu Pro Gly His>

1120        1130        1140        1150        1160
 *     *     *     *     *     *     *     *     *     *
ATG GGC TTC TCA GGG GAC TTC CAG TCA TTT GTC AAA GAC TGC CTT ACT
TAC CCG AAG AGT CCC CTG AAG GTC AGT AAA CAG TTT CTG ACG GAA TGA
Met Gly Phe Ser Gly Asp Phe Gln Ser Phe Val Lys Asp Cys Leu Thr>

1170        1180        1190        1200        1210
     *     *     *     *     *     *     *     *     *     *
    AAA GAT CAC AGG AAG AGA CCA AAG TAT AAT AAG CTA CTT GAA CAC AGC
    TTT CTA GTG TCC TTC TCT GGT TTC ATA TTA TTC GAT GAA CTT GTG TCG
    Lys Asp His Arg Lys Arg Pro Lys Tyr Asn Lys Leu Leu Glu His Ser>

1220        1230        1240        1250        1260
     *     *     *     *     *     *     *     *     *
    TTC ATC AAG CAC TAT GAG ATA CTC GAG GTG GAT GTC GCG TCC TGG TTT
    AAG TAG TTC GTG ATA CTC TAT GAG CTC CAC CTA CAG CGC AGG ACC AAA
    Phe Ile Lys His Tyr Glu Ile Leu Glu Val Asp Val Ala Ser Trp Phe>

1270        1280        1290        1300        1310
         *     *     *     *     *     *     *     *     *     *
        AAG GAT GTC ATG GCG AAG ACC GAG TCC CCA AGG ACT AGT GGA GTC CTG
        TTC CTA CAG TAC CGC TTC TGG CTC AGG GGT TCC TGA TCA CCT CAG GAC
```

FIG. 13C

Mouse MKK7c

Lys Asp Val Met Ala Lys Thr Glu Ser Pro Arg Thr Ser Gly Val Leu>

```
         1320        1330        1340        1350        1360
           *           *           *           *           *
AGT CAG CAC CAT CTG CCC TTC TTC AGG TA  GCCTCATGGC AGCGGCCAGC
TCA GTC GTG GTA GAC GGG AAG AAG TCC AT  CGGAGTACCG TCGCCGGTCG
Ser Gln His His Leu Pro Phe Phe Arg>  (SEQ ID NO: 28)

1370        1380        1390        1400        1410        1420
           *           *           *           *           *           *
CCCGCAGGGG CCCCGGGCCA CGGCCACCGA CCCCCCCCCC AACCTGGCCA ACCCAGCTGC
GGGCGTCCCC GGGGCCCGGT GCCGGTGGCT GGGGGGGGGG TTGGACCGGT TGGGTCGACG 1430        1440        1450        1460        1470        1480
           *           *           *           *           *           *
CCATCAGGGG ACCTGGGACC TGGACGACTG CCAAGGACTG AGGACAGAAA GTAGGGGGTT
GGTAGTCCCC TGGACCCTGG ACCTGCTGAC GGTTCCTGAC TCCTGTCTTT CATCCCCCAA 1490        1500        1510        1520        1530        1540
           *           *           *           *           *           *
CCCATCCAGC TCTGACTCCC TGCCTACCAG CTGTGGACAA AAGGGCATGC TGGTTCCTAA
GGGTAGGTCG AGACTGAGGG ACGGATGGTC GACACCTGTT TTCCCGTACG ACCAAGGATT 1550        1560        1570        1580        1590        1600
           *           *           *           *           *           *
TCCCTCCCAC TCTGGGGTCA GCCAGCAGTG TGAGCCCCAT CCCACCCCGA CAGACACTGT
AGGGAGGGTG AGACCCCAGT CGGTCGTCAC ACTCGGGGTA GGGTGGGGCT GTCTGTGACA 1610        1620        1630        1640
           *           *           *           *
GAACGGAAGA CAGCAGGCCA AAAAAAAAAA AAAAAAAAAA AAA  (SEQ ID NO: 27)
CTTGCCTTCT GTCGTCCGGT TTTTTTTTTT TTTTTTTTTT TTT
```

FIG. 13D

MKK7d
Sequence Range: 1 to 1578

```
         10         20         30         40         50         60
         *          *          *          *          *          *
GGAAAGGCAG CCTCCTGTAG GTGAAAATTC TGTTCACTAC CTGGCCACCT GGCCTGACTG
CCTTTCCGTC GGAGGACATC CACTTTTAAG ACAAGTGATG GACCGGTGGA CCGGACTGAC 70         80         90        100        110        120
         *          *          *          *          *          *
ACCTTCACAG CTTGATCATC TTCCTGAAGA GGCATTCAGG ATTCCCTCCA TCCCTACCCC
TGGAAGTGTC GAACTAGTAG AAGGACTTCT CCGTAAGTCC TAAGGGAGGT AGGGATGGGG 130        140        150        160        170        180
         *          *          *          *          *          *
TTCTGGACAA AGTCTTCCAC GTTTCCTTCC TGGAGTTTC TTCCAGGAAC TGGAGATACC
AAGACCTGTT TCAGAAGGTG CAAAGGAAGG ACCCTCAAAG AAGGTCCTTG ACCTCTATGG 190        200        210        220        230        240
         *          *          *          *          *          *
CAGAGCCCTG CAACTCCCAC TGGCCAACGA TGGGGGCAGC CGCTCACCAT CCTCAGAGAG
GTCTCGGGAC GTTGAGGGTG ACCGGTTGCT ACCCCCGTCG GCGAGTGGTA GGAGTCTCTC 250        260        270        280            290
         *          *          *          *             *          *
CTCCCCACAG CACCCTACAC CCCCCACCCG GCCCCGCCAC ATG CTG GGG CTC CCA
GAGGGGTGTC GTGGGATGTG GGGGTGGGC CGGGGCGGTG TAC GAC CCC GAG GGT
                                             Met Leu Gly Leu Pro>

300         310         320         330         340
       *           *           *           *           *
TCA ACC TTG TTC ACA CCG CGC AGT ATG GAG AGC ATC GAG ATT GAC CAG
AGT TGG AAC AAG TGT GGC GCG TCA TAC CTC TCG TAG CTC TAA CTG GTC
Ser Thr Leu Phe Thr Pro Arg Ser Met Glu Ser Ile Glu Ile Asp Gln>

350         360         370         380         390
       *           *           *           *           *
AAG CTG CAG GAG ATC ATG AAG CAG ACA GGG TAC CTG ACT ATC GGG GGC
TTC GAC GTC CTC TAG TAC TTC GTC TGT CCC ATG GAC TGA TAG CCC CCG
Lys Leu Gln Glu Ile Met Lys Gln Thr Gly Tyr Leu Thr Ile Gly Gly>

400         410         420         430
       *           *           *           *
CAG CGT TAT CAG GCA GAA ATC AAT GAC TTG GAG AAC TTG GGT GAG ATG
GTC GCA ATA GTC CGT CTT TAG TTA CTG AAC CTC TTG AAC CCA CTC TAC
Gln Arg Tyr Gln Ala Glu Ile Asn Asp Leu Glu Asn Leu Gly Glu Met>

440         450         460         470         480
 *           *           *           *           *
GGC AGT GGT ACC TGT GGT CAG GTG TGG AAG ATG CGG TTC CGG AAG ACA
CCG TCA CCA TGG ACA CCA GTC CAC ACC TTC TAC GCC AAG GCC TTC TGT
Gly Ser Gly Thr Cys Gly Gln Val Trp Lys Met Arg Phe Arg Lys Thr>

490         500         510         520         530
       *           *           *           *           *
GGC CAC ATC ATT GCT GTT AAG CAA ATG CGG CGC TCT GGG AAC AAG GAA
CCG GTG TAG TAA CGA CAA TTC GTT TAC GCC GCG AGA CCC TTG TTC CTT
Gly His Ile Ile Ala Val Lys Gln Met Arg Arg Ser Gly Asn Lys Glu>
```

FIG. 14A

MKK7d

```
     540         550         560         570         580
      *           *           *           *           *
GAG AAT AAG CGC ATT TTG ATG GAC CTG GAT GTA GTA CTC AAG AGC CAT
CTC TTA TTC GCG TAA AAC TAC CTG GAC CTA CAT CAT GAG TTC TCG GTA
Glu Asn Lys Arg Ile Leu Met Asp Leu Asp Val Val Leu Lys Ser His>

590         600         610         620         630
           *           *           *           *           *
GAC TGC CCT TAC ATC GTT CAG TGC TTT GGC ACC TTC ATC ACC AAC ACA
CTG ACG GGA ATG TAG CAA GTC ACG AAA CCG TGG AAG TAG TGG TTG TGT
Asp Cys Pro Tyr Ile Val Gln Cys Phe Gly Thr Phe Ile Thr Asn Thr>

640         650         660         670
        *           *           *           *
GAC GTC TTT ATT GCC ATG GAG CTC ATG GGC ACA TGT GCA GAG AAG CTG
CTG CAG AAA TAA CGG TAC CTC GAG TAC CCG TGT ACA CGT CTC TTC GAC
Asp Val Phe Ile Ala Met Glu Leu Met Gly Thr Cys Ala Glu Lys Leu>

680         690         700         710         720
  *           *           *           *           *
AAG AAA CGA ATG CAG GGC CCC ATT CCA GAG CGA ATC CTG GGC AAG ATG
TTC TTT GCT TAC GTC CCG GGG TAA GGT CTC GCT TAG GAC CCG TTC TAC
Lys Lys Arg Met Gln Gly Pro Ile Pro Glu Arg Ile Leu Gly Lys Met>

730         740         750         760         770
  *           *           *           *           *
ACT GTG GCG ATT GTG AAA GCA CTG TAC TAT CTG AAG GAG AAG CAT GGC
TGA CAC CGC TAA CAC TTT CGT GAC ATG ATA GAC TTC CTC TTC GTA CCG
Thr Val Ala Ile Val Lys Ala Leu Tyr Tyr Leu Lys Glu Lys His Gly>

780         790         800         810         820
        *           *           *           *           *
GTC ATC CAT CGC GAT GTC AAA CCC TCC AAC ATC CTG CTA GAT GAG CGG
CAG TAG GTA GCG CTA CAG TTT GGG AGG TTG TAG GAC GAT CTA CTC GCC
Val Ile His Arg Asp Val Lys Pro Ser Asn Ile Leu Leu Asp Glu Arg>

830         840         850         860         870
        *           *           *           *           *
GGC CAG ATC AAG CTC TGT GAC TTT GGC ATC AGT GGC CGC CTT GTT GAC
CCG GTC TAG TTC GAG ACA CTG AAA CCG TAG TCA CCG GCG GAA CAA CTG
Gly Gln Ile Lys Leu Cys Asp Phe Gly Ile Ser Gly Arg Leu Val Asp>

880         890         900         910
        *           *           *           *
TCC AAA GCC AAA ACA CGG AGT GCT GGC TGT GCT GCC TAT ATG GCT CCC
AGG TTT CGG TTT TGT GCC TCA CGA CCG ACA CGA CGG ATA TAC CGA GGG
Ser Lys Ala Lys Thr Arg Ser Ala Gly Cys Ala Ala Tyr Met Ala Pro>

920         930         940         950         960
 *           *           *           *           *
GAG CGC ATC GAC CCT CCA GAT CCC ACC AAG CCT GAC TAT GAC ATC CGA
CTC GCG TAG CTG GGA GGT CTA GGG TGG TTC GGA CTG ATA CTG TAG GCT
```

FIG. 14B

MKK7d
Glu Arg Ile Asp Pro Pro Asp Pro Thr Lys Pro Asp Tyr Asp Ile Arg>

```
         970         980         990        1000        1010
          *           *           *           *           *       *
    GCT GAT GTG TGG AGC CTG GGC ATC TCA CTG GTG GAG CTG GCA ACA GGA
    CGA CTA CAC ACC TCG GAC CCG TAG AGT GAC CAC CTC GAC CGT TGT CCT
    Ala Asp Val Trp Ser Leu Gly Ile Ser Leu Val Glu Leu Ala Thr Gly>

1020        1030        1040        1050        1060
          *           *           *           *           *
    CAG TTC CCC TAT AAG AAC TGC AAG ACG GAC TTT GAG GTC CTC ACC AAA
    GTC AAG GGG ATA TTC TTG ACG TTC TGC CTG AAA CTC CAG GAG TGG TTT
    Gln Phe Pro Tyr Lys Asn Cys Lys Thr Asp Phe Glu Val Leu Thr Lys>

1070        1080        1090        1100        1110
             *           *           *           *           *       *
    GTC CTA CAG GAA GAG CCC CCA CTC CTG CCT GGT CAC ATG GGC TTC TCA
    CAG GAT GTC CTT CTC GGG GGT GAG GAC GGA CCA GTG TAC CCG AAG AGT
    Val Leu Gln Glu Glu Pro Pro Leu Leu Pro Gly His Met Gly Phe Ser>

1120        1130        1140        1150
               *           *           *           *           *
    GGG GAC TTC CAG TCA TTT GTC AAA GAC TGC CTT ACT AAA GAT CAC AGG
    CCC CTG AAG GTC AGT AAA CAG TTT CTG ACG GAA TGA TTT CTA GTG TCC
    Gly Asp Phe Gln Ser Phe Val Lys Asp Cys Leu Thr Lys Asp His Arg>

1160        1170        1180        1190        1200
     *           *           *           *           *       *
    AAG AGA CCA AAG TAT AAT AAG CTA CTT GAA CAC AGC TTC ATC ATC AAG
    TTC TCT GGT TTC ATA TTA TTC GAT GAA CTT GTG TCG AAG TAG TAG TTC
    Lys Arg Pro Lys Tyr Asn Lys Leu Leu Glu His Ser Phe Ile Ile Lys>

1210        1220        1230        1240        1250
     *           *           *           *           *       *
    CAC TAT GAG ATA CTC GAG GTG GAT GTC GCG TCC TGG TTT AAG GAT GTC
    GTG ATA CTC TAT GAG CTC CAC CTA CAG CGC AGG ACC AAA TTC CTA CAG
    His Tyr Glu Ile Leu Glu Val Asp Val Ala Ser Trp Phe Lys Asp Val>

1260        1270        1280        1290        1300
          *           *           *           *           *   *
    ATG GCG AAG ACC GAG TCC CCA AGG ACT AGT GGA GTC CTG AGT CAG CAC
    TAC CGC TTC TGG CTC AGG GGT TCC TGA TCA CCT CAG GAC TCA GTC GTG
    Met Ala Lys Thr Glu Ser Pro Arg Thr Ser Gly Val Leu Ser Gln His>

1310        1320        1330        1340        1350
             *           *           *           *           *       *
    CAT CTG CCC TTC TTC AGT GGG AGT CTG GAG GAG TCT CCC ACT TCC CCA
    GTA GAC GGG AAG AAG TCA CCC TCA GAC CTC CTC AGA GGG TGA AGG GGT
    His Leu Pro Phe Phe Ser Gly Ser Leu Glu Glu Ser Pro Thr Ser Pro>

1360        1370        1380        1390
                 *           *           *           *           *
        CCT TCT CCC AAG TCC TTC CCT CTG TCA CCA GCC ATC CCT CAG GCC CAG
```

FIG. 14C

MKK7d

```
GGA AGA GGG TTC AGG AAG GGA GAC AGT GGT CGG TAG GGA GTC CGG GTC
Pro Ser Pro Lys Ser Phe Pro Leu Ser Pro Ala Ile Pro Gln Ala Gln>
```

```
         1400       1410       1420       1430       1440       1450
           *          *          *          *          *          *
     GCA GAG TGG GTC TCG GGC AGG TAGGGACCTG GAGTGGCCTG GTCCCACCCT
     CGT CTC ACC CAG AGC CCG TCC ATCCCTGGAC CTCACCGGAC CAGGGTGGGA
     Ala Glu Trp Val Ser Gly Arg>  (SEQ ID NO: 30)
```

```
           1460       1470       1480       1490       1500       1510
             *          *          *          *          *          *
     CTGACCTCCT CCTCAGGCCA CCAGTGTTGC CCTCTTCCCT TTTTAAAACA AAATACCCTT
     GACTGGAGGA GGAGTCCGGT GGTCACAACG GGAGAAGGGA AAAATTTTGT TTTATGGGAA
```

```
           1520       1530       1540       1550       1560       1570
             *          *          *          *          *          *
     GTTTGTAAAT CCTTAGACGC TTGAGAATAA AACCCTTCCC TTTTCTTCCG AAAAAAAAAA
     CAAACATTTA GGAATCTGCG AACTCTTATT TTGGGAAGGG AAAAGAAGGC TTTTTTTTTT
             *
     AAAAAAAA   (SEQ ID NO: 29)
     TTTTTTTT
```

FIG. 14D

MKK7e
Sequence Range: 1 to 1598

```
          10         20         30         40         50         60
           *          *          *          *          *          *
     AGCGCAGGCG CAGTGCGGTG TTTGTCTACC CCGGACTGAC GGGTGGCCTG GCGGTGAGCG
     TCGCGTCCGC GTCACGCCAC AAACAGATGG GGCCTGACTG CCCACCGGAC CGCCACTCGC 70         80         90        100        110
                *          *          *          *          *
     GCGGCAGCGG CGGCGGGGAA G ATG GCG GCG TCC TCC CTG GAG CAG AAG CTG
     CGCCGTCGCC GCCGCCCCTT C TAC CGC CGC AGG AGG GAC CTC GTC TTC GAC
                              Met Ala Ala Ser Ser Leu Glu Gln Lys Leu>

120        130        140        150
                *          *          *          *          *
     TCC CGC CTG GAA GCC AAG CTG AAG CAG GAG AAC CGT GAG GCC CGC AGG
     AGG GCG GAC CTT CGG TTC GAC TTC GTC CTC TTG GCA CTC CGG GCG TCC
     Ser Arg Leu Glu Ala Lys Leu Lys Gln Glu Asn Arg Glu Ala Arg Arg>

160        170        180        190        200
         *          *          *          *          *          *
     AGG ATC GAC CTC AAC TTG GAT ATC AGC CCA CAG CGG CCC AGG CCC ACC
     TCC TAG CTG GAG TTG AAC CTA TAG TCG GGT GTC GCC GGG TCC GGG TGG
     Arg Ile Asp Leu Asn Leu Asp Ile Ser Pro Gln Arg Pro Arg Pro Thr>

210        220        230        240        250
         *          *          *          *          *          *
     CTG CAA CTC CCA CTG GCC AAC GAT GGG GGC AGC CGC TCA CCA TCC TCA
     GAC GTT GAG GGT GAC CGG TTG CTA CCC CCG TCG GCG AGT GGT AGG AGT
     Leu Gln Leu Pro Leu Ala Asn Asp Gly Gly Ser Arg Ser Pro Ser Ser>

260        270        280        290        300
             *          *          *          *          *
     GAG AGC TCC CCA CAG CAC CCT ACA CCC CCC ACC CGG CCC CGC CAC ATG
     CTC TCG AGG GGT GTC GTG GGA TGT GGG GGG TGG GCC GGG GCG GTG TAC
     Glu Ser Ser Pro Gln His Pro Thr Pro Pro Thr Arg Pro Arg His Met>

310        320        330        340        350
             *          *          *          *          *
     CTG GGG CTC CCA TCA ACC TTG TTC ACA CCG CGC AGT ATG GAG AGC ATC
     GAC CCC GAG GGT AGT TGG AAC AAG TGT GGC GCG TCA TAC CTC TCG TAG
     Leu Gly Leu Pro Ser Thr Leu Phe Thr Pro Arg Ser Met Glu Ser Ile>

360        370        380        390
                *          *          *          *          *
     GAG ATT GAC CAG AAG CTG CAG GAG ATC ATG AAG CAG ACA GGG TAC CTG
     CTC TAA CTG GTC TTC GAC GTC CTC TAG TAC TTC GTC TGT CCC ATG GAC
     Glu Ile Asp Gln Lys Leu Gln Glu Ile Met Lys Gln Thr Gly Tyr Leu>

400        410        420        430        440
         *          *          *          *          *          *
     ACT ATC GGG GGC CAG CGT TAT CAG GCA GAA ATC AAT GAC TTG GAG AAC
     TGA TAG CCC CCG GTC GCA ATA GTC CGT CTT TAG TTA CTG AAC CTC TTG
     Thr Ile Gly Gly Gln Arg Tyr Gln Ala Glu Ile Asn Asp Leu Glu Asn>
```

FIG. 15A

Mouse MKK7e

```
       450          460          470          480          490
        *            *            *            *            *
  *         *            *            *            *            *
TTG GGT GAG ATG GGC AGT GGT ACC TGT GGT CAG GTG TGG AAG ATG CGG
AAC CCA CTC TAC CCG TCA CCA TGG ACA CCA GTC CAC ACC TTC TAC GCC
Leu Gly Glu Met Gly Ser Gly Thr Cys Gly Gln Val Trp Lys Met Arg>

500          510          520          530          540
        *            *            *            *            *
  *         *            *            *            *            *
TTC CGG AAG ACA GGC CAC ATC ATT GCT GTT AAG CAA ATG CGG CGC TCT
AAG GCC TTC TGT CCG GTG TAG TAA CGA CAA TTC GTT TAC GCC GCG AGA
Phe Arg Lys Thr Gly His Ile Ile Ala Val Lys Gln Met Arg Arg Ser>

550          560          570          580          590
        *            *            *            *            *
  *         *            *            *            *            *
GGG AAC AAG GAA GAG AAT AAG CGC ATT TTG ATG GAC CTG GAT GTA GTA
CCC TTG TTC CTT CTC TTA TTC GCG TAA AAC TAC CTG GAC CTA CAT CAT
Gly Asn Lys Glu Glu Asn Lys Arg Ile Leu Met Asp Leu Asp Val Val>

600          610          620          630
               *            *            *            *
         *            *            *            *            *
CTC AAG AGC CAT GAC TGC CCT TAC ATC GTT CAG TGC TTT GGC ACC TTC
GAG TTC TCG GTA CTG ACG GGA ATG TAG CAA GTC ACG AAA CCG TGG AAG
Leu Lys Ser His Asp Cys Pro Tyr Ile Val Gln Cys Phe Gly Thr Phe>

640          650          660          670          680
  *            *            *            *            *
       *            *            *            *            *
ATC ACC AAC ACA GAC GTC TTT ATT GCC ATG GAG CTC ATG GGC ACA TGT
TAG TGG TTG TGT CTG CAG AAA TAA CGG TAC CTC GAG TAC CCG TGT ACA
Ile Thr Asn Thr Asp Val Phe Ile Ala Met Glu Leu Met Gly Thr Cys>

690          700          710          720          730
  *            *            *            *            *
       *            *            *            *            *
GCA GAG AAG CTG AAG AAA CGA ATG CAG GGC CCC ATT CCA GAG CGA ATC
CGT CTC TTC GAC TTC TTT GCT TAC GTC CCG GGG TAA GGT CTC GCT TAG
Ala Glu Lys Leu Lys Lys Arg Met Gln Gly Pro Ile Pro Glu Arg Ile>

740          750          760          770          780
        *            *            *            *            *
  *         *            *            *            *            *
CTG GGC AAG ATG ACT GTG GCG ATT GTG AAA GCA CTG TAC TAT CTG AAG
GAC CCG TTC TAC TGA CAC CGC TAA CAC TTT CGT GAC ATG ATA GAC TTC
Leu Gly Lys Met Thr Val Ala Ile Val Lys Ala Leu Tyr Tyr Leu Lys>

790          800          810          820          830
        *            *            *            *            *
  *         *            *            *            *            *
GAG AAG CAT GGC GTC ATC CAT CGC GAT GTC AAA CCC TCC AAC ATC CTG
CTC TTC GTA CCG CAG TAG GTA GCG CTA CAG TTT GGG AGG TTG TAG GAC
Glu Lys His Gly Val Ile His Arg Asp Val Lys Pro Ser Asn Ile Leu>

840          850          860          870
               *            *            *            *
         *            *            *            *            *
CTA GAT GAG CGG GGC CAG ATC AAG CTC TGT GAC TTT GGC ATC AGT GGC
GAT CTA CTC GCC CCG GTC TAG TTC GAG ACA CTG AAA CCG TAG TCA CCG
Leu Asp Glu Arg Gly Gln Ile Lys Leu Cys Asp Phe Gly Ile Ser Gly>
```

FIG. 15B

Mouse MKK7e

```
      880            890            900            910            920
       *       *      *       *      *       *      *       *      *       *
      CGC CTT GTT GAC TCC AAA GCC AAA ACA CGG AGT GCT GGC TGT GCT GCC
      GCG GAA CAA CTG AGG TTT CGG TTT TGT GCC TCA CGA CCG ACA CGA CGG
      Arg Leu Val Asp Ser Lys Ala Lys Thr Arg Ser Ala Gly Cys Ala Ala>

930            940            950            960            970
       *       *      *       *      *       *      *       *      *       *
      TAT ATG GCT CCC GAG CGC ATC GAC CCT CCA GAT CCC ACC AAG CCT GAC
      ATA TAC CGA GGG CTC GCG TAG CTG GGA GGT CTA GGG TGG TTC GGA CTG
      Tyr Met Ala Pro Glu Arg Ile Asp Pro Pro Asp Pro Thr Lys Pro Asp>

980            990           1000           1010           1020
         *       *      *       *      *       *      *       *      *       *
      TAT GAC ATC CGA GCT GAT GTG TGG AGC CTG GGC ATC TCA CTG GTG GAG
      ATA CTG TAG GCT CGA CTA CAC ACC TCG GAC CCG TAG AGT GAC CAC CTC
      Tyr Asp Ile Arg Ala Asp Val Trp Ser Leu Gly Ile Ser Leu Val Glu>

1030           1040           1050           1060           1070
          *       *      *       *      *       *      *       *      *       *
      CTG GCA ACA GGA CAG TTC CCC TAT AAG AAC TGC AAG ACG GAC TTT GAG
      GAC CGT TGT CCT GTC AAG GGG ATA TTC TTG ACG TTC TGC CTG AAA CTC
      Leu Ala Thr Gly Gln Phe Pro Tyr Lys Asn Cys Lys Thr Asp Phe Glu>

1080           1090           1100           1110
              *       *      *       *      *       *      *       *      *
             GTC CTC ACC AAA GTC CTA CAG GAA GAG CCC CCA CTC CTG CCT GGT CAC
             CAG GAG TGG TTT CAG GAT GTC CTT CTC GGG GGT GAG GAC GGA CCA GTG
             Val Leu Thr Lys Val Leu Gln Glu Glu Pro Pro Leu Leu Pro Gly His>

1120           1130           1140           1150           1160
      *       *      *       *      *       *      *       *      *       *
     ATG GGC TTC TCA GGG GAC TTC CAG TCA TTT GTC AAA GAC TGC CTT ACT
     TAC CCG AAG AGT CCC CTG AAG GTC AGT AAA CAG TTT CTG ACG GAA TGA
     Met Gly Phe Ser Gly Asp Phe Gln Ser Phe Val Lys Asp Cys Leu Thr>

1170           1180           1190           1200           1210
          *       *      *       *      *       *      *       *      *       *
         AAA GAT CAC AGG AAG AGA CCA AAG TAT AAT AAG CTA CTT GAA CAC AGC
         TTT CTA GTG TCC TTC TCT GGT TTC ATA TTA TTC GAT GAA CTT GTG TCG
         Lys Asp His Arg Lys Arg Pro Lys Tyr Asn Lys Leu Leu Glu His Ser>

1220           1230           1240           1250           1260
             *       *      *       *      *       *      *       *      *       *
            TTC ATC ATC AAG CAC TAT GAG ATA CTC GAG GTG GAT GTC GCG TCC TGG
            AAG TAG TAG TTC GTG ATA CTC TAT GAG CTC CAC CTA CAG CGC AGG ACC
            Phe Ile Ile Lys His Tyr Glu Ile Leu Glu Val Asp Val Ala Ser Trp>

1270           1280           1290           1300           1310
                 *       *      *       *      *       *      *       *      *       *
                TTT AAG GAT GTC ATG GCG AAG ACC GAG TCC CCA AGG ACT AGT GGA GTC
                AAA TTC CTA CAG TAC CGC TTC TGG CTC AGG GGT TCC TGA TCA CCT CAG
```

FIG. 15C

Mouse MKK7e

```
    Phe Lys Asp Val Met Ala Lys Thr Glu Ser Pro Arg Thr Ser Gly Val>

1320          1330          1340          1350
             *             *             *             *         *
    CTG AGT CAG CAC CAT CTG CCC TTC TTC AGT GGG AGT CTG GAG GAG TCT
    GAC TCA GTC GTG GTA GAC GGG AAG AAG TCA CCC TCA GAC CTC CTC AGA
    Leu Ser Gln His His Leu Pro Phe Phe Ser Gly Ser Leu Glu Glu Ser>

1360          1370          1380          1390          1400
    *             *             *             *             *         *
    CCC ACT TCC CCA CCT TCT CCC AAG TCC TTC CCT CTG TCA CCA GCC ATC
    GGG TGA AGG GGT GGA AGA GGG TTC AGG AAG GGA GAC AGT GGT CGG TAG
    Pro Thr Ser Pro Pro Ser Pro Lys Ser Phe Pro Leu Ser Pro Ala Ile>

1410          1420          1430          1440          1450          1460
       *             *             *             *             *             *
    CCT CAG GCC CAG GCA GAG TGG GTC TCG GGC AGG TAGGGACCTG GAGTGGCCTG
    GGA GTC CGG GTC CGT CTC ACC CAG AGC CCG TCC ATCCTGGAC CTCACCGGAC
    Pro Gln Ala Gln Ala Glu Trp Val Ser Gly Arg> (SEQ ID NO: 32)

1470       1480       1490       1500       1510       1520
             *          *          *          *          *          *
    GTCCCACCCT CTGACCTCCT CCTCAGGCCA CCAGTGTTGC CCTCTTCCCT TTTTAAAACA
    CAGGGTGGGA GACTGGAGGA GGAGTCCGGT GGTCACAACG GGAGAAGGGA AAAATTTTGT 1530       1540       1550       1560       1570       1580
             *          *          *          *          *          *
    AAATACCCTT GTTTGTAAAT CCTTAGACGC TTGAGAATAA AACCCTTCCC TTTTCTTCCG
    TTTATGGGAA CAAACATTTA GGAATCTGCG AACTCTTATT TTGGGAAGGG AAAAGAAGGC

1590
             *          *
    AAAAAAAAAA AAAAAAAA (SEQ ID NO: 31)
    TTTTTTTTTT TTTTTTTT
```

FIG. 15D

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 2030 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: Coding Sequence
      (B) LOCATION: 338...1291

(xi) SEQUENCE DESCRIPTION: SEQ ID NO:1:

```
TGGCTGGCAA TGGCCTTGCT GACCTCGAGC CGGGCCCACG TGGGGACCTT TGGAGCACAG      60

CCTACGATCC TGGTGCAAGG CCGGTGGATG CAGAGGCCAG TCCATATACC ACCCAGGCCT     120

GCGAGGAGCG TGGTCCCCAC CCATCCAGCC CATATGTGCA AGTGCCCTTG ACAGAGAGGC     180

TGGTCATATC CATGGTGACC ATTTATGGGC CACAACAGGT CCCCATCTGC GCAGTGAACC     240

CTGTGCTGAG CACCTTGCAG ACGTGATCTT GCTTCGTCCT GCAGCACTGT GCGGGGCAGG     300

AAAATCCAAG AGGAAGAAGG ATCTACGGAT ATCCTGC ATG TCC AAG CCA CCC GCA      355
                                    Met Ser Lys Pro Pro Ala
                                      1               5

CCC AAC CCC ACA CCC CCC CGG AAC CTG GAC TCC CGG ACC TTC ATC ACC       403
Pro Asn Pro Thr Pro Pro Arg Asn Leu Asp Ser Arg Thr Phe Ile Thr
         10                  15                  20

ATT GGA GAC AGA AAC TTT GAG GTG GAG GCT GAT GAC TTG GTG ACC ATC       451
Ile Gly Asp Arg Asn Phe Glu Val Glu Ala Asp Asp Leu Val Thr Ile
             25                  30                  35

TCA GAA CTG GGC CGT GGA GCC TAT GGG GTG GTA GAG AAG GTG CGG CAC       499
Ser Glu Leu Gly Arg Gly Ala Tyr Gly Val Val Glu Lys Val Arg His
     40                  45                  50

GCC CAG AGC GGC ACC ATC ATG GCC GTG AAG CGG ATC CGG GCC ACC GTG       547
Ala Gln Ser Gly Thr Ile Met Ala Val Lys Arg Ile Arg Ala Thr Val
 55                  60                  65                  70
```

```
AAC TCA CAG GAG CAG AAG CGG CTG CTC ATG GAC CTG GAC ATC AAC ATG      595
Asn Ser Gln Glu Gln Lys Arg Leu Leu Met Asp Leu Asp Ile Asn Met
                75                  80                  85

CGC ACG GTC GAC TGT TTC TAC ACT GTC ACC TTC TAC GGG GCA CTA TTC      643
Arg Thr Val Asp Cys Phe Tyr Thr Val Thr Phe Tyr Gly Ala Leu Phe
                90                  95                 100

AGA GAG GGA GAC GTG TGG ATC TGC ATG GAG CTC ATG GAC ACA TCC TTG      691
Arg Glu Gly Asp Val Trp Ile Cys Met Glu Leu Met Asp Thr Ser Leu
            105                 110                 115

GAC AAG TTC TAC CGG AAG GTG CTG GAT AAA AAC ATG ACA ATT CCA GAG      739
Asp Lys Phe Tyr Arg Lys Val Leu Asp Lys Asn Met Thr Ile Pro Glu
        120                 125                 130

GAC ATC CTT GGG GAG ATT GCT GTG TCT ATC GTG CGG GCC CTG GAG CAT      787
Asp Ile Leu Gly Glu Ile Ala Val Ser Ile Val Arg Ala Leu Glu His
135                 140                 145                 150

CTG CAC AGC AAG CTG TCG GTG ATC CAC AGA GAT GTG AAG CCC TCC AAT      835
Leu His Ser Lys Leu Ser Val Ile His Arg Asp Val Lys Pro Ser Asn
                155                 160                 165

GTC CTT ATC AAC AAG GAG GGC CAT GTG AAG ATG TGT GAC TTT GGC ATC      883
Val Leu Ile Asn Lys Glu Gly His Val Lys Met Cys Asp Phe Gly Ile
            170                 175                 180

AGT GGC TAC TTG GTG GAC TCT GTG GCC AAG ACG ATG GAT GCC GGC TGC      931
Ser Gly Tyr Leu Val Asp Ser Val Ala Lys Thr Met Asp Ala Gly Cys
        185                 190                 195

AAG CCC TAC ATG GCC CCT GAG AGG ATC AAC CCA GAG CTG AAC CAG AAG      979
Lys Pro Tyr Met Ala Pro Glu Arg Ile Asn Pro Glu Leu Asn Gln Lys
    200                 205                 210

GGC TAC AAT GTC AAG TCC GAC GTC TGG AGC CTG GGC ATC ACC ATG ATT     1027
Gly Tyr Asn Val Lys Ser Asp Val Trp Ser Leu Gly Ile Thr Met Ile
215                 220                 225                 230

GAG ATG GCC ATC CTG CGG TTC CCT TAC GAG TCC TGG GGG ACC CCG TTC     1075
Glu Met Ala Ile Leu Arg Phe Pro Tyr Glu Ser Trp Gly Thr Pro Phe
                235                 240                 245

CAG CAG CTG AAG CAG GTG GTG GAG GAG CCG TCC CCC CAG CTC CCA GCC     1123
Gln Gln Leu Lys Gln Val Val Glu Glu Pro Ser Pro Gln Leu Pro Ala
            250                 255                 260

GAC CGT TTC TCC CCC GAG TTT GTG GAC TTC ACT GCT CAG TGC CTG AGG     1171
Asp Arg Phe Ser Pro Glu Phe Val Asp Phe Thr Ala Gln Cys Leu Arg
        265                 270                 275

AAG AAC CCC GCA GAG CGT ATG AGC TAC CTG GAG CTG ATG GAG CAC CCC     1219
Lys Asn Pro Ala Glu Arg Met Ser Tyr Leu Glu Leu Met Glu His Pro
    280                 285                 290

TTC TTC ACC TTG CAC AAA ACC AAG AAG ACG GAC ATT GCT GCC TTC GTG     1267
Phe Phe Thr Leu His Lys Thr Lys Lys Thr Asp Ile Ala Ala Phe Val
295                 300                 305                 310

AAG AAG ATC CTG GGA GAA GAC TCA TAGGGGCTGG GCCTCGGACC CCACTCCGGC    1321
Lys Lys Ile Leu Gly Glu Asp Ser
                315

CCTCCAGAGC CCCACAGCCC CATCTGCGGG GGCAGTGCTC ACCCACACCA TAAGCTACTG   1381

CCATCCTGGC CCAGGGCATC TGGGAGGAAC CGAGGGGGCT GCTCCCACCT GGCTCTGTGG   1441

CGAGCCATTT GTCCCAAGTG CCAAAGAAGC AGACCATTGG GGCTCCCAGC CAGGCCCTTG   1501

TCGGCCCCAC CAGTGCCTCT CCCTGCTGCT CCTAGGACCC GTCTCCAGCT GCTGAGATCC   1561

TGGACTGAGG GGGCCTGGAT GCCCCCTGTG GATGCTGCTG CCCCTGCACA GCAGGCTGCC   1621

AGTGCCTGGG TGGATGGGCC ACCGCCTTGC CCAGCCTGGA TGCCATCCAA GTTGTATATT   1681

TTTTTAATCT CTCGACTGAA TGGACTTTGC ACACTTTGGC CCAGGGTGGC CACACCTCTA   1741
```

```
TCCCGGCTTT GGTGCGGGGT ACACAAGAGG GGATGAGTTG TGTGAATACC CCAAGACTCC    1801

CATGAGGGAG ATGCCATGAG CCGCCCAAGG CCTTCCCCTG GCACTGGCAA ACAGGGCCTC    1861

TGCGGAGCAC ACTGGCTCAC CCAGTCCTGC CCGCCACCGT TATCGGTGTC ATTCACCTTT    1921

CGTGTTTTTT TTAATTTATC CTCTGTTGAT TTTTTCTTTT GCTTTATGGG TTTGGCTTGT    1981

TTTTCTTGCA TGGTTTGGAG CTGATCGCTT CTCCCCCACC CCCTAGGGG               2030
```

(2) INFORMATION FOR SEQ ID NO:2:

(i) SEQUENCE CHARACTERISTICS:
        (A) LENGTH: 318 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

```
Met Ser Lys Pro Pro Ala Pro Asn Pro Thr Pro Pro Arg Asn Leu Asp
  1               5                  10                  15

Ser Arg Thr Phe Ile Thr Ile Gly Asp Arg Asn Phe Glu Val Glu Ala
                 20                  25                  30

Asp Asp Leu Val Thr Ile Ser Glu Leu Gly Arg Gly Ala Tyr Gly Val
             35                  40                  45

Val Glu Lys Val Arg His Ala Gln Ser Gly Thr Ile Met Ala Val Lys
         50                  55                  60

Arg Ile Arg Ala Thr Val Asn Ser Gln Glu Gln Lys Arg Leu Leu Met
 65                  70                  75                  80

Asp Leu Asp Ile Asn Met Arg Thr Val Asp Cys Phe Tyr Thr Val Thr
                 85                  90                  95

Phe Tyr Gly Ala Leu Phe Arg Glu Gly Asp Val Trp Ile Cys Met Glu
                100                 105                 110

Leu Met Asp Thr Ser Leu Asp Lys Phe Tyr Arg Lys Val Leu Asp Lys
            115                 120                 125

Asn Met Thr Ile Pro Glu Asp Ile Leu Gly Glu Ile Ala Val Ser Ile
130                 135                 140

Val Arg Ala Leu Glu His Leu His Ser Lys Leu Ser Val Ile His Arg
145                 150                 155                 160

Asp Val Lys Pro Ser Asn Val Leu Ile Asn Lys Glu Gly His Val Lys
                165                 170                 175

Met Cys Asp Phe Gly Ile Ser Gly Tyr Leu Val Asp Ser Val Ala Lys
            180                 185                 190

Thr Met Asp Ala Gly Cys Lys Pro Tyr Met Ala Pro Glu Arg Ile Asn
        195                 200                 205

Pro Glu Leu Asn Gln Lys Gly Tyr Asn Val Lys Ser Asp Val Trp Ser
    210                 215                 220

Leu Gly Ile Thr Met Ile Glu Met Ala Ile Leu Arg Phe Pro Tyr Glu
225                 230                 235                 240

Ser Trp Gly Thr Pro Phe Gln Gln Leu Lys Gln Val Val Glu Glu Pro
                245                 250                 255

Ser Pro Gln Leu Pro Ala Asp Arg Phe Ser Pro Glu Phe Val Asp Phe
            260                 265                 270

Thr Ala Gln Cys Leu Arg Lys Asn Pro Ala Glu Arg Met Ser Tyr Leu
        275                 280                 285

Glu Leu Met Glu His Pro Phe Phe Thr Leu His Lys Thr Lys Lys Thr
```

```
                    290                 295                 300
Asp Ile Ala Ala Phe Val Lys Lys Ile Leu Gly Glu Asp Ser
305                 310                 315
```

(2) INFORMATION FOR SEQ ID NO:3:

(i) SEQUENCE CHARACTERISTICS:
        (A) LENGTH: 1602 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 244...1245

(xi) SEQUENCE DESCRIPTION: SEQ ID NO:3:

```
TAGCTGCAGC ACAGCCTTCC CTAACGTTGC AACTGGGGGA AAAATCACTT TCCAGTCTGT        60

TTTGCAAGGT GTGCATTTCC ATCTTGATTC CCTGAAAGTC CATCTGCTGC ATCGGTCAAG       120

AGAAACTCCA CTTGCATGAA GATTGCACGC CTGCAGCTTG CATCTTTGTT GCAAAACTAG       180

CTACAGAAGA GAAGCAAGGC AAAGTCTTTT GTGCTCCCCT CCCCCATCAA AGGAAAGGGG       240

AAA ATG TCT CAG TCG AAA GGC AAG AAG CGA AAC CCT GGC CTT AAA ATT        288
    Met Ser Gln Ser Lys Gly Lys Lys Arg Asn Pro Gly Leu Lys Ile
    1               5                   10                  15

CCA AAA GAA GCA TTT GAA CAA CCT CAG ACC AGT TCC ACA CCA CCT AGA        336
Pro Lys Glu Ala Phe Glu Gln Pro Gln Thr Ser Ser Thr Pro Pro Arg
                20                  25                  30

GAT TTA GAC TCC AAG GCT TGC ATT TCT ATT GGA AAT CAG AAC TTT GAG        384
Asp Leu Asp Ser Lys Ala Cys Ile Ser Ile Gly Asn Gln Asn Phe Glu
            35                  40                  45

GTG AAG GCA GAT GAC CTG GAG CCT ATA ATG GAA CTG GGA CGA GGT GCG        432
Val Lys Ala Asp Asp Leu Glu Pro Ile Met Glu Leu Gly Arg Gly Ala
        50                  55                  60

TAC GGG GTG GTG GAG AAG ATG CGG CAC GTG CCC AGC GGG CAG ATC ATG        480
Tyr Gly Val Val Glu Lys Met Arg His Val Pro Ser Gly Gln Ile Met
    65                  70                  75

GCA GTG AAG CGG ATC CGA GCC ACA GTA AAT AGC CAG GAA CAG AAA CGG        528
Ala Val Lys Arg Ile Arg Ala Thr Val Asn Ser Gln Glu Gln Lys Arg
80                  85                  90                  95

CTA CTG ATG GAT TTG GAT ATT TCC ATG AGG ACG GTG GAC TGT CCA TTC        576
Leu Leu Met Asp Leu Asp Ile Ser Met Arg Thr Val Asp Cys Pro Phe
                100                 105                 110

ACT GTC ACC TTT TAT GGC GCA CTG TTT CGG GAG GGT GAT GTG TGG ATC        624
Thr Val Thr Phe Tyr Gly Ala Leu Phe Arg Glu Gly Asp Val Trp Ile
            115                 120                 125

TGC ATG GAG CTC ATG GAT ACA TCA CTA GAT AAA TTC TAC AAA CAA GTT        672
Cys Met Glu Leu Met Asp Thr Ser Leu Asp Lys Phe Tyr Lys Gln Val
        130                 135                 140

ATT GAT AAA GGC CAG ACA ATT CCA GAG GAC ATC TTA GGG AAA ATA GCA        720
Ile Asp Lys Gly Gln Thr Ile Pro Glu Asp Ile Leu Gly Lys Ile Ala
    145                 150                 155

GTT TCT ATT GTA AAA GCA TTA GAA CAT TTA CAT AGT AAG CTG TCT GTC        768
Val Ser Ile Val Lys Ala Leu Glu His Leu His Ser Lys Leu Ser Val
160                 165                 170                 175

ATT CAC AGA GAC GTC AAG CCT TCT AAT GTA CTC ATC AAT GCT CTC GGT        816
Ile His Arg Asp Val Lys Pro Ser Asn Val Leu Ile Asn Ala Leu Gly
                180                 185                 190

CAA GTG AAG ATG TGC GAT TTT GGA ATC AGT GGC TAC TTG GTG GAC TCT        864
```

-continued

```
Gln Val Lys Met Cys Asp Phe Gly Ile Ser Gly Tyr Leu Val Asp Ser
            195                 200                 205

GTT GCT AAA ACA ATT GAT GCA GGT TGC AAA CCA TAC ATG GCC CCT GAA          912
Val Ala Lys Thr Ile Asp Ala Gly Cys Lys Pro Tyr Met Ala Pro Glu
        210                 215                 220

AGA ATA AAC CCA GAG CTC AAC CAG AAG GGA TAC AGT GTG AAG TCT GAC          960
Arg Ile Asn Pro Glu Leu Asn Gln Lys Gly Tyr Ser Val Lys Ser Asp
225                 230                 235

ATT TGG AGT CTG GGC ATC ACG ATG ATT GAG TTG GCC ATC CTT CGA TTT         1008
Ile Trp Ser Leu Gly Ile Thr Met Ile Glu Leu Ala Ile Leu Arg Phe
240                 245                 250                 255

CCC TAT GAT TCA TGG GGA ACT CCA TTT CAG CAG CTC AAA CAG GTG GTA         1056
Pro Tyr Asp Ser Trp Gly Thr Pro Phe Gln Gln Leu Lys Gln Val Val
            260                 265                 270

GAG GAG CCA TCG CCA CAA CTC CCA GCA GAC AAG TTC TCT GCA GAG TTT         1104
Glu Glu Pro Ser Pro Gln Leu Pro Ala Asp Lys Phe Ser Ala Glu Phe
        275                 280                 285

GTT GAC TTT ACC TCA CAG TGC TTA AAG AAG AAT TCC AAA GAA CGG CCT         1152
Val Asp Phe Thr Ser Gln Cys Leu Lys Lys Asn Ser Lys Glu Arg Pro
    290                 295                 300

ACA TAC CCA GAG CTA ATG CAA CAT CCA TTT TTC ACC CTA CAT GAA TCC         1200
Thr Tyr Pro Glu Leu Met Gln His Pro Phe Phe Thr Leu His Glu Ser
305                 310                 315

AAA GGA ACA GAT GTG GCA TCT TTT GTA AAA CTG ATT CTT GGA GAC TAAAA       1250
Lys Gly Thr Asp Val Ala Ser Phe Val Lys Leu Ile Leu Gly Asp
320                 325                 330

AGCAGTGGAC TTAATCGGTT GACCCTACTG TGGATTGGTG GGTTTCGGGG TGAAGCAAGT       1310

TCACTACAGC ATCAATAGAA AGTCATCTTT GAGATAATTT AACCCTGCCT CTCAGAGGGT       1370

TTTCTCTCCC AATTTTCTTT TTACTCCCCC TCTTAAGGGG GCCTTGGAAT CTATAGTATA       1430

GAATGAACTG TCTAGATGGA TGAATTATGA TAAAGGCTTA GGACTTCAAA AGGTGATTAA       1490

ATATTTAATG ATGTGTCATA TGAGTCCTCA AAAAAAAAAA AAAAAAAAAA AAAAAAAAAA       1550

AAAAAAAAAA AAAAAAAAAA AAAAAAAAAA AAAAAAAAAA AAAAAAAAAA AA              1602

(2) INFORMATION FOR SEQ ID NO:4:

(i) SEQUENCE CHARACTERISTICS:
        (A) LENGTH: 334 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

Met Ser Gln Ser Lys Gly Lys Lys Arg Asn Pro Gly Leu Lys Ile Pro
1               5                   10                  15

Lys Glu Ala Phe Glu Gln Pro Gln Thr Ser Ser Thr Pro Pro Arg Asp
            20                  25                  30

Leu Asp Ser Lys Ala Cys Ile Ser Ile Gly Asn Gln Asn Phe Glu Val
        35                  40                  45

Lys Ala Asp Asp Leu Glu Pro Ile Met Glu Leu Gly Arg Gly Ala Tyr
    50                  55                  60

Gly Val Val Glu Lys Met Arg His Val Pro Ser Gly Gln Ile Met Ala
65                  70                  75                  80

Val Lys Arg Ile Arg Ala Thr Val Asn Ser Gln Glu Gln Lys Arg Leu
                85                  90                  95
```

```
Leu Met Asp Leu Asp Ile Ser Met Arg Thr Val Asp Cys Pro Phe Thr
            100                 105                 110
Val Thr Phe Tyr Gly Ala Leu Phe Arg Glu Gly Asp Val Trp Ile Cys
        115                 120                 125
Met Glu Leu Met Asp Thr Ser Leu Asp Lys Phe Tyr Lys Gln Val Ile
    130                 135                 140
Asp Lys Gly Gln Thr Ile Pro Glu Asp Ile Leu Gly Lys Ile Ala Val
145                 150                 155                 160
Ser Ile Val Lys Ala Leu Glu His Leu His Ser Lys Leu Ser Val Ile
                165                 170                 175
His Arg Asp Val Lys Pro Ser Asn Val Leu Ile Asn Ala Leu Gly Gln
            180                 185                 190
Val Lys Met Cys Asp Phe Gly Ile Ser Gly Tyr Leu Val Asp Ser Val
        195                 200                 205
Ala Lys Thr Ile Asp Ala Gly Cys Lys Pro Tyr Met Ala Pro Glu Arg
    210                 215                 220
Ile Asn Pro Glu Leu Asn Gln Lys Gly Tyr Ser Val Lys Ser Asp Ile
225                 230                 235                 240
Trp Ser Leu Gly Ile Thr Met Ile Glu Leu Ala Ile Leu Arg Phe Pro
                245                 250                 255
Tyr Asp Ser Trp Gly Thr Pro Phe Gln Gln Leu Lys Gln Val Val Glu
            260                 265                 270
Glu Pro Ser Pro Gln Leu Pro Ala Asp Lys Phe Ser Ala Glu Phe Val
        275                 280                 285
Asp Phe Thr Ser Gln Cys Leu Lys Lys Asn Ser Lys Glu Arg Pro Thr
    290                 295                 300
Tyr Pro Glu Leu Met Gln His Pro Phe Phe Thr Leu His Glu Ser Lys
305                 310                 315                 320
Gly Thr Asp Val Ala Ser Phe Val Lys Leu Ile Leu Gly Asp
                325                 330
```

(2) INFORMATION FOR SEQ ID NO:5:

(i) SEQUENCE CHARACTERISTICS:
        (A) LENGTH: 3498 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 40...1128

(xi) SEQUENCE DESCRIPTION: SEQ ID NO:5:

```
CTAGGGTCCC CGGCGCCAGG CCACCCGGCC GTCAGCAGC ATG CAG GGT AAA CGC      54
                                          Met Gln Gly Lys Arg
                                            1               5

AAA GCA CTG AAG TTG AAT TTT GCA AAT CCA CCT TTC AAA TCT ACA GCA    102
Lys Ala Leu Lys Leu Asn Phe Ala Asn Pro Pro Phe Lys Ser Thr Ala
            10                  15                  20

AGG TTT ACT CTG AAT CCC AAT CCT ACA GGA GTT CAA AAC CCA CAC ATA    150
Arg Phe Thr Leu Asn Pro Asn Pro Thr Gly Val Gln Asn Pro His Ile
        25                  30                  35

GAG AGA CTG AGA ACA CAC AGC ATT GAG TCA TCA GGA AAA CTG AAG ATC    198
Glu Arg Leu Arg Thr His Ser Ile Glu Ser Ser Gly Lys Leu Lys Ile
    40                  45                  50

TCC CCT GAA CAA CAC TGG GAT TTC ACT GCA GAG GAC TTG AAA GAC CTT    246
```

```
Ser Pro Glu Gln His Trp Asp Phe Thr Ala Glu Asp Leu Lys Asp Leu
    55                  60                  65

GGA GAA ATT GGA CGA GGA GCT TAT GGT TCT GTC AAC AAA ATG GTC CAC      294
Gly Glu Ile Gly Arg Gly Ala Tyr Gly Ser Val Asn Lys Met Val His
 70                  75                  80                  85

AAA CCA AGT GGG CAA ATA ATG GCA GTT AAA AGA ATT CGG TCA ACA GTG      342
Lys Pro Ser Gly Gln Ile Met Ala Val Lys Arg Ile Arg Ser Thr Val
                 90                  95                 100

GAT GAA AAA GAA CAA AAA CAA CTT CTT ATG GAT TTG GAT GTA GTA ATG      390
Asp Glu Lys Glu Gln Lys Gln Leu Leu Met Asp Leu Asp Val Val Met
                105                 110                 115

CGG AGT AGT GAT TGC CCA TAC ATT GTT CAG TTT TAT GGT GCA CTC TTC      438
Arg Ser Ser Asp Cys Pro Tyr Ile Val Gln Phe Tyr Gly Ala Leu Phe
            120                 125                 130

AGA GAG GGT GAC TGT TGG ATC TGT ATG GAA CTC ATG TCT ACC TCG TTT      486
Arg Glu Gly Asp Cys Trp Ile Cys Met Glu Leu Met Ser Thr Ser Phe
135                 140                 145

GAT AAG TTT TAC AAA TAT GTA TAT AGT GTA TTA GAT GAT GTT ATT CCA      534
Asp Lys Phe Tyr Lys Tyr Val Tyr Ser Val Leu Asp Asp Val Ile Pro
150                 155                 160                 165

GAA GAA ATT TTA GGC AAA ATC ACT TTA GCA ACT GTG AAA GCA CTA AAC      582
Glu Glu Ile Leu Gly Lys Ile Thr Leu Ala Thr Val Lys Ala Leu Asn
            170                 175                 180

CAC TTA AAA GAA AAC TTG AAA ATT ATT CAC AGA GAT ATC AAA CCT TCC      630
His Leu Lys Glu Asn Leu Lys Ile Ile His Arg Asp Ile Lys Pro Ser
                185                 190                 195

AAT ATT CTT CTG GAC AGA AGT GGA AAT ATT AAG CTC TGT GAC TTC GGC      678
Asn Ile Leu Leu Asp Arg Ser Gly Asn Ile Lys Leu Cys Asp Phe Gly
                200                 205                 210

ATC AGT GGA CAG CTT GTG GAC TCT ATT GCC AAG ACA AGA GAT GCT GGC      726
Ile Ser Gly Gln Leu Val Asp Ser Ile Ala Lys Thr Arg Asp Ala Gly
        215                 220                 225

TGT AGG CCA TAC ATG GCA CCT GAA AGA ATA GAC CCA AGC GCA TCA CGA      774
Cys Arg Pro Tyr Met Ala Pro Glu Arg Ile Asp Pro Ser Ala Ser Arg
230                 235                 240                 245

CAA GGA TAT GAT GTC CGC TCT GAT GTC TGG AGT TTG GGG ATC ACA TTG      822
Gln Gly Tyr Asp Val Arg Ser Asp Val Trp Ser Leu Gly Ile Thr Leu
            250                 255                 260

TAT GAG TTG GCC ACA GGC CGA TTT CCT TAT CCA AAG TGG AAT AGT GTA      870
Tyr Glu Leu Ala Thr Gly Arg Phe Pro Tyr Pro Lys Trp Asn Ser Val
            265                 270                 275

TTT GAT CAA CTA ACA CAA GTC GTG AAA GGA GAT CCT CCG CAG CTG AGT      918
Phe Asp Gln Leu Thr Gln Val Val Lys Gly Asp Pro Pro Gln Leu Ser
            280                 285                 290

AAT TCT GAG GAA AGG GAA TTC TCC CCG AGT TTC ATC AAC TTT GTC AAC      966
Asn Ser Glu Glu Arg Glu Phe Ser Pro Ser Phe Ile Asn Phe Val Asn
295                 300                 305

TTG TGC CTT ACG AAG GAT GAA TCC AAA AGG CCA AAG TAT AAA GAG CTT     1014
Leu Cys Leu Thr Lys Asp Glu Ser Lys Arg Pro Lys Tyr Lys Glu Leu
310                 315                 320                 325

CTG AAA CAT CCC TTT ATT TTG ATG TAT GAA GAA CGT GCC GTT GAG GTC     1062
Leu Lys His Pro Phe Ile Leu Met Tyr Glu Glu Arg Ala Val Glu Val
                330                 335                 340

GCA TGC TAT GTT TGT AAA ATC CTG GAT CAA ATG CCA GCT ACT CCC AGC     1110
Ala Cys Tyr Val Cys Lys Ile Leu Asp Gln Met Pro Ala Thr Pro Ser
            345                 350                 355

TCT CCC ATG TAT GTC GAT TGATATCGYT GCTACATCAG ACTCTAGAAA AAAGGGCT   1166
Ser Pro Met Tyr Val Asp
                360
```

-continued

```
GAGAGGAAGC AAGACGTAAA GAATTTTCAT CCCGTATCAC AGTGTTTTTA TTGCTCGCCC      1226

AGACACCATG TGCAATAAGA TTGGTGTTCG TTTCCATCAT GTCTGTATAC TCCTGTCACC      1286

TAGAACGTGC ATCCTTGTAA TACCTGATTG ATCACACAGT GTTAGTGCTG GTCAGAGAGA      1346

CCTCATCCTG CTCTTTTGTG ATGAACATAT TCATGAAATG TGGAAGTCAG TACGATCAAG      1406

TTGTTGACTG TGATTAGATC ACATCTTAAA TTCATTTCTA GACTCAAAAC CTGGAGATGC      1466

AGCTACTGGA ATGGTGTTTT GTCAGACTTC CAAATCCTGG AAGGACACAG TGATGAATGT      1526

ACTATATCTG AACATAGAAA CTCGGGCTTG AGTGAGAAGA GCTTGCACAG CCAACGAGAC      1586

ACATTGCCTT CTGGAGCTGG GAGACAAAGG AGGAATTTAC TTTCTTCACC AAGTGCAATA      1646

GATTACTGAT GTGATATTCT GTTGCTTTAC AGTTACAGTT GATGTTTGGG GATCGATGTG      1706

CTCAGCCAAA TTTCCTGTTT GAAATATCAT GTTAAATTAG AATGAATTTA TCTTTACCAA      1766

AAACCATGTT GCGTTCAAAG AGGTGAACAT TAAAATATAG AGACAGGACA GAATGTGTTC      1826

TTTTCTCCTC TACCAGTCCT ATTTTTCAAT GGGAAGACTC AGGAGTCTGC CACTTGTCAA      1886

AGAAGGTGCT GATCCTAAGA ATTTTTCATT CTCAGAATTC GGTGTGCTGC CAACTTGATG      1946

TTCCACCTGC CACAAACCAC CAGGACTGAA AGAAGAAAAC AGTACAGAAG GCAAAGTTTA      2006

CAGATGTTTT TAATTCTAGT ATTTTATCTG GAACAACTTG TAGCAGCTAT ATATTTCCCC      2066

TTGGTCCCAA GCCTGATACT TTAGCCATCA TAACTCACTA ACAGGGAGAA GTAGCTAGTA      2126

GCAATGTGCC TTGATTGATT AGATAAAGAT TTCTAGTAGG CAGCAAAAGA CCAAATCTCA      2186

GTTGTTTGCT TCTTGCCATC ACTGGTCCAG GTCTTCAGTT TCCGAATCTC TTTCCCTTCC      2246

CCTGTGGTCT ATTGTCGCTA TGTGACTTGC GCTTAATCCA ATATTTTGCC TTTTTTCTAT      2306

ATCAAAAAAC CTTTACAGTT AGCAGGGATG TTCCTTACCG AGGATTTTTA ACCCCCAATC      2366

TCTCATAATC GCTAGTGTTT AAAAGGCTAA GAATAGTGGG GCCCAACCGA TGTGGTAGGT      2426

GATAAAGAGG CATCTTTTCT AGAGACACAT TGGACCAGAT GAGGATCCGA AACGGCAGCC      2486

TTTACGTTCA TCACCTGCTA GAACCTCTCG TAGTCCATCA CCATTTCTTG GCATTGGAAT      2546

TCTACTGGAA AAAAATACAA AAAGCAAAAC AAAACCCTCA GCACTGTTAC AAGAGGCCAT      2606

TTAAGTATCT TGTGCTTCTT CACTTACCCA TTAGCCAGGT TCTCATTAGG TTTTGCTTGG      2666

GCCTCCCTGG CACTGAACCT TAGGCTTTGT ATGACAGTGA AGCAGCACTG TGAGTGGTTC      2726

AAGCACACTG GAATATAAAA CAGTCATGGC CTGAGATGCA GGTGATGCCA TTACAGAACC      2786

AAATCGTGGC ACGTATTGCT GTGTCTCCTC TCAGAGTGAC AGTCATAAAT ACTGTCAAAC      2846

AATAAAGGGA GAATGGTGCT GTTTAAAGTC ACATCCCTGT AAATTGCAGA ATTCAAAAGT      2906

GATTATCTCT TTGATCTACT TGCCTCATTT CCCTATCTTC TCCCCCACGG TATCCTAAAC      2966

TTTAGACTTC CCACTGTTCT GAAAGGAGAC ATTGCTCTAT GTCTGCCTTC GACCACAGCA      3026

AGCCATCATC CTCCATTGCT CCCGGGGACT CAAGAGGAAT CTGTTTCTCT GCTGTCAACT      3086

TCCCATCTGG CTCAGCATAG GGTCACTTTG CCATTATGCA AATGGAGATA AAGCAATTC      3146

TGGCTGTCCA GGAGCTAATC TGACCGTTCT ATTGTGTGGA TGACCACATA AGAAGGCAAT      3206

TTTAGTGTAT TAATCATAGA TTATTATAAA CTATAAACTT AAGGGCAAGG AGTTTATTAC      3266

AATGTATCTT TATTAAAACA AAAGGGTGTA TAGTGTTCAC AAACTGTGAA AATAGTGTAA      3326

GAACTGTACA TTGTGAGCTC TGGTTATTTT TCTCTTGTAC CATAGAAAAA TGTATAAAAA      3386

TTATCAAAAA GCTAATGTGC AGGGATATTG CCTTATTTGT CTGTAAAAAA TGGAGCTCAG      3446

TAACATAACT GCTTCTTGGA GCTTTGGAAT ATTTTATCCT GTATTCTTGT TT              3498
```

(2) INFORMATION FOR SEQ ID NO:6:

(i) SEQUENCE CHARACTERISTICS:
        (A) LENGTH: 363 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:6:

```
Met Gln Gly Lys Arg Lys Ala Leu Lys Leu Asn Phe Ala Asn Pro Pro
 1               5                  10                  15

Phe Lys Ser Thr Ala Arg Phe Thr Leu Asn Pro Asn Pro Thr Gly Val
             20                  25                  30

Gln Asn Pro His Ile Glu Arg Leu Arg Thr His Ser Ile Glu Ser Ser
         35                  40                  45

Gly Lys Leu Lys Ile Ser Pro Glu Gln His Trp Asp Phe Thr Ala Glu
 50                  55                  60

Asp Leu Lys Asp Leu Gly Glu Ile Gly Arg Gly Ala Tyr Gly Ser Val
 65                  70                  75                  80

Asn Lys Met Val His Lys Pro Ser Gly Gln Ile Met Ala Val Lys Arg
                 85                  90                  95

Ile Arg Ser Thr Val Asp Glu Lys Glu Gln Lys Gln Leu Leu Met Asp
                100                 105                 110

Leu Asp Val Val Met Arg Ser Ser Asp Cys Pro Tyr Ile Val Gln Phe
            115                 120                 125

Tyr Gly Ala Leu Phe Arg Glu Gly Asp Cys Trp Ile Cys Met Glu Leu
        130                 135                 140

Met Ser Thr Ser Phe Asp Lys Phe Tyr Lys Tyr Val Tyr Ser Val Leu
145                 150                 155                 160

Asp Asp Val Ile Pro Glu Glu Ile Leu Gly Lys Ile Thr Leu Ala Thr
                165                 170                 175

Val Lys Ala Leu Asn His Leu Lys Glu Asn Leu Lys Ile Ile His Arg
            180                 185                 190

Asp Ile Lys Pro Ser Asn Ile Leu Leu Asp Arg Ser Gly Asn Ile Lys
        195                 200                 205

Leu Cys Asp Phe Gly Ile Ser Gly Gln Leu Val Asp Ser Ile Ala Lys
210                 215                 220

Thr Arg Asp Ala Gly Cys Arg Pro Tyr Met Ala Pro Glu Arg Ile Asp
225                 230                 235                 240

Pro Ser Ala Ser Arg Gln Gly Tyr Asp Val Arg Ser Asp Val Trp Ser
                245                 250                 255

Leu Gly Ile Thr Leu Tyr Glu Leu Ala Thr Gly Arg Phe Pro Tyr Pro
            260                 265                 270

Lys Trp Asn Ser Val Phe Asp Gln Leu Thr Gln Val Val Lys Gly Asp
        275                 280                 285

Pro Pro Gln Leu Ser Asn Ser Glu Glu Arg Glu Phe Ser Pro Ser Phe
290                 295                 300

Ile Asn Phe Val Asn Leu Cys Leu Thr Lys Asp Glu Ser Lys Arg Pro
305                 310                 315                 320

Lys Tyr Lys Glu Leu Leu Lys His Pro Phe Ile Leu Met Tyr Glu Glu
                325                 330                 335

Arg Ala Val Glu Val Ala Cys Tyr Val Cys Lys Ile Leu Asp Gln Met
            340                 345                 350
```

Pro Ala Thr Pro Ser Ser Pro Met Tyr Val Asp
        355                 360

(2) INFORMATION FOR SEQ ID NO:7:

(i) SEQUENCE CHARACTERISTICS:
        (A) LENGTH: 3554 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 6...1184

(xi) SEQUENCE DESCRIPTION: SEQ ID NO:7:

| | | | | | | | | | | | | |
|---|---|---|---|---|---|---|---|---|---|---|---|---|
| CAACA | ATG | GCG | GCT | CCG | AGC | CCG | AGC | GGT | GGC | GGC | AGC | GGC ACC CCC | 50 |
| | Met | Ala | Ala | Pro | Ser | Pro | Ser | Gly | Gly | Gly | Ser | Gly Thr Pro | |
| | 1 | | | 5 | | | | 10 | | | | 15 | |

```
CAACA ATG GCG GCT CCG AGC CCG AGC GGT GGC GGC AGC GGC ACC CCC          50
      Met Ala Ala Pro Ser Pro Ser Gly Gly Gly Ser Gly Thr Pro
      1           5               10                  15

GGC CCC GTA GGG TCC CCG GCG CCA GGC CAC CCG GCC GTC AGC AGC ATG        98
Gly Pro Val Gly Ser Pro Ala Pro Gly His Pro Ala Val Ser Ser Met
                20              25                  30

CAG GGT AAA CGC AAA GCA CTG AAG TTG AAT TTT GCA AAT CCA CCT TTC       146
Gln Gly Lys Arg Lys Ala Leu Lys Leu Asn Phe Ala Asn Pro Pro Phe
            35              40                  45

AAA TCT ACA GCA AGG TTT ACT CTG AAT CCC AAT CCT ACA GGA GTT CAA       194
Lys Ser Thr Ala Arg Phe Thr Leu Asn Pro Asn Pro Thr Gly Val Gln
        50              55                  60

AAC CCA CAC ATA GAG AGA CTG AGA ACA CAC AGC ATT GAG TCA TCA GGA       242
Asn Pro His Ile Glu Arg Leu Arg Thr His Ser Ile Glu Ser Ser Gly
65              70                  75

AAA CTG AAG ATC TCC CCT GAA CAA CAC TGG GAT TTC ACT GCA GAG GAC       290
Lys Leu Lys Ile Ser Pro Glu Gln His Trp Asp Phe Thr Ala Glu Asp
80              85                  90                  95

TTG AAA GAC CTT GGA GAA ATT GGA CGA GGA GCT TAT GGT TCT GTC AAC       338
Leu Lys Asp Leu Gly Glu Ile Gly Arg Gly Ala Tyr Gly Ser Val Asn
                100                 105                 110

AAA ATG GTC CAC AAA CCA AGT GGG CAA ATA ATG GCA GTT AAA AGA ATT       386
Lys Met Val His Lys Pro Ser Gly Gln Ile Met Ala Val Lys Arg Ile
                115                 120                 125

CGG TCA ACA GTG GAT GAA AAA GAA CAA AAA CAA CTT CTT ATG GAT TTG       434
Arg Ser Thr Val Asp Glu Lys Glu Gln Lys Gln Leu Leu Met Asp Leu
            130                 135                 140

GAT GTA GTA ATG CGG AGT AGT GAT TGC CCA TAC ATT GTT CAG TTT TAT       482
Asp Val Val Met Arg Ser Ser Asp Cys Pro Tyr Ile Val Gln Phe Tyr
        145                 150                 155

GGT GCA CTC TTC AGA GAG GGT GAC TGT TGG ATC TGT ATG GAA CTC ATG       530
Gly Ala Leu Phe Arg Glu Gly Asp Cys Trp Ile Cys Met Glu Leu Met
160                 165                 170                 175

TCT ACC TCG TTT GAT AAG TTT TAC AAA TAT GTA TAT AGT GTA TTA GAT       578
Ser Thr Ser Phe Asp Lys Phe Tyr Lys Tyr Val Tyr Ser Val Leu Asp
                180                 185                 190

GAT GTT ATT CCA GAA GAA ATT TTA GGC AAA ATC ACT TTA GCA ACT GTG       626
Asp Val Ile Pro Glu Glu Ile Leu Gly Lys Ile Thr Leu Ala Thr Val
                195                 200                 205

AAA GCA CTA AAC CAC TTA AAA GAA AAC TTG AAA ATT ATT CAC AGA GAT       674
Lys Ala Leu Asn His Leu Lys Glu Asn Leu Lys Ile Ile His Arg Asp
            210                 215                 220

ATC AAA CCT TCC AAT ATT CTT CTG GAC AGA AGT GGA AAT ATT AAG CTC       722
Ile Lys Pro Ser Asn Ile Leu Leu Asp Arg Ser Gly Asn Ile Lys Leu
        225                 230                 235
```

-continued

| | |
|---|---|
| TGT GAC TTC GGC ATC AGT GGA CAG CTT GTG GAC TCT ATT GCC AAG ACA<br>Cys Asp Phe Gly Ile Ser Gly Gln Leu Val Asp Ser Ile Ala Lys Thr<br>240                         245                       250                      255 | 770 |
| AGA GAT GCT GGC TGT AGG CCA TAC ATG GCA CCT GAA AGA ATA GAC CCA<br>Arg Asp Ala Gly Cys Arg Pro Tyr Met Ala Pro Glu Arg Ile Asp Pro<br>                      260                      265                     270 | 818 |
| AGC GCA TCA CGA CAA GGA TAT GAT GTC CGC TCT GAT GTC TGG AGT TTG<br>Ser Ala Ser Arg Gln Gly Tyr Asp Val Arg Ser Asp Val Trp Ser Leu<br>                       275                     280                     285 | 866 |
| GGG ATC ACA TTG TAT GAG TTG GCC ACA GGC CGA TTT CCT TAT CCA AAG<br>Gly Ile Thr Leu Tyr Glu Leu Ala Thr Gly Arg Phe Pro Tyr Pro Lys<br>                290                     295                     300 | 914 |
| TGG AAT AGT GTA TTT GAT CAA CTA ACA CAA GTC GTG AAA GGA GAT CCT<br>Trp Asn Ser Val Phe Asp Gln Leu Thr Gln Val Val Lys Gly Asp Pro<br>305                         310                       315 | 962 |
| CCG CAG CTG AGT AAT TCT GAG GAA AGG GAA TTC TCC CCG AGT TTC ATC<br>Pro Gln Leu Ser Asn Ser Glu Glu Arg Glu Phe Ser Pro Ser Phe Ile<br>320                         325                     330                   335 | 1010 |
| AAC TTT GTC AAC TTG TGC CTT ACG AAG GAT GAA TCC AAA AGG CCA AAG<br>Asn Phe Val Asn Leu Cys Leu Thr Lys Asp Glu Ser Lys Arg Pro Lys<br>                      340                     345                     350 | 1058 |
| TAT AAA GAG CTT CTG AAA CAT CCC TTT ATT TTG ATG TAT GAA GAA CGT<br>Tyr Lys Glu Leu Leu Lys His Pro Phe Ile Leu Met Tyr Glu Glu Arg<br>               355                     360                     365 | 1106 |
| GCC GTT GAG GTC GCA TGC TAT GTT TGT AAA ATC CTG GAT CAA ATG CCA<br>Ala Val Glu Val Ala Cys Tyr Val Cys Lys Ile Leu Asp Gln Met Pro<br>                     370                     375                   380 | 1154 |
| GCT ACT CCC AGC TCT CCC ATG TAT GTC GAT TGATATCGYT GCTACATCAG ACT<br>Ala Thr Pro Ser Ser Pro Met Tyr Val Asp<br>385                                  390 | 1207 |
| CTAGAAAAAA GGGCTGAGAG GAAGCAAGAC GTAAAGAATT TCATCCCGT ATCACAGTGT | 1267 |
| TTTTATTGCT CGCCCAGACA CCATGTGCAA TAAGATTGGT GTTCGTTTCC ATCATGTCTG | 1327 |
| TATACTCCTG TCACCTAGAA CGTGCATCCT TGTAATACCT GATTGATCAC ACAGTGTTAG | 1387 |
| TGCTGGTCAG AGAGACCTCA TCCTGCTCTT TTGTGATGAA CATATTCATG AAATGTGGAA | 1447 |
| GTCAGTACGA TCAAGTTGTT GACTGTGATT AGATACATC TTAAATTCAT TTCTAGACTC | 1507 |
| AAAACCTGGA GATGCAGCTA CTGGAATGGT GTTTTGTCAG ACTTCCAAAT CCTGGAAGGA | 1567 |
| CACAGTGATG AATGTACTAT ATCTGAACAT AGAAACTCGG GCTTGAGTGA AAGAGCTTG | 1627 |
| CACAGCCAAC GAGACACATT GCCTTCTGGA GCTGGGAGAC AAAGGAGGAA TTTACTTTCT | 1687 |
| TCACCAAGTG CAATAGATTA CTGATGTGAT ATTCTGTTGC TTTACAGTTA CAGTTGATGT | 1747 |
| TTGGGGATCG ATGTGCTCAG CCAAATTTCC TGTTTGAAAT ATCATGTTAA ATTAGAATGA | 1807 |
| ATTTATCTTT ACCAAAAACC ATGTTGCGTT CAAAGAGGTG AACATTAAAA TATAGAGACA | 1867 |
| GGACAGAATG TGTTCTTTTC TCCTCTACCA GTCCTATTTT TCAATGGGAA GACTCAGGAG | 1927 |
| TCTGCCACTT GTCAAAGAAG GTGCTGATCC TAAGAATTTT TCATTCTCAG AATTCGGTGT | 1987 |
| GCTGCCAACT TGATGTTCCA CCTGCCACAA ACCACCAGGA CTGAAAGAAG AAAACAGTAC | 2047 |
| AGAAGGCAAA GTTTACAGAT GTTTTTAATT CTAGTATTTT ATCTGGAACA ACTTGTAGCA | 2107 |
| GCTATATATT TCCCCTTGGT CCCAAGCCTG ATACTTTAGC CATCATAACT CACTAACAGG | 2167 |
| GAGAAGTAGC TAGTAGCAAT GTGCCTTGAT TGATTAGATA AAGATTTCTA GTAGGCAGCA | 2227 |
| AAAGACCAAA TCTCAGTTGT TTGCTTCTTG CCATCACTGG TCCAGGTCTT CAGTTTCCGA | 2287 |
| ATCTCTTTCC CTTCCCCTGT GGTCTATTGT CGCTATGTGA CTTGCGCTTA ATCCAATATT | 2347 |

```
TTGCCTTTTT TCTATATCAA AAAACCTTTA CAGTTAGCAG GGATGTTCCT TACCGAGGAT    2407

TTTTAACCCC CAATCTCTCA TAATCGCTAG TGTTTAAAAG GCTAAGAATA GTGGGGCCCA    2467

ACCGATGTGG TAGGTGATAA AGAGGCATCT TTTCTAGAGA CACATTGGAC CAGATGAGGA    2527

TCCGAAACGG CAGCCTTTAC GTTCATCACC TGCTAGAACC TCTCGTAGTC CATCACCATT    2587

TCTTGGCATT GGAATTCTAC TGGAAAAAAA TACAAAAAGC AAAACAAAAC CCTCAGCACT    2647

GTTACAAGAG GCCATTTAAG TATCTTGTGC TTCTTCACTT ACCCATTAGC CAGGTTCTCA    2707

TTAGGTTTTG CTTGGGCCTC CCTGGCACTG AACCTTAGGG TTTGTATGAC AGTGAAGCAG    2767

CACTGTGAGT GGTTCAAGCA CACTGGAATA TAAAACAGTC ATGGCCTGAG ATGCAGGTGA    2827

TGCCATTACA GAACCAAATC GTGGCACGTA TTGCTGTGTC TCCTCTCAGA GTGACAGTCA    2887

TAAATACTGT CAAACAATAA AGGGAGAATG GTGCTGTTTA AAGTCACATC CCTGTAAATT    2947

GCAGAATTCA AAAGTGATTA TCTCTTTGAT CTACTTGCCT CATTTCCCTA TCTTCTCCCC    3007

CACGGTATCC TAAACTTTAG ACTTCCCACT GTTCTGAAAG GAGACATTGC TCTATGTCTG    3067

CCTTCGACCA CAGCAAGCCA TCATCCTCCA TTGCTCCCGG GGACTCAAGA GGAATCTGTT    3127

TCTCTGCTGT CAACTTCCCA TCTGGCTCAG CATAGGGTCA CTTTGCCATT ATGCAAATGG    3187

AGATAAAAGC AATTCTGGCT GTCCAGGAGC TAATCTGACC GTTCTATTGT GTGGATGACC    3247

ACATAAGAAG GCAATTTTAG TGTATTAATC ATAGATTATT ATAAACTATA AACTTAAGGG    3307

CAAGGAGTTT ATTACAATGT ATCTTTATTA AACAAAAGG GTGTATAGTG TTCACAAACT    3367

GTGAAAATAG TGTAAGAACT GTACATTGTG AGCTCTGGTT ATTTTTCTCT TGTACCATAG    3427

AAAAATGTAT AAAAATTATC AAAAAGCTAA TGTGCAGGGA TATTGCCTTA TTTGTCTGTA    3487

AAAAATGGAG CTCAGTAACA TAACTGCTTC TTGGAGCTTT GGAATATTTT ATCCTGTATT    3547

CTTGTTT                                                               3554
```

(2) INFORMATION FOR SEQ ID NO:8:

(i) SEQUENCE CHARACTERISTICS:
        (A) LENGTH: 393 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

```
Met Ala Ala Pro Ser Pro Ser Gly Gly Gly Ser Gly Thr Pro Gly
 1               5                  10                  15

Pro Val Gly Ser Pro Ala Pro Gly His Pro Ala Val Ser Ser Met Gln
                20                  25                  30

Gly Lys Arg Lys Ala Leu Lys Leu Asn Phe Ala Asn Pro Pro Phe Lys
            35                  40                  45

Ser Thr Ala Arg Phe Thr Leu Asn Pro Asn Pro Thr Gly Val Gln Asn
        50                  55                  60

Pro His Ile Glu Arg Leu Arg Thr His Ser Ile Glu Ser Ser Gly Lys
    65                  70                  75                  80

Leu Lys Ile Ser Pro Glu Gln His Trp Asp Phe Thr Ala Glu Asp Leu
                85                  90                  95

Lys Asp Leu Gly Glu Ile Gly Arg Gly Ala Tyr Gly Ser Val Asn Lys
                100                 105                 110

Met Val His Lys Pro Ser Gly Gln Ile Met Ala Val Lys Arg Ile Arg
            115                 120                 125
```

```
Ser Thr Val Asp Glu Lys Glu Gln Lys Gln Leu Leu Met Asp Leu Asp
    130                 135                 140

Val Val Met Arg Ser Ser Asp Cys Pro Tyr Ile Val Gln Phe Tyr Gly
145                 150                 155                 160

Ala Leu Phe Arg Glu Gly Asp Cys Trp Ile Cys Met Glu Leu Met Ser
                165                 170                 175

Thr Ser Phe Asp Lys Phe Tyr Lys Tyr Val Tyr Ser Val Leu Asp Asp
                180                 185                 190

Val Ile Pro Glu Glu Ile Leu Gly Lys Ile Thr Leu Ala Thr Val Lys
            195                 200                 205

Ala Leu Asn His Leu Lys Glu Asn Leu Lys Ile Ile His Arg Asp Ile
            210                 215                 220

Lys Pro Ser Asn Ile Leu Leu Asp Arg Ser Gly Asn Ile Lys Leu Cys
225                 230                 235                 240

Asp Phe Gly Ile Ser Gly Gln Leu Val Asp Ser Ile Ala Lys Thr Arg
                245                 250                 255

Asp Ala Gly Cys Arg Pro Tyr Met Ala Pro Glu Arg Ile Asp Pro Ser
                260                 265                 270

Ala Ser Arg Gln Gly Tyr Asp Val Arg Ser Asp Val Trp Ser Leu Gly
            275                 280                 285

Ile Thr Leu Tyr Glu Leu Ala Thr Gly Arg Phe Pro Tyr Pro Lys Trp
            290                 295                 300

Asn Ser Val Phe Asp Gln Leu Thr Gln Val Val Lys Gly Asp Pro Pro
305                 310                 315                 320

Gln Leu Ser Asn Ser Glu Glu Arg Glu Phe Ser Pro Ser Phe Ile Asn
                325                 330                 335

Phe Val Asn Leu Cys Leu Thr Lys Asp Glu Ser Lys Arg Pro Lys Tyr
                340                 345                 350

Lys Glu Leu Leu Lys His Pro Phe Ile Leu Met Tyr Glu Glu Arg Ala
            355                 360                 365

Val Glu Val Ala Cys Tyr Val Cys Lys Ile Leu Asp Gln Met Pro Ala
            370                 375                 380

Thr Pro Ser Ser Pro Met Tyr Val Asp
385                 390
```

(2) INFORMATION FOR SEQ ID NO:9:

(i) SEQUENCE CHARACTERISTICS:
        (A) LENGTH: 3576 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 10...1206

(xi) SEQUENCE DESCRIPTION: SEQ ID NO:9:

```
CTCCCAACA ATG GCG GCT CCG AGC CCG AGC GGC GGC GGC GGC TCC GGG GGC     51
          Met Ala Ala Pro Ser Pro Ser Gly Gly Gly Gly Ser Gly Gly
            1               5                  10

GGC AGC GGC AGC GGC ACC CCC GGC CCC GTA GGG TCC CCG GCG CCA GGC        99
Gly Ser Gly Ser Gly Thr Pro Gly Pro Val Gly Ser Pro Ala Pro Gly
 15                  20                  25                  30

CAC CCG GCC GTC AGC AGC ATG CAG GGT AAA CGC AAA GCA CTG AAG TTG      147
His Pro Ala Val Ser Ser Met Gln Gly Lys Arg Lys Ala Leu Lys Leu
```

```
                35                  40                  45
AAT TTT GCA AAT CCA CCT TTC AAA TCT ACA GCA AGG TTT ACT CTG AAT       195
Asn Phe Ala Asn Pro Pro Phe Lys Ser Thr Ala Arg Phe Thr Leu Asn
            50                  55                  60

CCC AAT CCT ACA GGA GTT CAA AAC CCA CAC ATA GAG AGA CTG AGA ACA       243
Pro Asn Pro Thr Gly Val Gln Asn Pro His Ile Glu Arg Leu Arg Thr
        65                  70                  75

CAC AGC ATT GAG TCA TCA GGA AAA CTG AAG ATC TCC CCT GAA CAA CAC       291
His Ser Ile Glu Ser Ser Gly Lys Leu Lys Ile Ser Pro Glu Gln His
    80                  85                  90

TGG GAT TTC ACT GCA GAG GAC TTG AAA GAC CTT GGA GAA ATT GGA CGA       339
Trp Asp Phe Thr Ala Glu Asp Leu Lys Asp Leu Gly Glu Ile Gly Arg
95                  100                 105                 110

GGA GCT TAT GGT TCT GTC AAC AAA ATG GTC CAC AAA CCA AGT GGG CAA       387
Gly Ala Tyr Gly Ser Val Asn Lys Met Val His Lys Pro Ser Gly Gln
                115                 120                 125

ATA ATG GCA GTT AAA AGA ATT CGG TCA ACA GTG GAT GAA AAA GAA CAA       435
Ile Met Ala Val Lys Arg Ile Arg Ser Thr Val Asp Glu Lys Glu Gln
            130                 135                 140

AAA CAA CTT CTT ATG GAT TTG GAT GTA GTA ATG CGG AGT AGT GAT TGC       483
Lys Gln Leu Leu Met Asp Leu Asp Val Val Met Arg Ser Ser Asp Cys
        145                 150                 155

CCA TAC ATT GTT CAG TTT TAT GGT GCA CTC TTC AGA GAG GGT GAC TGT       531
Pro Tyr Ile Val Gln Phe Tyr Gly Ala Leu Phe Arg Glu Gly Asp Cys
    160                 165                 170

TGG ATC TGT ATG GAA CTC ATG TCT ACC TCG TTT GAT AAG TTT TAC AAA       579
Trp Ile Cys Met Glu Leu Met Ser Thr Ser Phe Asp Lys Phe Tyr Lys
175                 180                 185                 190

TAT GTA TAT AGT GTA TTA GAT GAT GTT ATT CCA GAA GAA ATT TTA GGC       627
Tyr Val Tyr Ser Val Leu Asp Asp Val Ile Pro Glu Glu Ile Leu Gly
                195                 200                 205

AAA ATC ACT TTA GCA ACT GTG AAA GCA CTA AAC CAC TTA AAA GAA AAC       675
Lys Ile Thr Leu Ala Thr Val Lys Ala Leu Asn His Leu Lys Glu Asn
            210                 215                 220

TTG AAA ATT ATT CAC AGA GAT ATC AAA CCT TCC AAT ATT CTT CTG GAC       723
Leu Lys Ile Ile His Arg Asp Ile Lys Pro Ser Asn Ile Leu Leu Asp
        225                 230                 235

AGA AGT GGA AAT ATT AAG CTC TGT GAC TTC GGC ATC AGT GGA CAG CTT       771
Arg Ser Gly Asn Ile Lys Leu Cys Asp Phe Gly Ile Ser Gly Gln Leu
    240                 245                 250

GTG GAC TCT ATT GCC AAG ACA AGA GAT GCT GGC TGT AGG CCA TAC ATG       819
Val Asp Ser Ile Ala Lys Thr Arg Asp Ala Gly Cys Arg Pro Tyr Met
255                 260                 265                 270

GCA CCT GAA AGA ATA GAC CCA AGC GCA TCA CGA CAA GGA TAT GAT GTC       867
Ala Pro Glu Arg Ile Asp Pro Ser Ala Ser Arg Gln Gly Tyr Asp Val
                275                 280                 285

CGC TCT GAT GTC TGG AGT TTG GGG ATC ACA TTG TAT GAG TTG GCC ACA       915
Arg Ser Asp Val Trp Ser Leu Gly Ile Thr Leu Tyr Glu Leu Ala Thr
            290                 295                 300

GGC CGA TTT CCT TAT CCA AAG TGG AAT AGT GTA TTT GAT CAA CTA ACA       963
Gly Arg Phe Pro Tyr Pro Lys Trp Asn Ser Val Phe Asp Gln Leu Thr
        305                 310                 315

CAA GTC GTG AAA GGA GAT CCT CCG CAG CTG AGT AAT TCT GAG GAA AGG      1011
Gln Val Val Lys Gly Asp Pro Pro Gln Leu Ser Asn Ser Glu Glu Arg
    320                 325                 330

GAA TTC TCC CCG AGT TTC ATC AAC TTT GTC AAC TTG TGC CTT ACG AAG      1059
Glu Phe Ser Pro Ser Phe Ile Asn Phe Val Asn Leu Cys Leu Thr Lys
335                 340                 345                 350

GAT GAA TCC AAA AGG CCA AAG TAT AAA GAG CTT CTG AAA CAT CCC TTT      1107
```

```
                Asp Glu Ser Lys Arg Pro Lys Tyr Lys Glu Leu Leu Lys His Pro Phe
                                355                 360                 365

ATT TTG ATG TAT GAA GAA CGT GCC GTT GAG GTC GCA TGC TAT GTT TGT              1155
Ile Leu Met Tyr Glu Glu Arg Ala Val Glu Val Ala Cys Tyr Val Cys
            370                 375                 380

AAA ATC CTG GAT CAA ATG CCA GCT ACT CCC AGC TCT CCC ATG TAT GTC              1203
Lys Ile Leu Asp Gln Met Pro Ala Thr Pro Ser Ser Pro Met Tyr Val
        385                 390                 395

GAT TGATATCGCT GCTACATCAG ACTCTAGAAA AAGGGCTGA GAGGAAGCAA GACGTA             1262
Asp

AAGAATTTTC ATCCCGTATC ACAGTGTTTT TATTGCTCGC CCAGACACCA TGTGCAATAA            1322

GATTGGTGTT CGTTTCCATC ATGTCTGTAT ACTCCTGTCA CCTAGAACGT GCATCCTTGT            1382

AATACCTGAT TGATCACACA GTGTTAGTGC TGGTCAGAGA GACCTCATCC TGCTCTTTTG            1442

TGATGAACAT ATTCATGAAA TGTGGAAGTC AGTACGATCA AGTTGTTGAC TGTGATTAGA            1502

TCACATCTTA AATTCATTTC TAGACTCAAA ACCTGGAGAT GCAGCTACTG GAATGGTGTT            1562

TTGTCAGACT TCCAAATCCT GGAAGGACAC AGTGATGAAT GTACTATATC TGAACATAGA            1622

AACTCGGGCT TGAGTGAGAA GAGCTTGCAC AGCCAACGAG ACACATTGCC TTCTGGAGCT            1682

GGGAGACAAA GGAGGAATTT ACTTTCTTCA CCAAGTGCAA TAGATTACTG ATGTGATATT            1742

CTGTTGCTTT ACAGTTACAG TTGATGTTTG GGGATCGATG TGCTCAGCCA AATTTCCTGT            1802

TTGAAATATC ATGTTAAATT AGAATGAATT TATCTTTACC AAAAACCATG TTGCGTTCAA            1862

AGAGGTGAAC ATTAAAATAT AGAGACAGGA CAGAATGTGT TCTTTTCTCC TCTACCAGTC            1922

CTATTTTTCA ATGGGAAGAC TCAGGAGTCT GCCACTTGTC AAAGAAGGTG CTGATCCTAA            1982

GAATTTTTCA TTCTCAGAAT TCGGTGTGCT GCCAACTTGA TGTTCCACCT GCCACAAACC            2042

ACCAGGACTG AAAGAAGAAA ACAGTACAGA AGGCAAAGTT TACAGATGTT TTTAATTCTA            2102

GTATTTTATC TGGAACAACT TGTAGCAGCT ATATATTTCC CCTTGGTCCC AAGCCTGATA            2162

CTTTAGCCAT CATAACTCAC TAACAGGGAG AAGTAGCTAG TAGCAATGTG CCTTGATTGA            2222

TTAGATAAAG ATTTCTAGTA GGCAGCAAAA GACCAAATCT CAGTTGTTTG CTTCTTGCCA            2282

TCACTGGTCC AGGTCTTCAG TTTCCGAATC TCTTTCCCTT CCCCTGTGGT CTATTGTCGC            2342

TATGTGACTT GCGCTTAATC CAATATTTTG CCTTTTTTCT ATATCAAAAA ACCTTTACAG            2402

TTAGCAGGGA TGTTCCTTAC CGAGGATTTT TAACCCCCAA TCTCTCATAA TCGCTAGTGT            2462

TTAAAAGGCT AAGAATAGTG GGGCCCAACC GATGTGGTAG GTGATAAAGA GGCATCTTTT            2522

CTAGAGACAC ATTGGACCAG ATGAGGATCC GAAACGGCAG CCTTTACGTT CATCACCTGC            2582

TAGAACCTCT CGTAGTCCAT CACCATTTCT TGGCATTGGA ATTCTACTGG AAAAAAATAC            2642

AAAAAGCAAA ACAAAACCCT CAGCACTGTT ACAAGAGGCC ATTTAAGTAT CTTGTGCTTC            2702

TTCACTTACC CATTAGCCAG GTTCTCATTA GGTTTTGCTT GGGCCTCCCT GGCACTGAAC            2762

CTTAGGCTTT GTATGACAGT GAAGCAGCAC TGTGAGTGGT TCAAGCACAC TGGAATATAA            2822

AACAGTCATG GCCTGAGATG CAGGTGATGC CATTACAGAA CCAAATCGTG GCACGTATTG            2882

CTGTGTCTCC TCTCAGAGTG ACAGTCATAA ATACTGTCAA ACAATAAAGG GAGAATGGTG            2942

CTGTTTAAAG TCACATCCCT GTAAATTGCA GAATTCAAAA GTGATTATCT CTTTGATCTA            3002

CTTGCCTCAT TTCCCTATCT TCTCCCCCAC GGTATCCTAA ACTTTAGACT TCCCACTGTT            3062

CTGAAAGGAG ACATTGCTCT ATGTCTGCCT TCGACCACAG CAAGCCATCA TCCTCCATTG            3122

CTCCCGGGGA CTCAAGAGGA ATCTGTTTCT CTGCTGTCAA CTTCCCATCT GGCTCAGCAT            3182

AGGGTCACTT TGCCATTATG CAAATGGAGA TAAAAGCAAT TCTGGCTGTC CAGGAGCTAA            3242
```

```
TCTGACCGTT CTATTGTGTG GATGACCACA TAAGAAGGCA ATTTTAGTGT ATTAATCATA    3302

GATTATTATA AACTATAAAC TTAAGGGCAA GGAGTTTATT ACAATGTATC TTTATTAAAA    3362

CAAAAGGGTG TATAGTGTTC ACAAACTGTG AAAATAGTGT AAGAACTGTA CATTGTGAGC    3422

TCTGGTTATT TTTCTCTTGT ACCATAGAAA AATGTATAAA AATTATCAAA AAGCTAATGT    3482

GCAGGGATAT TGCCTTATTT GTCTGTAAAA AATGGAGCTC AGTAACATAA CTGCTTCTTG    3542

GAGCTTTGGA ATATTTTATC CTGTATTCTT GTTT                                3576
```

(2) INFORMATION FOR SEQ ID NO:10:

(i) SEQUENCE CHARACTERISTICS:
        (A) LENGTH: 399 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:10:

```
Met Ala Ala Pro Ser Pro Ser Gly Gly Gly Ser Gly Gly Gly Ser
  1               5                  10                  15

Gly Ser Gly Thr Pro Gly Pro Val Gly Ser Pro Ala Pro Gly His Pro
                 20                  25                  30

Ala Val Ser Ser Met Gln Gly Lys Arg Lys Ala Leu Lys Leu Asn Phe
             35                  40                  45

Ala Asn Pro Pro Phe Lys Ser Thr Ala Arg Phe Thr Leu Asn Pro Asn
         50                  55                  60

Pro Thr Gly Val Gln Asn Pro His Ile Glu Arg Leu Arg Thr His Ser
 65                  70                  75                  80

Ile Glu Ser Ser Gly Lys Leu Lys Ile Ser Pro Glu Gln His Trp Asp
                 85                  90                  95

Phe Thr Ala Glu Asp Leu Lys Asp Leu Gly Glu Ile Gly Arg Gly Ala
            100                 105                 110

Tyr Gly Ser Val Asn Lys Met Val His Lys Pro Ser Gly Gln Ile Met
            115                 120                 125

Ala Val Lys Arg Ile Arg Ser Thr Val Asp Glu Lys Glu Gln Lys Gln
        130                 135                 140

Leu Leu Met Asp Leu Asp Val Val Met Arg Ser Ser Asp Cys Pro Tyr
145                 150                 155                 160

Ile Val Gln Phe Tyr Gly Ala Leu Phe Arg Glu Gly Asp Cys Trp Ile
                165                 170                 175

Cys Met Glu Leu Met Ser Thr Ser Phe Asp Lys Phe Tyr Lys Tyr Val
            180                 185                 190

Tyr Ser Val Leu Asp Asp Val Ile Pro Glu Glu Ile Leu Gly Lys Ile
        195                 200                 205

Thr Leu Ala Thr Val Lys Ala Leu Asn His Leu Lys Glu Asn Leu Lys
    210                 215                 220

Ile Ile His Arg Asp Ile Lys Pro Ser Asn Ile Leu Leu Asp Arg Ser
225                 230                 235                 240

Gly Asn Ile Lys Leu Cys Asp Phe Gly Ile Ser Gly Gln Leu Val Asp
                245                 250                 255

Ser Ile Ala Lys Thr Arg Asp Ala Gly Cys Arg Pro Tyr Met Ala Pro
            260                 265                 270

Glu Arg Ile Asp Pro Ser Ala Ser Arg Gln Gly Tyr Asp Val Arg Ser
```

```
            275                 280                 285
Asp Val Trp Ser Leu Gly Ile Thr Leu Tyr Glu Leu Ala Thr Gly Arg
    290                 295                 300
Phe Pro Tyr Pro Lys Trp Asn Ser Val Phe Asp Gln Leu Thr Gln Val
305                 310                 315                 320
Val Lys Gly Asp Pro Pro Gln Leu Ser Asn Ser Glu Glu Arg Glu Phe
                325                 330                 335
Ser Pro Ser Phe Ile Asn Phe Val Asn Leu Cys Leu Thr Lys Asp Glu
                340                 345                 350
Ser Lys Arg Pro Lys Tyr Lys Glu Leu Leu Lys His Pro Phe Ile Leu
            355                 360                 365
Met Tyr Glu Glu Arg Ala Val Glu Val Ala Cys Tyr Val Cys Lys Ile
    370                 375                 380
Leu Asp Gln Met Pro Ala Thr Pro Ser Ser Pro Met Tyr Val Asp
385                 390                 395

(2) INFORMATION FOR SEQ ID NO:11:

(i) SEQUENCE CHARACTERISTICS:
         (A) LENGTH: 393 amino acids
         (B) TYPE: amino acid
         (D) TOPOLOGY: linear (ii) MOLECULE TYPE: protein (xi) SEQUENCE DESCRIPTION: SEQ ID NO:11:

Met Pro Lys Lys Lys Pro Thr Pro Ile Gln Leu Asn Pro Ala Pro Asp
  1               5                  10                  15
Gly Ser Ala Val Asn Gly Thr Ser Ser Ala Glu Thr Asn Leu Glu Ala
                 20                  25                  30
Leu Gln Lys Lys Leu Glu Glu Leu Glu Leu Asp Glu Gln Gln Arg Lys
            35                  40                  45
Arg Leu Glu Ala Phe Leu Thr Gln Lys Gln Lys Val Gly Glu Leu Lys
        50                  55                  60
Asp Asp Asp Phe Glu Lys Ile Ser Glu Leu Gly Ala Gly Asn Gly Gly
 65                  70                  75                  80
Val Val Phe Lys Val Ser His Lys Pro Ser Gly Leu Val Met Ala Arg
                 85                  90                  95
Lys Leu Ile His Leu Glu Ile Lys Pro Ala Ile Arg Asn Gln Ile Ile
                100                 105                 110
Arg Glu Leu Gln Val Leu His Glu Cys Asn Ser Pro Tyr Ile Val Gly
            115                 120                 125
Phe Tyr Gly Ala Phe Tyr Ser Asp Gly Glu Ile Ser Ile Cys Met Glu
        130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                165                 170                 175
Leu Thr Tyr Leu Arg Glu Lys His Lys Ile Met His Arg Asp Val Lys
                180                 185                 190
Pro Ser Asn Ile Leu Val Asn Ser Arg Gly Glu Ile Lys Leu Cys Asp
            195                 200                 205
Phe Gly Val Ser Gly Gln Leu Ile Asp Ser Met Ala Asn Ser Phe Val
        210                 215                 220
Gly Thr Arg Ser Tyr Met Ser Pro Glu Arg Leu Gln Gly Thr His Tyr
225                 230                 235                 240
```

-continued

```
Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
                260                 265                 270

Leu Met Phe Gly Cys Gln Val Glu Gly Asp Ala Ala Glu Thr Pro Pro
                275                 280                 285

Arg Pro Arg Thr Pro Gly Arg Pro Leu Ser Ser Tyr Gly Met Asp Ser
            290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
                355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390
```

(2) INFORMATION FOR SEQ ID NO:12:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:12:

```
Met Leu Ala Arg Arg Lys Pro Val Leu Pro Ala Leu Thr Ile Asn Pro
 1               5                  10                  15

Thr Ile Ala Glu Gly Pro Ser Pro Thr Ser Glu Gly Ala Ser Glu Ala
                20                  25                  30

Asn Leu Val Asp Leu Gln Lys Lys Leu Glu Glu Leu Glu Leu Asp Glu
            35                  40                  45

Gln Gln Lys Lys Arg Leu Glu Ala Phe Leu Thr Gln Lys Ala Lys Val
        50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
                100                 105                 110

Asn Gln Ile Ile Arg Glu Leu Gln Val Leu His Glu Cys Asn Ser Pro
            115                 120                 125

Tyr Ile Val Gly Phe Tyr Gly Ala Phe Tyr Ser Asp Gly Glu Ile Ser
        130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
                180                 185                 190
```

```
Arg Asp Val Lys Pro Ser Asn Ile Leu Val Asn Ser Arg Gly Glu Ile
            195                 200                 205

Lys Leu Cys Asp Phe Gly Val Ser Gly Gln Leu Ile Asp Ser Met Ala
            210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
            245                 250                 255

Leu Val Glu Leu Ala Val Gly Arg Tyr Pro Ile Pro Pro Asp Ala
            260                 265                 270

Lys Glu Leu Glu Ala Ile Phe Gly Arg Pro Val Val Asp Gly Glu Glu
            275                 280                 285

Gly Glu Pro His Ser Ile Ser Pro Arg Pro Arg Pro Pro Gly Arg Pro
            290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
            325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
            355                 360                 365

Ile Lys Arg Ser Glu Val Glu Glu Val Asp Phe Ala Gly Trp Leu Cys
            370                 375                 380

Lys Thr Leu Arg Leu Asn Gln Pro Gly Thr Pro Thr Arg Thr Ala Val
385                 390                 395                 400

(2) INFORMATION FOR SEQ ID NO:13:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:13:

Gly Thr Thr Pro Arg Thr Gly Asn Ser Asn Asn Ser Asn Ser Gly Ser
1               5                   10                  15

Ser Gly Gly Gly Gly Leu Phe Ala Asn Phe Ser Lys Tyr Val Asp Ile
            20                  25                  30

Lys Ser Gly Ser Leu Asn Phe Ala Gly Lys Leu Ser Leu Ser Ser Lys
            35                  40                  45

Gly Ile Asp Phe Ser Asn Gly Ser Ser Ser Arg Ile Thr Leu Asp Glu
        50                  55                  60

Leu Glu Phe Leu Asp Glu Leu Gly His Gly Asn Tyr Gly Asn Val Ser
65                  70                  75                  80

Lys Val Leu His Lys Pro Thr Asn Val Ile Met Ala Thr Lys Glu Val
            85                  90                  95

Arg Leu Glu Leu Asp Glu Ala Lys Phe Arg Gln Ile Leu Met Glu Leu
            100                 105                 110

Glu Val Leu His Lys Cys Asn Ser Pro Tyr Ile Val Asp Phe Tyr Gly
            115                 120                 125

Ala Phe Phe Ile Glu Gly Ala Val Tyr Met Cys Met Glu Tyr Met Asp
        130                 135                 140

Gly Gly Ser Leu Asp Lys Ile Tyr Asp Glu Ser Ser Glu Ile Gly Gly
```

```
              145                 150                 155                 160
         Ile Asp Glu Pro Gln Leu Ala Phe Ile Ala Asn Ala Val Ile His Gly
                         165                 170                 175

Leu Lys Glu Leu Lys Glu Gln His Asn Ile Ile His Arg Asp Val Lys
                     180                 185                 190

Pro Thr Asn Ile Leu Cys Ser Ala Asn Gln Gly Thr Val Lys Leu Cys
                     195                 200                 205

Asp Phe Gly Val Ser Gly Asn Leu Val Ala Ser Leu Ala Lys Thr Met
                 210                 215                 220

Asn Ile Gly Cys Gln Ser Tyr Met Ala Pro Glu Arg Ile Lys Ser Leu
         225                 230                 235                 240

Asn Pro Asp Arg Ala Thr Tyr Thr Val Gln Ser Asp Ile Trp Ser Leu
                         245                 250                 255

Gly Leu Ser Ile Leu Glu Met Ala Leu Gly Arg Tyr Pro Tyr Pro Pro
                     260                 265                 270

Glu Thr Tyr Asp Asn Ile Phe Ser Gln Leu Ser Ala Ile Val Asp Gly
                     275                 280                 285

Pro Pro Pro Arg Leu Pro Ser Asp Lys Phe Ser Ser Asp Ala Gln Asp
                 290                 295                 300

Phe Val Ser Leu Cys Leu Gln Lys Ile Pro Glu Arg Arg Pro Thr Tyr
         305                 310                 315                 320

Ala Ala Leu Thr Glu His Pro Trp Leu Val Lys Tyr Arg Asn Gln Asp
                         325                 330                 335

Val His Met Ser Glu Tyr Ile Thr Glu Arg Leu Glu Arg Arg Asn Lys
                     340                 345                 350

Ile Leu Arg Glu Arg Gly Glu Asn Gly Leu Ser Lys Asn Val Pro
                     355                 360                 365

(2) INFORMATION FOR SEQ ID NO:14:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:14:

TTYTAYGGNG CNTTYTTYAT HGA                                                23

(2) INFORMATION FOR SEQ ID NO:15:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:15:

ATBCTYTCNG GNGCCATKTA                                                    20

(2) INFORMATION FOR SEQ ID NO:16:

(i) SEQUENCE CHARACTERISTICS:
              (A) LENGTH: 8 amino acids
              (B) TYPE: amino acid
              (D) TOPOLOGY: linear
```

(ii) MOLECULE TYPE: peptide (xi) SEQUENCE DESCRIPTION: SEQ ID NO:16:

```
Asp Tyr Lys Asp Asp Asp Lys
 1               5
```

(2) INFORMATION FOR SEQ ID NO:17:

(i) SEQUENCE CHARACTERISTICS:
        (A) LENGTH: 1623 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 281...1318

(xi) SEQUENCE DESCRIPTION: SEQ ID NO:17:

```
GGAAAGGCAG CCTCCTGTAG GTGAAAATTC TGTTCACTAC CTGGCCACCT GGCCTGACTG          60

ACCTTCACAG CTTGATCATC TTCCTGAAGA GGCATTCAGG ATTCCCTCCA TCCCTACCCC         120

TTCTGGACAA AGTCTTCCAC GTTTCCTTCC TGGGAGTTTC TTCCAGGAAC TGGAGATACC         180

CAGAGCCCTG CAACTCCCAC TGGCCAACGA TGGGGGCAGC CGCTCACCAT CCTCAGAGAG         240

CTCCCCACAG CACCCTACAC CCCCCACCCG GCCCCGCCAC ATG CTG GGG CTC CCA          295
                                             Met Leu Gly Leu Pro
                                              1               5

TCA ACC TTG TTC ACA CCG CGC AGT ATG GAG AGC ATC GAG ATT GAC CAG          343
Ser Thr Leu Phe Thr Pro Arg Ser Met Glu Ser Ile Glu Ile Asp Gln
             10                  15                  20

AAG CTG CAG GAG ATC ATG AAG CAG ACA GGG TAC CTG ACT ATC GGG GGC          391
Lys Leu Gln Glu Ile Met Lys Gln Thr Gly Tyr Leu Thr Ile Gly Gly
         25                  30                  35

CAG CGT TAT CAG GCA GAA ATC AAT GAC TTG GAG AAC TTG GGT GAG ATG          439
Gln Arg Tyr Gln Ala Glu Ile Asn Asp Leu Glu Asn Leu Gly Glu Met
     40                  45                  50

GGC AGT GGT ACC TGT GGT CAG GTG TGG AAG ATG CGG TTC CGG AAG ACA          487
Gly Ser Gly Thr Cys Gly Gln Val Trp Lys Met Arg Phe Arg Lys Thr
 55                  60                  65

GGC CAC ATC ATT GCT GTT AAG CAA ATG CGG CGC TCT GGG AAC AAG GAA          535
Gly His Ile Ile Ala Val Lys Gln Met Arg Arg Ser Gly Asn Lys Glu
 70                  75                  80                  85

GAG AAT AAG CGC ATT TTG ATG GAC CTG GAT GTA GTA CTC AAG AGC CAT          583
Glu Asn Lys Arg Ile Leu Met Asp Leu Asp Val Val Leu Lys Ser His
             90                  95                 100

GAC TGC CCT TAC ATC GTT CAG TGC TTT GGC ACC TTC ATC ACC AAC ACA          631
Asp Cys Pro Tyr Ile Val Gln Cys Phe Gly Thr Phe Ile Thr Asn Thr
        105                 110                 115

GAC GTC TTT ATT GCC ATG GAG CTC ATG GGC ACA TGT GCA GAG AAG CTG          679
Asp Val Phe Ile Ala Met Glu Leu Met Gly Thr Cys Ala Glu Lys Leu
    120                 125                 130

AAG AAA CGA ATG CAG GGC CCC ATT CCA GAG CGA ATC CTG GGC AAC ATG          727
Lys Lys Arg Met Gln Gly Pro Ile Pro Glu Arg Ile Leu Gly Asn Met
135                 140                 145

ACT GTG GCG ATT GTG AAA GCA CTG TAC TAT CTG AAG GAG AAG CAT GGC          775
Thr Val Ala Ile Val Lys Ala Leu Tyr Tyr Leu Lys Glu Lys His Gly
150                 155                 160                 165

GTC ATC CAT CGC GAT GTC AAA CCC TCC AAC ATC CTG CTA GAT GAG CGG          823
Val Ile His Arg Asp Val Lys Pro Ser Asn Ile Leu Leu Asp Glu Arg
            170                 175                 180
```

-continued

```
GGC CAG ATC AAG CTC TGT GAC TTT GGC ATC AGT GGC CGC CTT GTT GAC        871
Gly Gln Ile Lys Leu Cys Asp Phe Gly Ile Ser Gly Arg Leu Val Asp
            185                 190                 195

TCC AAA GCC AAA ACA CGG AGT GCT GGC TGT GCT GCC TAT ATG GCT CCC        919
Ser Lys Ala Lys Thr Arg Ser Ala Gly Cys Ala Ala Tyr Met Ala Pro
            200                 205                 210

GAG CGC ATC GAC CCT CCA GAT CCC ACC AAG CCT GAC TAT GAC ATC CGA        967
Glu Arg Ile Asp Pro Pro Asp Pro Thr Lys Pro Asp Tyr Asp Ile Arg
            215                 220                 225

GCT GAT GTG TGG AGC CTG GGC ATC TCA CTG GTG GAG CTG GCA ACA GGA       1015
Ala Asp Val Trp Ser Leu Gly Ile Ser Leu Val Glu Leu Ala Thr Gly
230                 235                 240                 245

CAG TTC CCC TAT AAG AAC TGC AAG ACG GAC TTT GAG GTC CTC ACC AAA       1063
Gln Phe Pro Tyr Lys Asn Cys Lys Thr Asp Phe Glu Val Leu Thr Lys
            250                 255                 260

GTC CTA CAG GAA GAG CCC CCA CTC CTG CCT GGT CAC ATG GGC TTC TCA       1111
Val Leu Gln Glu Glu Pro Pro Leu Leu Pro Gly His Met Gly Phe Ser
            265                 270                 275

GGG GAC TTC CAG TCA TTT GTC AAA GAC TGC CTT ACT AAA GAT CAC AGG       1159
Gly Asp Phe Gln Ser Phe Val Lys Asp Cys Leu Thr Lys Asp His Arg
            280                 285                 290

AAG AGA CCA AAG TAT AAT AAG CTA CTT GAA CAC AGC TTC ATC AAG CAC       1207
Lys Arg Pro Lys Tyr Asn Lys Leu Leu Glu His Ser Phe Ile Lys His
            295                 300                 305

TAT GAG ATA CTC GAG GTG GAT GTC GCG TCC TGG TTT AAG GAT GTC ATG       1255
Tyr Glu Ile Leu Glu Val Asp Val Ala Ser Trp Phe Lys Asp Val Met
310                 315                 320                 325

GCG AAG ACC GAG TCC CCA AGG ACT AGT GGA GTC CTG AGT CAG CAC CAT       1303
Ala Lys Thr Glu Ser Pro Arg Thr Ser Gly Val Leu Ser Gln His His
            330                 335                 340

CTG CCC TTC TTC AGG TAGCCTCATG GCAGCGGCCA GCCCCGCAGG GGCCCCGGGC C     1359
Leu Pro Phe Phe Arg
            345

ACGGCCACCG ACCCCCCCCC CAACCTGGCC AACCCAGCTG CCCATCAGGG GACCTGGGAC    1419

CTGGACGACT GCCAAGGACT GAGGACAGAA AGTAGGGGGT TCCCATCCAG CTCTGACTCC    1479

CTGCCTACCA GCTGTGGACA AAAGGGCATG CTGGTTCCTA ATCCCTCCCA CTCTGGGGTC    1539

AGCCAGCAGT GTGAGCCCCA TCCCACCCCG ACAGACACTG TGAACGGAAG ACAGCAGGCC    1599

AAAAAAAAAA AAAAAAAAAA AAAA                                          1623

(2) INFORMATION FOR SEQ ID NO:18:

(i) SEQUENCE CHARACTERISTICS:
        (A) LENGTH: 346 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:18:

Met Leu Gly Leu Pro Ser Thr Leu Phe Thr Pro Arg Ser Met Glu Ser
  1               5                  10                  15

Ile Glu Ile Asp Gln Lys Leu Gln Glu Ile Met Lys Gln Thr Gly Tyr
            20                  25                  30

Leu Thr Ile Gly Gly Gln Arg Tyr Gln Ala Glu Ile Asn Asp Leu Glu
        35                  40                  45

Asn Leu Gly Glu Met Gly Ser Gly Thr Cys Gly Gln Val Trp Lys Met
```

```
            50                  55                  60
Arg Phe Arg Lys Thr Gly His Ile Ile Ala Val Lys Gln Met Arg Arg
 65                  70                  75                  80

Ser Gly Asn Lys Glu Glu Asn Lys Arg Ile Leu Met Asp Leu Asp Val
                 85                  90                  95

Val Leu Lys Ser His Asp Cys Pro Tyr Ile Val Gln Cys Phe Gly Thr
                100                 105                 110

Phe Ile Thr Asn Thr Asp Val Phe Ile Ala Met Glu Leu Met Gly Thr
                115                 120                 125

Cys Ala Glu Lys Leu Lys Lys Arg Met Gln Gly Pro Ile Pro Glu Arg
130                 135                 140

Ile Leu Gly Asn Met Thr Val Ala Ile Val Lys Ala Leu Tyr Tyr Leu
145                 150                 155                 160

Lys Glu Lys His Gly Val Ile His Arg Asp Val Lys Pro Ser Asn Ile
                165                 170                 175

Leu Leu Asp Glu Arg Gly Gln Ile Lys Leu Cys Asp Phe Gly Ile Ser
                180                 185                 190

Gly Arg Leu Val Asp Ser Lys Ala Lys Thr Arg Ser Ala Gly Cys Ala
                195                 200                 205

Ala Tyr Met Ala Pro Glu Arg Ile Asp Pro Pro Asp Pro Thr Lys Pro
210                 215                 220

Asp Tyr Asp Ile Arg Ala Asp Val Trp Ser Leu Gly Ile Ser Leu Val
225                 230                 235                 240

Glu Leu Ala Thr Gly Gln Phe Pro Tyr Lys Asn Cys Lys Thr Asp Phe
                245                 250                 255

Glu Val Leu Thr Lys Val Leu Gln Glu Glu Pro Pro Leu Leu Pro Gly
                260                 265                 270

His Met Gly Phe Ser Gly Asp Phe Gln Ser Phe Val Lys Asp Cys Leu
                275                 280                 285

Thr Lys Asp His Arg Lys Arg Pro Lys Tyr Asn Lys Leu Leu Glu His
290                 295                 300

Ser Phe Ile Lys His Tyr Glu Ile Leu Glu Val Asp Val Ala Ser Trp
305                 310                 315                 320

Phe Lys Asp Val Met Ala Lys Thr Glu Ser Pro Arg Thr Ser Gly Val
                325                 330                 335

Leu Ser Gln His His Leu Pro Phe Phe Arg
                340                 345

(2) INFORMATION FOR SEQ ID NO:19:

(i) SEQUENCE CHARACTERISTICS:
        (A) LENGTH: 1465 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 3...1169

(xi) SEQUENCE DESCRIPTION: SEQ ID NO:19:

GC ACG AGC CCT GCT CCT GCC CCG TCC CAG CGA GCA GCC CTG CAA CTC        47
   Thr Ser Pro Ala Pro Ala Pro Ser Gln Arg Ala Ala Leu Gln Leu
    1               5                  10                  15

CCA CTG GCC AAC GAT GGG GGC AGC CGC TCA CCA TCC TCA GAG AGC TCC       95
Pro Leu Ala Asn Asp Gly Gly Ser Arg Ser Pro Ser Ser Glu Ser Ser
```

```
                    20                      25                     30
CCA CAG CAC CCT ACA CCC CCC ACC CGG CCC CGC CAC ATG CTG GGG CTC    143
Pro Gln His Pro Thr Pro Pro Thr Arg Pro Arg His Met Leu Gly Leu
            35                      40                 45

CCA TCA ACC TTG TTC ACA CCG CGC AGT ATG GAG AGC ATC GAG ATT GAC    191
Pro Ser Thr Leu Phe Thr Pro Arg Ser Met Glu Ser Ile Glu Ile Asp
        50                      55                  60

CAG AAG CTG CAG GAG ATC ATG AAG CAG ACA GGG TAC CTG ACT ATC GGG    239
Gln Lys Leu Gln Glu Ile Met Lys Gln Thr Gly Tyr Leu Thr Ile Gly
    65                      70                  75

GGC CAG CGT TAT CAG GCA GAA ATC AAT GAC TTG GAG AAC TTG GGT GAG    287
Gly Gln Arg Tyr Gln Ala Glu Ile Asn Asp Leu Glu Asn Leu Gly Glu
80                      85                  90                 95

ATG GGC AGT GGT ACC TGT GGT CAG GTG TGG AAG ATG CGG TTC CGG AAG    335
Met Gly Ser Gly Thr Cys Gly Gln Val Trp Lys Met Arg Phe Arg Lys
                100                     105                 110

ACA GGC CAC ATC ATT GCT GTT AAG CAA ATG CGG CGC TCT GGG AAC AAG    383
Thr Gly His Ile Ile Ala Val Lys Gln Met Arg Arg Ser Gly Asn Lys
            115                     120                 125

GAA GAG AAT AAG CGC ATT TTG ATG GAC CTG GAT GTA GTA CTC AAG AGC    431
Glu Glu Asn Lys Arg Ile Leu Met Asp Leu Asp Val Val Leu Lys Ser
        130                     135                 140

CAT GAC TGC CCT TAC ATC GTT CAG TGC TTT GGC ACC TTC ATC ACC AAC    479
His Asp Cys Pro Tyr Ile Val Gln Cys Phe Gly Thr Phe Ile Thr Asn
    145                     150                 155

ACA GAC GTC TTT ATT GCC ATG GAG CTC ATG GGC ACA TGT GCA GAG AAG    527
Thr Asp Val Phe Ile Ala Met Glu Leu Met Gly Thr Cys Ala Glu Lys
160                     165                 170                 175

CTG AAG AAA CGA ATG CAG GGC CCC ATT CCA GAG CGA ATC CTG GGC AAG    575
Leu Lys Lys Arg Met Gln Gly Pro Ile Pro Glu Arg Ile Leu Gly Lys
                180                     185                 190

ATG ACT GTG GCG ATT GTG AAA GCA CTG TAC TAT CTG AAG GAG AAG CAT    623
Met Thr Val Ala Ile Val Lys Ala Leu Tyr Tyr Leu Lys Glu Lys His
            195                     200                 205

GGC GTC ATC CAT CGC GAT GTC AAA CCC TCC AAC ATC CTG CTA GAT GAG    671
Gly Val Ile His Arg Asp Val Lys Pro Ser Asn Ile Leu Leu Asp Glu
        210                     215                 220

CGG GGC CAG ATC AAG CTC TGT GAC TTT GGC ATC AGT GGC CGC CTT GTT    719
Arg Gly Gln Ile Lys Leu Cys Asp Phe Gly Ile Ser Gly Arg Leu Val
    225                     230                 235

GAC TCC AAA GCC AAA ACA CGG AGT GCT GGC TGT GCT GCC TAT ATG GCT    767
Asp Ser Lys Ala Lys Thr Arg Ser Ala Gly Cys Ala Ala Tyr Met Ala
240                     245                 250                 255

CCC GAG CGC ATC GAC CCT CCA GAT CCC ACC AAG CCT GAC TAT GAC ATC    815
Pro Glu Arg Ile Asp Pro Pro Asp Pro Thr Lys Pro Asp Tyr Asp Ile
                260                     265                 270

CGA GCT GAT GTG TGG AGC CTG GGC ATC TCA CTG GTG GAG CTG GCA ACA    863
Arg Ala Asp Val Trp Ser Leu Gly Ile Ser Leu Val Glu Leu Ala Thr
            275                     280                 285

GGA CAG TTC CCC TAT AAG AAC TGC AAG ACG GAC TTT GAG GTC CTC ACC    911
Gly Gln Phe Pro Tyr Lys Asn Cys Lys Thr Asp Phe Glu Val Leu Thr
        290                     295                 300

AAA GTC CTA CAG GAA GAG CCC CCA CTC CTG CCT GGT CAC ATG GGC TTC    959
Lys Val Leu Gln Glu Glu Pro Pro Leu Leu Pro Gly His Met Gly Phe
    305                     310                 315

TCA GGG GAC TTC CAG TCA TTT GTC AAA GAC TGC CTT ACT AAA GAT CAC    1007
Ser Gly Asp Phe Gln Ser Phe Val Lys Asp Cys Leu Thr Lys Asp His
320                     325                 330                 335

AGG AAG AGA CCA AAG TAT AAT AAG CTA CTT GAA CAC AGC TTC ATC AAG    1055
```

```
Arg Lys Arg Pro Lys Tyr Asn Lys Leu Leu Glu His Ser Phe Ile Lys
                340                 345                 350

CAC TAT GAG ATA CTC GAG GTG GAT GTC GCG TCC TGG TTT AAG GAT GTC          1103
His Tyr Glu Ile Leu Glu Val Asp Val Ala Ser Trp Phe Lys Asp Val
                355                 360                 365

ATG GCG AAG ACC GAG TCC CCA AGG ACT AGT GGA GTC CTG AGT CAG CAC          1151
Met Ala Lys Thr Glu Ser Pro Arg Thr Ser Gly Val Leu Ser Gln His
        370                 375                 380

CAT CTG CCC TTC TTC AGG TAGCCTCATG GCAGCGGCCA GCCCCGCAGG GGCCCCGG        1207
His Leu Pro Phe Phe Arg
    385

GCCACGGCCA CCGACCCCCC CCCCAACCTG GCCAACCCAG CTGCCCATCA GGGGACCTGG        1267

GACCTGGACG ACTGCCAAGG ACTGAGGACA GAAAGTAGGG GGTTCCCATC CAGCTCTGAC        1327

TCCCTGCCTA CCAGCTGTGG ACAAAAGGGC ATGCTGGTTC CTAATCCCTC CCACTCTGGG        1387

GTCAGCCAGC AGTGTGAGCC CCATCCCACC CCGACAGACA CTGTGAACGG AAGACAGCAA        1447

AAAAAAAAAA AAAAAAA                                                       1465
```

(2) INFORMATION FOR SEQ ID NO:20:

(i) SEQUENCE CHARACTERISTICS:
        (A) LENGTH: 389 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:20:

```
Thr Ser Pro Ala Pro Ala Pro Ser Gln Arg Ala Ala Leu Gln Leu Pro
 1               5                  10                  15

Leu Ala Asn Asp Gly Gly Ser Arg Ser Pro Ser Ser Glu Ser Ser Pro
                20                  25                  30

Gln His Pro Thr Pro Pro Thr Arg Pro Arg His Met Leu Gly Leu Pro
            35                  40                  45

Ser Thr Leu Phe Thr Pro Arg Ser Met Glu Ser Ile Glu Ile Asp Gln
 50                  55                  60

Lys Leu Gln Glu Ile Met Lys Gln Thr Gly Tyr Leu Thr Ile Gly Gly
65                  70                  75                  80

Gln Arg Tyr Gln Ala Glu Ile Asn Asp Leu Glu Asn Leu Gly Glu Met
                85                  90                  95

Gly Ser Gly Thr Cys Gly Gln Val Trp Lys Met Arg Phe Arg Lys Thr
            100                 105                 110

Gly His Ile Ile Ala Val Lys Gln Met Arg Arg Ser Gly Asn Lys Glu
        115                 120                 125

Glu Asn Lys Arg Ile Leu Met Asp Leu Asp Val Val Leu Lys Ser His
    130                 135                 140

Asp Cys Pro Tyr Ile Val Gln Cys Phe Gly Thr Phe Ile Thr Asn Thr
145                 150                 155                 160

Asp Val Phe Ile Ala Met Glu Leu Met Gly Thr Cys Ala Glu Lys Leu
                165                 170                 175

Lys Lys Arg Met Gln Gly Pro Ile Pro Glu Arg Ile Leu Gly Lys Met
            180                 185                 190

Thr Val Ala Ile Val Lys Ala Leu Tyr Tyr Leu Lys Glu Lys His Gly
        195                 200                 205

Val Ile His Arg Asp Val Lys Pro Ser Asn Ile Leu Leu Asp Glu Arg
```

-continued

```
                    210                 215                 220
Gly Gln Ile Lys Leu Cys Asp Phe Gly Ile Ser Gly Arg Leu Val Asp
225                 230                 235                 240

Ser Lys Ala Lys Thr Arg Ser Ala Gly Cys Ala Ala Tyr Met Ala Pro
                    245                 250                 255

Glu Arg Ile Asp Pro Pro Asp Pro Thr Lys Pro Asp Tyr Asp Ile Arg
                    260                 265                 270

Ala Asp Val Trp Ser Leu Gly Ile Ser Leu Val Glu Leu Ala Thr Gly
                    275                 280                 285

Gln Phe Pro Tyr Lys Asn Cys Lys Thr Asp Phe Glu Val Leu Thr Lys
                    290                 295                 300

Val Leu Gln Glu Glu Pro Pro Leu Leu Pro Gly His Met Gly Phe Ser
305                 310                 315                 320

Gly Asp Phe Gln Ser Phe Val Lys Asp Cys Leu Thr Lys Asp His Arg
                    325                 330                 335

Lys Arg Pro Lys Tyr Asn Lys Leu Leu Glu His Ser Phe Ile Lys His
                    340                 345                 350

Tyr Glu Ile Leu Glu Val Asp Val Ala Ser Trp Phe Lys Asp Val Met
                    355                 360                 365

Ala Lys Thr Glu Ser Pro Arg Thr Ser Gly Val Leu Ser Gln His His
                    370                 375                 380

Leu Pro Phe Phe Arg
385
```

(2) INFORMATION FOR SEQ ID NO:21:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:21:

```
Ser Ala Ser Ser Ser Ser Ser Ala Ser Ala Phe Ala Ser Ala Ala
1               5                   10                  15

Pro Ala Thr Gly Thr Phe Gly Gly Thr Tyr Thr Pro Pro Thr Thr Arg
                    20                  25                  30

Val Ser Arg Ala Thr Pro Thr Leu Pro Met Leu Ser Ser Gly Pro Gly
                    35                  40                  45

Gly Gly Leu Asn Arg Thr Arg Pro Asn Ile Leu Pro Leu Pro Thr Pro
    50                  55                  60

Pro His Pro Pro Val Ser Glu Thr Asp Met Lys Leu Lys Ile Ile Met
65                  70                  75                  80

Glu Gln Thr Gly Lys Leu Asn Ile Asn Gly Arg Gln Tyr Pro Thr Asp
                    85                  90                  95

Ile Asn Asp Leu Lys His Leu Gly Asp Leu Gly Asn Gly Thr Ser Gly
                    100                 105                 110

Asn Val Val Lys Met Met His Leu Ser Ser Asn Thr Ile Ile Ala Val
                    115                 120                 125

Lys Gln Met Arg Arg Thr Gly Asn Ala Glu Glu Asn Lys Arg Ile Leu
    130                 135                 140

Met Asp Leu Asp Val Val Leu Lys Ser His Asp Cys Lys Tyr Ile Val
145                 150                 155                 160

Lys Cys Leu Gly Cys Phe Val Arg Asp Pro Asp Val Trp Ile Cys Met
                    165                 170                 175
```

```
Glu Leu Met Ser Met Cys Phe Asp Lys Leu Leu Lys Leu Ser Lys Lys
            180                 185                 190

Pro Val Pro Glu Gln Ile Leu Gly Lys Val Thr Val Ala Thr Val Asn
                195                 200                 205

Ala Leu Ser Tyr Leu Lys Asp Lys His Gly Val Ile His Arg Asp Val
            210                 215                 220

Lys Pro Ser Asn Ile Leu Ile Asp Glu Arg Gly Asn Ile Lys Leu Cys
225                 230                 235                 240

Asp Phe Gly Ile Ser Gly Arg Leu Val Asp Ser Lys Ala Lys Thr Arg
                245                 250                 255

Ser Ala Gly Cys Ala Ala Tyr Met Ala Pro Glu Arg Ile Asp Pro Lys
            260                 265                 270

Lys Pro Lys Tyr Asp Ile Arg Ala Asp Val Trp Ser Leu Gly Ile Thr
            275                 280                 285

Leu Val Glu Leu Ala Thr Ala Arg Ser Pro Tyr Glu Gly Cys Asn Thr
            290                 295                 300

Asp Phe Glu Val Leu Thr Lys Val Leu Asp Ser Glu Pro Pro Cys Leu
305                 310                 315                 320

Pro Tyr Gly Glu Gly Tyr Asn Phe Ser Gln Gln Phe Arg Asp Phe Val
                325                 330                 335

Ile Lys Cys Leu Thr Lys Asn His Gln Asp Arg Pro Lys Tyr Pro Glu
            340                 345                 350

Leu Leu Ala Gln Pro Phe Ile Arg Ile Tyr Glu Ser Ala Lys Val Asp
            355                 360                 365

Val Pro Asn Gln Ser Ile Lys Asp Asn Arg Leu Arg Ala Asn Gly Asp
            370                 375                 380

Pro Thr Leu Gln Arg Leu Pro Asn Ser
385                 390

(2) INFORMATION FOR SEQ ID NO:22:

(i) SEQUENCE CHARACTERISTICS:
        (A) LENGTH: 405 amino acids
        (B) TYPE: amino acid
        (D) TOPOLOGY: linear (ii) MOLECULE TYPE: protein (xi) SEQUENCE DESCRIPTION: SEQ ID NO:22:

Ile Gly Gln Val Leu Pro Glu Ala Thr Thr Ala Phe Glu Tyr Glu
  1                 5                  10                  15

Asp Glu Asp Gly Asp Arg Ile Thr Val Arg Ser Asp Glu Glu Met Lys
                20                  25                  30

Ala Met Leu Ser Tyr Tyr Ser Thr Val Met Glu Gln Gln Val Asn
             35                  40                  45

Gly Gln Leu Ile Glu Pro Leu Gln Ile Phe Pro Arg Ala Cys Lys Pro
     50                  55                  60

Pro Gly Glu Arg Asn Ile His Gly Leu Lys Val Asn Thr Arg Ala Gly
 65                  70                  75                  80

Pro Ser Gln His Ser Ser Pro Ala Val Ser Asp Ser Leu Pro Ser Asn
             85                  90                  95

Ser Leu Lys Lys Ser Ser Ala Glu Leu Lys Lys Ile Leu Ala Asn Gly
            100                 105                 110

Gln Met Asn Glu Gln Asp Ile Arg Tyr Arg Asp Thr Leu Gly His Gly
            115                 120                 125
```

```
Asn Gly Gly Thr Val Glu Lys Met Arg His Val Pro Ser Gly Lys Ile
            130                 135                 140

Leu Ala Val Lys Val Ile Leu Leu Asp Ile Thr Leu Glu Leu Gln Lys
145                 150                 155                 160

Gln Ile Met Ser Glu Leu Glu Ile Leu Ile Lys Cys Asp Ser Ser Tyr
                165                 170                 175

Ile Ile Gly Phe Tyr Gly Ala Phe Phe Val Glu Asn Arg Ile Ser Ile
            180                 185                 190

Cys Thr Glu Phe Met Asp Gly Ser Leu Asp Asp Ile Gly Lys Met
            195                 200                 205

Pro Glu His Val Leu Gly Arg Ile Ala Val Ala Val Val Lys Gly Leu
            210                 215                 220

Thr Tyr Lys Gly Leu Thr Tyr Leu Trp Ser Leu Lys Ile Leu His Arg
225                 230                 235                 240

Asp Val Lys Pro Ser Asn Met Val Asn Thr Arg Gly Gln Val Lys Leu
                245                 250                 255

Cys Asp Phe Gly Val Ser Thr Gln Leu Val Asn Ser Ile Ala Lys Thr
            260                 265                 270

Tyr Val Gly Thr Asn Ala Tyr Met Ala Pro Glu Arg Ile Ser Gly Glu
            275                 280                 285

Gln Tyr Gly Ile His Ser Asp Val Trp Ser Leu Gly Ile Thr Met Ile
            290                 295                 300

Glu Leu Ala Thr Gly Arg Phe Pro Tyr Pro Lys Trp Asn Ser Val Leu
305                 310                 315                 320

Gln Leu Leu Gln Cys Ile Val Asp Glu Asp Ser Pro Val Leu Pro Val
                325                 330                 335

Gly Glu Phe Ser Glu Pro Phe Val His Phe Ile Thr Gln Cys Met Arg
            340                 345                 350

Thr Gln Pro Lys Glu Arg Pro Ala Pro Glu Glu Leu Met Gly His Pro
            355                 360                 365

Phe Ile Val Gln Phe Asn Asp Gly Asn Ala Ala Val Val Ser Met Trp
370                 375                 380

Val Cys Arg Ala Leu Glu Glu Arg Arg Thr Ser Arg Gly Pro Arg Glu
385                 390                 395                 400

Ala Ala Ala Gly His
                405

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

ATNGCNGTNA ARCARATG                                              18

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:24:

```
ATNCKYTCNG GNGCCATRTA                                              20
```

(2) INFORMATION FOR SEQ ID NO:25:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 62...841

(xi) SEQUENCE DESCRIPTION: SEQ ID NO:25:

```
TGTTTGTCTG CCGGACTGAC GGGCGGCCGG GCGGTGCGCG GCGGCGGTGG CGGCGGGGAA       60

G ATG GCG GCG TCC TCC CTG GAA CAG AAG CTG TCC CGC CTG GAA GCA AAG      109
  Met Ala Ala Ser Ser Leu Glu Gln Lys Leu Ser Arg Leu Glu Ala Lys
   1               5                  10                  15

CTG AAG CAG GAG AAC CGG GAG GCC CGG CGG AGG ATC GAC CTC AAC CTG        157
Leu Lys Gln Glu Asn Arg Glu Ala Arg Arg Arg Ile Asp Leu Asn Leu
              20                  25                  30

GAT ATC AGC CCC CAG CGG CCC AGG CCC ACC CTG CAG CTC CCG CTG GCC        205
Asp Ile Ser Pro Gln Arg Pro Arg Pro Thr Leu Gln Leu Pro Leu Ala
         35                  40                  45

AAC GAT GGG GGC AGC CGC TCG CCA TCC TCA GAG AGC TCC CCG CAG CAC        253
Asn Asp Gly Gly Ser Arg Ser Pro Ser Ser Glu Ser Ser Pro Gln His
     50                  55                  60

CCC ACG CCC CCC GCC CGG CCC CGC CAC ATG CTG GGG CTC CCG TCA ACC        301
Pro Thr Pro Pro Ala Arg Pro Arg His Met Leu Gly Leu Pro Ser Thr
 65                  70                  75                  80

CTG TTC ACA CCC CGC AGC ATG GAG AGC ATT GAG ATT GAC CAG AAG CTG        349
Leu Phe Thr Pro Arg Ser Met Glu Ser Ile Glu Ile Asp Gln Lys Leu
                 85                  90                  95

CAG GAG ATC ATG AAG CAG ACG GGC TAC CTG ACC ATC GGG GGC CAG CGC        397
Gln Glu Ile Met Lys Gln Thr Gly Tyr Leu Thr Ile Gly Gly Gln Arg
             100                 105                 110

TAC CAG GCA GAA ATC AAC GAC CTG GAG AAC TTG GGC GAG ATG GGC AGC        445
Tyr Gln Ala Glu Ile Asn Asp Leu Glu Asn Leu Gly Glu Met Gly Ser
         115                 120                 125

GGC ACC TGC GGC CAG GTG TGG AAG ATG CGC TTC CGG AAG ACC GGC CAC        493
Gly Thr Cys Gly Gln Val Trp Lys Met Arg Phe Arg Lys Thr Gly His
     130                 135                 140

GTC ATT GCC GTT AAG CAA ATG CGG CGC TCC GGG AAC AAG GAG GAG AAC        541
Val Ile Ala Val Lys Gln Met Arg Arg Ser Gly Asn Lys Glu Glu Asn
145                 150                 155                 160

AAG CGC ATC CTC ATG GAC CTG GAT GTG GTG CTG AAG AGC CAC GAC TGC        589
Lys Arg Ile Leu Met Asp Leu Asp Val Val Leu Lys Ser His Asp Cys
                 165                 170                 175

CCC TAC ATC GTG CAG TGC TTT GGG ACG TTC ATC ACC AAC ACG GAC GTC        637
Pro Tyr Ile Val Gln Cys Phe Gly Thr Phe Ile Thr Asn Thr Asp Val
             180                 185                 190

TTC ATC GCC ATG GAG CTC ATG GGC ACC TGC GCT GAG AAG CTC AAG AAG        685
Phe Ile Ala Met Glu Leu Met Gly Thr Cys Ala Glu Lys Leu Lys Lys
         195                 200                 205

CGG ATG CAG GGC CCC ATC CCC GAG CGC ATT CTG GGC AAG ATG ACA GTG        733
Arg Met Gln Gly Pro Ile Pro Glu Arg Ile Leu Gly Lys Met Thr Val
     210                 215                 220
```

```
GCG ATT GTG AAG GCG CTG TAC TAC CTG AAG GAG AAG CAC GGT GTC ATC      781
Ala Ile Val Lys Ala Leu Tyr Tyr Leu Lys Glu Lys His Gly Val Ile
225                 230                 235                 240

CAC CGC GAC GTC AAG CCC TCC AAC ATC CTG CTG GAC GAG CGG GGC CAG      829
His Arg Asp Val Lys Pro Ser Asn Ile Leu Leu Asp Glu Arg Gly Gln
                245                 250                 255

ATC AAG CTG TGC GA                                                   843
Ile Lys Leu Cys
260

(2) INFORMATION FOR SEQ ID NO:26:

(i) SEQUENCE CHARACTERISTICS:
        (A) LENGTH: 260 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:26:

Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Ile Asp Leu Asn Leu
            20                  25                  30

Asp Ile Ser Pro Gln Arg Pro Arg Pro Thr Leu Gln Leu Pro Leu Ala
        35                  40                  45

Asn Asp Gly Gly Ser Arg Ser Pro Ser Ser Glu Ser Ser Pro Gln His
    50                  55                  60

Pro Thr Pro Pro Ala Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
                85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
        115                 120                 125

Gly Thr Cys Gly Gln Val Trp Lys Met Arg Phe Arg Lys Thr Gly His
    130                 135                 140

Val Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
        195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys
            260
```

(2) INFORMATION FOR SEQ ID NO:27:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 82...1338

(xi) SEQUENCE DESCRIPTION: SEQ ID NO:27:

```
AGCGCAGGCG CAGTGCGGTG TTTGTCTACC CCGGACTGAC GGGTGGCCTG GCGGTGAGCG              60

GCGGCAGCGG CGGCGGGAA G ATG GCG GCG TCC TCC CTG GAG CAG AAG CTG               111
                       Met Ala Ala Ser Ser Leu Glu Gln Lys Leu
                        1               5                  10

TCC CGC CTG GAA GCC AAG CTG AAG CAG GAG AAC CGT GAG GCC CGC AGG              159
Ser Arg Leu Glu Ala Lys Leu Lys Gln Glu Asn Arg Glu Ala Arg Arg
             15                  20                  25

AGG ATC GAC CTC AAC TTG GAT ATC AGC CCA CAG CGG CCC AGG CCC ACC              207
Arg Ile Asp Leu Asn Leu Asp Ile Ser Pro Gln Arg Pro Arg Pro Thr
                 30                  35                  40

CTG CAA CTC CCA CTG GCC AAC GAT GGG GGC AGC CGC TCA CCA TCC TCA              255
Leu Gln Leu Pro Leu Ala Asn Asp Gly Gly Ser Arg Ser Pro Ser Ser
             45                  50                  55

GAG AGC TCC CCA CAG CAC CCT ACA CCC CCC ACC CGG CCC CGC CAC ATG              303
Glu Ser Ser Pro Gln His Pro Thr Pro Pro Thr Arg Pro Arg His Met
 60                  65                  70

CTG GGG CTC CCA TCA ACC TTG TTC ACA CCG CGC AGT ATG GAG AGC ATC              351
Leu Gly Leu Pro Ser Thr Leu Phe Thr Pro Arg Ser Met Glu Ser Ile
 75                  80                  85                  90

GAG ATT GAC CAG AAG CTG CAG GAG ATC ATG AAG CAG ACA GGG TAC CTG              399
Glu Ile Asp Gln Lys Leu Gln Glu Ile Met Lys Gln Thr Gly Tyr Leu
                 95                 100                 105

ACT ATC GGG GGC CAG CGT TAT CAG GCA GAA ATC AAT GAC TTG GAG AAC              447
Thr Ile Gly Gly Gln Arg Tyr Gln Ala Glu Ile Asn Asp Leu Glu Asn
             110                 115                 120

TTG GGT GAG ATG GGC AGT GGT ACC TGT GGT CAG GTG TGG AAG ATG CGG              495
Leu Gly Glu Met Gly Ser Gly Thr Cys Gly Gln Val Trp Lys Met Arg
125                 130                 135

TTC CGG AAG ACA GGC CAC ATC ATT GCT GTT AAG CAA ATG CGG CGC TCT              543
Phe Arg Lys Thr Gly His Ile Ile Ala Val Lys Gln Met Arg Arg Ser
            140                 145                 150

GGG AAC AAG GAA GAG AAT AAG CGC ATT TTG ATG GAC CTG GAT GTA GTA              591
Gly Asn Lys Glu Glu Asn Lys Arg Ile Leu Met Asp Leu Asp Val Val
155                 160                 165                 170

CTC AAG AGC CAT GAC TGC CCT TAC ATC GTT CAG TGC TTT GGC ACC TTC              639
Leu Lys Ser His Asp Cys Pro Tyr Ile Val Gln Cys Phe Gly Thr Phe
                175                 180                 185

ATC ACC AAC ACA GAC GTC TTT ATT GCC ATG GAG CTC ATG GGC ACA TGT              687
Ile Thr Asn Thr Asp Val Phe Ile Ala Met Glu Leu Met Gly Thr Cys
            190                 195                 200

GCA GAG AAG CTG AAG AAA CGA ATG CAG GGC CCC ATT CCA GAG CGA ATC              735
Ala Glu Lys Leu Lys Lys Arg Met Gln Gly Pro Ile Pro Glu Arg Ile
205                 210                 215

CTG GGC AAG ATG ACT GTG GCG ATT GTG AAA GCA CTG TAC TAT CTG AAG              783
Leu Gly Lys Met Thr Val Ala Ile Val Lys Ala Leu Tyr Tyr Leu Lys
        220                 225                 230

GAG AAG CAT GGC GTC ATC CAT CGC GAT GTC AAA CCC TCC AAC ATC CTG              831
```

```
CTA GAT GAG CGG GGC CAG ATC AAG CTC TGT GAC TTT GGC ATC AGT GGC        879
Leu Asp Glu Arg Gly Gln Ile Lys Leu Cys Asp Phe Gly Ile Ser Gly
            255                 260                 265

CGC CTT GTT GAC TCC AAA GCC AAA ACA CGG AGT GCT GGC TGT GCT GCC        927
Arg Leu Val Asp Ser Lys Ala Lys Thr Arg Ser Ala Gly Cys Ala Ala
            270                 275                 280

TAT ATG GCT CCC GAG CGC ATC GAC CCT CCA GAT CCC ACC AAG CCT GAC        975
Tyr Met Ala Pro Glu Arg Ile Asp Pro Pro Asp Pro Thr Lys Pro Asp
            285                 290                 295

TAT GAC ATC CGA GCT GAT GTG TGG AGC CTG GGC ATC TCA CTG GTG GAG       1023
Tyr Asp Ile Arg Ala Asp Val Trp Ser Leu Gly Ile Ser Leu Val Glu
            300                 305                 310

CTG GCA ACA GGA CAG TTC CCC TAT AAG AAC TGC AAG ACG GAC TTT GAG       1071
Leu Ala Thr Gly Gln Phe Pro Tyr Lys Asn Cys Lys Thr Asp Phe Glu
315                 320                 325                 330

GTC CTC ACC AAA GTC CTA CAG GAA GAG CCC CCA CTC CTG CCT GGT CAC       1119
Val Leu Thr Lys Val Leu Gln Glu Glu Pro Pro Leu Leu Pro Gly His
            335                 340                 345

ATG GGC TTC TCA GGG GAC TTC CAG TCA TTT GTC AAA GAC TGC CTT ACT       1167
Met Gly Phe Ser Gly Asp Phe Gln Ser Phe Val Lys Asp Cys Leu Thr
            350                 355                 360

AAA GAT CAC AGG AAG AGA CCA AAG TAT AAT AAG CTA CTT GAA CAC AGC       1215
Lys Asp His Arg Lys Arg Pro Lys Tyr Asn Lys Leu Leu Glu His Ser
            365                 370                 375

TTC ATC AAG CAC TAT GAG ATA CTC GAG GTG GAT GTC GCG TCC TGG TTT       1263
Phe Ile Lys His Tyr Glu Ile Leu Glu Val Asp Val Ala Ser Trp Phe
            380                 385                 390

AAG GAT GTC ATG GCG AAG ACC GAG TCC CCA AGG ACT AGT GGA GTC CTG       1311
Lys Asp Val Met Ala Lys Thr Glu Ser Pro Arg Thr Ser Gly Val Leu
395                 400                 405                 410

AGT CAG CAC CAT CTG CCC TTC TTC AGG TAGCCTCATG GCAGCGGCCA GCCCCGC     1365
Ser Gln His His Leu Pro Phe Phe Arg
            415

AGGGGCCCCG GGCCACGGCC ACCGACCCCC CCCCCAACCT GGCCAACCCA GCTGCCCATC    1425

AGGGGACCTG GGACCTGGAC GACTGCCAAG GACTGAGGAC AGAAAGTAGG GGGTTCCCAT    1485

CCAGCTCTGA CTCCCTGCCT ACCAGCTGTG GACAAAAGGG CATGCTGGTT CCTAATCCCT    1545

CCCACTCTGG GGTCAGCCAG CAGTGTGAGC CCCATCCCAC CCCGACAGAC ACTGTGAACG    1605

GAAGACAGCA GGCCAAAAAA AAAAAAAAAA AAAAAAA                             1643
```

(2) INFORMATION FOR SEQ ID NO:28:

(i) SEQUENCE CHARACTERISTICS:
        (A) LENGTH: 419 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:28:

```
Met Ala Ala Ser Ser Leu Glu Gln Lys Leu Ser Arg Leu Glu Ala Lys
1               5                   10                  15

Leu Lys Gln Glu Asn Arg Glu Ala Arg Arg Ile Asp Leu Asn Leu
            20                  25                  30

Asp Ile Ser Pro Gln Arg Pro Arg Pro Thr Leu Gln Leu Pro Leu Ala
            35                  40                  45
```

Asn Asp Gly Gly Ser Arg Ser Pro Ser Ser Glu Ser Ser Pro Gln His
        50                      55                      60

Pro Thr Pro Pro Thr Arg Pro Arg His Met Leu Gly Leu Pro Ser Thr
65                      70                      75                      80

Leu Phe Thr Pro Arg Ser Met Glu Ser Ile Glu Ile Asp Gln Lys Leu
                85                      90                      95

Gln Glu Ile Met Lys Gln Thr Gly Tyr Leu Thr Ile Gly Gly Gln Arg
            100                     105                     110

Tyr Gln Ala Glu Ile Asn Asp Leu Glu Asn Leu Gly Glu Met Gly Ser
        115                     120                     125

Gly Thr Cys Gly Gln Val Trp Lys Met Arg Phe Arg Lys Thr Gly His
    130                     135                     140

Ile Ile Ala Val Lys Gln Met Arg Arg Ser Gly Asn Lys Glu Glu Asn
145                     150                     155                     160

Lys Arg Ile Leu Met Asp Leu Asp Val Val Leu Lys Ser His Asp Cys
                165                     170                     175

Pro Tyr Ile Val Gln Cys Phe Gly Thr Phe Ile Thr Asn Thr Asp Val
            180                     185                     190

Phe Ile Ala Met Glu Leu Met Gly Thr Cys Ala Glu Lys Leu Lys Lys
        195                     200                     205

Arg Met Gln Gly Pro Ile Pro Glu Arg Ile Leu Gly Lys Met Thr Val
    210                     215                     220

Ala Ile Val Lys Ala Leu Tyr Tyr Leu Lys Glu Lys His Gly Val Ile
225                     230                     235                     240

His Arg Asp Val Lys Pro Ser Asn Ile Leu Leu Asp Glu Arg Gly Gln
                245                     250                     255

Ile Lys Leu Cys Asp Phe Gly Ile Ser Gly Arg Leu Val Asp Ser Lys
            260                     265                     270

Ala Lys Thr Arg Ser Ala Gly Cys Ala Ala Tyr Met Ala Pro Glu Arg
        275                     280                     285

Ile Asp Pro Pro Asp Pro Thr Lys Pro Asp Tyr Asp Ile Arg Ala Asp
    290                     295                     300

Val Trp Ser Leu Gly Ile Ser Leu Val Glu Leu Ala Thr Gly Gln Phe
305                     310                     315                     320

Pro Tyr Lys Asn Cys Lys Thr Asp Phe Glu Val Leu Thr Lys Val Leu
                325                     330                     335

Gln Glu Glu Pro Pro Leu Leu Pro Gly His Met Gly Phe Ser Gly Asp
            340                     345                     350

Phe Gln Ser Phe Val Lys Asp Cys Leu Thr Lys Asp His Arg Lys Arg
        355                     360                     365

Pro Lys Tyr Asn Lys Leu Leu Glu His Ser Phe Ile Lys His Tyr Glu
    370                     375                     380

Ile Leu Glu Val Asp Val Ala Ser Trp Phe Lys Asp Val Met Ala Lys
385                     390                     395                     400

Thr Glu Ser Pro Arg Thr Ser Gly Val Leu Ser Gln His His Leu Pro
                405                     410                     415

Phe Phe Arg (2) INFORMATION FOR SEQ ID NO:29:

(i) SEQUENCE CHARACTERISTICS:
        (A) LENGTH: 1578 base pairs
        (B) TYPE: nucleic acid
        (C) STRANDEDNESS: double

```
            (D) TOPOLOGY: linear (ii) MOLECULE TYPE: cDNA (ix) FEATURE:
            (A) NAME/KEY: Coding Sequence
            (B) LOCATION: 281...1420

(xi) SEQUENCE DESCRIPTION: SEQ ID NO:29:

GGAAAGGCAG CCTCCTGTAG GTGAAAATTC TGTTCACTAC CTGGCCACCT GGCCTGACTG        60

ACCTTCACAG CTTGATCATC TTCCTGAAGA GGCATTCAGG ATTCCCTCCA TCCCTACCCC       120

TTCTGGACAA AGTCTTCCAC GTTTCCTTCC TGGGAGTTTC TTCCAGGAAC TGGAGATACC       180

CAGAGCCCTG CAACTCCCAC TGGCCAACGA TGGGGGCAGC CGCTCACCAT CCTCAGAGAG       240

CTCCCCACAG CACCCTACAC CCCCCACCCG GCCCCGCCAC ATG CTG GGG CTC CCA         295
                                             Met Leu Gly Leu Pro
                                             1               5

TCA ACC TTG TTC ACA CCG CGC AGT ATG GAG AGC ATC GAG ATT GAC CAG         343
Ser Thr Leu Phe Thr Pro Arg Ser Met Glu Ser Ile Glu Ile Asp Gln
                10                  15                  20

AAG CTG CAG GAG ATC ATG AAG CAG ACA GGG TAC CTG ACT ATC GGG GGC         391
Lys Leu Gln Glu Ile Met Lys Gln Thr Gly Tyr Leu Thr Ile Gly Gly
            25                  30                  35

CAG CGT TAT CAG GCA GAA ATC AAT GAC TTG GAG AAC TTG GGT GAG ATG         439
Gln Arg Tyr Gln Ala Glu Ile Asn Asp Leu Glu Asn Leu Gly Glu Met
        40                  45                  50

GGC AGT GGT ACC TGT GGT CAG GTG TGG AAG ATG CGG TTC CGG AAG ACA         487
Gly Ser Gly Thr Cys Gly Gln Val Trp Lys Met Arg Phe Arg Lys Thr
    55                  60                  65

GGC CAC ATC ATT GCT GTT AAG CAA ATG CGG CGC TCT GGG AAC AAG GAA         535
Gly His Ile Ile Ala Val Lys Gln Met Arg Arg Ser Gly Asn Lys Glu
70                  75                  80                  85

GAG AAT AAG CGC ATT TTG ATG GAC CTG GAT GTA GTA CTC AAG AGC CAT         583
Glu Asn Lys Arg Ile Leu Met Asp Leu Asp Val Val Leu Lys Ser His
                90                  95                 100

GAC TGC CCT TAC ATC GTT CAG TGC TTT GGC ACC TTC ATC ACC AAC ACA         631
Asp Cys Pro Tyr Ile Val Gln Cys Phe Gly Thr Phe Ile Thr Asn Thr
               105                 110                 115

GAC GTC TTT ATT GCC ATG GAG CTC ATG GGC ACA TGT GCA GAG AAG CTG         679
Asp Val Phe Ile Ala Met Glu Leu Met Gly Thr Cys Ala Glu Lys Leu
           120                 125                 130

AAG AAA CGA ATG CAG GGC CCC ATT CCA GAG CGA ATC CTG GGC AAG ATG         727
Lys Lys Arg Met Gln Gly Pro Ile Pro Glu Arg Ile Leu Gly Lys Met
       135                 140                 145

ACT GTG GCG ATT GTG AAA GCA CTG TAC TAT CTG AAG GAG AAG CAT GGC         775
Thr Val Ala Ile Val Lys Ala Leu Tyr Tyr Leu Lys Glu Lys His Gly
150                 155                 160                 165

GTC ATC CAT CGC GAT GTC AAA CCC TCC AAC ATC CTG CTA GAT GAG CGG         823
Val Ile His Arg Asp Val Lys Pro Ser Asn Ile Leu Leu Asp Glu Arg
                170                 175                 180

GGC CAG ATC AAG CTC TGT GAC TTT GGC ATC AGT GGC CGC CTT GTT GAC         871
Gly Gln Ile Lys Leu Cys Asp Phe Gly Ile Ser Gly Arg Leu Val Asp
            185                 190                 195

TCC AAA GCC AAA ACA CGG AGT GCT GGC TGT GCT GCC TAT ATG GCT CCC         919
Ser Lys Ala Lys Thr Arg Ser Ala Gly Cys Ala Ala Tyr Met Ala Pro
        200                 205                 210

GAG CGC ATC GAC CCT CCA GAT CCC ACC AAG CCT GAC TAT GAC ATC CGA         967
Glu Arg Ile Asp Pro Pro Asp Pro Thr Lys Pro Asp Tyr Asp Ile Arg
    215                 220                 225

GCT GAT GTG TGG AGC CTG GGC ATC TCA CTG GTG GAG CTG GCA ACA GGA        1015
```

```
Ala Asp Val Trp Ser Leu Gly Ile Ser Leu Val Glu Leu Ala Thr Gly
230                 235                 240                 245

CAG TTC CCC TAT AAG AAC TGC AAG ACG GAC TTT GAG GTC CTC ACC AAA         1063
Gln Phe Pro Tyr Lys Asn Cys Lys Thr Asp Phe Glu Val Leu Thr Lys
                250                 255                 260

GTC CTA CAG GAA GAG CCC CCA CTC CTG CCT GGT CAC ATG GGC TTC TCA         1111
Val Leu Gln Glu Glu Pro Pro Leu Leu Pro Gly His Met Gly Phe Ser
            265                 270                 275

GGG GAC TTC CAG TCA TTT GTC AAA GAC TGC CTT ACT AAA GAT CAC AGG         1159
Gly Asp Phe Gln Ser Phe Val Lys Asp Cys Leu Thr Lys Asp His Arg
        280                 285                 290

AAG AGA CCA AAG TAT AAT AAG CTA CTT GAA CAC AGC TTC ATC ATC AAG         1207
Lys Arg Pro Lys Tyr Asn Lys Leu Leu Glu His Ser Phe Ile Ile Lys
    295                 300                 305

CAC TAT GAG ATA CTC GAG GTG GAT GTC GCG TCC TGG TTT AAG GAT GTC         1255
His Tyr Glu Ile Leu Glu Val Asp Val Ala Ser Trp Phe Lys Asp Val
310                 315                 320                 325

ATG GCG AAG ACC GAG TCC CCA AGG ACT AGT GGA GTC CTG AGT CAG CAC         1303
Met Ala Lys Thr Glu Ser Pro Arg Thr Ser Gly Val Leu Ser Gln His
                330                 335                 340

CAT CTG CCC TTC TTC AGT GGG AGT CTG GAG GAG TCT CCC ACT TCC CCA         1351
His Leu Pro Phe Phe Ser Gly Ser Leu Glu Glu Ser Pro Thr Ser Pro
                345                 350                 355

CCT TCT CCC AAG TCC TTC CCT CTG TCA CCA GCC ATC CCT CAG GCC CAG         1399
Pro Ser Pro Lys Ser Phe Pro Leu Ser Pro Ala Ile Pro Gln Ala Gln
            360                 365                 370

GCA GAG TGG GTC TCG GGC AGG TAGGGACCTG GAGTGGCCTG GTCCCACCCT CTGA       1454
Ala Glu Trp Val Ser Gly Arg
    375                 380

CCTCCTCCTC AGGCCACCAG TGTTGCCCTC TTCCCTTTTT AAAACAAAAT ACCCTTGTTT       1514

GTAAATCCTT AGACGCTTGA GAATAAAACC CTTCCCTTTT CTTCCGAAAA AAAAAAAAA        1574

AAAA                                                                    1578
```

(2) INFORMATION FOR SEQ ID NO:30:

(i) SEQUENCE CHARACTERISTICS:
        (A) LENGTH: 380 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:30:

```
Met Leu Gly Leu Pro Ser Thr Leu Phe Thr Pro Arg Ser Met Glu Ser
1               5                   10                  15

Ile Glu Ile Asp Gln Lys Leu Gln Glu Ile Met Lys Gln Thr Gly Tyr
                20                  25                  30

Leu Thr Ile Gly Gly Gln Arg Tyr Gln Ala Glu Ile Asn Asp Leu Glu
            35                  40                  45

Asn Leu Gly Glu Met Gly Ser Gly Thr Cys Gly Gln Val Trp Lys Met
        50                  55                  60

Arg Phe Arg Lys Thr Gly His Ile Ile Ala Val Lys Gln Met Arg Arg
65                  70                  75                  80

Ser Gly Asn Lys Glu Glu Asn Lys Arg Ile Leu Met Asp Leu Asp Val
                85                  90                  95

Val Leu Lys Ser His Asp Cys Pro Tyr Ile Val Gln Cys Phe Gly Thr
            100                 105                 110
```

```
Phe Ile Thr Asn Thr Asp Val Phe Ile Ala Met Glu Leu Met Gly Thr
        115                 120                 125
Cys Ala Glu Lys Leu Lys Lys Arg Met Gln Gly Pro Ile Pro Glu Arg
130                 135                 140
Ile Leu Gly Lys Met Thr Val Ala Ile Val Lys Ala Leu Tyr Tyr Leu
145                 150                 155                 160
Lys Glu Lys His Gly Val Ile His Arg Asp Val Lys Pro Ser Asn Ile
                165                 170                 175
Leu Leu Asp Glu Arg Gly Gln Ile Lys Leu Cys Asp Phe Gly Ile Ser
            180                 185                 190
Gly Arg Leu Val Asp Ser Lys Ala Lys Thr Arg Ser Ala Gly Cys Ala
        195                 200                 205
Ala Tyr Met Ala Pro Glu Arg Ile Asp Pro Pro Asp Pro Thr Lys Pro
210                 215                 220
Asp Tyr Asp Ile Arg Ala Asp Val Trp Ser Leu Gly Ile Ser Leu Val
225                 230                 235                 240
Glu Leu Ala Thr Gly Gln Phe Pro Tyr Lys Asn Cys Lys Thr Asp Phe
                245                 250                 255
Glu Val Leu Thr Lys Val Leu Gln Glu Glu Pro Pro Leu Leu Pro Gly
            260                 265                 270
His Met Gly Phe Ser Gly Asp Phe Gln Ser Phe Val Lys Asp Cys Leu
        275                 280                 285
Thr Lys Asp His Arg Lys Arg Pro Lys Tyr Asn Lys Leu Leu Glu His
290                 295                 300
Ser Phe Ile Ile Lys His Tyr Glu Ile Leu Glu Val Asp Val Ala Ser
305                 310                 315                 320
Trp Phe Lys Asp Val Met Ala Lys Thr Glu Ser Pro Arg Thr Ser Gly
                325                 330                 335
Val Leu Ser Gln His His Leu Pro Phe Phe Ser Gly Ser Leu Glu Glu
            340                 345                 350
Ser Pro Thr Ser Pro Pro Ser Pro Lys Ser Phe Pro Leu Ser Pro Ala
        355                 360                 365
Ile Pro Gln Ala Gln Ala Glu Trp Val Ser Gly Arg
370                 375                 380

(2) INFORMATION FOR SEQ ID NO:31:

(i) SEQUENCE CHARACTERISTICS:
        (A) LENGTH: 1598 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 82...1440

(xi) SEQUENCE DESCRIPTION: SEQ ID NO:31:

AGCGCAGGCG CAGTGCGGTG TTTGTCTACC CCGGACTGAC GGGTGGCCTG GCGGTGAGCG     60

GCGGCAGCGG CGGCGGGGAA G ATG GCG GCG TCC TCC CTG GAG CAG AAG CTG    111
                       Met Ala Ala Ser Ser Leu Glu Gln Lys Leu
                         1               5                  10

TCC CGC CTG GAA GCC AAG CTG AAG CAG GAG AAC CGT GAG GCC CGC AGG    159
Ser Arg Leu Glu Ala Lys Leu Lys Gln Glu Asn Arg Glu Ala Arg Arg
            15                  20                  25
```

```
AGG ATC GAC CTC AAC TTG GAT ATC AGC CCA CAG CGG CCC AGG CCC ACC        207
Arg Ile Asp Leu Asn Leu Asp Ile Ser Pro Gln Arg Pro Arg Pro Thr
                30                  35                  40

CTG CAA CTC CCA CTG GCC AAC GAT GGG GGC AGC CGC TCA CCA TCC TCA        255
Leu Gln Leu Pro Leu Ala Asn Asp Gly Gly Ser Arg Ser Pro Ser Ser
            45                  50                  55

GAG AGC TCC CCA CAG CAC CCT ACA CCC CCC ACC CGG CCC CGC CAC ATG        303
Glu Ser Ser Pro Gln His Pro Thr Pro Pro Thr Arg Pro Arg His Met
        60                  65                  70

CTG GGG CTC CCA TCA ACC TTG TTC ACA CCG CGC AGT ATG GAG AGC ATC        351
Leu Gly Leu Pro Ser Thr Leu Phe Thr Pro Arg Ser Met Glu Ser Ile
75                  80                  85                  90

GAG ATT GAC CAG AAG CTG CAG GAG ATC ATG AAG CAG ACA GGG TAC CTG        399
Glu Ile Asp Gln Lys Leu Gln Glu Ile Met Lys Gln Thr Gly Tyr Leu
                95                  100                 105

ACT ATC GGG GGC CAG CGT TAT CAG GCA GAA ATC AAT GAC TTG GAG AAC        447
Thr Ile Gly Gly Gln Arg Tyr Gln Ala Glu Ile Asn Asp Leu Glu Asn
            110                 115                 120

TTG GGT GAG ATG GGC AGT GGT ACC TGT GGT CAG GTG TGG AAG ATG CGG        495
Leu Gly Glu Met Gly Ser Gly Thr Cys Gly Gln Val Trp Lys Met Arg
        125                 130                 135

TTC CGG AAG ACA GGC CAC ATC ATT GCT GTT AAG CAA ATG CGG CGC TCT        543
Phe Arg Lys Thr Gly His Ile Ile Ala Val Lys Gln Met Arg Arg Ser
140                 145                 150

GGG AAC AAG GAA GAG AAT AAG CGC ATT TTG ATG GAC CTG GAT GTA GTA        591
Gly Asn Lys Glu Glu Asn Lys Arg Ile Leu Met Asp Leu Asp Val Val
155                 160                 165                 170

CTC AAG AGC CAT GAC TGC CCT TAC ATC GTT CAG TGC TTT GGC ACC TTC        639
Leu Lys Ser His Asp Cys Pro Tyr Ile Val Gln Cys Phe Gly Thr Phe
                175                 180                 185

ATC ACC AAC ACA GAC GTC TTT ATT GCC ATG GAG CTC ATG GGC ACA TGT        687
Ile Thr Asn Thr Asp Val Phe Ile Ala Met Glu Leu Met Gly Thr Cys
            190                 195                 200

GCA GAG AAG CTG AAG AAA CGA ATG CAG GGC CCC ATT CCA GAG CGA ATC        735
Ala Glu Lys Leu Lys Lys Arg Met Gln Gly Pro Ile Pro Glu Arg Ile
        205                 210                 215

CTG GGC AAG ATG ACT GTG GCG ATT GTG AAA GCA CTG TAC TAT CTG AAG        783
Leu Gly Lys Met Thr Val Ala Ile Val Lys Ala Leu Tyr Tyr Leu Lys
220                 225                 230

GAG AAG CAT GGC GTC ATC CAT CGC GAT GTC AAA CCC TCC AAC ATC CTG        831
Glu Lys His Gly Val Ile His Arg Asp Val Lys Pro Ser Asn Ile Leu
235                 240                 245                 250

CTA GAT GAG CGG GGC CAG ATC AAG CTC TGT GAC TTT GGC ATC AGT GGC        879
Leu Asp Glu Arg Gly Gln Ile Lys Leu Cys Asp Phe Gly Ile Ser Gly
                255                 260                 265

CGC CTT GTT GAC TCC AAA GCC AAA ACA CGG AGT GCT GGC TGT GCT GCC        927
Arg Leu Val Asp Ser Lys Ala Lys Thr Arg Ser Ala Gly Cys Ala Ala
            270                 275                 280

TAT ATG GCT CCC GAG CGC ATC GAC CCT CCA GAT CCC ACC AAG CCT GAC        975
Tyr Met Ala Pro Glu Arg Ile Asp Pro Pro Asp Pro Thr Lys Pro Asp
        285                 290                 295

TAT GAC ATC CGA GCT GAT GTG TGG AGC CTG GGC ATC TCA CTG GTG GAG       1023
Tyr Asp Ile Arg Ala Asp Val Trp Ser Leu Gly Ile Ser Leu Val Glu
300                 305                 310

CTG GCA ACA GGA CAG TTC CCC TAT AAG AAC TGC AAG ACG GAC TTT GAG       1071
Leu Ala Thr Gly Gln Phe Pro Tyr Lys Asn Cys Lys Thr Asp Phe Glu
315                 320                 325                 330

GTC CTC ACC AAA GTC CTA CAG GAA GAG CCC CCA CTC CTG CCT GGT CAC       1119
Val Leu Thr Lys Val Leu Gln Glu Glu Pro Pro Leu Leu Pro Gly His
                335                 340                 345
```

```
ATG GGC TTC TCA GGG GAC TTC CAG TCA TTT GTC AAA GAC TGC CTT ACT        1167
Met Gly Phe Ser Gly Asp Phe Gln Ser Phe Val Lys Asp Cys Leu Thr
            350                 355                 360

AAA GAT CAC AGG AAG AGA CCA AAG TAT AAT AAG CTA CTT GAA CAC AGC        1215
Lys Asp His Arg Lys Arg Pro Lys Tyr Asn Lys Leu Leu Glu His Ser
            365                 370                 375

TTC ATC ATC AAG CAC TAT GAG ATA CTC GAG GTG GAT GTC GCG TCC TGG        1263
Phe Ile Ile Lys His Tyr Glu Ile Leu Glu Val Asp Val Ala Ser Trp
        380                 385                 390

TTT AAG GAT GTC ATG GCG AAG ACC GAG TCC CCA AGG ACT AGT GGA GTC        1311
Phe Lys Asp Val Met Ala Lys Thr Glu Ser Pro Arg Thr Ser Gly Val
395                 400                 405                 410

CTG AGT CAG CAC CAT CTG CCC TTC TTC AGT GGG AGT CTG GAG GAG TCT        1359
Leu Ser Gln His His Leu Pro Phe Phe Ser Gly Ser Leu Glu Glu Ser
                415                 420                 425

CCC ACT TCC CCA CCT TCT CCC AAG TCC TTC CCT CTG TCA CCA GCC ATC        1407
Pro Thr Ser Pro Pro Ser Pro Lys Ser Phe Pro Leu Ser Pro Ala Ile
            430                 435                 440

CCT CAG GCC CAG GCA GAG TGG GTC TCG GGC AGG TAGGGACCTG GAGTGGCCTG      1460
Pro Gln Ala Gln Ala Glu Trp Val Ser Gly Arg
            445                 450

GTCCCACCCT CTGACCTCCT CCTCAGGCCA CCAGTGTTGC CCTCTTCCCT TTTTAAAACA     1520

AAATACCCTT GTTTGTAAAT CCTTAGACGC TTGAGAATAA AACCCTTCCC TTTTCTTCCG     1580

AAAAAAAAAA AAAAAAA                                                     1598

(2) INFORMATION FOR SEQ ID NO:32:

(i) SEQUENCE CHARACTERISTICS:
        (A) LENGTH: 453 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:32:

Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Ile Asp Leu Asn Leu
            20                  25                  30

Asp Ile Ser Pro Gln Arg Pro Arg Pro Thr Leu Gln Leu Pro Leu Ala
            35                  40                  45

Asn Asp Gly Gly Ser Arg Ser Pro Ser Ser Glu Ser Ser Pro Gln His
        50                  55                  60

Pro Thr Pro Pro Thr Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
                85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
            115                 120                 125

Gly Thr Cys Gly Gln Val Trp Lys Met Arg Phe Arg Lys Thr Gly His
        130                 135                 140

Ile Ile Ala Val Lys Gln Met Arg Arg Ser Gly Asn Lys Glu Glu Asn
145                 150                 155                 160
```

-continued

```
Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
        195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
        275                 280                 285

Ile Asp Pro Pro Asp Pro Thr Lys Pro Asp Tyr Asp Ile Arg Ala Asp
    290                 295                 300

Val Trp Ser Leu Gly Ile Ser Leu Val Glu Leu Ala Thr Gly Gln Phe
305                 310                 315                 320

Pro Tyr Lys Asn Cys Lys Thr Asp Phe Glu Val Leu Thr Lys Val Leu
                325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
        355                 360                 365

Pro Lys Tyr Asn Lys Leu Leu Glu His Ser Phe Ile Ile Lys His Tyr
    370                 375                 380

Glu Ile Leu Glu Val Asp Val Ala Ser Trp Phe Lys Asp Val Met Ala
385                 390                 395                 400

Lys Thr Glu Ser Pro Arg Thr Ser Gly Val Leu Ser Gln His His Leu
                405                 410                 415

Pro Phe Phe Ser Gly Ser Leu Glu Glu Ser Pro Thr Ser Pro Pro Ser
            420                 425                 430

Pro Lys Ser Phe Pro Leu Ser Pro Ala Ile Pro Gln Ala Gln Ala Glu
        435                 440                 445

Trp Val Ser Gly Arg
    450
```

(2) INFORMATION FOR SEQ ID NO:33:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:33:

```
Met Xaa Ser Pro Ala Pro Ala Pro Ser Gln Arg Ala Ala Leu Gln Leu
 1               5                  10                  15

Pro Leu Ala Asn Asp Gly Gly Ser Arg Ser Pro Ser Ser Glu Ser Ser
                20                  25                  30

Pro Gln His Pro Thr Pro Pro Thr Arg Pro Arg His
            35                  40
```

-continued (2) INFORMATION FOR SEQ ID NO:34:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO:34:

```
Glu Gly Gly Gly Val Lys His Met Ala Lys Leu Tyr Val Phe Tyr Gly
 1               5                  10                  15

Ala Gly Cys Met Glu Met Ser Asp Ile Glu Leu Leu Leu His Arg Asp
                20                  25                  30

Lys Pro Asn Leu Gly Lys Cys Asp Phe Gly Ser Gly Leu Ser Ala Gly
            35                  40                  45

Tyr Met Pro Glu Arg Tyr Val Ser Asp Trp Ser Gly Glu Ala Arg Pro
        50                  55                  60

Phe Leu Val Pro Leu Phe Phe Cys Leu Lys Arg Leu His
 65                 70                  75
```

CYTOKINE-, STRESS-, AND ONCOPROTEIN-ACTIVATED HUMAN PROTEIN KINASE KINASES

CROSS-REFERENCE TO RELATED APPLICATION

This application is a continuation-in-part of U.S. patent Ser. No. 08/530,950, filed Sep. 19, 1995 now U.S. Pat. No. 5,736,381, which is a continuation-in-part of application Ser. No. 08/446,083, filed May 19, 1995 now U.S. Pat. No. 5,804,427, which applications are incorporated herein by reference in their entirety.

STATEMENT AS TO FEDERALLY SPONSORED RESEARCH

This invention was made in part with National Cancer Institute research grant CA 58396 and CA 65861. The Federal government has certain rights in the invention.

BACKGROUND OF THE INVENTION

This invention relates to protein kinases.

Mitogen-activated protein (MAP) kinases are important mediators of signal transduction from the cell surface to the nucleus. Multiple MAP kinases have been described in yeast including SMK1, HOG1, MPK1, FUS3, and KSS1. In mammals, the MAP kinases identified are extracellular signal-regulated MAP kinase (ERK), c-Jun amino-terminal kinase (JNK), and p38 kinase (Davis (1994) Trends Biochem. Sci. 19:470). These MAP kinase isoforms are activated by dual phosphorylation on threonine and tyrosine.

Activating Transcription Factor-2 (ATF2), ATFa, and cAMP Response Element Binding Protein (CRE-BPa) are related transcription factors that bind to similar sequences located in the promoters of many genes (Ziff (1990) Trends in Genet. 6:69). The binding of these transcription factors leads to increased transcriptional activity. ATF2 binds to several viral proteins, including the oncoprotein Ela (Liu and Green (1994) Nature 368:520), the hepatitis B virus X protein (Maguire et al. (1991) Science 252:842), and the human T cell leukemia virus 1 tax protein (Wagner and Green (1993) Science 262:395). ATF2 also interacts with the tumor suppressor gene product Rb (Kim et al. (1992) Nature 358:331), the high mobility group protein HMG(I)Y (Du et al. (1993) Cell 74:887), and the transcription factors nuclear NF-κB (Du et al. (1993) Cell 74:887) and c-Jun (Benbrook and Jones (1990) Oncogene 5:295).

SUMMARY OF THE INVENTION

The invention is based on the identification and isolation of a new group of human mitogen-activated protein kinase kinases (MKKs). The MKK isoforms described herein, MKK3, MKK6, MKK4 (including MKK4-α, -β, and -γ), MKK7 (including murine MKK7, human MKK7, MKK7b, MKK7c, MKK7d, and MKK7e) have serine, threonine, and tyrosine kinase activity. MKK3, MKK4, and MKK6 specifically phosphorylate the human MAP kinase p38 at $Thr^{180}$ and $Tyr^{182}$. The MKK4 isoforms also phosphorylate the human MAP kinases JNK (including JNK1, JNK2, and JNK5) at $Thr^{183}$ and $Tyr^{185}$. The MKK7 isoforms phosphorylate JNK at $Thr^{183}$ and $Tyr^{185}$.

Accordingly, the invention features a substantially pure human MKK polypeptide having serine, threonine, and tyrosine kinase activity that specifically phosphorylates human p38 MAP kinase. MKK3 has the amino acid sequence of SEQ ID NO:2. The invention further includes MKK6 having the amino acid sequence of SEQ ID NO:4 and having serine, threonine, and tyrosine kinase activity that specifically phosphorylates human p38 MAP kinase.

The invention further features a substantially pure human MKK polypeptide having serine, threonine, and tyrosine kinase activity that specifically phosphorylates human p38 MAP kinase and JNK. MKK4 isoform MKK4-α has the amino acid sequence of SEQ ID NO:6. MKK4 isoform MKK4-β has the amino acid sequence of SEQ ID NO:8. MKK4 isoform MKK4-y has the amino acid sequence of SEQ ID NO:10.

The invention also features a substantially pure MKK polypeptide (MKK7) having serine, threonine, and tyrosine kinase activity that specifically phosphorylates mitogen-activated protein kinase JNK. MKK isoforms MKK7 (murine) and MKK7 (human) have the amino acid sequences of SEQ ID NOS:18 and 26, respectively. The MKK7 isoforms MKK7b, MKK7c, MKK7d, and MKK7e have the amino acid sequences of SEQ ID NO:20, SEQ ID NO:28, SEQ ID NO:30, and SEQ ID NO:32, respectively.

As used herein, the term "mitogen-activating protein kinase kinase" or "MKK" means a protein kinase which possesses the characteristic activity of phosphorylating and activating a human mitogen-activating protein kinase. Examples of MKKs include MKK3 and MKK6, which specifically phosphorylate and activate p38 MAP kinase at $Thr^{180}$ and $Tyr^{182}$, MKK4 isoforms which specifically phosphorylate and activate p38 MAP kinase at $Thr^{180}$ and $Tyr^{182}$, and JNK at $Thr^{183}$ and $Tyr^{185}$, and MKK7 isoforms which specifically phosphorylate JNK at $Thr^{183}$ and $Tyr^{185}$.

An "MKK7" is a mammalian isoform of mitogen-activated protein kinase kinase (MKK) polypeptide having serine, threonine, and tyrosine kinase activity, and phosphorylating mitogen-activated protein (MAP) kinase JNK but not p38.

The invention includes the specific p38 and JNK MKKs disclosed, as well as closely related MKKs which are identified and isolated by the use of probes or antibodies prepared from the polynucleotide and amino acid sequences disclosed for the MKKs of the invention. This can be done using standard techniques, e.g., by screening a genomic, cDNA, or combinatorial chemical library with a probe having all or a part of the nucleic acid sequences of the disclosed MKKs. The invention further includes synthetic polynucleotides having all or part of the amino acid sequence of the MKKs herein described.

The term "polypeptide" means any chain of amino acids, regardless of length or post-translational modification (e.g., glycosylation or phosphorylation), and includes natural proteins as well as synthetic or recombinant polypeptides and peptides.

The term "substantially pure," when referring to a polypeptide, means a polypeptide that is at least 60%, by weight, free from the proteins and naturally-occurring organic molecules with which it is naturally associated. A substantially pure MKK polypeptide (e.g., human) is at least 75%, more preferably at least 90%, and most preferably at least 99%, by weight, MKK polypeptide. A substantially pure MKK can be obtained, for example, by extraction from a natural source; by expression of a recombinant nucleic acid encoding a MKK polypeptide, or by chemically synthesizing the protein. Purity can be measured by any appropriate method, e.g., column chromatography, polyacrylamide gel electrophoresis, or HPLC analysis.

In one aspect, the invention features isolated polynucleotides which encode the MKKs of the invention. In one embodiment, the polynucleotide is the nucleotide sequence of SEQ ID NO:1. In other embodiments, the polynucleotide is the nucleotide sequence of SEQ ID NO:3, SEQ ID NO:5, SEQ ID NO:7, SEQ ID NO:9, SEQ ID NO:17, SEQ ID NO:19, SEQ ID NO:25, SEQ ID NO:27, SEQ ID NO:29, or SEQ ID NO:31, respectively.

As used herein, "polynucleotide" refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

An "isolated" polynucleotide is a nucleic acid molecule that is separated in some way from sequences in the naturally occurring genome of an organism. Thus, the term "isolated polynucleotide" includes any nucleic acid molecules that are not naturally occuring. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences, such as those described herein, or more stringent conditions. One skilled in the art can select posthybridization washing conditions, including temperature and salt concentrations, which reduce the number of nonspecific hybridizations such that only highly complementary sequences are identified e.g., hybridization in 50% formadide at 42° C., followed by washing in 0.2× and 0.1% SDS at 68° C. (Sambrook et al. (1989) in *Molecular Cloning*, 2d ed.; Cold Spring Harbor Laboratory Press, Cold Spring Harbor, N.Y.

The isolated polynucleotide sequences of the invention also include sequences complementary to the polynucleotides encoding MKK (antisense sequences). Antisense nucleic acids are DNA or RNA molecules that are complementary to at least a portion of a specific mRNA molecule (Weintraub (1990) Scientific American 262:40). The invention includes all antisense polynucleotides that inhibit production of MKK polypeptides. In the cell, the antisense nucleic acids hybridize to the corresponding mRNA, forming a double-stranded molecule. Antisense oligomers of about 15 nucleotides are preferred, since they are easily synthesized and introduced into a target MKK-producing cell. The use of antisense methods to inhibit the translation of genes is known in the art, and is described, e.g., in Marcus-Sakura Anal. Biochem., 172:289 (1988).

In addition, ribozyme nucleotide sequences for MKK are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific mRNA species, and 18-base recognition sequences are preferable to shorter recognition sequences.

The MKK polypeptides can also be used to produce antibodies that are immunoreactive or bind epitopes of the MKK polypeptides. Accordingly, one aspect of the invention features antibodies to the MKK polypeptides of the invention. The antibodies of the invention include polyclonal antibodies which include pooled monoclonal antibodies with different epitopic specificities, as well as distinct monoclonal antibody preparations. Monoclonal antibodies are made from antigen-containing fragments of the MKK polypeptide by methods known in the art (see, for example, Kohler et al. (1975) Nature 256:495).

The term "antibody" as used herein includes intact molecules as well as fragments thereof, such as Fa, $F(ab')_2$, and Fv, which are capable of binding an epitopic determinant. Antibodies that specifically bind MKK polypeptides can be prepared using intact polypeptides or fragments containing small peptides of interest as the immunizing antigen. The polypeptide or peptide used to immunize an animal can be derived from translated cDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

A molecule (e.g., antibody) that "specifically binds" is one that binds to a particular polypeptide, e.g., MKK7, but that does not substantially recoginze or bind to other molecules in a sample, e.g., a biological sample which includes MKK7. References to constructs made of an antibody (or fragment thereof) coupled to a compound comprising a detectable marker include constructs made by any technique, including chemical means and recombinant techniques.

The invention also features methods of identifying subjects at risk for MKK-mediated disorders by measuring activation of the MKK signal transduction pathway. Activation of the MKK signal transduction pathway can be determined by measuring MKK synthesis; activation of MKK isoforms; activation of MKK substrates p38 or JNK isoforms; or activation of p38 and JNK substrates such as ATF2, ATFa, CRE-BPa, and c-Jun. The term "JNK" or "JNK isoforms" includes JNK1, JNK2, and JNK3. The term "MKK substrate" as used herein includes MKK substrates, as well as MKK substrate substrates, e.g., p38, JNK, ATF2, and c-Jun.

In one embodiment, activation of the MKK signal transduction pathway is determined by measuring activation of the appropriate MKK signal transduction pathway substrates (for example, selected from p38, JNK isoforms, ATF2, ATFa, CRE-BPa, or c-Jun). MKK activity is measured by the rate of substrate phosphorylation as determined by quantitation of the rate of labelled phosphorus (e.g., [$^{32}$]P or [$^{33}$]P) incorporation. This can also be measured using phosphorylation-specific reagents, such as antibodies. The specificity of MKK substrate phosphorylation can be tested by measuring p38 activation, JNK activation, or both, or by employing mutated p38 or JNK molecules that lack the sites for MKK phosphorylations. Altered phosphorylation of the substrate relative to control values indicates alteration of the MKK signal transduction pathway, and increased risk in a subject of an MKK-mediated disorder. MKK activation of p38 and JNK can be detected in a coupled assay with the MKK signal transduction substrate ATF2, or related compounds such as ATFa and CRE-BPa. Activation can also be detected with the substrate c-Jun. When ATF2 is included in the assay, it is present as an intact protein or as a fragment of the intact protein, e.g., the activation domain (residues 1–109, or a portion thereof). ATF2 is incubated with a test sample in which MKK activity is to be measured and [$\gamma$-$^{32}$pP]ATP, under conditions sufficient to allow the phosphorylation of ATF2. ATF2 is then isolated and the amount of phosphorylation quantitated. In a specific embodiment, ATF2 is isolated by immunoprecipitation, resolved by SDS-PAGE, and detected by autoradiography.

In another embodiment, activation of the MKK signal transduction pathway is determined by measuring the level of MKK expression in a test sample. In a specific embodiment, the level of MKK expression is measured by Western blot analysis. The proteins present in a sample are fractionated by gel electrophoresis, transferred to a membrane, and probed with labeled antibodies to MKK. In another specific embodiment, the level of MKK expression is measured by Northern blot analysis. Total cellular or polyadenylated [poly(A)$^+$] mRNA is isolated from a test sample. The RNA is fractionated by electrophoresis and transferred to a membrane. The membrane is probed with labeled MKK cDNA. In another embodiment, MKK expression is measured by quantitative PCR applied to expressed mRNA.

The MKKs of the invention are useful for screening reagents that modulate MKK activity. MKKs are activated by phosphorylation. Accordingly, in one aspect, the invention features methods for identifying a reagent which modulates MKK activity, by incubating MKK with the test reagent and measuring the effect of the test reagent on MKK synthesis, phosphorylation, function, or activity. In one embodiment, the test reagent is incubated with MKK and [$^{32}$] P-ATP, and the rate of MKK phosphorylation determined, as described above. In another embodiment, the test reagent is incubated with a cell transfected with an MKK polynucleotide expression vector, and the effect of the test reagent on MKK transcription is measured by Northern blot analysis, as described above. In a further embodiment, the effect of the test reagent on MKK synthesis is measured by Western blot analysis using an antibody to MKK. In still another embodiment, the effect of a reagent on MKK activity is measured by incubating MKK with the test reagent, [$^{32}$] P-ATP, and a substrate in the MKK signal transduction pathway, including one or more of p38, JNK, and ATF2. The rate of substrate phosphorylation is determined as described above.

The term "modulation of MKK activity" includes inhibitory or stimulatory effects.

The invention is particularly useful for screening reagents that inhibit MKK activity. Such reagents are useful for the treatment or prevention of MKK-mediated disorders, for example, inflammation and oxidative damage.

The invention further features a method of treating a MKK-mediated disorder by administering to a subject in need thereof, an effective dose of a therapeutic reagent that inhibits the activity of MKK.

An "MKK-mediated disorder" is a pathological condition resulting, at least in part, from excessive activation of an MKK signal transduction pathway. The MKK signal transduction pathways are activated by several factors, including inflammation and stress. MKK-mediated disorders include, for example, ischemic heart disease, burns due to heat or radiation (UV, X-ray, $\gamma$, $\beta$, etc.), kidney failure, liver damage due to oxidative stress or alcohol, respiratory distress syndrome, septic shock, rheumatoid arthritis, autoimmune disorders, and other types of inflammatory diseases.

A "therapeutic reagent" any compound or molecule that achieves the desired effect on an MKK-mediated disorder when administered to a subject in need thereof.

MKK-mediated disorders further include proliferative disorders, particularly disorders that are stress-related. Examples of stress-related MKK-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents inhibit the activity or expression of MKK inhibit cell growth or cause apoptosis.

A therapeutic reagent that "inhibits MKK activity" interferes with a MKK-mediated signal transduction pathway. For example, a therapeutic reagent can alter the protein kinase activity of MKK, decrease the level of MKK transcription or translation, e.g., an antisense polynucleotide able to bind MKK mRNA, or suppress MKK phosphorylation of p38, JNK, or ATF2, thus disrupting the MKK-mediated signal transduction pathway. Examples of such reagents include antibodies that bind specifically to MKK polypeptides, and fragments of MKK polypeptides that competitively inhibit MKK polypeptide activity.

A therapeutic reagent that "enhances MKK activity" supplements a MKK-mediated signal transduction pathway. Examples of such reagents include the MKK polypeptides themselves, which can be administered in instances where the MKK-mediated disorder is caused by under expression of the MKK polypeptide, or expression of a mutant MKK polypeptide. In addition, portions of DNA encoding an MKK polypeptide can be introduced into cells that under express an MKK polypeptide.

A "therapeutically effective amount" is an amount of a reagent sufficient to decrease or prevent the symptoms associated with the MKK-mediated disorder.

Therapeutic reagents for treatment of MKK-mediated disorders identified by the methods of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the MKK-mediated disorder. These methods include the use of viral vectors (e.g., retrovirus, adenovirus, vaccinia virus, or herpes virus), colloid dispersions, and liposomes.

The materials of the invention are ideally suited for the preparation of a kit for the detection of the level or activity of MKK. Accordingly, the invention features a kit comprising an antibody that binds MKK, or a nucleic acid probe that hybridizes to a MKK polynucleotide, and suitable buffers. The probe or monoclonal antibody can be labeled to detect binding to a MKK polynucleotide or protein. In a preferred embodiment, the kit features a labeled antibody to MKK.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, and from the claims.

DETAILED DESCRIPTION

The drawings will first be described.

Drawings

FIG. 1 is a comparison of the amino acid sequences of MKK3 (SEQ ID NO:2), MKK4-α (SEQ ID NO:6), the human MAP kinase kinases MEK1 (SEQ ID NO:11) and MEK2 (SEQ ID NO:12), and the yeast HOG1 MAP kinase kinase PBS2 (SEQ ID NO:13). Sequences were compared using the PILE-UP program (version 7.2; Wisconsin Genetics Computer Group). The protein sequences are presented in single letter code (A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp, and Y, Tyr). The PBS2 sequence is truncated at both the $NH_2$— (<) and COOH— (>) termini. Gaps introduced into the sequences to optimize the alignment are illustrated by a dash. Identical residues are indicated by a period. The sites of activating phosphorylation in MEK are indicated by asterisks.

FIG. 2A is a dendrogram showing the relationship between members of the human and yeast MAP kinase kinases. The dendrogram was created by the unweighted pair-group method with the use of arithmetic averages (PILE-UP program). The human (hu) MAP kinase kinases MEK1, MEK2, MKK3, and MKK4; the Saccharomyces cerevisiae (sc) MAP kinase kinases PBS2, MKK1, and STE7; and the Saccharomyces pombe (sp) MAP kinase kinases WIS1 and BYR1 are presented.

FIG. 2B is a dendrogram showing the relationship between MKKs. The dendrogram was created as described for FIG. 2A.

FIG. 3 is a schematic representation of the ERK, p38, and JNK signal transduction pathways. MEK1 and MEK2 are activators of the ERK subgroup of MAP kinase. MKK3 and MKK4 are activators of the p38 MAP kinase. MKK4 is identified as an activator of both the p38 and JNK subgroups of MAP kinase.

FIGS. 4A–4D are a representation of the nucleic acid (SEQ ID NO:1) and amino acid sequences (SEQ ID NO:2) for MKK3.

FIGS. 5A–5C are a representation of the nucleic acid (SEQ ID NO:3) and amino acid sequences (SEQ ID NO:4) for MKK6.

FIGS. 6A–6F are a representation of the nucleic acid (SEQ ID NO:5) and amino acid sequences (SEQ ID NO:6) for MKK4β.

FIGS. 7A–7F are a representation of the nucleic acid (SEQ ID NO:7) and amino acid sequences (SEQ ID NO:8) for MKK4α.

FIGS. 8A–8F are a representation of the nucleic acid (SEQ ID NO:9) and amino acid sequences (SEQ ID NO:10) for MKK4γ.

FIG. 9 is a representation of the deduced primary structure of MKK7 (SEQ ID NO:18) compared with hep (SEQ ID NO:21), the MAP kinase kinases MEK1 (MKK1; SEQ ID NO:11), MEK2 (MKK2; SEQ ID NO:12), MKK3 (SEQ ID NO:2), MKK4T (SEQ ID NO:10), MKK5 (SEQ ID NO:22), and MKK6 (SEQ ID NO:4) using the PILE-UP program (version 7,2; Wisconsin Genetics Computer Group). Gaps introduced into the sequences to optimize the alignment are illustrated with a dash (-). Identity is indicated with a dot (.). The sites of activating phosphorylation of MAP kinase kinases (2, 27, 37, and 38) are indicated with asterisks (*).

FIGS. 10A–10D are a representation of the nucleic acid (SEQ ID NO:17) and amino acid (SEQ ID NO:18) sequences for MKK7.

FIGS. 11A–11D are a representation of the nucleic acid (SEQ ID NO:19) and amino acid (SEQ ID NO:20) sequences of MKK7b.

FIGS. 12A–12B are a representation of the nucleic acid (SEQ ID NO:25) and amino acid (SEQ ID NO:26) sequences of human MKK7.

FIGS. 13A–13D are a representation of the nucleic acid (SEQ ID NO:27) and amino acid (SEQ ID NO:28) sequences of murine MKK7c.

FIGS. 14A–14D are a representation of the nucleic acid (SEQ ID NO:29) and amino acid (SEQ ID NO:30) sequences of murine MKK7d.

FIGS. 15A–15D are a representation of the nucleic acid (SEQ ID NO:31) and amino acid (SEQ ID NO:32) sequences of murine MKK7e.

Figure 16A:
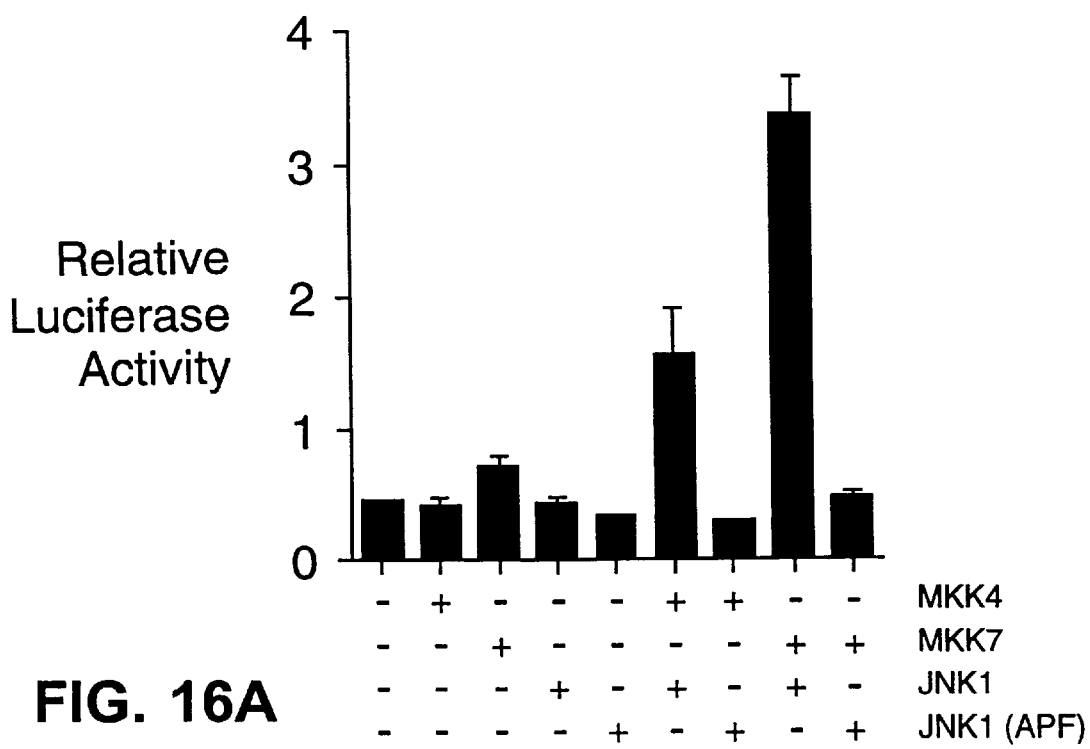

FIG. 16A is a graph of data from a transfection assay in which cells were co-transfected with AP-1 reporter plasmid pTRE-Luciferase with expression vectors for MKK4, MKK7, JNK1, JNK1(APF), or control vector.

Figure 16B:
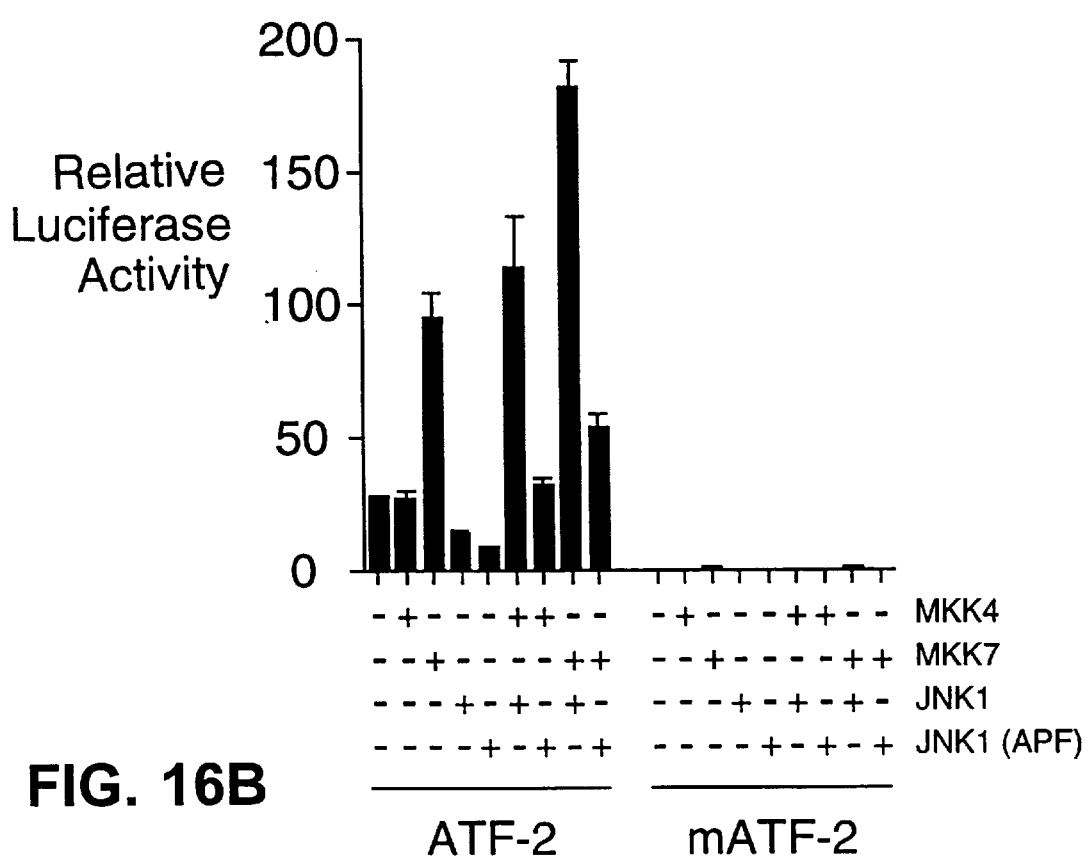

FIG. 16B is a graph of a transfection assay in which cells were co-transfected with a GAL4-ATF2 fusion vector and an expression vector for MKK4, MKK7, JNK1, JNK1(APF), or control vector.

HUMAN MITOGEN-ACTIVATED PROTEIN KINASE KINASES

The human MAP kinase kinases MKK3 and MKK4 (MKK3/4), and MKK7, described herein mediate the transduction of specific signals from the cell surface to the nucleus along specific pathways. These signal transduction pathways are initiated by factors such as cytokines, UV radiation, osmotic shock, and oxidative stress. Activation of MKK3/4, MKK6, and MKK7 results in activation of the MAP kinases. p38 is activated by MKK3 and MKK4. JNK is activated by MKK4 and MKK7. p38 and JNK in turn activate a group of related transcription factors such as ATF2, ATFa, and CRE-BPa. These transcription factors in turn activate expression of specific genes. For example, ATF2 in known to activate expression of human T cell leukemia virus 1 (Wagner and -Green (1993) Science 262:395), transforming growth factor-b2 (Kim et al. (1992) supra), interferon-β (Du et al. (1993) Cell 74:887), and E-selectin (DeLuca et al. (1994) J. Biol. Chem. 269:19193). In addition, ATF2 is implicated in the function of a T cell-specific enhancer (Georgopoulos et al. (1992) Mol. Cell. Biol. 12:747).

The JNK group of MAP kinases is activated by exposure of cells to environmental stress or by treatment of cells with pro-inflammatory cytokines (Gupta et al. (1994) EMBO J. 15:2760–2770; Dérijard et al. (1991) Cell 76:1025– 1037;

Kyriakis et al. (1994) Nature 369:156–160; Sluss et al. (1994) Mol. Cell. Biol. 14:8376–8384; Kallunki et al. (1994) Genes & Dev. 8:2996–3007). Targets of the JNK signal transduction pathway include the transcription factors ATF2 and c-jun (Whitmarsh & Davis (1996) J. Mol. Med. 74:589–607). These transcription factors are members of the bZIP group that bind as homo- and hetero-dimeric complexes to AP-1 and AP-1-like sites in the promoters of many genes (Curran & Franza (1988) Cell 55:395–397). JNK binds to an $NH_2$-terminal region of ATF2 and c-Jun and phosphorylates two sites within the activation domain of each transcription factor (Dérijard et al. (1994) Cell 76:1025–1037; van Dam et al. (1995) EMBO J. 14:1798–1811; Livingstone et al. (1995) EMBO J. 14:1785–1797). This phosphorylation leads to increased transcriptional activity (Whitmarsh, supra). Together, these biochemical studies indicate that the JNK signal transduction pathway contributes to the regulation of AP-1 transcriptional activity in response to cytokines and environmental stress (Whitmarsh, supra). Strong support for this hypothesis is provided by genetic evidence indicating that the JNK signaling pathway is required for the normal regulation of AP-1 transcriptional activity (Yang et al. (1997) Proc. Natl. Acad. Sci. USA, 94:3004–3009).

JNK is activated by dual phosphorylation on Thr-183 and Tyr-185 (Dérijard, supra). MKK4 (also known as SEK1) was the first MAP kinase kinase identified as a component of the JNK signal transduction pathway (Dérijard et al. (1995) Science 267:682–685; Lin et al. (1995) Science 268:286–290; Sanchez et al. (1994) Nature 372:794–798). Biochemical studies demonstrate that MKK4 phosphorylates and activates JNK (Dérijard et al. (1995) Science 267:682–685; Lin et al. (1995) Science 268:286–290; Sanchez et al. (1994) Nature 372:794–798). However, the function of MKK4 may not be restricted to the JNK signal transduction pathway because MKK4 also phosphorylates and activates p38 MAP kinase (Dérijard et al. (1995) Science 267:682-685; Lin et al. (1995) Science 268:286–290). This specificity of MKK4 to activate both JNK and p38 MAP kinase provides a mechanism that may account for the co-ordinate activation of these MAP kinases in cells treated with cytokines or environmental stress (Davis (1994) Trends Biochem. Sci. 19:470–473). However, this co-ordinate activation is not always observed. For example, JNK activation in the liver correlates with decreased p38 MAP kinase activity (Mendelson et al. (1996) Proc. Natl. Acad. Sci. USA 93:12908–12913). These data suggest that the properties of MKK4 are insufficient to account for the regulation of JNK in vivo.

The isolation of human MKKs is described in Example 1, Example 22, Dérijard et al. ((1995) Science 267:682–685, hereby specifically incorporated by reference), and Raingeaud et al. ((1995) Mol. Cell. Biol. 16:1247–1255). Distinctive regions of the yeast PBS2 sequence were used to design polymerase chain reaction (PCR) primers. Amplification of human brain mRNA with these primers resulted in the formation of specific products which were cloned into a plasmid vector and sequenced. Two different complementary DNAs (cDNAs) that encoded human protein kinases were identified: one encoding a 36 kD protein (MKK3), and one encoding a 44 kD protein (MKK4). MKK4 includes 3 isoforms that vary slightly at the $NH_2$-terminal, identified as α, β, and γ. The amino acid sequences of MKK3 (SEQ ID NO:2), MKK4-α (SEQ ID NO:6), MKK4-β (SEQ ID NO:8), and MKK4-γ (SEQ ID NO:10) are shown in FIG. 1. The nucleic acid and amino acid sequences of MKK3 (FIG. 4), MKK6 (FIG. 5), MKK4-α (FIG. 6), MKK4-β (FIG. 7), and MKK4-γ (FIG. 8) are also provided. MKK6 was isolated from a human skeletal muscle library by cross-hybridization with MKK3. Except for differences at the N-terminus, MKK6 is highly homologous to MKK3. Other human MKK3 and MKK4 isoforms that exist can be identified by the method described in Example 1.

The expression of these human MKK isoforms was examined by Northern (RNA) blot analysis of mRNA isolated from eight adult human tissues (Example 2). Both protein kinases were found to be widely expressed in human tissues, with the highest expression seen in skeletal muscle tissue.

The substrate specificity of MKK3 was investigated in an in vitro phosphorylation assay with recombinant epitope-tagged MAP kinases (JNK1, p38, and ERK2) as substrates (Example 3). MKK3 phosphorylated p38, but did not phosphorylate JNK1 or ERK2. Phosphoaminoacid analysis of p38 demonstrated the presence of a phosphothreonine and phosphotyrosine. Mutational analysis of p38 demonstrated that replacement of phosphorylation sites $Thr^{180}$ and $Tyr^{182}$ with Ala and Phe, respectively, blocked p38 phosphorylation. These results establish that MKK3 functions in vitro as a p38 MAP kinase kinase.

Studies of the in vitro substrate specificity of MKK4 are described in Example 4. MKK4 incubated with [$\gamma$-$^{32}$P]ATP, and JNK1, p38, or ERK2 was found to phosphorylate :both p38 and JNK1. MKK4 activation of JNK and p38 was also studied by incubating MKK4 with wild-type or mutated JNK1 or p38. The p38 substrate ATF2 was included in each assay. MKK4 was found to exhibit less autophosphorylation than MKK3. MKK4 was also found to be a substrate for activated MAP kinase. Unlike MKK3, MKK4 was also found to activate JNK1. MKK4 incubated with wild-type JNK1, but not mutated JNK1, resulted in increased phosphorylation of ATF2. These results establish that MKK4 is a p38 MAP kinase kinase that also phosphorylates the JNK subgroup of MAP kinases.

In vivo activation of p38 by UV-stimulated MKK3 is described in Example 5. Cells expressing MKK3 were exposed in the presence or absence of UV radiation. MKK3 was isolated by immunoprecipitation and used for protein kinase assays with the substrates p38 or JNK. ATF2 was included in some assays as a substrate for p38 and JNK. MKK3 from non-activated cultured COS cells caused a small amount of phosphorylation of p38 MAP kinase, resulting from basal activity of MKK3. MKK3 from UV-irradiated cells caused increased phosphorylation of p38 MAP kinase, but not of JNK1. An increase in p38 activity was also detected in assays in which ATF2 was included as a substrate. These results establish that MKK3 is activated by UV radiation.

The effect of expression of MKK3 and MKK4 on p38 activity was examined in COS-1 cells (Example 6). Cells were transfected with a vector encoding p38 and a MEK1, MKK3, or MKK4. Some of the cells were also exposed to EGF or UV radiation. p38 was isolated by immunoprecipitation and assayed for activity with [$\gamma$-$^{32}$p]ATP and ATF2. The expression of the ERK activator MEK1 did not alter p38 phosphorylation of ATF2. In contrast, expression of MKK3 or MKK4 caused increased activity of p38 MAP kinase. The activation of p38 caused by MKK3 and MKK4 was similar to that observed in UV-irradiated cells, and was much greater than that detected in EGF-treated cells. These in vitro results provide evidence that MKK3 and MKK4 activate p38 in vivo.

A series of experiments was conducted to examine the potential regulation of ATF2 by JNK1. These experiments are described in Gupta et al. (1995) Science 267:389–393, hereby specifically incorporated by reference. The effect of UV radiation on ATF2 phosphorylation was investigated in COS-1 cells transfected with and without epitope-tagged JNK1 (Example 7). Cells were exposed to UV radiation, and JNK1 and JNK2 visualized by in-gel protein kinase assay with the substrate ATF2. JNK1 and JNK2 were detected in transfected and non-transfected cells exposed to UV radiation; however, JNK1 levels were higher in the transfected cells. These results demonstrate that ATF2 is a substrate for the JNK1 and JNK2 protein kinases, and that these protein kinases are activated in cells exposed to UV light.

The site of JNK1 phosphorylation of ATF2 was examined by deletion analysis (Example 8). Progressive $NH_2$-terminal domain deletion GST-ATF2 fusion proteins were generated, and phosphorylation by JNK1 isolated from UV-irradiated cells was examined. The results showed that JNK1 requires the presence of ATF2 residues 1–60 for phosphorylation of the $NH_2$-terminal domain of ATF2.

The ATF2 residues required for binding of JNK1 were similarly examined. JNK1 was incubated with immobilized ATF2, unbound JNK1 was removed by extensive washing, and bound JNK1 was detected by incubation with $[\gamma^{-32}p]$ ATP. Results indicate that residues 20 to 60 of ATF2 are required for binding and phosphorylation by JNK1. A similar binding interaction between ATF2 and the 55 kD JNK2 protein kinase has also been observed.

Phosphorylation by JNK1 was shown to reduce the electrophoretic mobility of ATF2 (Example 9). Phosphoamino acid analysis of the full-length ATF2 molecule (residues 1–505) demonstrated that JNK phosphorylated both Thr and Ser residues. The major sites of Thr and Ser phosphorylation were located in the $NH_2$ and COOH terminal domains, respectively. The $NH_2$-terminal sites of phosphorylation were identified as $Thr^{69}$ and $Thr^{71}$ by phosphopeptide mapping and mutational analysis. These sites of Thr phosphorylation are located in a region of ATF2 that is distinct from the sub-domain required for JNK binding (residues 20 to 60).

The reduced electrophoretic mobility seen with phosphorylation of ATF2 was investigated further (Example 10). JNK1 was activated in CHO cells expressing JNK1 by treatment with UV radiation, pro-inflammatory cytokine interleukin-1 (IL-1), or serum. A decreased electrophoretic mobility of JNK1-activated ATF2 was observed in cells treated with UV radiation and IL-1. Smaller effects were seen after treatment of cells with serum. These results indicate that ATF2 is an in vivo substrate for JNK1.

The effect of UV radiation on the properties of wild-type ($Thr^{69,71}$) and phosphorylation-defective ($Ala^{69,71}$) ATF2 molecules was investigated (Example 11). Exposure to UV caused a decrease in the electrophoretic mobility of both endogenous and over-expressed wild-type ATF2. This change in electrophoretic mobility was associated with increased ATF2 phosphorylation. Both the electrophoretic mobility shift and increased phosphorylation were blocked by the replacement of $Thr^{69}$ and $Thr^{71}$ with Ala in ATF2. This mutation also blocked the phosphorylation of ATF2 on Thr residues in vivo.

Transcriptional activities of fusion proteins consisting of the GAL4 DNA binding domain and wild-type or mutant ATF2 were examined (Example 12). Point mutations at $Thr^{69}$ and/or $Thr^{71}$ of ATF2 significantly decreased the transcriptional activity of ATF2 relative to the wild-type molecule, indicating the physiological relevance of phosphorylation at these sites for activity.

The binding of JNK1 to the $NH_2$-terminal activation domain of ATF2 (described in Example 8) suggested that a catalytically inactive JNK1 molecule could function as a dominant inhibitor of the wild-type JNK1 molecule. This hypothesis was investigated by examining the effect of a catalytically inactive JNK1 molecule on ATF2 function (Example 13). A catalytically-inactive JNK1 mutant was constructed by replacing the sites of activating $Thr^{183}$ and $Tyr^{185}$ phosphorylation with Ala and Phe, respectively ($Ala^{183}$, $Phe^{185}$, termed "dominant-negative"). Expression of wild-type JNK1 caused a small increase in serum-stimulated ATF2 transcriptional activity. In contrast, dominant-negative JNK1 inhibited both control and serum-stimulated ATF2 activity. This inhibitory effect results from the non-productive binding of the JNK1 mutant to the ATF2 activation domain, effectively blocking ATF2 phosphorylation.

The tumor suppressor gene product Rb binds to ATF2 and increases ATF2-stimulated gene expression (Kim et al. (1992) Nature 358:331). Similarly, the adenovirus oncoprotein E1A associates with the DNA binding domain of ATF2 and increases ATF2-stimulated gene expression by a mechanism that requires the $NH_2$-terminal activation domain of ATF2 (Liu and Green (1994) Nature 368:520). ATF2 transcriptional activity was investigated with the luciferase reporter gene system in control, Rb-treated, and E1A-treated cells expressing wild-type or mutant ATF2 molecules (Example 14). Rb and E1A were found to increase ATF2-stimulated gene expression of both wild-type and mutant ATF2. However, mutant ATF2 caused a lower level of reporter gene expression than did wild-type ATF2. Together, these results indicate a requirement for ATF2 phosphorylation (on $Thr^{69}$ and $Thr^{71}$) plus either Rb or E1A for maximal transcriptional activity. Thus, Rb and E1A act in concert with ATF2 phosphorylation to control transcriptional activity.

A series of experiments were conducted to examine the action of p38 activation and to establish the relationship of the p38 MAP kinase pathway to the ERK and JNK signal transduction pathways (Raingeaud et al. (1995) J. Biol. Chem. 270:7420, hereby specifically incorporated by reference). Initially, the substrate specificity of p38 was investigated by incubating p38 with proteins that have been demonstrated to be substrates for the ERK and/or JNK groups of MAP kinases (Example 15). We examined the phosphorylation of MBP (Erickson et al. (1990) J. Biol. Chem. 265:19728), EGF-R (Northwood et al. (1991) J. Biol. Chem. 266:15266), cytoplasmic phospholipase $A_2$ ($cPLA_2$) (Lin et al. (1993) Cell 72:269), c-Myc (Alvarez et al. (1991) J. Biol. Chem. 266:15277), IκB, c-Jun, and wild-type ($Thr^{69,71}$) or mutated ($Ala^{69,71}$) ATF2. p38 phosphorylated MBP and EGF-R, and to a lesser extent IκB, but not the other ERK substrates, demonstrating that the substrate specificity of p38 differs from both the ERK and JNK groups of MAP kinases. Wild-type ATF2, but not mutated ATF2 ($Ala^{69,71}$), was found to be an excellent p38 substrate.

The phosphorylation of ATF2 by p38 was associated with an electrophoretic mobility shift of ATF2 during polyacrylamide gel electrophoresis. We tested the hypothesis that p38 phosphorylates ATF2 at the same sites as JNK1 by replacing $Thr^{69}$ and $Thr^{71}$ with Ala ($Ala^{69,71}$). It was found that p38 did not phosphorylate mutated ATF2, which demonstrates that p38 phosphorylates ATF2 within the $NH_2$-terminal activation domain on $Thr^{69}$ and $Thr^7$.

A comparison of the binding of JNK and p38 to ATF2 was conducted by incubating extracts of cells expressing JNK1 or p38 with epitope alone (GST) or GST-ATF2 (residues 1–109 containing the activation domain) (Example 16). Bound protein kinases were detected by Western blot analysis. The results demonstrate that both p38 and JNK bind to the ATF2 activation domain.

EGF and phorbol ester are potent activators of the ERK signal transduction pathway (Egan and Weinberg (1993) Nature 365:781), causing maximal activation of the ERK sub-group of MAP kinases. These treatments, however, cause only a small increase in JNK protein kinase activity (Dérijard et al. (1994) supra; Hibi et al. (1993) supra). The effects of EGF or phorbol esters, as well UV radiation, osmotic shock, interleukin-l, tumor necrosis factor, and LPS, on p38 activity were all tested (Example 17). Significantly, EGF and phorbol ester caused only a modest increase in p38 protein kinase activity, whereas environmental stress (UV radiation and osmotic shock) caused a marked increase in the activity of both p38 and JNK. Both p38 and JNK were activated in cells treated with pro-inflammatory cytokines (TNF and IL-1) or endotoxic LPS. Together, these results indicate that p38, like JNK, is activated by a stress-induced signal transduction pathway.

ERKs and JNKs are activated by dual phosphorylation within the motifs Thr-Glu-Tyr and Thr-Pro-Tyr, respectively. In contrast, p38 contains the related sequence Thr-Gly-Tyr. To test whether this motif is relevant to the activation of p38, the effect of the replacement of Thr-Gly-Tyr with Ala-Gly-Phe was examined (Example 18). The effect of UV radiation on cells expressing wild-type ($Thr^{180}$, $Tyr^{182}$) or mutant p38 ($Ala^{180}$, $Phe^{182}$) was studied. Western blot analysis using an anti-phosphotyrosine antibody demonstrated that exposure to UV radiation caused an increase in the Tyr phosphorylation of p38. The increased Tyr phosphorylation was confirmed by phosphoamino acid analysis of p38 isolated from [$\gamma$-$^{32}$p]phosphate-labeled cells. This analysis also demonstrated that UV radiation caused increased Thr phosphorylation of p38. Significantly, the increased phosphorylation on $Thr^{180}$ and $Tyr^{182}$ was blocked by the $Ala^{180}$/$Phe^{182}$ mutation. This result demonstrates that UV radiation causes increased activation of p38 by dual phosphorylation.

It has recently been demonstrated that ERK activity is regulated by the mitogen-induced dual specificity phosphatases MKP1 and PAC1 (Ward et al. (1994) Nature 367:651). The activation of p38 by dual phosphorylation (Example 18) raises the possibility that p38 may also be regulated by dual specificity phosphatases. We examined the effect of MKP1 and PAC1 on p38 MAP kinase activation (Example 19). Cells expressing human MKP1 and PAC1 were treated with and without UV radiation, and p38 activity measured. The expression of PAC1 or MKP1 was found to inhibit p38 activity. The inhibitory effect of MKP1 was greater than PAC1. In contrast, cells transfected with a catalytically inactive mutant phosphatase (mutant PAC1 $Cys^{257}$/Ser) did not inhibit p38 MAP kinase. These results demonstrate that p38 can be regulated by dual specificity phosphatases PAC1 and MKP1.

The sub-cellular distribution of p38 MAP kinase was examined by indirect immunofluorescence microscopy (Example 20). Epitope-tagged p38 MAP kinase was detected using the M2 monoclonal antibody. Specific staining of cells transfected with epitope-tagged p38 MAP kinase was observed at the cell surface, in the cytoplasm, and in the nucleus. Marked changes in cell surface and nuclear p38 MAP kinase were not observed following UV irradiation, but an increase in the localization of cytoplasmic p38 MAP kinase to the perinuclear region was detected.

A series of experiments were conducted to study the activation of JNK by hyper-osmotic media (Example 21). These experiments were reported by Galcheva-Gargova et al. (1994) Science 265:806, hereby specifically incorporated by reference. CHO cells expressing epitope-tagged JNK1 were incubated with 0–1000 mM sorbitol, and JNK1 activity measured in an immune complex kinase assay with the substrate c-Jun. Increased JNK1 activity was observed in cells incubated for 1 hour with 100 mM sorbitol. Increased JNK1 activity was observed within 5 minutes of exposure to 300 mM sorbitol. Maximal activity was observed 15 to 30 minutes after osmotic shock with a progressive decline in JNK1 activity at later times. The activation of JNK by osmotic shock was studied in cells expressing wild-type ($Thr^{183}$, $Tyr^{185}$) or mutated ($Ala^{183}$, $Phe^{185}$) JNK1. JNK1 activity was measured after incubation for 15 minutes with or without 300 mM sorbitol. Cells expressing wild-type JNK1 showed increased JNK1 activity, while cells expressing mutated JNK1 did not. These results demonstrate that the JNK signal transduction pathway is activated in cultured mammalian cells exposed to hyper-osmotic media.

Figure 3:
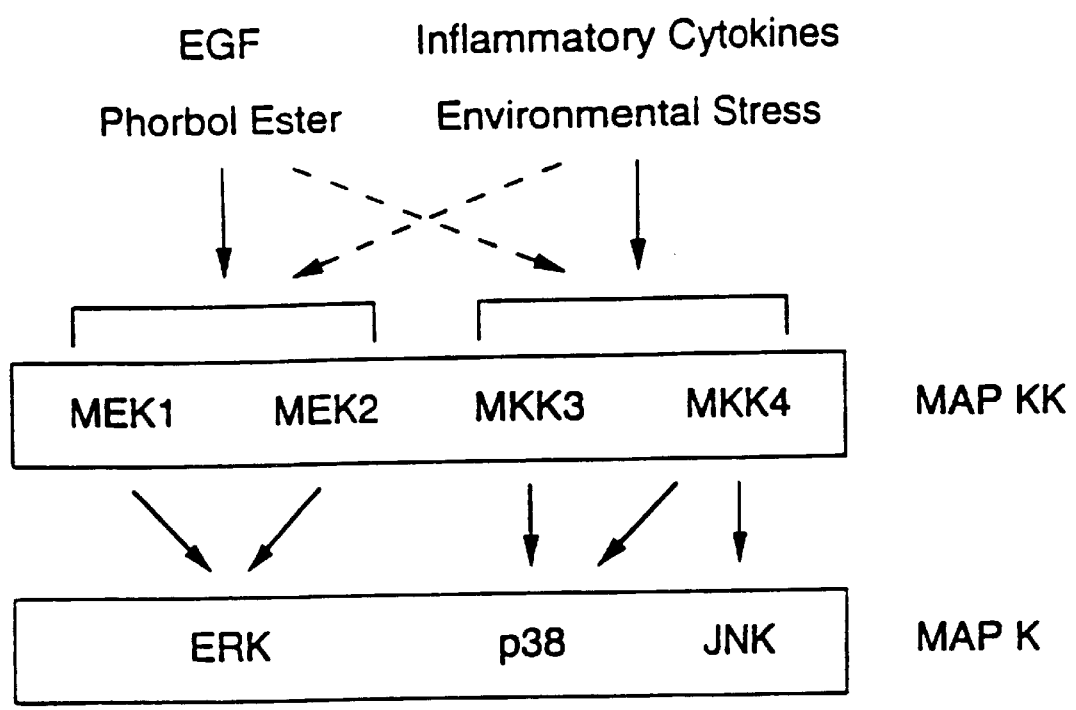

The results of the above-described experiments are illustrated in FIG. 3, which diagrams the ERK, p38, and JNK MAP kinase signal transduction pathways. ERKs are potently activated by treatment of cells with EGF or phorbol esters. In contrast, p38 is only slightly activated under these conditions (Example 15). However, UV radiation, osmotic stress, and inflammatory cytokines cause a marked increase in p38 activity. This difference in the pattern of activation of ERK and p38 suggests that these MAP kinases are regulated by different signal transduction pathways. The molecular basis for the separate identity of these signal transduction pathways is established by the demonstration that the MAP kinase kinases that activate ERK (MEK1 and MEK2) and p38 (MKK3, MKK4, and MKK6) are distinct.

The isolation of murine and human MKK7 is described in Example 22. Distinctive regions of the Drosophila MAP kinase kinase hep sequence were used to design polymerase chain reaction (PCR) primers. Amplification of murine testis mRNA with these primers resulted in the formation of specific products which were cloned into a plasmid vector and sequenced. One sequence related to hep was identified and used to screen a murine testis library. Five DNAs (cDNAs) that encoded protein kinases were identified: one encoding a MAP protein kinase kinase (MKK7). The others encoded various splice variants: MKK7b (a partial sequence appears in FIG. 11), MKK7c (FIG. 13), MKK7d (FIG. 14), MKK7e (FIG. 15). The deduced amino acid sequences of MKK7 (SEQ ID NO:18) and hep (SEQ ID NO:21) are shown in FIG. 9, and compared to the MAP kinase kinases MEK1 (SEQ ID NO:11), MEK2 (SEQ ID NO:12), MKK3 (SEQ ID NO:2), MKK4 (SEQ ID NO:10), MKK5 (SEQ ID NO:22), and MKK6 (SEQ ID NO:4). A human MKK7 was identified by screening a human cDNA library with a full-length (mouse) MKK7 cDNA probe. The identified partial sequence (lacking the 3'end) is homologous to mouse MKK7c.

The expression of MKK7 and MKK4 isoforms was examined by Northern (RNA) blot analysis of poly A+ mRNA isolated from eight murine tissues (Example 23). Both protein kinases were found to be widely expressed.

The substrate specificity of MKK7 was investigated in an in vitro phosphorylation assay with recombinant, epitope-tagged MAP kinases (JNK1, p38, and ERK2) as substrates (Example 24). MKK7 phosphorylated JNK, but did not phosphorylate p38 or ERK2. MKK7 was phosphorylated by p38 and JNK1.

MKK7 was found to specifically activate JNK protein kinase in vivo (Example 25). CHO cells were co-transfected with an epitope-tagged MAP kinase (JNK1, p38, or ERK2) together with an empty expression vector or an expression vector encoding MKK1, MKK4, MKK6, or MKK7 and the product of the phosphorylation reaction analyzed. MKK7 activated only JNK1, and did so to a greater extent than did MKK4.

To test whether MKK7 could cause increased AP-1 transcriptional activity, a co-transfection assay was employed (Example 26). Co-expression of MKK7 with JNK caused an increase in AP-1 reporter gene expression that was greater than the increase seen with MKK4 and JNK. A similar result was seen when ATF2 was used as the reporter gene. In addition, MKK7 alone was able to increase expression of ATF2 (FIG. 16).

MKK isoforms are useful for screening reagents which modulate MKK activity. Described in the Use section following the Examples are methods for identifying reagents capable of inhibiting or activating MKK activity.

The discovery of human MKK isoforms and MKK-mediated signal transduction pathways is clinically significant for the treatment of MKK-mediated disorders. One use of the MKK isoforms is in a method for screening reagents able to inhibit or prevent the activation of the MKK-MAP kinase-ATF2 pathways.

EXAMPLES

The following examples are meant to illustrate, not limit, the invention.

Example 1
MKK Protein Kinases

The primary sequences of MKK3 and MKK4 were deduced from the sequence of cDNA clones isolated from a human fetal brain library.

The primers TTYTAYGGNGCNTTYTTYATHGA (SEQ ID NO:14) and ATBCTYTCNGGNGCCATKTA (SEQ ID NO:15) were designed based on the sequence of PBS2 (Brewster et al. (1993) Science 259:1760; Maeda et al. (1994) Nature 369:242). The primers were used in a PCR reaction with human brain mRNA as template. Two sequences that encoded fragments of PBS2-related protein kinases were identified. Full-length human cDNA clones were isolated by screening of a human fetal brain library (Dérijard et al. (1995) Science 267:682–685). The cDNA clones were examined by sequencing with an Applied Biosystems model 373A machine. The largest clones obtained for MKK3 (2030 base pairs (bp)) and MKK4 (3576 bp) contained the entire coding region of these protein kinases.

The primary structures of MKK3 (SEQ ID NO:2) and MKK4-α (SEQ ID NO:6) are shown in FIG. 1. An in-frame termination codon is located in the 5' untranslated region of the MKK3 cDNA, but not in the 5' region of the MKK4 cDNA. The MKK4 protein sequence presented starts at the second in-frame initiation codon.

These sequences were compared to those of the human MAP kinase kinases MEK1 (SEQ ID NO:11) and MEK2 (SEQ ID NO:12) (Zheng and Guan (1993) J. Biol. Chem 268:11435) and of the yeast MAP kinase kinase PBS2 (SEQ ID NO:13) (Boguslawaski and Polazzi (1987) Proc. Natl. Acad. Sci. USA 84:5848) (FIG. 1). The identity and similarity of the kinases with human MKK3 (between subdomains I and XI) were calculated with the BESTFIT program (version 7.2; Wisconsin Genetics Computer Group) (percent of identity to percent of similarity): MEK1, 41%/63%; MEK2, 41%/62%; MKK4o, 52%/73%; and PBS2, 40%/59%). The identity and similarity of the kinases with human MKK4(were calculated to be as follows (percent of identity to percent of similarity): MEK1, 44%/63%; MEK2, 45%/61%; MKK3, 52%/73%; and PBS2, 44%/58%.

The cDNA sequences of MKK3 and MKK4T have been deposited in GenBank with accession numbers L36719 and L36870, respectively. The MKK4T cDNA sequence contains both the cDNA sequences of MKK4α and MKK4β, which are generated in vivo from alternate splicing sites. One of ordinary skill in the art can readily determine the amino acid sequences of MKK3 and MKK4 isoforms from the deposited cDNA sequences.

Example 2
Expression of MKK3 and MKK4 mRNA in Adult Human Tissue

Northern blot analysis was performed with polyadenylated [poly(A)$^+$] mRNA (2 μg) isolated from human heart, brain, placenta, lung, liver, muscle, kidney, and pancreas tissues. The mRNA was fractionated by denaturing agarose gel electrophoresis and was transferred to a nylon membrane. The blot was probed with the MKK3 and MKK4 cDNA labeled by random priming with [α-$^{32}$P]ATP (deoxyadenosine triphosphate) (Amersham International PLC). MKK3 and MKK4 were expressed in all tissues examined; the highest expression of MKK3 and MKK4 was found in skeletal muscle tissue.

Figure 2A:
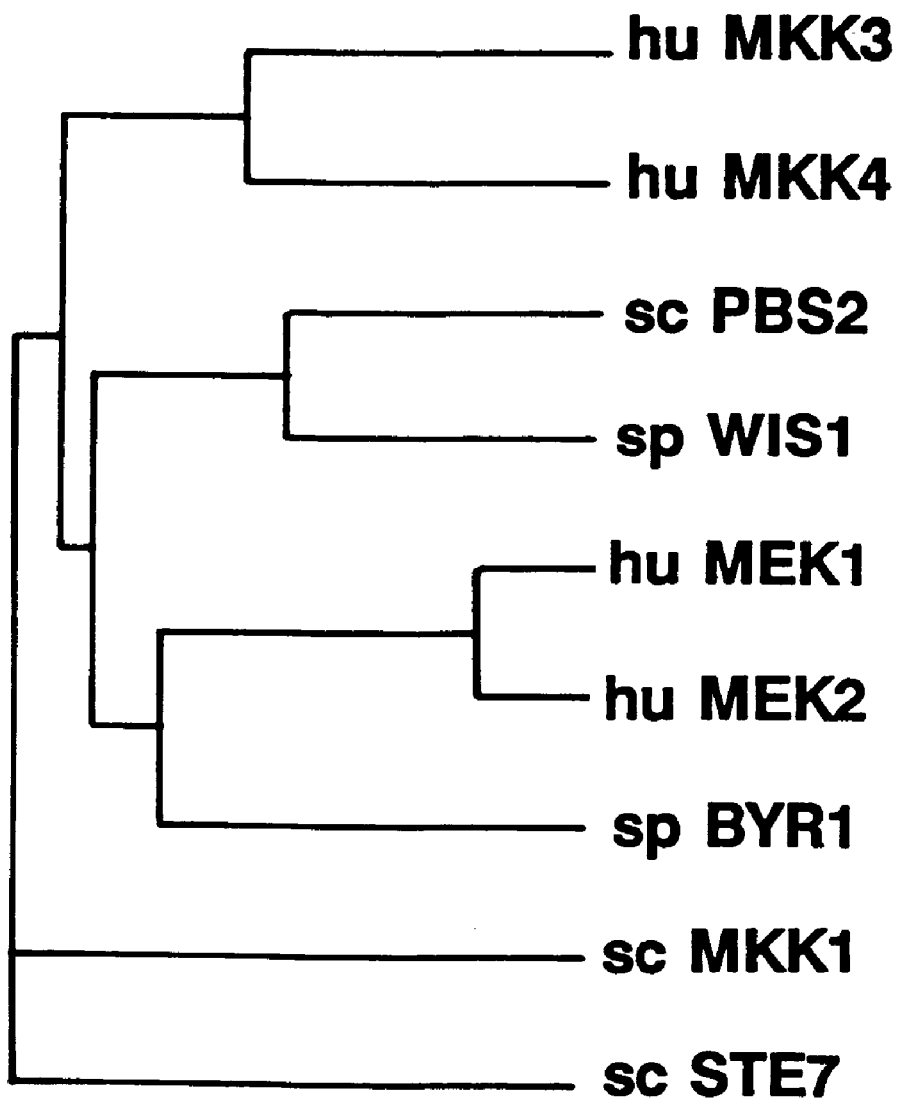
Figure 2B:
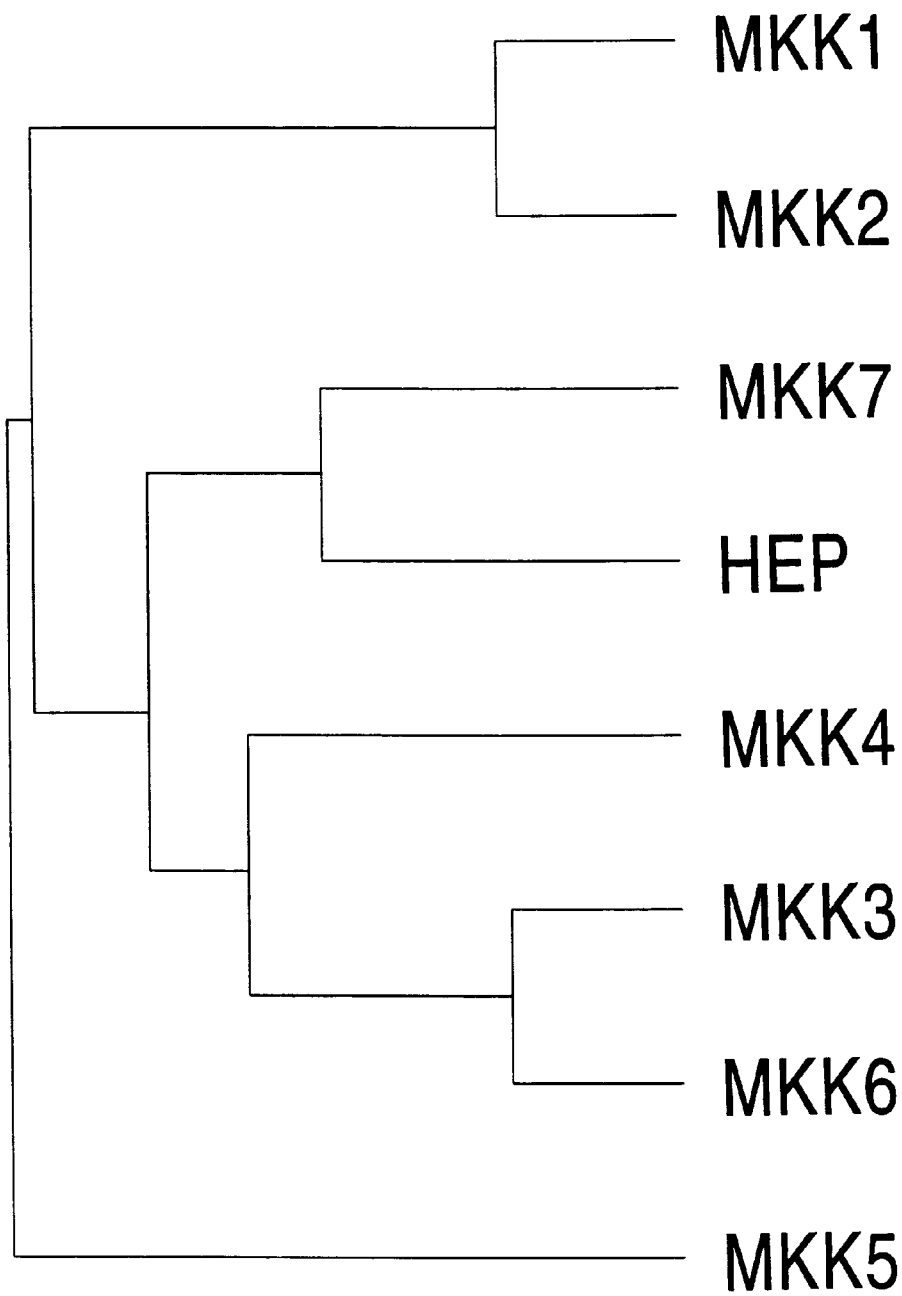

The relation between members of the human and yeast MAP kinase kinase group is presented as a dendrogram (FIG. 2). MKK3/4 form a unique subgroup of human MAP kinase kinases.

Example 3
In Vitro Phosphorylation of p38 MAP kinase by MKK3

GST-JNK1, and GST-ERK2 have been described (Dérijard et al. (1994) supra; Gupta et al. (1995) Science 267:389; Wartmann and Davis (1994) J. Biol. Chem. 269:6695, each herein specifically incorporated by reference). GST-p38 MAP kinase was prepared from the expression vector pGSTag (Dressier et al. (1992) Biotechniques 13:866) and a PCR fragment containing the coding region of the p38 MAP kinase cDNA. GST-MKK3 and MKK4 were prepared with pGEX3X (Pharmacia-LKB Biotechnology) and PCR fragments containing the coding region of the MKK3 and MKK4 cDNAs. The GST fusion proteins were purified by affinity chromatography with the use of GSH-agarose (Smith and Johnson (1988) Gene 67:31). The expression vectors pCMV-Flag-JNK1 and pCMV-MEK1 have been described (Dérijard et al. (1994) supra; Wartmann and Davis (1994) supra). The plasmid pCMV-Flag-p38 MAP kinase was prepared with the expression vector pCMV5 (Andersson et al. (1989) J. Biol. Chem. 264:8222) and the p38 MAP kinase cDNA. The expression vectors for MKK3 and MKK4 were prepared by subcloning of the cDNAs into the polylinker of pCDNA3 (Invitrogen). The Flag epitope (Asp-Tyr-Lys-Asp-Asp-Asp-Asp-Lys (SEQ ID NO:16); Immunex, Seattle, Wash.) was inserted between codons 1 and 2 of the kinases by insertional overlapping PCR (Ho et al. (1989) Gene 77:51).

Protein kinase assays were performed in kinase buffer (25 mM 4-(2-hydroxyethyl)-1-piperazineethansulfonic acid, pH 7.4, 25 mM P-glycerophosphate, 25 mM MgCl$_2$, 2 mM dithiothreitol, and 0.1 mM orthovanadate). Recombinant GST-MKK3 was incubated with [γ-$^{32}$P]ATP and buffer, GST-JNK1, GST-p38 MAP kinase, or GST-ERK2. The assays were initiated by the addition of 1 μg of substrate proteins and 50 μM [γ-$^{32}$P]ATP (10 Ci/mmol) in a final volume of 25 μl. The reactions were terminated after 30 minutes at 25oC by addition of Laemmli sample buffer. The phosphorylation of the substrate proteins was examined after SDS-polyacrylamide gel electrophoresis (SDS-PAGE) by autoradiography. Phosphoaminoacid analysis was performed by partial acid hydrolysis and thin-layer chromatography (Dérijard et al. (1994) supra; Alvarez et al. (1991) J. Biol. Chem. 266:15277). Autophosphorylation of MKK3 was observed in all groups. MKK3 phosphorylated p38 MAP kinase, but not JNK1 or ERK2.

A similar insertional overlapping PCR procedure was used to replace $Thr^{180}$ and $Tyr^{182}$ of p38, with Ala and Phe, respectively. The sequence of all plasmids was confirmed by automated sequencing on an Applied Biosystems model 373A machine. GST-MKK3 was incubated with $[\gamma\text{-}^{32}P]ATP$ and buffer, wild-type GST-p38 MAP kinase (TGY), or mutated GST-p38 MAP kinase (AGF). The phosphorylated proteins were resolved by SDS-PAGE and detected by autoradiography. Only phosphorylation of wild-type p38 was observed.

Example 4

In Vitro Phosphorylation and Activation of JNK and p38 MAP Kinase by MKK4

Protein kinase assays were conducted as described in Example 3. Recombinant GST-MKK4 was incubated with $[\gamma\text{-}^{32}P]ATP$ and buffer, GST-JNK1, GST-p38 MAP kinase, or GST-ERK2. JNK1 and p38 were phosphorylated, as was MKK4 incubated with JNK1 and p38.

GST-MKK4 was incubated with $[\gamma\text{-}^{32}P]ATP$ and buffer, wild-type JNK1 ($Thr^{183}$, $Tyr^{185}$), or mutated GST-JNK1 ($Ala^{183}$, $Phe^{185}$). The JNK1 substrate ATF2 (Gupta et al. (1995) supra) was included in each incubation. ATF2 was phosphorylated in the presence of MKK4 and wild-type JNK1. The results establish that MKK4 phosphorylates and activates both p38 and JNK1.

Example 5

Phosphorylation and Activation of p38 MAP Kinase by UV-stimulated MKK3

Epitope-tagged MKK3 was expressed in COS-1 cells maintained in Dulbecco's modified Eagle's medium supplemented with fetal bovine serum (5%)(Gibco-BRL). The cells were transfected with the lipofectamine reagent according to the manufacturer's recommendations (Gibco-BRL) and treated with UV radiation or EGF as described (Dérijard et al. (1994) supra).

The cells were exposed in the absence and presence of UV-C (40 J/m$^2$). The cells were solubilized with lysis buffer (20 mM tris, pH 7.4, 1% TRITON® X-100, 10% glycerol, 137 mM NaCl, 2 mM EDTA, 25 mM β-glycerophosphate, 1 mM Na orthovanadate, 1 mM phenylmethylsulfonyl fluoride, and leupeptin (10 µg/ml)) and centrifuged at 100,000×g for 15 minutes at 4° C. MKK3 was isolated by immunoprecipitation. The epitope-tagged protein kinases were incubated for 1 hour at 4° C with the M2 antibody to the Flag epitope (IBI-Kodak) bound to protein G-Sepharose (Pharmacia-LKB Biotechnology). The immunoprecipitates were washed twice with lysis buffer and twice with kinase buffer.

Protein kinase assays were conducted with the substrate GST-p38 MAP kinase or JNK1. ATF2 was included in some assays. Basal levels of MKK3 phosphorylation of p38 MAP kinase were observed. UV-irradiation resulted in increased phosphorylation of p38 MAP kinase, but not of JNK1. The increased p38 MAP kinase activity resulted in increased phosphorylation of ATF2.

Example 6

Activation of p38 MAP Kinase in Cells Expressing MKK3 and MKK4

COS-1 cells were transfected with epitope-tagged p38 MAP kinase, together with an empty expression vector or an expression vector encoding MEK1, MKK3, or MKK4α. Some of the cultures were exposed to UV radiation (40 J/m$^2$) or treated with 10 nM EGF. p38 MAP kinase was isolated by immunoprecipitation with M2 monoclonal antibody, and the protein kinase activity was measured in the immunecomplex with $[\gamma\text{-}^{32}P]ATP$ and ATF2 as substrates. The product of the phosphorylation reaction was visualized after SDS-PAGE by autoradiography. ATF2 was not phosphorylated in the control MEK1, or EGF-treated groups, but was phosphorylated in the MKK3, MKK4, and UV-irradiated groups. MKK3 and MKK4 phosphorylation of ATF2 was similar to that seen with p38 MAP kinase isolated from UV-irradiated cells.

Example 7

Phosphorylation of ATF2 by JNK1 and JNK2 COS-1 cells were maintained in Dulbecco's modified Eagle's medium supplemented with bovine serum albumin (5%) (Gibco-BRL). Metabolic labeling with $[^{32}P]$ was performed by incubation of cells for 3 hours in phosphate-free modified Eagle's medium (Flow Laboratories Inc.) supplemented with $[^{32}p]$ orthophosphate (2 mCi/ml) (Dupont-NEN). COS-1 cells were transfected without (Mock) and with epitope-tagged JNK1 (JNK1). Plasmid expression vectors encoding the JNK1 cDNA have previously been described (Dérijard et al. (1994) Cell 76:1025, herein specifically incorporated by reference). Plasmid DNA was transfected into COS-1 cells by the lipofectamine method (Gibco-BRL). After 48 hours of incubation, some cultures were exposed to 40 J/m$^2$ W radiation and incubated for 1 hour at 37° C.

Cells were lysed in 20 mM Tris, pH 7.5, 25 mM β-glycerophosphate, 10% glycerol, 1% Triton® X-100, 0.5% (w/v) deoxycholate, 0.1% (w/v) SDS, 0.137 M NaCl, 2 mM pyrophosphate, 1 mM orthovanadate, 2 mM EDTA, 10 pg/ml leupeptin, 1 mM PMSF. Soluble extracts were prepared by centrifugation in a microfuge for 20 minutes at 4° C. JNK1 immunoprecipitates were also prepared by reaction with a rabbit antiserum prepared with recombinant JNK1 as an antigen.

In-gel protein kinase assays were performed with cell lysates and JNK1 immunoprecipitates after SDS-PAGE by renaturation of protein kinases, polymerization of the substrate (GST-ATF2, residues 1–505) in the gel, and incubation with $[\gamma\text{-}^{32}P]ATP$ (Dérijard et al. (1994) supra). The incorporation of $[^{32}P]$phosphate was visualized by autoradiography and quantitated with a Phosphorimager and ImageQuant software (Molecular Dynamics Inc., Sunnyvale, Calif.). The cell lysates demonstrate the presence of 46 kD and 55 kD protein kinases that phosphorylate ATF2 in extracts prepared from UV-irradiated cells. The 46 kD and 55 kD protein kinases were identified as JNK1 and JNK2, respectively.

Example 8

Binding of JNK1 to ATF2 and Phosphorylation of the NH$_2$-Terminal Activation Domain The site of JNK1 phosphorylation of ATF2 was investigated by generation of progressive NH$_2$-terminal domain deletions of ATF2. Plasmid expression vectors encoding ATF2 (pECE-ATF2) (Liu and Green (1994) and (1990)), have been described. Bacterial expression vectors for GST-ATF2 fusion proteins were constructed by sub-cloning ATF2 cDNA fragments from a polymerase chain reaction (PCR) into pGEX-3X (Pharmacia-LKB Biotechnology Inc.). The sequence of all constructed plasmids was confirmed by automated sequencing with an Applied Biosystems model 373A machine. The GST-ATF2 proteins were purified as described (Smith and Johnson (1988) Gene 67:31), resolved by SDS-PAGE and stained with Coomassie blue. GST-ATF2 fusion proteins contained residues 1–505, 1–349, 350–505, 1–109, 20–109, 40–109, and 60–109.

The phosphorylation of GST-ATF2 fusion proteins by JNK1 isolated from UV-irradiated cells was examined in an immunocomplex kinase assay. Immunecomplex kinase assays were performed with Flag epitope-tagged JNK1 and the monoclonal antibody M2 (IBI-Kodak) as described by Dérijard et al. (1994) supra) . Immunecomplex protein kinase assays were also performed with a rabbit antiserum prepared with recombinant JNK1 as an antigen. The cells were solubilized with 20 mM Tris, pH 7.5, 10% glycerol, 1% Tritons X-100, 0.137 M NaCl, 25 mM $\beta$-glycerophosphate, 2 mM EDTA, 1 mM orthovanadate, 2 mM pyrophosphate, 10 $\mu$g/ml leupeptin, and 1 mM PMSF. JNK1 was immunoprecipitated with protein G-Sepharose bound to a rabbit polyclonal antibody to JNK or the M2 monoclonal antibody to the Flag epitope. The beads were washed three times with lysis buffer and once with kinase buffer (20 mM Hepes, pH 7.6, 20 mM $MgCl_2$, 25 mM $\beta$-glycerophosphate, 100 $\mu$M Na orthovanadate, 2 mM dithiothreitol). The kinase assays were performed at 25° C. for 10 minutes with 1 $\mu$g of substrate, 20 $\mu$M adenosine triphosphate and 10 $\mu$Ci of $[\gamma-^{32}P]ATP$ in 30 $\mu$l of kinase buffer. The reactions were terminated with Laemmli sample buffer and the products were resolved by SDS-PAGE (10% gel). JNK1 phosphorylates GST-ATF2 fusion proteins containing residues 1–505, 1–349, 1–109, 20–109, and 40–109, but not 60–109. These results indicate that the presence of ATF2 residues 1–60 are required for phosphorylation by JNK.

The binding of immobilized GST-ATF2 fusion proteins was examined in a solid-phase kinase assay as described by Hibi et al. ((1993) Genes Dev. 7:2135, herein specifically incorporated by reference). JNK1 from UV-irradiated cells was incubated with GST-ATF2 fusion proteins bound to GSH-agarose. The agarose beads were washed extensively to remove the unbound JNK1. Phosphorylation of the GST-ATF2 fusion proteins by the bound JNK1 protein kinase was examined by addition of $[\gamma-^{32}P]ATP$. JNK1 bound GST-ATF2 fusion proteins containing residues 1–505, 1–349, 1–109, 20–109, and 40–109, indicating that the presence of residues 20–60 were required for binding of JNK1 to ATF2.

Example 9

Phosphorylation of the $NH_2$-terminal Activation Domain of ATF2 on $Thr^{69}$ and $Thr^{71}$ by JNK1

The effect of UV radiation on the properties of wild-type ($Thr^{69,71}$) and phosphorylation-defective ($Ala^{69,71}$) ATF2 molecules was examined. Mock-transfected and JNK1-transfected COS cells were treated without and with 40 $J/m^2$ UV radiation. The epitope-tagged JNK1 was isolated by immunoprecipitation with the M2 monoclonal antibody. The phosphorylation of GST-ATF2 (residues 1 to 109) was examined in an immunocomplex kinase assay as described above. The GST-ATF2 was resolved from other proteins by SDS-PAGE and stained with Coomassie blue. The phosphorylation of GST-ATF2 was detected by autoradiography. JNK1-transfected cells, but not mock-transfected cells, phosphorylated ATF2. JNK1 phosphorylation of ATF2 was greater in cells exposed to UV radiation. Phosphorylation of ATF2 by JNK1 was associated with a decreased electrophoretic mobility.

In a separate experiment, GST fusion proteins containing full-length ATF2 (residues 1 to 505), an $NH_2$-terminal fragment (residues 1 to 109), and a COOH-terminal fragment (residues 95 to 505) were phosphorylated with JNK1 and the sites of phosphorylation analyzed by phosphoamino acid analysis. The methods used for phosphopeptide mapping and phosphoamino acid analysis have been described (Alvarez et al. (1991) J. Biol. Chem. 266:15277). The horizontal dimension of the peptide maps was electrophoresis and the vertical dimension was chromatography. The $NH_2$-terminal sites of phosphorylation were identified as $Thr^{69}$ and $Thr^{71}$ by phosphopeptide mapping and mutational analysis. Site-directed mutagenesis was performed as described above, replacing $Thr^{69}$ and $Thr^{71}$ with Ala. Phosphorylation of mutated ATF2 was not observed.

Example 10

Reduced Electrophoretic Mobility of JNK-Activated ATF2

CHO cells were maintained in Ham's F12 medium supplemented with 5% bovine serum albumin (Gibco-BRL). Cells were labeled and transfected with JNK1 as described above. CHO cells were treated with UV-C (40 $J/m^2$), IL-1$\alpha$ (10 ng/ml) (Genzyme), or fetal bovine serum (20%) (Gibco-BRL). The cells were incubated for 30 minutes at 37° C. prior to harvesting. The electrophoretic mobility of ATF2 after SDS-PAGE was examined by protein immuno-blot analysis. A shift in ATF2 electrophoretic mobility was observed in cells treated with UV, IL-1, and serum. These results indicate that JNK1 activation is associated with an electrophoretic mobility shift of ATF2, further suggesting that ATF2 is an in vivo substrate for JNK1.

Example 11

Increased ATF2 Phosphorylation After Activation of JNK

COS-1 cells were transfected without (control) and with an ATF2 expression vector (ATF2), as described above (Hai et al. (1989) supra) . The effect of exposure of the cells to 40 $J/m^2$ UV-C was examined. After irradiation, the cells were incubated for 0 or 30 minutes (control) or 0, 15, 30, and 45 minutes (ATF2) at 37° C. and then collected. The electrophoretic mobility of ATF2 during SDS-PAGE was examined by protein immuno-blot analysis as described above. The two electrophoretic mobility forms of ATF2 were observed in ATF2-transfected cells, but not in control cells.

The phosphorylation state of wild-type ($Thr^{69,71}$) ATF2 and mutated ($Ala^{69,71}$) ATF2 was examined in cells labeled with $[^{32}P]$, treated without and with 40 $J/m^2$ UV-C, and then incubated at 37° C. for 30 minutes (Hai et al. (1989) supra). The ATF2 proteins were isolated by immunoprecipitation and analyzed by SDS-PAGE and autoradiography. The phosphorylated ATF2 proteins were examined by phosphoamino acid analysis as described above. Both forms of ATF2 contained phosphoserine, but only wild-type ATF2 contained phosphothreonine.

Tryptic phosphopeptide mapping was used to compare ATF2 phosphorylated in vitro by JNK1 with ATF2 phosphorylated in COS-1 cells. A map was also prepared with a sample composed of equal amounts of in vivo and in vitro phosphorylated ATF2 (Mix). Mutation of ATF2 at $Thr^{69}$ and $Thr^{71}$ resulted in the loss of two tryptic phosphopeptides in maps of ATF2 isolated from UV-irradiated cells. These phosphopeptides correspond to mono- and bis-phosphorylated peptides containing $Thr^{69}$ and $Thr^{71}$. Both of these phosphopeptides were found in maps of ATF2 phosphorylated by JNK1 in vitro.

Example 12

Inhibition of ATF2-Stimulated Gene Expression by Mutation of the Phosphorylation Sites $Thr^{69}$ and $Thr^{71}$ A fusion protein consisting of ATF2 and the GAL4 DNA binding domain was expressed in CHO cells as described above. The activity of the GAL4-ATF2 fusion protein was measured in co-transfection assays with the reporter plasmid pG5E1bLuc (Seth et al. (1992) J. Biol. Chem. 267:24796, hereby specifically incorporated by reference). The reporter plasmid contains five GAL4 sites cloned upstream of a minimal promoter element and the firefly luciferase gene. Transfection efficiency was monitored with a control plasmid that expresses β-galactosidase (pCH110; Pharmacia-LKB Biotechnology). The luciferase and β-galactosidase activity detected in cell extracts was measured as the mean activity ratio of three experiments (Gupta et al. (1993) Proc. Natl. Acad. Sci. USA 90:3216, hereby specifically incorporated by reference). The results, shown in Table 1, demonstrate the importance of phosphorylation at $Thr^{69}$ and $Thr^{71}$ for transcriptional activity.

TABLE 1

INHIBITION OF ATF-2 STIMULATED GENE EXPRESSION BY MUTATION OF THE PHOSPHORYLATION SITES $THR^{69,71}$

| PROTEIN | LUCIFERASE ACTIVITY (Light Units/OD) |
| --- | --- |
| GAL4 | 45 |
| GAL4-ATF2 (wild type) | 320,000 |
| GAL4-ATF2 ($Ala^{69}$) | 24,000 |
| GAL4-ATF2 ($Ala^{71}$) | 22,000 |
| GAL4-ATF2 ($Ala^{69,71}$) | 29,000 |
| GAL4-ATF2 ($Glu^{69}$) | 27,000 |

Example 13
Effect of Dominant-Negative JNK1 Mutant on ATF2 Function

The luciferase reporter plasmid system was used to determine the effect of point mutations at the ATF2 phosphorylation sites $Thr^{69}$ and $Thr^{71}$ in serum-treated CHO cells transfected with wild-type ($Thr^{183}$, $Tyr^{185}$) or mutant ($Ala^{183}$, $Phe^{185}$) JNK1. Control experiments were done with mock-transfected cells. The CHO cells were serum-starved for 18 hours and then incubated without or with serum for 4 hours. Expression of wild-type ATF2 caused a small increase in serum-stimulated ATF2 transcriptional activity. In contrast, mutant JNK1 inhibited both control and serum-stimulated ATF2 activity.

Example 14
Effect of Tumor Suppressor Gene Product Rb and Adenovirus Oncoprotein E1A on ATF2-Stimulated Gene Expression The effect of expression of the Rb tumor suppressor gene product and adenovirus oncoprotein E1A on ATF2 transcriptional activity were investigated with a luciferase reporter plasmid and GAL4-ATF2 (residues 1-505), as described above. Cells were transfected with wild-type ($Thr^{69,71}$) or mutated ($Ala^{69,71}$) ATF2. No effect of Rb or E1A on luciferase activity was detected in the absence of GAL4-ATF2. Rb and E1A were found to increase ATF2-stimulated gene expression of both wild-type and mutated ATF2. However, mutated ATF2 caused a lower level of reporter gene expression than did wild-type ATF2. These results indicate a requirement for ATF2 phosphorylation (on $Thr^{69}$ and $Thr^{71}$) plus either Rb or E1A for maximal transcriptional activity.

Example 15
Substrate Specificity of p38 MAP Kinase

Substrate phosphorylation by p38 MAP kinase was examined by incubation of bacterially-expressed p38 MAP kinase with IκB, cMyc, EGF-R, cytoplasmic phospholipase $A_2$ ($cPLA_2$), c-jun, and mutated ATF2 ($Thr^{69,71}$) and ATP[γ-$^{32}$P] (Raingeaud et al. (1995) J. Biol. Chem 270:7420, herein specifically incorporated by reference). GST-IκB was provided by Dr D. Baltimore (Massachusetts Institute of Technology). GST-cMyc (Alvarez et al. (1991) J. Biol. Chem. 266:15277), GST-EGF-R (residues 647–688) (Koland et al. (1990) Biochem. Biophys. Res. Commun. 166:90), and GST-c-Jun (Dérijard et al. (1994) supra) have been described. The phosphorylation reaction was terminated after 30 minutes by addition of Laemmli sample buffer. The phosphorylated proteins were resolved by SDS-PAGE and detected by autoradiography. The rate phosphorylation of the substrate proteins was quantitated by PhosphorImager (Molecular Dynamics Inc.) analysis. The relative phosphorylation of ATF2, MBP, EGF-R, and IκB was 1.0, 0.23, 0.04, and 0.001, respectively.

Example 16
Binding of p38 MAP Kinase to ATF2

Cell extracts expressing epitope-tagged JNK1 and p38 MAP kinase were incubated with a GST fusion protein containing the activation domain of ATF2 (residues 1–109) immobilized on GSH agarose. The supernatant was removed and the agarose was washed extensively. Western blot analysis of the supernatant and agarose-bound fractions was conducted as follows: proteins were fractionated by SDS-PAGE, electrophoretically transferred to an Immobilon-P membrane, and probed with monoclonal antibodies to phosphotyrosine (PY20) and the Flag epitope (M2). Immunocomplexes were detected using enhanced chemiluminescence (Amersham International PLC). Control experiments were performed using immobilized GST.

Example 17
p38 MAP Kinase and JNK1 Activation by Pro-Inflammatory Cytokines and Environmental Stress The effect of phorbol ester, EGF, UV radiation, osmotic stress, IL-1, tumor necrosis factor (TNF), and LPS on p38 MAP kinase and JNK1 activity were measured in immunecomplex protein kinase assays using ATP [γ-$^{32}$P] and ATF2 as substrates. TNFα and IL-1α were from Genzyme Corp. Lipolysaccharide (LPS) was isolated from lyophilized *Salmonella minesota* Re595 bacteria as described (Mathison et a. (1988) J. Clin. Invest. 81:1925). Phorbol myristate acetate was from Sigma. EGF was purified from mouse salivary glands (Davis (1988) J. Biol. Chem. 263:9462). Kinase assays were performed using immunoprecipitates of p38 and JNK. The immunocomplexes were washed twice with kinase buffer (described above), and the assays initiated by the addition of 1 μg of ATF2 and 50 μM [γ-$^{32}$P]ATP (10 Ci/mmol) in a final volume of 25 μl. The reactions were terminated after 30 minutes at 30° C. by addition of Laemmli sample buffer. The phosphorylation of ATF2 was examined after SDS-PAGE by autoradiography, and the rate of ATF2 phosphorylation quantitated by PhosphorImager analysis.

The results are shown in Table 2. Exposure of HeLa cells to 10 nM phorbol myristate acetate very weakly activated p38 and JNK1. Similarly, treatment with 10 nM EGF only weakly activated p38 and JNK1. By contrast, treatment with 40 J/m$^2$ UV-C, 300 mM sorbitol, 10 ng/ml interleukin-1, and 10 ng/ml TNFA strongly activated p38 and JNK1 activity. The effect of LPS on the activity of p38 was examined using CHO cells that express human CD14. Exposure of CHO cells to 10 ng/ml LPS only slightly activated p38 and JNK1 activity.

TABLE 2 p38 AND JNK1 ACTIVATION BY PRO-INFLAMMATORY CYTOKINES AND ENVIRONMENTAL STRESS.

| | Relative Protein Kinase Activity | |
|---|---|---|
| | JNK | p38 |
| Control | 1.0 | 1.0 |
| Epidermal Growth Factor (10 nM) | 1.9 | 2.1 |
| Phorbol Ester (10 nM) | 2.3 | 2.9 |
| Lipopolysaccharide (10 ng/ml) | 3.6 | 3.7 |
| Osmotic Shock (300 mM sorbitol) | 18.1 | 4.2 |
| Tumor Necrosis Factor (10 ng/ml) | 19.3 | 10.3 |
| Interleukin-1 (10 ng/ml) | 8.9 | 6.2 |
| UV (40 J/m$^2$) | 7.4 | 17.1 |

Example 18
p38 MAP Kinase Activation by Dual Phosphorylation on Tyr and Thr

COS-1 cells expressing wild-type (Thr$^{180}$, Tyr$^{182}$) or mutated (Ala$^{180}$, Phe$^{182}$) p38 MAP kinase were treated without and with UV-C (40 J/m$^2$). The cells were harvested 30 minutes following exposure with or without UV radiation. Control experiments were performed using mock-transfected cells. The level of expression of epitope-tagged p38 MAP kinase and the state of Tyr phosphorylation of p38 MAP kinase was examined by Western blot analysis using the M2 monoclonal antibody and the phosphotyrosine monoclonal antibody PY20. Immune complexes were detected by enhanced chemiluminescence.

Wild-type and mutant p38 were expressed at similar levels. Western blot analysis showed that UV radiation caused an increase in the Tyr phosphorylation of p38. The increased Tyr phosphorylation was confirmed by phospho-amino acid analysis of p38 isolated from [$^{32}$P]phosphate-labeled cells. The results also showed that UV radiation increased Thr phosphorylation of p38. The increased phosphorylation on Tyr and Thr was blocked by mutated p38. Wild-type and mutated p38 were isolated from the COS-1 cells by immunoprecipitation. Protein kinase activity was measured in the immune complex using [γ-$^{32}$P]ATP and GST-ATF2 as substrates. The phosphorylated GST-ATF2 was detected after SDS-PAGE by autoradiography. UV radiation resulted in a marked increase in the activity of wild-type p38, while the mutant p38 was found to be catalytically inactive. These results show that p38 is activated by dual phosphorylation within the Thr-Gly-Tyr motif.

Example 19
MAP Kinase Phosphatase Inhibits p38 MAP kinase Activation

The cells were treated without and with 40 J/m$^2$ UV-C. Control experiments were performed using mock-transfected cells (control) and cells transfected with the catalytically inactive mutated phosphatase mPAC1 (Cys$^{257}$/Ser) and human MKP1. The activity of p38 MAP kinase was measured with an immunecomplex protein kinase assay employing [γ-$^{32}$P]ATP and GST-ATF2 as substrates. The expression of PAC1 or MKP1 was found to inhibit p38 phosphorylation, demonstrating that p38 can be regulated by the dual specificity phosphatases PAC1 and MKP1.

Example 20
Subcellular Distribution of p38 MAP Kinase

Epitope-tagged p38 MAP kinase was expressed in COS cells. The cells were treated without or with 40 J/m$^2$ UV radiation and then incubated for 60 minutes at 37° C. The p38 MAP kinase was detected by indirect immunofluorescence using the M2 monoclonal antibody. The images were acquired by digital imaging microscopy and processed for image restoration.

Immunocytochemistry

Coverslips (22 mm×22 mm No. 1; Gold Seal Cover Glass; Becton-Dickinson) were pre-treated by boiling in 0.1 N HCl for 10 minutes, rinsed in distilled water, autoclaved and coated with 0.01% poly-L-lysine (Sigma; St. Louis Mo.). The coverslips were placed at the bottom of 35 mm multi-well tissue culture plates (Becton Dickinson, UK). Transfected COS-1 cells were plated directly on the coverslips and allowed to adhere overnight in Dulbecco's modified Eagle's medium supplemented with 5% fetal calf serum (Gibco-BRL). Twenty-four hours post-transfection, the cells were rinsed once and incubated at 37° C. for 30 minutes in 25 mM Hepes, pH 7.4, 137 mM NaCl, 6 mM KCl, 1 mM MgCl$_2$, 1 mM CaCl$_2$, 10 mM glucose. The cells were rinsed once with phosphate-buffered saline and the coverslips removed from the tissue culture wells. Cells were fixed in fresh 4% paraformaldehyde in phosphate-buffered saline for 15 minutes at 220C. The cells were permeabilized with 0.25% Triton® X-100 in phosphate-buffered saline for 5 minutes and washed three times in DWB solution (150 mM NaCl, 15 mM Na citrate, pH 7.0, 2% horse serum, 1% (w/v) bovine serum albumin, 0.05% Triton® X-100) for 5 minutes. The primary antibody (M2 anti-FLAG monoclonal antibody, Eastman-Kodak Co., New Haven, Conn.) was diluted 1:250 in DWB and applied to the cells in a humidified environment at 22° C. for 1 hour. The cells were again washed three times as above and fluorescein isothiocyanate-conjugated goat anti-mouse Ig secondary antibody (Kirkegaard & Perry Laboratories Inc. Gaithersburg, MD) was applied at a 1:250 dilution for 1 hour at 22° C. in a humidified environment. The cells were then washed three times in DWB and then mounted onto slides with Gel-Mount (Biomeda Corp. Foster City, Calif.) for immunofluorescence analysis. Control experiments were performed to assess the specificity of the observed immunofluorescence. No fluorescence was detected when the transfected cells were stained in the absence of the primary M2 monoclonal antibody, or mock-transfected cells.

Digital Imaging Microscopy and Image Restoration

Digital images of the fluorescence distribution in single cells were obtained using a Nikon 60× Planapo objective (numerical aperture=1.4) on a Zeiss IM-35 microscope equipped for epifluorescence as previously described (Carrington et al. (1990) in: *Non-invasive Techniques in Cell Biology*, Fosbett & Grinstein, eds., Wiley-Liss, NY; pp. 53–72; Fay et al. (1989) J. Microsci. 153:133–149). Images of various focal planes were obtained with a computer controlled focus mechanism and a thermoelectrically cooled charged-coupled device camera (model 220; Photometrics Ltd., Tucson, Ariz.). The exposure of the sample to the excitation source was determined by a computer-controlled shutter and wavelength selector system (MVI, Avon, Mass.). The charge-coupled device camera and microscope functions were controlled by a microcomputer, and the data acquired from the camera were transferred to a Silicon Graphics model 4D/GTX workstation (Mountainview, Calif.) for image processing. Images were corrected for non-uniformities in sensitivity and for the dark current of the charge coupled device detector. The calibration of the microscopy blurring was determined by measuring the instrument's point spread function as a series of optical sections at 0.125 μm intervals of a 0.3 μm diameter fluorescently labeled latex bead (Molecular Probes Inc.). The image restoration algorithm used is based upon the theory of ill-posed problems and obtains quantitative dye density values within the cell that are substantially more accurate than those in an unprocessed image (Carrington et al. (1990) supra; Fay et al. (1989) supra). After image processing, individual optical sections of cells were inspected and analyzed using computer graphics software on a Silicon Graphics workstation. p38 MAP kinase was observed at the cell surface, in the cytoplasm, and in the nucleus. After irradiation, an increased localization of cytoplasmic p38 to the perinuclear region was detected.

Example 21

Activation of the MKK Signal Transduction Pathway by Osmotic Shock

CHO cells were co-transfected with the plasmid pCMV-Flag-Jnk1 and pRSV-Neo (Dérijard et al. (1994) supra). A stable cell line expressing epitope-tagged Jnk1 (Flag; Immunex Corp.) was isolated by selection with Geneticin (Gibco-BRL). The cells were incubated with 0, 100, 150, 300, 600, or 1000 mM sorbitol for 1 hour at 37° C. The cells were collected in lysis buffer (20 mM Tris, pH 7.4, 1% TRITON® X-100, 2 mM EDTA, 137 mM NaCl, 25 mM β-glycerophosphate, 1 mM orthovanadate, 2 mM pyrophosphate, 10% glycerol, 1 mM phenylmethylsulfonyl fluoride, 10 μg/ml leupeptin) and a soluble extract was obtained by centrifugation at 100,000 g for 30 minutes at 4° C. The epitope-tagged JNK1 was isolated by immunoprecipitation with the monoclonal antibody M2 (Immunex Corp.). The immunoprecipitates were washed extensively with lysis buffer. Immunecomplex kinase assays were done in 25 μl of 25 mM Hepes, pH 7.4, 25 mM MgCl$_2$, 25 mM β-glycerophosphate, 2 mM dithiothreitol, 100 μM orthovanadate, and 50 μM ATP [γ-$^{32}$p] (10 Ci/mmole) with 2.5 μg of bacterially expressed c-Jun (residues 1–79) fused to glutathione-S-transferase (GST) as a substrate. The phosphorylation of c-Jun was examined after SDS-PAGE by autoradiography and PhosphorImager (Molecular Dynamics Inc.) analysis. JNK1 activation was observed at all concentrations of sorbitol exposure.

The time course of JNK1 protein kinase activation was measured in cells incubated in medium supplemented with 300 mM sorbitol as described above. Increased JNK1 activity was observed within 5 minutes of exposure to sorbitol, with maximum activity occurring after 15–30 minutes.

Mutation of JNK1 at the phosphorylation sites Thr$^{183}$ and Tyr$^{185}$ blocked the activation of JNK1 protein kinase activity by osmotic shock. CHO cells were transfected with vector, wild-type JNK1 (Thr$^{183}$, Tyr$^{185}$), and mutated JNK1 (Ala$^{183}$, Phe$^{185}$). The cells were incubated in medium supplemented without or with 300 mM sorbitol for 15 minutes before measurement of JNK1 protein kinase activity as described above. JNK1 activation was seen in the wild-type but not mutated JNK1.

Example 22

Molecular Cloning of MKK7

RT-PCR was employed to identify a fragment of a novel mammalian MAP kinase kinase. The primers designed for the protocol, ATNGCNGTNAARCARATG (SEQ ID NO:23) and ATNCKYTCNGGNGCCATRTA (SEQ ID NO:24), were based on the sequence of the Drosophila MAP kinase kinase hep (Glise et al. (1995) Cell 83:451–461). Murine testis mRNA was used as the template. A single product (461 bp) was detected following RT-PCR amplification of murine testis mRNA. Sequence analysis identified this PCR product as a fragment of a novel mammalian MAP kinase kinase. Full-length murine cDNA clones were isolated by screening a murine testis library (Stratagene Inc.). The cDNA clones were examined by sequencing with an Applied Biosystems model 373A machine. A group of seven clones was identified by sequence analysis to contain a single long open reading frame that encoded a putative protein kinase (FIG. 9 and FIG. 10; SEQ ID NO:17 and SEQ ID NO:18). In-frame termination codons were detected in the 5' and 3' regions of these clones. This sequence includes protein kinase sub-domains I–XI and is related to the MAP kinase kinase group. The novel protein kinase was designated MKK7. The sites of activating phosphorylation of MAP kinase kinases located in sub-domain VIII are conserved in MKK7. Comparison of MKK7 with other members of the mammalian MAP kinase kinase group demonstrates that MKK7 is related to the JNK activator MKK4.

One additional cDNA clone isolated from the X phage library differed from the other seven clones. This clone contained the same 3' untranslated region and coding region of MKK7, but had a different 5' region that lacked an in-frame termination codon. This clone represents an alternatively spliced form of MKK7 (MKK7b; FIG. 11; SEQ ID NO:19). The MKK7b cDNA clone does not have an initiation codon in the alternative 5' region; this cDNA therefore encodes the same MKK7 protein kinase as the other clones that were isolated. However, if the MKK7b cDNA clone is not full-length it is possible that additional 5' sequence may include an in-frame initiation codon. If true, MKK7b is predicted to fuse the sequence M-[?]-SPAPA PSQRAALQLPLANDGGSRSPSSESSPQHPTPPTRPRH- (SEQ ID NO:33) to the initiating methionine of MKK7 (FIG. 9). Although the Drosophila MAP kinase kinase hep shares substantial sequence similarity with MKK7, the sequence of the NH$_2$-terminal extension of MKK7b is not conserved in the hep protein kinase. Three additional clones encoded MKK7 splice variants that differ in the 5' and 3' regions. These clones (MKK7c (FIG. 13), MKK7d (FIG. 14), and MKK7e (FIG. 15)) are full-length because of the presence of in-frame termination codons in the 5' and 3' regions.

A human cDNA library was screened with a full-length mouse MKK7 cDNA probe. A single clone was identified and squenced. A partial MKK7 sequence was identified (FIG. 12; SEQ ID NO:25 and SEQ ID NO:26) that is missing the 3' end. The sequence is most homologous to mouse MKK7c.

The sequences of MKK7, MKK7b, hep, and human MKK7 cDNAs have been deposited in Genbank with accession numbers U93030, U93031, U93032, and AF00319 respectively.

Example 23

Expression of MKK7

MKK7 expression was examined by Northern blot analysis of mRNA isolated from different tissues. The analysis was done with poly A+ mRNA (2 μg) isolated from different tissues and fractionated by denaturing agarose gel electrophoresis and transferred to a nylon membrane (Clontech). The blot was probed with MKK4 and MKK7 cDNAs labeled by random priming with [α-$^{32}$p]dATP (Amersham International PLC).

MKK7 was found to be widely expressed in murine tissues. A single MKK7 transcript (approximately 4.0-kb) was detected in all of the tissues examined, except for testis where two MKK7 transcripts (4.0 kb and 1.6 kb) were detected. The highest levels of MKK7 expression were in testis. Significant expression of MKK7 was also observed in heart, brain, lung, liver, and kidney. This contrasts with MKK4 expression which was highest in brain although significant amounts of expression were observed in brain, liver, muscle, heart, and kidney. Although MKK4 and MKK7 are co-expressed, the relative abundance of each MAP kinase kinase is different in each of the tissues examined.

Example 24
Specific Activation of JNK by MKK7 in vitro

To examine the specificity of MKK7, in vitro protein kinase assays were performed. A bacterial MKK7 expression vector was prepared by sub-cloning an MKK7 cDNA (Eco RI and Pvu II fragment) into the Eco RI and Sma I sites of pGEX-5X1 (Pharmacia-LKB). The glutathione-S-transferase (GST) fusion protein was purified by affinity chromatography (Smith and Johnson (1988) Gene 67:31–40). The recombinant proteins GST-ATF2 (Gupta et al. (1995) Science 267:389–393), GST-cJun (Dérijard (1994) supra), GST-cMyc (Alvarez et al. (1991) J. Biol. Chem. 266:15277–15285), GST-ERK2 (Seth et al. (1992) J. Biol. Chem. 267:24796–24804), GST-p38, (Raingeaud et al. (1995) J. Biol. Chem. 270:7420–7426), and GST-JNK1 (Dérijard (1994) supra) have been described.

Protein kinase assays were performed in kinase buffer (25 mM 4-(2-hydroxyethyl)-1-piperazineethansulfonic acid (pH 7.4), 25 mM β-glycerophosphate, 25 mM $MgCl_2$, 2 mM dithiothreitol, 0.1 mM orthovanadate). The assays were initiated by the addition of 1 μg of substrate proteins and 50 μM [γ-32P]ATP (10 Ci/mmol) in a final volume of 25 Al. The reactions were terminated after 30 minutes at 25° C. by addition of Laemmli sample buffer. The phosphorylation of the substrate proteins was examined after SDS-polyacrylamide gel electrophoresis (PAGE) by autoradiography.

Recombinant MAP kinases were incubated with GST (control) or GST-MKK7 using the substrate ATP[γ-$^{32}$P] Recombinant MKK7 purified from bacteria was not observed to autophosphorylate. Incubation of the recombinant MKK7 with MAP kinases demonstrated that MKK7 phosphorylated JNK1, but not p38 or ERK2. MKK7 was phosphorylated by p38 and JNK1. The significance of the retrophosphorylation of the MAP kinase kinase by the MAP kinase is unclear, but similar retrophosphorylation has been detected in kinase assays using MKK4 (Dérijard (1995) supra) and the Drosophila JNK activator hep (Sluss (1996) supra).

To test whether the phosphorylation of JNK1 by MKK7 caused increased protein kinase activity, experiments using ATF2 as the JNK substrate were performed. GST-MKK7 was incubated in a protein kinase assay with recombinant JNK1. JNK activity was measured by including the JNK substrate ATF2 in each assay. ATF2 was not phosphorylated by MKK7, but was weakly phosphorylated by JNK1. Incubation of MKK7 with JNK1 caused phosphorylation of JNK1 and a large increase in ATF2 phosphorylation. These data indicate that MKK7 phosphorylates and activates JNK1. To confirm this conclusion, the effect of replacement of the JNK dual phosphorylation motif Thr-Pro-Tyr with Ala-Pro-Phe was examined. MKK7 did not phosphorylate the mutated JNK1 (APF) protein. Furthermore, MKK7 did not increase ATF2 phosphorylation by the mutated JNK1 protein kinase. Thus, MKK7 is a JNK activator in vitro.

Example 25
Specific Activation of JNK by MKK7 in vivo

To examine the specificity of MKK7 in vivo, cotransfection assays were performed. CHO cells were maintained in Dulbecco's modified Eagle's medium supplemented with fetal calf serum (5%; Gibco-BRL). The cells were transfected with the lipofectamine reagent according to the manufacturer's recommendations (Gibco-BRL) Dérijard (1994) supra). Cells were co-transfected with vectors encoding epitope-tagged JNK1 together with an empty expression vector (control) or an expression vector encoding MKK4 or MKK7. The epitope tag was derived from the hemagglutinin protein (HA) of the influenza virus. JNK1 was isolated by immunoprecipitation of cell lysates. The cells were solubilized with lysis buffer (20 mM Tris (pH 7.4), 1% TRITON X-1000, 10% glycerol, 137 mM NaCl, 2 mM EDTA, 25 mM γ-glycerophosphate, 1 mM Na orthovanadate, 2 mM pyrophosphate, 1 mM PMSF, 10 μg/ml leupeptin) and centrifuged at 100,000×g for 15 minutes at 4° C. The epitope-tagged protein kinases were immunoprecipitated by incubation for 3 hours at 4° C. with an anti-HA monoclonal antibody bound to protein-G Sepharose (Pharmacia-LKB Biotechnology Inc.). The immunoprecipitates were washed three times with lysis buffer (Gupta et al. (1995) Science 267:389–393). Protein kinase activity was measured in the immunecomplex with [γ-$^{32}$P]ATP and c-Jun as substrates. The product of the phosphorylation reaction was visualized after SDS-PAGE by autoradiography. The ERK2 and p38 MAP kinases were not activated by co-expressed MKK7. Control experiments demonstrated that the ERK2 and p38 MAP kinases were activated by their respective cognate MAP kinase kinases, MKK1 and MKK6. In contrast, MKK7 did activate JNK1. Interestingly, the activation of JNK1 by co-expressed MKK7 was greater than that caused by the previously described JNK activator MKK4. Together, these data establish that MKK7 can function as a specific activator of JNK in cultured cells.

Example 26
Activation of the JNK Signal Transduction Pathway by MKK7

The JNK signaling pathway is known to regulate AP-1 transcriptional activity (Whitmarsh (1996) supra). To test the hypothesis that the expression of MKK7 would cause increased AP-1 transcriptional activity, a co-transfection assay was employed using a luciferase reporter gene that contains three AP-1 sites cloned upstream of a minimal promoter element (Rincon and Flavell (1994) EMBO J. 13:4370–4381). Luciferase reporter gene expression was measured in co-transfection assays using the 0.5 μg of the reporter plasmid pTRE-luciferase (Rincon (1994) supra) and 0.25 μg of the γ-galactosidase expression vector pCH110 (Pharmacia-LKB). Experiments using GAL4 fusion proteins were performed using 0.25 μg of pGAL4-ATF2 (residues 1–109), 0.5 μg of the reporter plasmid pG5E1bLuc, and 0.25 μg of pCH110 (Gupta et al. (1995) supra) . The effect of protein kinases was examined by co-transfection with 0.3 μg of an empty expression vector or a protein kinase expression vector. The ERK2, p38, JNK1, MKK1, MKK3, MKK4, and MKK6 expression vectors have been described. The cells were harvested 36 hours post-transfection. The 0-galactosidase and luciferase activity in the cell lysates was measured as described (Gupta (1995) supra). Expression of MKK4, MKK7, or JNK1 did not cause marked changes in AP-1 reporter gene expression (FIG. 16A). In contrast, co-expression of MKK7 with JNK1 caused increased AP-1-dependent reporter gene expression. Consistent with the observation that MKK4 causes weaker activation of JNK than MKK7, co-expression of MKK4 with JNK caused a smaller increase in AP-1 reporter gene expression (FIG. 16A). Together, these data demonstrate that MKK7 can function as an activator of the JNK signal transduction pathway.

To further examine the effect of MKK7 on transcriptional activity, the effect of MKK7 on the transcription factor ATF2 was investigated. Previous studies have demonstrated that ATF2 is a target of the JNK signal transduction pathway (van Dam et al. (1995) supra; Gupta et al. (1995) supra; Livingstone et al (1995) supra). JNK phosphorylates two sites (Thr-69 and Thr-71) in the $NH_2$-terminal activation domain of ATF2 and increases transcriptional activity. A GAL4 fusion protein strategy was employed to monitor the transcriptional activity of the activation domain of ATF2 (Gupta (1995) supra). Measurement of reporter gene expression demonstrated that the co-expression of MKK4 with JNK1 caused increased transcriptional activity (FIG. 16B). A similar level of reporter gene expression was caused by expression of MKK7 and a larger increase was detected when MKK7 was co-expressed with JNK1. The more potent effect of MKK7, compared with MKK4, on transcriptional activity is consistent with the relative effects of MKK7 and MKK4 on JNK activation. To confirm that the increased reporter gene expression was mediated by ATF2 phosphorylation, the effect of replacement of the sites of ATF2 phosphorylation (Thr-69 and Thr-71) with Ala was examined. The mutated ATF2 protein was not regulated by MKK4, MKK7, or JNK1 (FIG. 16B). Together, these data demonstrate that MKK7 can regulate a physiological target of the JNK signaling pathway.

Use

The MKK polypeptides and polynucleotides of the invention are useful for identifying reagents that modulate the MKK signal transduction pathways. Reagents that modulate an MKK signal transduction pathway can be identified by their effect on MKK synthesis, MKK phosphorylation, or MKK activity. For example, the effect of a reagent on MKK activity can be measured by the in vitro kinase assays described above. MKK is incubated without (control) and with a test reagent under conditions sufficient to allow the components to react, then the effect of the test reagent on kinase activity is subsequently measured. Reagents that inhibit an MKK signal transduction pathway can be used in the treatment of MKK-mediated disorders. Reagents that stimulate an MKK signal transduction pathway can be used in a number of ways, including induction of programmed cell death (apoptosis) in tissues. For example, the elimination of UV damaged cells can be used to prevent cancer.

Generally, for identification of a reagent that inhibits the MKK signal transduction pathway, a kinase assay (see, for example, Example 3) is used. A range of reagent concentrations (e.g., 1.0 nM to 100 mM) are added to a test system that includes an MKK substrate and a radioactive marker such as $[\gamma\text{-}^{32}P]ATP$. Appropriate substrate molecules include p38, JNK1, JNK2, or ATF2. The incorporation of labelled phosphorus (e.g., $[^{32}P]$ or $[^{33}P]$) into the substrate is determined, and the results obtained with the test reagent compared to control values. Of particular interest are reagents that result in inhibition of $[^{32}P]$ incorporation of about 80% or more. Phosphorylation may also be examined using a reagent that is phosphorylation-dependent, for example, an antibody. Phosphorylation-dependent antibodies may be made using MKK7 phosphorylated on the activating sites, $Ser^{198}$ and $Thr^{202}$. This may be accomplished by immunizing animals with a synthetic peptide (for example, approximately 15 amino acids in length) corresponding to the MKK7 sequence with phosphorylated $Ser^{198}$ and $Thr^{202}$. Methods of producing such antibodies are known in the art. Such antibodies are useful for the detection of activated MKK7 in tissues and cell extracts (e.g. on Western blots) and may be used in a kit.

Assays that test the effect of a reagent on MKK synthesis can also be used to identify compounds that inhibit MKK signal transduction pathways. The effect of the test reagent on MKK expression is measured by, for example, Western blot analysis with an antibody specific for an MKK. Antibody binding is visualized by autoradiography or chemiluminescence, and is quantitated. The effect of the test reagent on MKK mRNA expression can be examined, for example, by Northern blot analysis using a polynucleotide probe or by polymerase chain reaction.

Reagents found to inhibit MKK signal transduction pathways can be used as therapeutic agents for the treatment of MKK-mediated disorders. Such reagents are also useful in drug design for elucidation of the specific molecular features needed to inhibit MKK signal transduction pathways.

In addition, the invention provides a method for the treatment of MKK-mediated stress-related and inflammatory disorders. The method includes administration of an effective amount of a therapeutic reagent that inhibits MKK function. Suitable reagents inhibit either MKK activity or expression. The concentration of the reagent to be administered is determined based on a number of factors, including the appropriate dosage, the route of administration, and the specific condition being treated. The appropriate dose of a reagent is determined by methods known to those skilled in the art including routine experimentation to optimize the dosage as necessary for the individual patient and specific MKK-mediated disorder being treated. Specific therapeutically effective amounts appropriate for administration are readily determined by one of ordinary skill in the art (see, for example, *Remington's Pharmaceutical Sciences.* 18th ed., Gennaro, ed., Mack Publishing Company, Easton, Pa., 1990). Dosages may range from about 0.1–10 mg/kilo/day.

The invention provides methods for both acute and prophylactic treatment of stress-related and inflammatory disorders. For example, it is envisioned that ischemic heart disease will be treated during episodes of ischemia and oxidative stress following reperfusion. In addition, a patient at risk for ischemia can be treated prior to ischemic episodes.

In another example, a therapeutic agent that inhibits MKK function or activity is administered to control inflammatory responses by inhibiting the secretion of inflammatory cytokines, including TNF and IL-1.

Stress-related proliferative disorders can also be treated by the method of the invention by administering a therapeutic reagent that inhibits MKK function or activity. Such therapeutic reagents can be used alone or in combination with other therapeutic reagents, for example, with chemotherapeutic agents in the treatment of malignancies. Indeed, the control of stress-activated MKK by the therapeutic reagents provided by this invention can modulate symptoms caused by other therapeutic strategies that induce stress.

The therapeutic reagents employed are compounds which inhibit MKK function or activity, including polynucleotides, polypeptides, and other molecules such as antisense oligonucleotides and ribozymes, which can be made according to the invention and techniques known to the art. Polyclonal or monoclonal antibodies (including fragments or derivatives thereof) that bind epitopes of MKK also can be employed as therapeutic reagents. Dominant-negative forms of MKK which effectively displace or compete with MKK for substrate binding and/or phosphorylation can be used to decrease protein kinase activity. Dominant-negative forms can be created by mutations within the catalytic domain of the protein kinases, using methods known in the art, and as described above (Example 13). The catalytic residues are conserved in all the MKK isoforms. For example, mutation of $Lys^{76}$ inhibits MKK7 activity. Similarly, mutation of the conserved sites of activating phosphorylation ($Ser^{198}$, Thr$^{202}$) inhibits MKK7 activity. These kinase-inactive forms of MKK7 act as dominant-negative inhibitors.

In some cases, augmentation of MKK activity is desirable, e.g., induction of apoptosis. The methods of the invention can be used to identify reagents capable of increasing MKK function or activity. Alternatively, increased activity is achieved by over-expression of MKK. When an MKK-mediated disorder is associated with under-expression of MKK, or expression of a mutant MKK polypeptide, a sense polynucleotide sequence (the DNA coding strand) or MKK polypeptide can be introduced into the cell to enhance normal MKK activity. If necessary, these treatments are targeted to specific cells by their mode of administration (e.g., by use of cell-type specific viral vectors), or by placing MKK7 nucleic acids in recombinant constructs with cell-type specific or inducible promoters by methods known in the art. For example, MKK7 nucleic acid-containing vectors can be constructed by recombinant DNA technology methods standard in the art. Vectors can be plasmid, viral, or others known in the art, used for replication and expression in mammalian cells. Expression of the sequence encoding the MKK7 nucleic acid can be by any promoter known in the art to act in mammalian, preferably human cells. Such promoters can be inducible or constitutive. Such promoters include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a polypeptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives can also be present, such as, for example, antimicrobials, antioxidants, chelating agents, and inert gases, and the like.

Polynucleotide sequences, including antisense sequences, can be therapeutically administered by various techniques known to those skilled in the art. Such therapy would achieve its therapeutic effect by introduction of the MKK polynucleotide into cells of mammals having a MKK-mediated disorder. Delivery of MKK polynucleotides can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Transgenic animals

MKK polypeptides can also be expressed in transgenic animals. These animals represent a model system for the study of disorders that are caused by or exacerbated by overexpression or underexpression of MKK, and for the development of therapeutic agents that modulate the expression or activity of MKK. For example, dominant-negative and constitutively activated alleles could be expressed in mice to establish physiological function.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred.

Any technique known in the art can be used to introduce a MKK transgene into animals to produce the founder lines of transgenic animals. Such techniques include, but are not limited to, pronuclear microinjection (U.S. Pat. No. 4,873, 191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983). Especially useful are the methods described in Yang et al. (*Proc. Natl Acac. Sci. USA* 94:3004–3009, 1997).

The present invention provides for transgenic animals that carry the MKK transgene in all their cells, as well as animals that carry the transgene in some, but not all of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the MKK transgene be integrated into the chromosomal site of the endogenous MKK gene, gene targeting is preferred. Briefly, when such a technique is to be used, vectors containing some nucleotide sequences homologous to an endogenous MKK gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous MKK gene in only that cell type (Gu et al., *Science* 265:103, 1984). The regulatory sequences required for such a cell-type specific inactivation will depend upon the particular cell type of interest, and will be apparent to those of skill in the art.

These techniques are useful for preparing "knock outs" having no functional MKK gene.

Once transgenic animals have been generated, the expression of the recombinant MKK gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of MKK gene-expressing tissue can also be evaluated immunocytochemically using antibodies specific for the MKK transgene product.

For a review of techniques that can be used to generate and assess transgenic animals, skilled artisans can consult Gordon (*Intl. Rev. Cytol.* 115:171–229, 1989), and may obtain additional guidance from, for example: Hogan et al. *Manipulating the Mouse Embryo*, Cold Spring Harbor Press, Cold Spring Harbor, N.Y., 1986);, Krimpenfort et al. (*Bio/Technology* 9:86, 1991), Palmiter et al. (*Cell* 41:343, 1985), Kraemer et al. (*Genetic Manipulation of the Early Mammalian Embryo*, Cold Spring Harbor Press, Cold Spring Harbor, N.Y., 1985), Hammer et al. (*Nature* 315:680, 1985), Purcel et al. (*Science,* 244:1281, 1986), Wagner et al. (U.S. Pat. No. 5,175,385), and Krimpenfort et al. (U.S. Pat. No. 5,175,384) (the latter two publications are hereby incorporated by reference).

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated polynucleotide sequence encoding a MMK7 polypeptide having serine, threonine, and tyrosine kinase activity, and phosphorylating MAP kinase JNK, but not p38 comprising a polynucleotide sequence that hybridizes to the sequence of SEQ ID NO:17, SEQ ID NO:19, SEQ ID NO:25, SEQ ID NO:27, SEQ ID NO:29, SEQ ID NO:31, or a complement thereof, the hybridization conditions comprising hybridization in 50% formamide at 42° C. and washing in 0.2× SSC and 0.1% SDS at 68° C.

2. An isolated polynucleotide sequence encoding a mitogen-activated protein kinase kinase 7 (MKK7) polypeptide having serine, threonine, and tyrosine kinase activity, and phosphorylating mitogen-activated Protein (MAP) kinase JNK, but not p38, wherein the MKK7 polypeptide sequence is selected from the group consisting of SEQ ID NO:18, SEQ ID NO:20, SEQ ID NO:26, SEQ ID NO:28, SEQ ID NO:30, and SEQ ID NO:32.

3. An isolated polynucleotide sequence encoding a mitogen-activated protein kinase kinase (MKK), the polynucleotide sequence comprising the sequence of SEQ ID NO:17, SEQ ID NO:19, SEQ ID NO:25, SEQ ID NO:27, SEQ ID NO:29, or SEQ ID NO:31, or degenerate variants thereof, or a polynucleotide sequence fully complementary to the sequence of SEQ ID NO:17, SEQ ID NO:19, SEQ ID NO:25, SEQ ID NO:27, SEQ ID NO:29, or SEQ ID NO:31, or degenerate variants thereof.

4. A recombinant expression vector containing a polynucleotide sequence of claim 1.

5. A recombinant host cell comprising a polynucleotide sequence of claim 1.

6. A recombinant expression vector containing a polynucleotide sequence of claim 2.

7. A recombinant host cell comprising a polynucleotide sequence of claim 2.

8. A recombinant expression vector containing a polynucleotide sequence of claim 3.

9. A recombinant host cell comprising a polynucleotide sequence of claim 3.

\* \* \* \* \*